US009034329B2

(12) United States Patent
Chang et al.

(10) Patent No.: US 9,034,329 B2
(45) Date of Patent: *May 19, 2015

(54) PREPARATION OF ANTIBODY OR AN ANTIBODY FRAGMENT-TARGETED IMMUNOLIPOSOMES FOR SYSTEMIC ADMINISTRATION OF THERAPEUTIC OR DIAGNOSTIC AGENTS AND USES THEREOF

(75) Inventors: Esther H. Chang, Potomac, MD (US); Kathleen F. Pirollo, Rockville, MD (US)

(73) Assignee: Georgetown University, Washington, DC (US)

( * ) Notice: Subject to any disclaimer, the term of this patent is extended or adjusted under 35 U.S.C. 154(b) by 1832 days.

This patent is subject to a terminal disclaimer.

(21) Appl. No.: 11/520,796

(22) Filed: Sep. 14, 2006

(65) Prior Publication Data

US 2007/0065499 A1 Mar. 22, 2007

Related U.S. Application Data

(63) Continuation-in-part of application No. 10/113,927, filed on Apr. 2, 2002, which is a continuation-in-part of application No. 09/914,046, filed as application No. PCT/US00/04392 on Feb. 22, 2000, now Pat. No. 7,479,276.

(60) Provisional application No. 60/121,133, filed on Feb. 22, 1999, provisional application No. 60/280,134, filed on Apr. 2, 2011.

(51) Int. Cl.
| A61K 39/395 | (2006.01) |
| A61K 9/127 | (2006.01) |
| C12P 21/08 | (2006.01) |
| C12N 15/11 | (2006.01) |
| C07K 16/28 | (2006.01) |
| G01N 33/53 | (2006.01) |

(52) U.S. Cl.
CPC ........... *C07K 16/2881* (2013.01); *A61K 9/1272* (2013.01); *C07K 2317/622* (2013.01)

(58) Field of Classification Search
None
See application file for complete search history.

(56) References Cited

U.S. PATENT DOCUMENTS

| 4,946,778 | A | 8/1990 | Ladner et al. |
| 5,688,488 | A | 11/1997 | Low et al. |
| 5,786,214 | A | 7/1998 | Holmberg |
| 5,977,322 | A | 11/1999 | Marks et al. |
| 6,071,533 | A | 6/2000 | Papahadjopoulos et al. |
| 6,099,842 | A | 8/2000 | Pastan et al. |
| 6,200,956 | B1 | 3/2001 | Scherman et al. |
| 6,210,707 | B1 | 4/2001 | Papahadjopoulos et al. |
| 6,693,086 | B1 | 2/2004 | Dow et al. |
| 6,794,128 | B2 | 9/2004 | Marks et al. |
| 7,022,336 | B2 | 4/2006 | Papahadjopoulos et al. |
| 7,741,300 | B2 | 6/2010 | Dow et al. |
| 7,780,882 | B2 * | 8/2010 | Chang et al. .................... 264/4.1 |
| 2001/0008759 | A1 | 7/2001 | Marks et al. |
| 2003/0044407 | A1 | 3/2003 | Chang et al. |
| 2004/0209366 | A1 | 10/2004 | Papahadjopoulos et al. |

FOREIGN PATENT DOCUMENTS

| EP | 0 451 972 | 10/1991 |
| JP | 09-110722 | 4/1997 |
| WO | WO 83/02069 | 6/1983 |
| WO | WO 95/14380 | 6/1995 |
| WO | WO 95/35301 | 12/1995 |
| WO | WO 97/28817 | 8/1997 |
| WO | WO 98/20857 | 5/1998 |
| WO | WO 99/25320 A1 | 5/1999 |
| WO | WO 99/59643 | 11/1999 |
| WO | WO 00/15649 A1 | 3/2000 |
| WO | WO 00/50008 | 8/2000 |

OTHER PUBLICATIONS

Aigner (J. Biomed. Biotechnol. pp. 1-15, vol. 2006, published online May 18, 2006).*
Martin, F.J. and Papahaduopoulos, D., "Irreversible Coupling of Immunoglobulin Fragments to Performed Vesicles. An improved method for liposome targeting," *J. Biol. Chem.* 257:286-288, American Society for Biochemistry and Molecular Biology (1982).
Spragg, D.D., et al., "Immunotargeting of liposomes to activated vascular endothelial cells: A strategy for site-selective delivery in the cardiovascular system," *Proc. Natl. Acad. Sci.* 94:8795-8800, National Academy of Sciences (1997).
Xu, L., et al., "Transferrin-Liposome-Mediated Systemic p53 Gene Therapy in Combination with Radiation Results in Regression of Human Head and Neck Cancer Xenografts," *Human Gene Therapy* 10:2941-2952, Mary Ann Liebert (1999).
Compagnon, B., et al., "Enhanced Gene Delivery and Expression in Human Hepatocellular Carcinoma Cells by Cationic Immunoliposomes," *J. Liposomes Res.* 7:127-141, Marcie Dekker, Inc. (1997).

(Continued)

*Primary Examiner* — Michael Szperka
*Assistant Examiner* — Marianne Dibrino
(74) *Attorney, Agent, or Firm* — Fanelli Haag PLLC

(57) ABSTRACT

The present invention provides methods of preparing an antibody- or antibody fragment-targeted cationic immunoliposome or polymer complex comprising (a) preparing an antibody or antibody fragment; (b) mixing said antibody or antibody fragment with a cationic liposome to form a cationic immunoliposome or with a cationic polymer to form a polyplex; and (c) mixing said cationic immunoliposome or said polyplex with a therapeutic or diagnostic agent to form said antibody- or antibody fragment-targeted cationic immunoliposome or polymer complex. The present invention also provides cationic immunoliposome or polymer complexes produced by such methods and compositions comprising such complexes. The present invention also provides methods for treating various diseases and disorders, including cancers, by administering the complexes and compositions of the invention to a patient.

66 Claims, 75 Drawing Sheets

(56) References Cited

OTHER PUBLICATIONS

De Kruif, J., et al., "Biosynthetically lipid-modified human scFv fragments from phage display libraries as targeting molecules for immunoliposomes," *FEBS Lett.* 399:232-236, Elsevier Science B.V. (1996).
Jiang, A., et al., "Cell-Type-Specific Gene Transfer into Human Cells with Retroviral Vectors that Display Single-Chain Antibodies," *J. Virol.* 72:10148-10156, American Society for Microbiology (1998).
Kobatake, E., et al., "A fluoroimmunoassay based on immunoliposomes containing genetically engineered lipid-tagged antibody," *Anal. Chem.* 69:1295-1298, American Chemical Society (1997).
Roh, H., et al., "HER2/neu antisense targeting of human breast carcinoma," *Oncogene* 19:6138-6143, Macmillan Publishers Ltd. (2000).
Shahinian, S., and Silvius, J.R., "A novel strategy affords high-yield coupling of antibody Fab' fragments to liposomes," *Biochim. Biophys. Acta* 1239:157-167, Elsevier Science B.V. (1995).
Xu, L., et al., "Transferrin-liposome-mediated p53 sensitization of squamous cell carcinoma of the head and neck to radiation in vitro" *Hum. Gene Ther.*8:467-475, M.A. Liebert (1997).
Yoshida, J., et al., "Simple preparation and characterization of cationic liposomes associated with a monoclonal antibody against glioma-associated antigen (immunoliposomes)," *J. Liposome Res.* 5:981-995, Marcel Dekker (1995).
Mamot, et al., "Targeting the epidermal growth factor receptor (EGFR)—a new therapeutic option in oncology?," *Swiss Med. Wkly.* 136:4-12, EMH Swiss Medical Publishers Ltd. (Jan. 2006).
Martin, F.J. and Papahadjopoulos, D., "Irreversible coupling of immunoglobulin fragments to preformed vesicles. An improved method for liposome targeting," *J. Biol. Chem.* 257:286-288, American Society for Biochemistry and Molecular Biology (1982).
Nilsson, B., et al., "Fusion proteins in biotechnology and structural biology," *Curr. Opin. Struct. Biol.* 2:569-575, Current Biology Ltd. (1992).
Wang, D., et al., "Generation and Characterization of an Anti-CD19 Single-Chain Fv Immunotoxin Composed of C-Terminal Disulfide-Linked dgRTA," *Bioconjugate Chem.* 8:878-884, American Chemical Society (1997).
Xu, L., et al., "Systemic Tumor-targeted Gene Delivery by Anti-Transferrin Receptor scFv-Immunoliposomes," *Mol. Cancer Ther.* 1:337-346, American Association for Cancer Research, Inc. (Mar. 2002).
Xu, L., et al., "Tumor-targeted p53-gene therapy enhances the efficacy of conventional chemo/radiotherapy," *Journal of Controlled Release* 74:115-128, Elsevier Science Ltd. (Jul. 2001).
Xu, L., et al., "Systemic p53 Gene Therapy of Cancer with Immunolipoplexes Targeted by Anti-Transferrin Receptor scFv," *Molecular Medicine* 7:723-734, The Johns Hopkins University Press (Feb. 2001).
Yu, W., et al., "Enhanced transfection efficiency of a systemically delivered tumor-targeting immunolipoplex by inclusion of a pH-sensitive histidylated oligolysine peptide," *Nucleic Acids Research* 32: e48, Oxford University Press (Mar. 2004), pp. 2-10.
Yu, D., et al., "Liposome-mediated in vivo E1A gene transfer suppressed dissemination of ovarian cancer cells that overexpress HER-2/neu," *Oncogene* 11:1383-1388, Stockton Press (1995).
Office Action in related co-pending U.S. Appl. No. 09/914,046, mailed on Jul. 28, 2005.
Office Action in related co-pending U.S. Appl. No. 09/914,046, mailed on Jun. 9, 2006.
Office Action in related co-pending U.S. Appl. No. 09/914,046, mailed on Dec. 6, 2006.
Office Action in related co-pending U.S. Appl. No. 09/914,046, mailed on Jul. 26, 2007.
Office Action in related co-pending U.S. Appl. No. 10/113,927 mailed on Feb. 7, 2008.
Office Action in related co-pending U.S. Appl. No. 10/113,927 mailed on Nov. 6, 2007.
Office Action in related co-pending U.S. Appl. No. 10/113,927 mailed on Jul. 27, 2007.
Office Action in related co-pending U.S. Appl. No. 10/113,927 mailed on Dec. 5, 2006.
Office Action in related co-pending U.S. Appl. No. 10/113,927 mailed on Sep. 22, 2005.
Allen, T.M., et al., "A new strategy for attachment of antibodies to sterically stabilized liposomes resulting in efficient targeting to cancer cells," *Biochim. Biophys. Acta* 1237:99-108, Elsevier Science Inc. (1995).
Allen, T.M., et al., "Antibody-Targeted Stealth® Liposomes" in *Stealth Liposomes*, Lasic, D.D. and Martin, F.J., eds., CRC Press Inc., Boca Raton, FL, pp. 233-244 (1995).
Aoki, K., et al., "Liposome-mediated in Vivo Gene Transfer of Antisense K-ras Construct Inhibits Pancreatic Tumor Dissemination in the Murine Peritoneal Cavity," *Cancer Res.* 55:3810-3816, American Association for Cancer Research (1995).
Bajoria, R., and Contractor, S.F., "Effect of Surface Charge of Small Unilamellar Liposomes on Uptake and Transfer of Carboxyfluorescein across the Perfused Human Term Placenta [Regular Articles]," *Pediatr. Res.* 42:520-527, International Pediatrics Research Foundation, Inc. (1997).
Bajoria, R., et al., "Endocytotic uptake of small unilamellar liposomes by human trophoblast cells in culture," *Hum. Reprod.* 12:1343-1348, European Society for Human Reproduction and Embryology (1997).
Bristow, R.G., et al., "The p53 gene as a modifier of intrinsic radiosensitivity: implications for radiotherapy," *Radiother. Oncol.* 40:197-223, Elsevier Scientific Publishers (1996).
Chen, L., et al., "Synergistic activation of p53 by inhibition of MDM2 expression and DNA damage," *Proc. Natl. Acad. Sci. USA* 95:195-200, National Academy of Sciences (1998).
Cheng, P.-W., "Receptor Ligand-Facilitated Gene Transfer: Enhancement of Liposome-Mediated Gene Transfer and Expression by Transferrin," *Hum. Gene Ther.* 7:275-282, Mary Ann Liebert, Inc. (1996).
Chiarugi, V., et al., "Cox-2, iNOS and p53 as play-makers of tumor angiogenesis (Review)," *Int. J. Mol. Med.* 2:715-719, D.A. Spandidos (1998).
Clark, P.R., and Hersh, E.M., "Cationic lipid-mediated gene transfer: Current concepts," *Curr. Opin. Mol. Ther.* 1:158-176, Current Drugs Ltd. (Apr. 1999).
Cristiano, R.J., and Curiel, D.T., "Strategies to accomplish gene delivery via the receptor-mediated endocytosis pathway," *Cancer Gene Ther.* 3:49-57, Appleton & Lange (1996).
Drummond, D.C., et al., "Optimizing Liposomes for Delivery of Chemotherapeutic Agents to Solid Tumors," *Pharmacol. Rev.* 51:691-743, The American Society for Pharmacology and Experimental Therapeutics (Dec. 1999).
Dubé, D., et al., "Preparation and Tumor Cell Uptake of Poly(N-isopropylacrylamide) Folate Conjugates," *Bioconjugate Chem.* 13:685-692, American Chemical Society (May-Jun. 2002).
Elliott, R.L., et al., "Breast Carcinoma and the Role of Iron Metabolism: A Cytochemical, Tissue Culture, and Ultrastructural Study," *Ann. N.Y. Acad. Sci.* 698:159-166, New York Academy of Sciences (1993).
Felgner, P.L., et al., "Improved Cationic Lipid Formulations for In Vivo Gene Therapy," *Ann. N.Y. Acad. Sci.* 772:126-139, New York Academy of Sciences (1995).
Forssen, E., and Willis, M., "Ligand-targeted liposomes," *Adv. Drug Deliv. Rev.* 29:249-271, Elsevier Science B.V. (1998).
Fujiwara, T., et al., "A Retroviral Wild-Type p53 Expression Vector Penetrates Human Lung Cancer Spheroids and Inhibits Growth by Inducing Apoptosis," *Cancer Res.* 53:4129-4133, American Association for Cancer Research (1993).
Fujiwara, T., et al., "Induction of Chemosensitivity in Human Lung Cancer Cells in vivo by Adenovirus-mediated Transfer of the Wild-Type p53 Gene," *Cancer Res.* 54:2287-2291, American Association for Cancer Research (1994).
Gershon, H., et al., "Mode of formation and structural features of DNA-cationic liposome complexes used for transfection," *Biochemistry* 32:7143-7151, American Chemical Society (1993).

(56) References Cited

OTHER PUBLICATIONS

Hamada, K., et al., "Adenovirus-mediated Transfer of a Wild-Type p53 Gene and Induction of Apoptosis in Cervical Cancer," *Cancer Res.* 56:3047-3054, American Association for Cancer Research (1996).

Huwyler, J., et al., "Brain drug delivery of small molecules using immunoliposomes," *Proc. Natl. Acad. Sci. USA* 93:14164-14169, National Academy of Sciences (1996).

Johnson, P., et al., "Expression of Wild-Type p53 Is Not Compatible with Continued Growth of p53-Negative Tumor Cells," *Mol. Cell Biol.* 11:1-11, American Society for Microbiology (1991).

Kerr, J.F.R., et al., "Apoptosis: Its Significance in Cancer and Cancer Therapy," *Cancer* 73:2013-2026, Wiley (1994).

Kirpotin, D., et al., "Sterically Stabilized Anti-HER2 Immunoliposomes: Design and Targeting to Human Breast Cancer Cells in Vitro," *Biochemistry* 36:66-75, American Chemical Society (1997).

Koning, G.A., et al., "Antiproliferative effect of immunoliposomes containing 5-fluorodeoxyuridine-dipalmitate on colon cancer cells," *Br. J. Cancer* 80:1718-1725, Cancer Research Campaign (Aug. 1999).

Koning, G.A., et al., "Selective transfer of a lipophilic prodrug of 5-fluorodeoxyuridine from immunoliposomes to colon cancer cells," *Biochim. Biophys. Acta* 1420:153-167, Elsevier Science B.V. (Aug. 1999).

Konishi, H., et al., "Targeting Strategy for Gene Delivery to Carcinoembryonic Antigen-Producing Cancer Cells by Retrovirus Displaying a Single-Chain Variable Fragment Antibody," *Hum. Gene Ther.* 9:235-248, Mary Ann Liebert, Inc. (1998).

Lasic, D.D., et al., "Sterically stabilized liposomes in cancer therapy and gene delivery," *Curr. Opin. Mol. Ther.* 1:177-185, Current Drugs Ltd. (Apr. 1999).

Lasic, D.D., and Papahadjopoulos, D., "Liposomes Revisited," *Science* 267:1275-1276, American Association for the Advancement of Science (1995).

Laukkanen, M.-L., et al., "Functional Immunoliposomes Harboring a Biosynthetically Lipid-Tagged Single-Chain Antibody," *Biochemistry* 33:11664-11670, American Chemical Society (1994).

Lee, R.J. and Huang, L., "Folate-targeted, Anionic Liposome-entrapped Polylysine-condensed DNA for Tumor Cell-specific Gene Transfer," *J. Biol. Chem.* 271:8481-8487, American Society for Biochemistry and Molecular Biology, Inc. (1996).

Lesoon-Wood, L.A., et al., "Systemic gene therapy with p53 reduces growth and metastases of a malignant human breast cancer in nude mice," *Hum. Gene Ther.* 6:395-405, M.A. Liebert (1995).

Lewis, J.G., et al., "A serum-resistant cytofectin for cellular delivery of antisense oligodeoxynucleotides and plasmid DNA," *Proc. Natl. Acad. Sci. USA* 93:3176-3181, National Academy of Sciences (1996).

Li, S., and Huang, L., "Functional Pleomorphism of Liposomal Gene Delivery Vectors—Lipoplex and Lipopolyplex," in *Liposomes—Rational Design*, Janoff, A.S., ed., Marcel Dekker, Inc., New York, NY, pp. 89-124 (1998).

Liu, T.J., et al., "Growth Suppression of Human Head and Neck Cancer Cells by the Introduction of a Wild-Type p53 Gene via a Recombinant Adenovirus," *Cancer Res.* 54:3662-3667, American Association for Cancer Research (1994).

Lowe, S.W., "Cancer therapy and p53," *Curr. Opin. Oncol.* 7:547-553, Rapid Science Publishers (1995).

Maclean, A.L., et al., "Immunoliposomes as targeted delivery vehicles for cancer therapeutics (Review)," *Int. J. Oncol.* 11:325-332, International Journal of Oncology (1997).

Martin, F., et al., "Retroviral Vector Targeting to Melanoma Cells by Single-Chain Antibody Incorporation in Envelope," *Human Gene Ther.* 9:737-746, Mary Ann Liebert, Inc. (1998).

Massing, U., "Cancer therapy with liposomal formulations of anticancer drugs," *Int. J. Clin. Pharmacol. Ther.* 35:87-90, Dustri-Verlag Dr. K. Feistle (1997).

Matlashewski, G., "p53: Twenty years on, Meeting Review," *Oncogene Rev.* 18:7618-7620, Stockton Press (Dec. 1999).

Miyamoto, T., et al., "Transferrin receptor in oral tumors," *Intl. J. Oral Maxillofac. Surg.* 23:430-433, Munksgaard (1994).

Miyashita, T., et al., "Tumor suppressor p53 is a regulator of bcl-2 and bax gene expression in vitro and in vivo," *Oncogene* 9:1799-1805, Macmillan Press Ltd. (1994).

Morishige, H., et al., "In vitro cytostatic effect of TNF (tumor necrosis factor) entrapped in immununoliposomes on cells normally insensitive to TNF," *Biochem. Biophys. Acta* 1151:59-68, Elsevier Science B.V. (1993).

Nag, A., et al., "A Colorimetric Estimation of Polyethyleneglycol-Conjugated Phospholipid in Stealth Liposomes," *Anal. Biochem.* 250:35-43, Academic Press (1997).

Nam, S.M., et al., "Sterically stabilized anti-$G_{M3}$, anti-Le$^x$ immunoliposomes: targeting to B16BL6, HRT-18 cancer cells," *Oncol. Res.* 11:9-16, Cognizant Communication (Jul. 1999).

Ng, K.-Y., et al., "The effects of polyethyleneglycol (PEG)-derived lipid on the activity of target-sensitive immunoliposome," *Int. J. Pharma.* 193:157-166, Elsevier Science B.V. (Jan. 2000).

Nicholson, I.C., et al., "Construction and Characterisation of a Functional CD19 Specific Single Chain Fv Fragment for Immunotherapy of B Lineage Leukaemia and Lymphoma," *Mol. Immunol.* 34:1157-1165, Elsevier Science Ltd. (1997).

Pagnan, G., et al., "GD2-Mediated Melanoma Cell Targeting and Cytotoxicity of Liposome-Entrapped Fenretinide," *Int. J. Cancer* 81:268-274, Wiley-Liss, Inc. (Apr. 1999).

Park, J.W., et al., "Development of anti-p185$^{HER2}$ immunoliposomes for cancer therapy," *Proc. Natl. Acad. Sci. USA* 92:1327-1331, National Academy of Sciences (1995).

Park, J.W., et al., "Immunoliposomes for cancer treatment," *Adv. Pharmacol.* 40:399-435, Academic Press (1997).

Park, J.W., et al., "Tumor targeting using anti-her2 immunoliposomes," *J. Control. Rel.* 74:95-113, Elsevier Science B.V. (Jul. 2001).

Pirollo, K.F., et al., "p53 mediated sensitization of squamous cell carcinoma of the head and neck to radiotherapy," *Oncogene* 14:1735-1746, Stockton Press (1997).

Pirollo, K.F., et al., "Immunoliposomes: A Targeted Delivery Tool for Cancer Treatment," in *Vector Targeting for Therapeutic Gene Delivery*, Curiel, D.T., and Douglas, J.T., eds., Wiley-Liss, Inc., Hoboken, NJ, pp. 33-62 (Aug. 2002).

Poon, R.Y.M, "Advances in Monoclonal Antibody Applications: Bispecific Antibodies" in *Biotechnology International: International Developments in the Biotechnology Industry*, Fox, F., and Connor, T.H., eds., Universal Medical Press, Inc., San Francisco, CA, pp. 113-128 (1997).

Rait, A.S., et al., "Inhibitory effects of the combination of HER-2 antisense oligonucleotide and chemotherapeutic agents used for the treatment of human breast cancer," *Cancer Gene Ther.* 8:728-739, Nature Publishing Group (Oct. 2001).

Ruley, H.E., "p53 and Response to Chemotherapy and Radiotherapy," in *Important Adv. Oncol.* 1996, DeVita, V.T., et al., eds., Lippincott-Raven Publishers, Philadelphia, PA, pp. 37-56 (1996).

Schier, R., et al., "In vitro and in vivo characterization of a human anti-c-erbB-2 single-chain Fv isolated from a filamentous phage antibody library," *Immunotechnology* 1:73-81, Elsevier Science B.V. (1995).

Sidransky, D., and Hollstein, M., "Clinical implications of the p53 gene," *Annu. Rev. Med.* 47:285-301, Annual Reviews, Inc. (1996).

Srivastava, S., et al., "Recombinant Adenovirus Vector Expressing Wild-type p53 is a Potent Inhibitor of Prostate Cancer Cell Proliferation," *Urology* 46:843-848, Excerpta Medica, Inc. (1995).

Suzuki, S., et al., "Modulation of doxorubicin resistance in a doxorubicin-resistant human leukaemia cell by an immunoliposome targeting transferring receptor," *Br. J. Cancer* 76:83-89, Cancer Research Campaign (1997).

The Journal of Gene Medicine Clinical Trials Database, "Gene Therapy Clinical Trials Worldwide," available online at http://www.wiley.co.uk/wileychi/genmed/clinical, John Wiley and Sons, Ltd., 2 pages (accessed Sep. 2001).

Thierry, A.R., et al., "Systemic gene therapy: Biodistribution and long-term expression of a transgene in mice," *Proc. Natl. Acad. Sci. USA* 92:9742-9746, National Academy of Science (1995).

(56) References Cited

OTHER PUBLICATIONS

Thorstensen, K. and Romslo, I., "The Transferrin Receptor: Its Diagnostic Value and its Potential as Therapeutic Target," *Scand. J. Clin. Lab. Invest.* 53 (*Suppl.* 215):113-120, Universitetsforlaget (1993).
Vertut-Doï, A., et al., "Binding and uptake of liposomes containing a poly(ethylene glycol) derivative of cholesterol (stealth liposomes) by the macrophage cell line J774: influence of PEG content and its molecular weight," *Biochim. Biophys. Acta* 1278:19-28, Elsevier Science B.V. (1996).
Volpert, O.V., et al., "Sequential development of an angiogenic phenotype by human fibroblasts progressing to tumorigenicity," *Oncogene* 14:1495-1502, Stockton Press (1997).
Weinberg, E.D., "Roles of Iron in Neoplasia: Promotion, Prevention, and Therapy," *Biol. Trace Element Res.* 34:123-140, Humana Press, Inc. (1992).
Wright, S.E., and Huang, L., "Bilayer stabilization of phosphatidylethanolamine by N-biotinylphosphatidylethanolamine," *Biochim. Biophys. Acta* 1103:172-178, Elsevier Science B.V. (1992).
Xu, L., et al., "Systemic p53 gene therapy in combination with radiation results in human tumor regression," *Tumor Targeting* 4:92-104, Stockton Press (Jul. 1999).
Xu, L., et al., "Transferrin-Liposome-Mediated Systemic p53 Gene Therapy in Combination with Radiation Results in Regression of Human Head and Neck Cancer Xenografts," *Hum. Gene Ther.* 10:2941-2952, Mary Ann Liebert, Inc. (Dec. 1999).
Xu, L., et al., "Self-Assembly of a Virus-Mimicking Nanostructure System for Efficient Tumor-Targeted Gene Delivery," *Hum. Gene Ther.* 13:469-481, Mary Ann Liebert, Inc. (Feb. 2002).
Yang, C., et al., "Adenovirus-mediated Wild-Type p53 Expression Induces Apoptosis and Suppresses Tumorigenesis of Prostatic Tumor Cells," *Cancer Res.* 55:4210-4213, American Association for Cancer Research (1995).
Yazdi, P.T., et al., "Influence of Cellular Trafficking on Protein Synthesis Inhibition of Immunotoxins Directed against the Transferrin Receptor," *Cancer Res.* 55:3763-3771, American Association for Cancer Research (1995).
Zhang, W.-W., et al., "Advances in Cancer Gene Therapy," *Adv. Pharmacol.* 32:289-341, Academic Press, Inc. (1995).
Hamada, K., et al., "Growth Inhibition of Human Cervical Cancer Cells with the Recombinant Adenovirus p53 in Vitro," *Gynecol. Oncol.* 60:373-379, Academic Press, Inc. (1996).
Hamada, K., et al., "Adenovirus-Mediated Transfer of HPV 16 E6/E7 Antisense RNA to Human Cervical Cancer Cells," *Gynecol. Oncol.* 63:219-227, Academic Press, Inc. (1996).
Database Medline, Accession No. NLM7621238, English language abstract for Zhang, W.W., et al., "High-efficiency gene transfer and high-level expression of wild-type p53 in human lung cancer cells mediated by recombinant adenovirus," *Cancer Gene Ther.* 1:5-13, Nature Publishing Group (1994).
Bauer, K. S., et al.: "Inhibition of Angiogenesis by Thalidomide Requires Metabolic Activation, Which is Species-Dependent," Biochemical Pharmacology, vol. 55, pp. 1827-1834, 1998.
Capitosti, S. M., et al.: "Thalidomide Analogues Demonstrate Dual Inhibition of Both Angiogenesis and Prostate Cancer," Bioorganic & Medicinal Chemistry, vol. 12, pp. 327-336, 2004.
Chackal-Roy, M., et al.: "Stimulation of Human Prostatic Carcinoma Cell Growth by Factors Present in Human Bone Marrow," The Journal of Clinical Investigation, vol. 84, pp. 43-50, 1989.
D'Amato, R. J., et al.: "Thalidomide is an Inhibitor of Angiogenesis," Proceedings of the National Academy of Sciences of the United States of America, vol. 91, pp. 4082-4085, 1994.
Dredge, K., et al.: "Immunological Effects of Thalidomide and Its Chemical and Functional Analogs," Critical Reviews in Immunology, vol. 22, pp. 425-437, 2002.
Dredge, K., et al.: "Novel Thalidomide Analogues Display Anti-Angiogenic Activity Independently of Immunomodulatory Effects," British Journal of Cancer, vol. 87, pp. 1166-1172, 2002.
Fernandes-Alnemri, T., et al.: "CPP32, a Novel Human Apoptotic Protein with Homology to Caenorhabditis elegans Cell Death Protein Ced-3 and Mammalian Interleukin-1 β-Converting Enzyme," Journal of Biological Chemistry, vol. 269, pp. 30761-30764, 1994.
Forsyth, C. J., et al.: "Thalidomide Responsive Chronic Pulmonary GVHD," Bone Marrow Tranplantation, vol. 17, pp. 291-293, 1996.
Hamel, E., et al.: "Antitumor 2,3-Ddiydro-2-(aryl)-4(1 H)-quinazolinone Derivatives. Interactions with Tubulin," Biochemical Pharmacology, vol. 51, pp. 53-59, 1995.
Heere-Ress, E., et al.: "Thalidomide Enhances the Anti-Tumor Activity of Standard Chemotherapy in a Human Melanoma Xenotransplantation Model," Journal of Investigative Dermatology, vol. 125, pp. 201-206, 2005.
Hour, M. - J., et al.: "6-Alkylamino- and 2,3-Dihydro-3'-methoxy-2-phenyl-4-quinazolinones and Related Compounds: Their Synthesis, Cytotoxicity, and Inhibition of Tubulin Polymerization," Journal of Medicinal Chemistry, vol. 43, pp. 4479-4487, 2000.
Jacobson, J. M., et al.: "Thalidomide for the Treatment of Oral Aphthous Ulcers in Patients with Human Immunodeficiency Virus Infection," New England Journal of Medicine, vol. 336, pp. 1487-1493, 1997.
Keer, H. N., et al.: "Elevated Transferrin Receptor Content in Human Prostate Cancer Cell Lines assessed In Vitro and In Vivo," Journal of Urology, vol. 143, pp. 381-385, 1990.
Kenyon, B. M., et al.: "Effects of Thalidomide and Related Metabolites in a Mouse Corneal Model of Neovascularization," Experimental Eye Research, vol. 64, pp. 971-978, 1997.
Lee, Y. J., et al.: "Docetaxel and Cisplatin as Primary Chemotherapy for Treatment of Locally Advanced Breast Cancers," Clinical Breast Cancer, vol. 5, pp. 371-376, 2004.
Lima, L. M., et al.: "Synthesis and Anti-Inflammatory Activity of Phthalimide Derivatives, Designed as New Thalidomide Analogues," Bioorganic & Medicinal Chemistry, vol. 10, pp. 3067-3073, 2002.
Marinina, J., et al.: "Stabilization of Vinca Alkaloids Encapsulated in Poly(lactide-co-glycolide) Microspheres," Pharmaceutical Research, vol. 17, pp. 677-683, 2000.
Mastrobattista, E., et al.: "Immunoliposomes for the Targeted Delivery of Antitumor Drugs," Advanced Drug Delivery Reviews, vol. 40, pp. 103-127, 1999.
Mattioli, R., et al.: "Long-Survival in Responding Patients with Metastatic Breast Cancer Treated with Doxorubicin-Docetaxel Combination. A Multicentre Phase II Trial," Anticancer Research, vol. 24, pp. 3257-3262, 2004.
May, P., et al.: "Twenty Years of p53 Research: Structural and Functional Aspects of the p53 Protein," Oncogene Reviews, vol. 18, pp. 7621-7636, 1999.
McCarthy, D. M., et al.: "Thalidomide for the Therapy of Graft-Versus-Host Disease Following Allogeneic Bone Marrow Transplantation," Biomedicine & Pharmacotherapy, vol. 43, pp. 693-697, 1989.
Miller, K. D,, et al.: "Taxanes in the Treatment of Breast Cancer: A Prodigy Comes of Age," Cancer Investigation, vol. 17, pp. 121-136, 1999.
Ng, S. S. W., et al.: "Antiangiogenic Activity of N-Substituted and Tetrafluorinated Thalidomide Analogues," Cancer Research, vol. 63, pp. 3189-3194, 2003.
Nguyen, M., et al.: "Thalidomide and Chemotherapy Combination: Preliminary Results of Preclinical and Clinical Studies," International Journal of Oncology, vol. 10, pp. 965-969, 1997.
Nicholson, D. W., et al.: "Identification and Inhibition of the ICE/CED-3 Protease Necessary for Mammalian Apotosis," Nature, vol. 376, pp. 37-43, 1995.
Reyes-Terán, G., et al.: Effects of Thalidomide on HIV-Associated Wasting Syndrome: A Randomized, Double-Blind, Placebo-Controlled Clinical Trial, AIDS, vol. 10, pp. 1501-1507, 1996.
Rossi, M. C., et al.: "Selective Stimulation of Prostatic Carcinoma Cell Proliferation by Tranderrin," Proceedings of the National Academy of Sciences of the United States of America, vol. 89, pp. 6197-6201, 1992.
Rowinsky, E. K., et al.: "Paclitaxel (Taxol)," New England Journal of Medicine, vol. 332, pp. 1004-1014, 1995.
Sachdeva, M. S., et al.: "Drug Targeting Systems for Cancer Chemotherapy," Expert Opinion on Investigational Drugs, vol. 7, pp. 1849-1964, 1998.

(56) References Cited

OTHER PUBLICATIONS

Sapra, P., et al.: "Improved Therapeutic Responses in Xenograft Model of Human B Lymphoma (Namalwa) for Liposomal Vincristine versus Liposomal Doxorubicin Targeted via Anti-CD19 IgG2a or Fab' Fragments," Clinical Cancer Research, vol. 10, pp. 1100-1111, 2004.

Simoes, S. et al.: "Enhancement of Cationic Liposome-Mediated Gene Delivery by Transferrin and Fusogenic Peptides," The 24$^{th}$ International Symposium on Controlled Release of Bioactive Materials, vol. 24, pp. 659-660, 1997.

Tewari, M., et al.: "Yama/CPP32β, a Mammalian Homolog of CED-3, Is a CrmA-Inhibitable Protease That Cleaves the Death Susbstrate Poly(ADP-Ribose) Polymerase," Cell, vol. 81, pp. 801-809, 1995.

Tseng, S., et al.: "Rediscovering Thalidomide: A Review of its Mechanism of Action, Side Effects, and Potential Uses," Journal of the American Academy of Dermatology, vol. 35, pp. 969-979, 1996.

Turk, M. J., et al.: "Characterization of a Novel pH-Sensitive Peptide that Enhances Drug Release from Folate-Targeted Liposomes at Endosomal pHs," Biochimica et Biophysica Acta, vol. 1559, pp. 56-68, 2002.

Venugopalan, P., et al.: "pH- Sensitive Liposomes: Mechanism of Triggered Release to Drug and Gene Delivery Prospects," Pharmazie, vol. 57, pp. 659-671, 2002.

Vogelsang, G. B., et al.: "Treatment and Prevention of Acute Graft-Versus-Host Disease with Thalidomide in a Rat Model," Transplantation, vol. 41, pp. 644-647, 1986.

Zignani, M., et al.: In Vitro Characterization of a Novel Polymeric-Based pH-Sensitive Liposome System, Biochimica et Biophysica Acta, vol. 1463, pp. 383-394, 2000.

Office Action in related U.S. Appl. No. 10/113,927, now Patent No. 7,780,882 mailed May 31, 2006.

Office Action in related U.S. Appl. No. 10/113,927, now U.S. Patent No. 7,780,882 mailed Nov. 25, 2008.

Notice of Allowance in related U.S. Appl. No. 10/113,927, now Patent No. 7,780,882 mailed Mar. 23, 2010.

Office Action in related co-pending U.S. Appl. No. 11/520,796 mailed Aug. 3, 2010.

Office Action in related co-pending U.S. Appl. No. 11/798,296 mailed Jan. 14, 2011.

Office Action in related co-pending U.S. Appl. No. 12/820,800, mailed Nov. 22, 2011, 12 pages.

Grayhack, J.T., et al. "Analysis of Specific Protiens in Prostatic Fluid Detecting Prostatic Malignancy," *The Journal of Urology* 121:295-299 (1979).

Joshee, N., et al., "Transferrin-Facilitated Lipofection Gene Delivery Strategy: Characterization of the Transfection Complexes and Intracellular Trafficking," *Human Gene Therapy* 13:1991-2004 (2002).

International Search Report for International Application No. PCT/US07/11407, ISA US, Alexandria VA, mailed on Oct. 10, 2007.

Office Action in related co-pending U.S. Appl. No. 12/820,800, mailed Mar. 17, 2011, 12 pages.

* cited by examiner

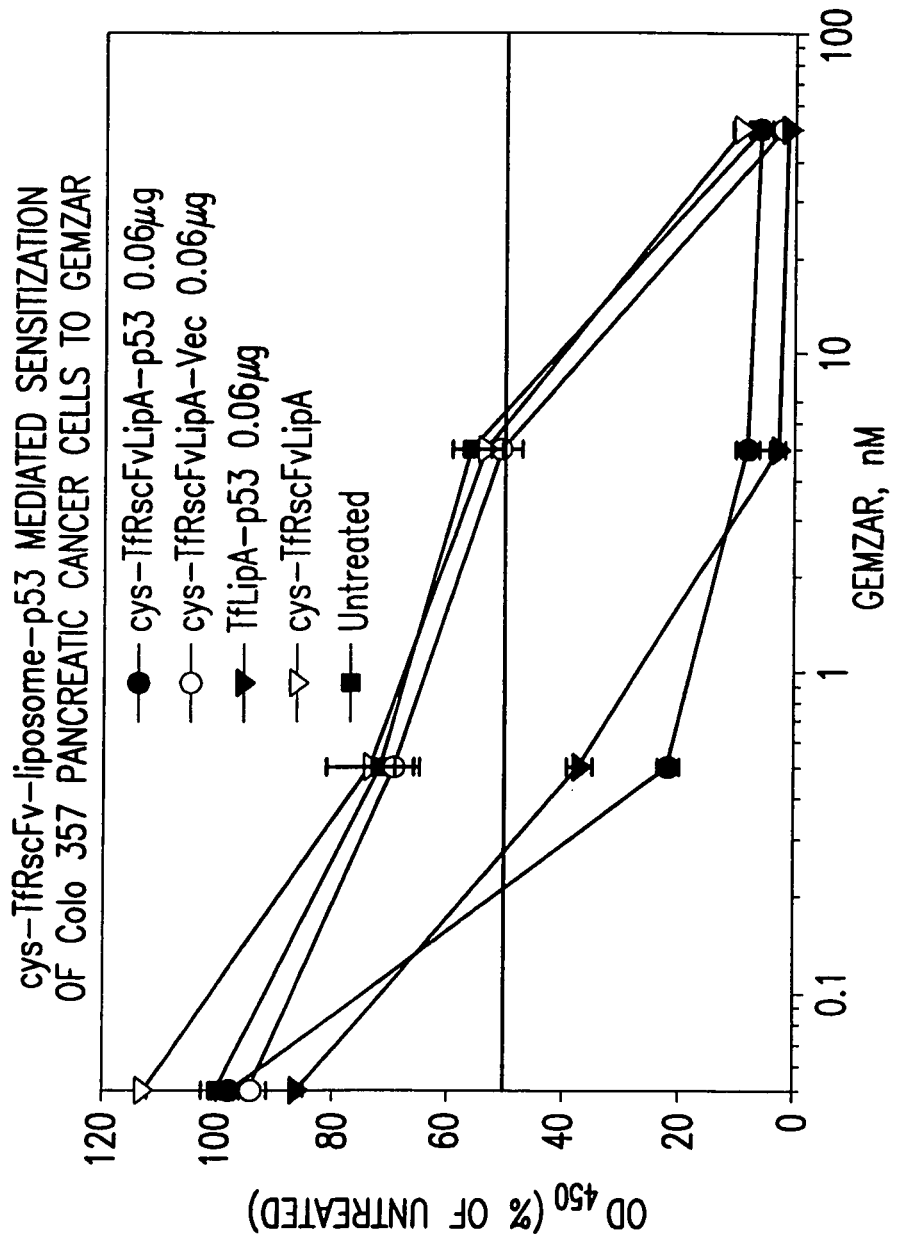

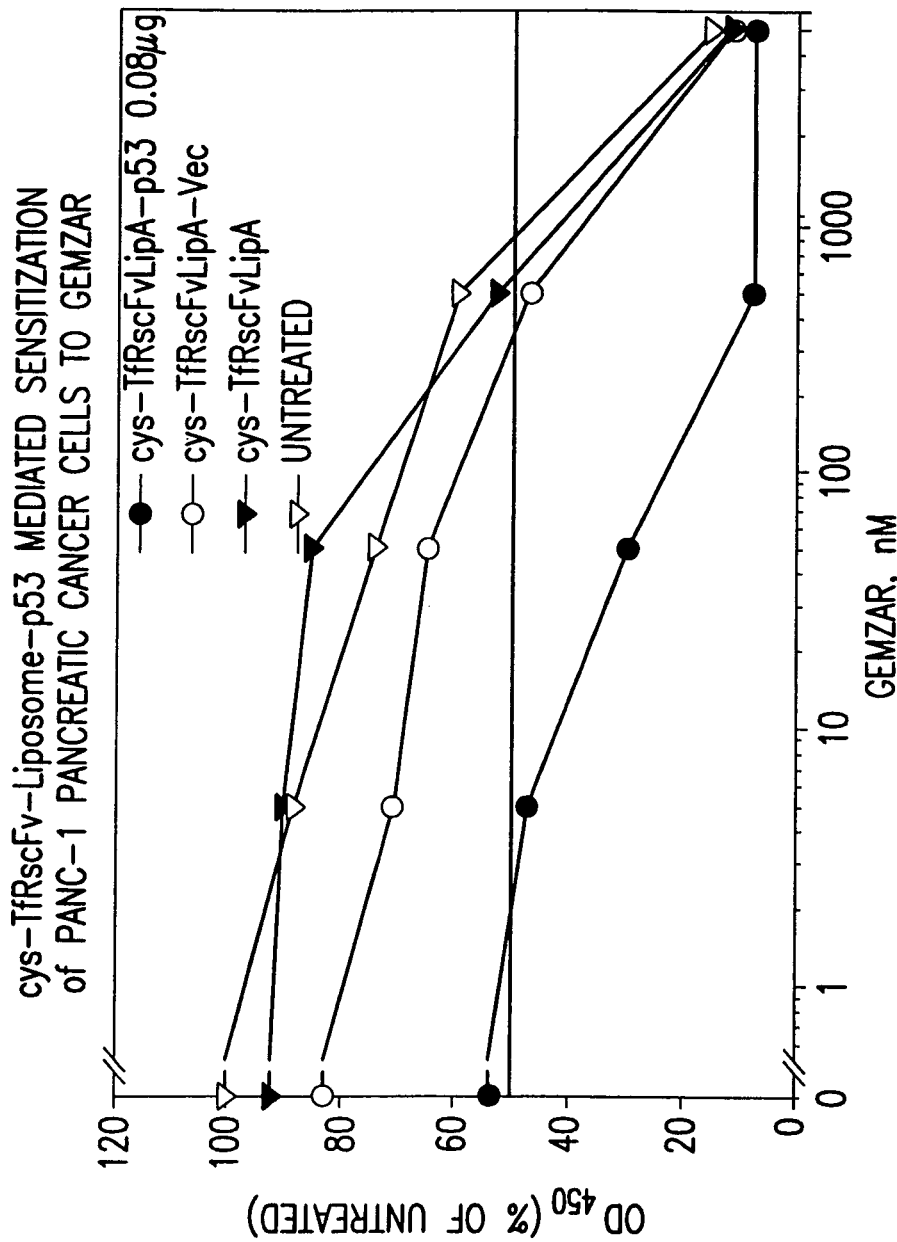

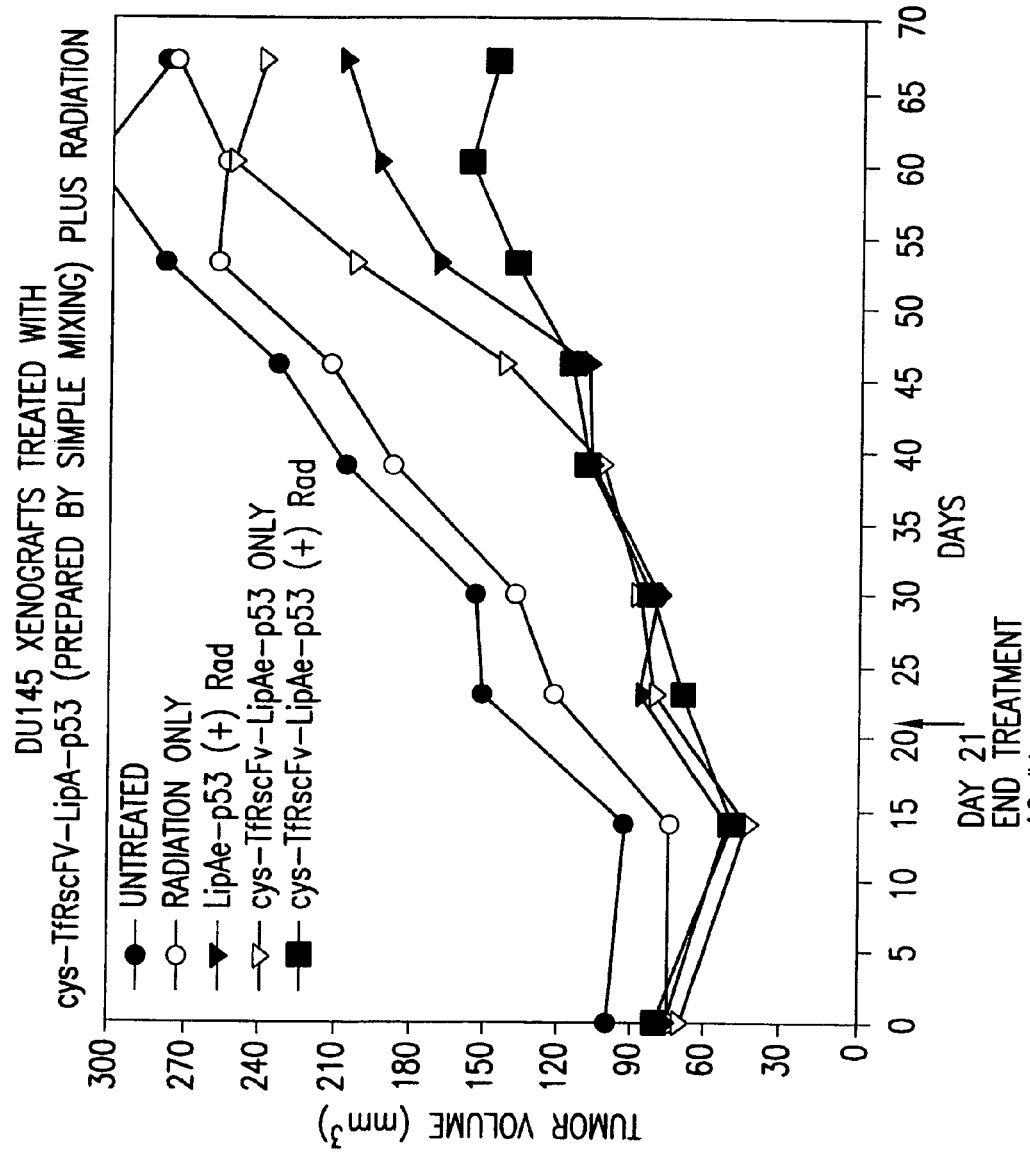

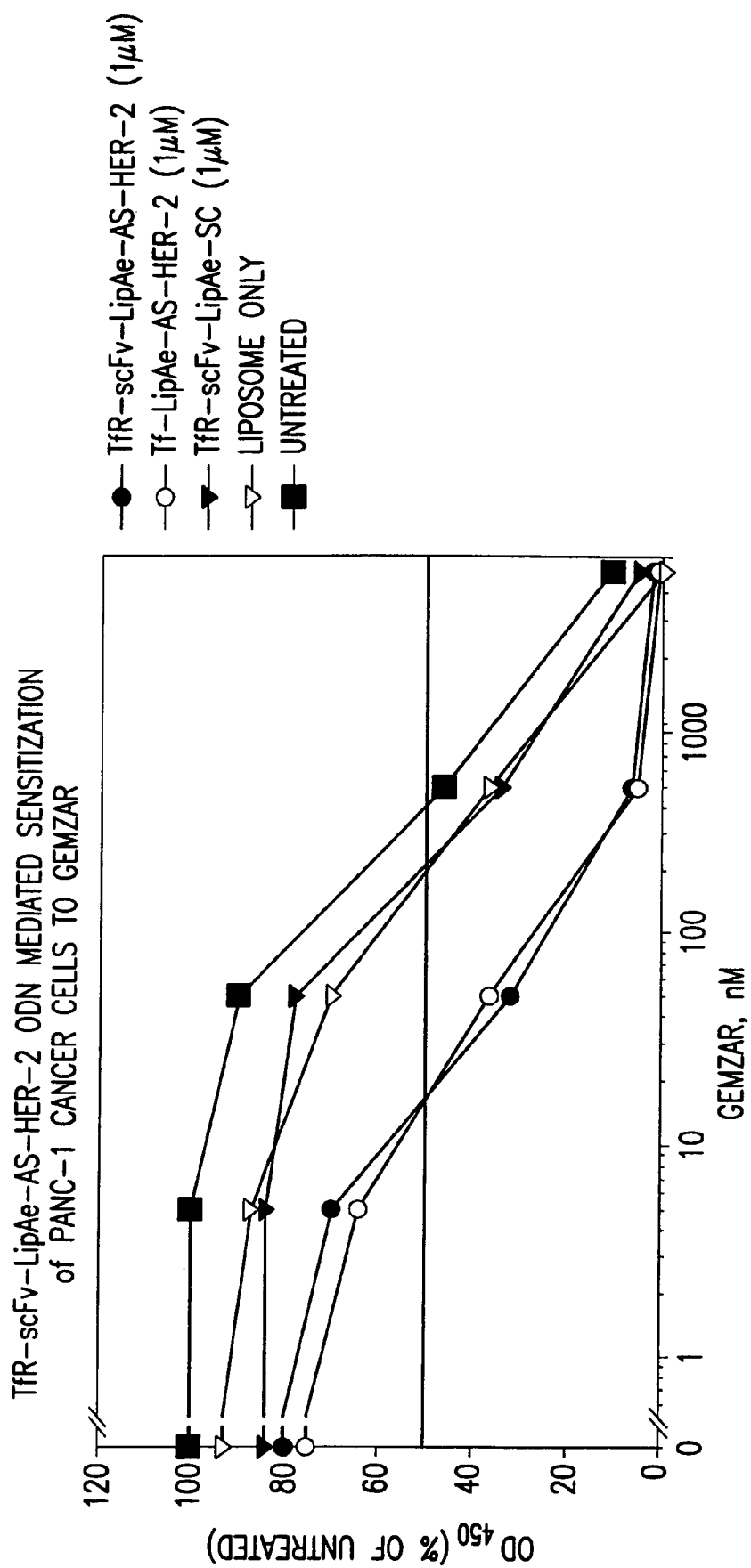

Fate of siRNA in blood of mice bearing human pancreatic cancer Xenografts by systemically Administered Immunonanocomplex

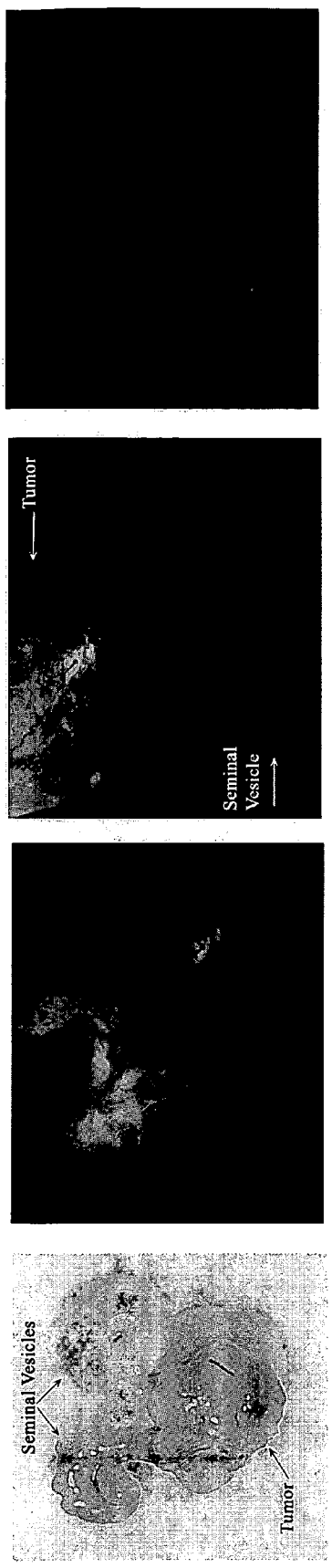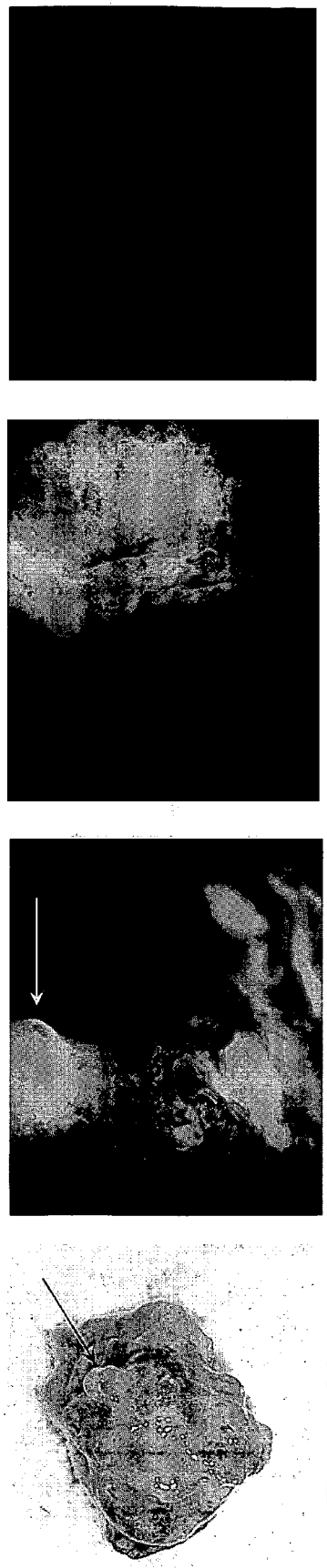
Figure 60

Figure 69. Tumor Elimination in Mice Bearing Pancreatic Cancer Xenograft Tumors after Treatment with the Combination of Ligand-Liposome-HER-2siRNA (Modified Hybrid) plus Gemzar

SEQUENCE LISTING

```
<160> NUMBER OF SEQ ID NOS: 22

<210> SEQ ID NO 1
<211> LENGTH: 21
<212> TYPE: RNA
<213> ORGANISM: Artificial Sequence
<220> FEATURE:
<223> OTHER INFORMATION: Chemically synthesized - HER-2 Duplex 1 Sense

<400> SEQUENCE: 1
ggagcuggcg gccuugugcc g                                                 21

<210> SEQ ID NO 2
<211> LENGTH: 21
<212> TYPE: RNA
<213> ORGANISM: Artificial Sequence
<220> FEATURE:
<223> OTHER INFORMATION: Chemically synthesized - HER-2 Duplex 1
      Antisense

<400> SEQUENCE: 2
gcacaaggcc gccagcucca u                                                 21

<210> SEQ ID NO 3
<211> LENGTH: 21
<212> TYPE: RNA
<213> ORGANISM: Artificial Sequence
<220> FEATURE:
<223> OTHER INFORMATION: Chemically synthesized - Construct 3 Sense

<400> SEQUENCE: 3
ucucugcggu gguuggcauu c                                                 21

<210> SEQ ID NO 4
<211> LENGTH: 21
<212> TYPE: RNA
<213> ORGANISM: Artificial Sequence
<220> FEATURE:
<223> OTHER INFORMATION: Chemically synthesized - Construct 3 Antisense
```

```
<400> SEQUENCE: 4
augccaacca ccgcagagac g                                              21

<210> SEQ ID NO 5
<211> LENGTH: 21
<212> TYPE: RNA
<213> ORGANISM: Artificial Sequence
<220> FEATURE:
<223> OTHER INFORMATION: Chemically synthesized - Control Sense

<400> SEQUENCE: 5
uucuccgaac gugucacguu u                                              21

<210> SEQ ID NO 6
<211> LENGTH: 21
<212> TYPE: RNA
<213> ORGANISM: Artificial Sequence
<220> FEATURE:
<223> OTHER INFORMATION: Chemically synthesized - Control Antisense

<400> SEQUENCE: 6
acgugacacg uucggagaau u                                              21

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized - Control HER-2 Modified
      Hybrid Sense
<220> FEATURE:
<221> NAME/KEY: misc_feature
<222> LOCATION: (2)..(2)
<223> OTHER INFORMATION: N is 2-deoxyinosine
<220> FEATURE:
<221> NAME/KEY: misc_feature
<222> LOCATION: (4)..(4)
<223> OTHER INFORMATION: N is 2-deoxyinosine
<220> FEATURE:
<221> NAME/KEY: misc_feature
<222> LOCATION: (16)..(16)
<223> OTHER INFORMATION: N is 2-deoxyinosine
<220> FEATURE:
<221> NAME/KEY: misc_feature
<222> LOCATION: (18)..(18)
<223> OTHER INFORMATION: N is 2-deoxyinosine
<220> FEATURE:
<221> NAME/KEY: misc_feature
<222> LOCATION: (5)..(14)
<223> OTHER INFORMATION: nucleic acids are RNA

<400> SEQUENCE: 7
tncnccgaac gugucncnt                                                 19

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized - Control HER-2 Modified
      Hybrid Antisense

<400> SEQUENCE: 8
acgugacacg uucggagaa                                                 19

<210> SEQ ID NO 9
<211> LENGTH: 19
<212> TYPE: DNA
```

```
<213> ORGANISM: Artificial Sequence
<220> FEATURE:
<223> OTHER INFORMATION: Chemically synthesized - HER-2 Modified Hybrid
      3 Sense
<220> FEATURE:
<221> NAME/KEY: misc_feature
<222> LOCATION: (2)..(2)
<223> OTHER INFORMATION: n is 2-deoxyinosine
<220> FEATURE:
<221> NAME/KEY: misc_feature
<222> LOCATION: (4)..(4)
<223> OTHER INFORMATION: n is 2-deoxyinosine
<220> FEATURE:
<221> NAME/KEY: misc_feature
<222> LOCATION: (16)..(16)
<223> OTHER INFORMATION: n is 2-deoxyinosine
<220> FEATURE:
<221> NAME/KEY: misc_feature
<222> LOCATION: (18)..(18)
<223> OTHER INFORMATION: n is 2-deoxyinosine
<220> FEATURE:
<221> NAME/KEY: misc_feature
<222> LOCATION: (6)..(14)
<223> OTHER INFORMATION: nucleic acids are RNA

<400> SEQUENCE: 9
tntntgcggu gguugncnt                                                19

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized - HER-2 Duplex 3 Sense

<400> SEQUENCE: 10
ucucugcggu gguuggcau                                                19

<210> SEQ ID NO 11
<211> LENGTH: 19
<212> TYPE: RNA
<213> ORGANISM: Artificial Sequence
<220> FEATURE:
<223> OTHER INFORMATION: Chemically synthesized - HER-2 Duplex 3
      Antisense

<400> SEQUENCE: 11
augccaacca ccgcagaga                                                19

<210> SEQ ID NO 12
<211> LENGTH: 21
<212> TYPE: DNA
<213> ORGANISM: Artificial Sequence
<220> FEATURE:
<223> OTHER INFORMATION: Chemically synthesized - HER-2 Hybrid 1 Sense

<400> SEQUENCE: 12
ggagctggcg gccttgtgcc g                                             21

<210> SEQ ID NO 13
<211> LENGTH: 21
<212> TYPE: RNA
<213> ORGANISM: Artificial Sequence
<220> FEATURE:
<223> OTHER INFORMATION: Chemically synthesized - HER-2 Hybrid 1
      Antisense

<400> SEQUENCE: 13
uaccucgacc gccggaacac g                                             21
```

```
<210> SEQ ID NO 14
<211> LENGTH: 19
<212> TYPE: DNA
<213> ORGANISM: Artificial Sequence
<220> FEATURE:
<223> OTHER INFORMATION: Chemically synthesized - HER-2 Hybrid 3 Sense

<400> SEQUENCE: 14
tctctgcggt ggttggcat                                              19

<210> SEQ ID NO 15
<211> LENGTH: 19
<212> TYPE: RNA
<213> ORGANISM: Artificial Sequence
<220> FEATURE:
<223> OTHER INFORMATION: Chemically synthesized - HER-2 Hybrid 3
      Antisense

<400> SEQUENCE: 15
augccaacca ccgcagaga                                              19

<210> SEQ ID NO 16
<211> LENGTH: 19
<212> TYPE: RNA
<213> ORGANISM: Artificial Sequence
<220> FEATURE:
<223> OTHER INFORMATION: Chemically synthesized - HER-2 Modified Hybrid
      3 Antisense

<400> SEQUENCE: 16
augccaacca ccgcagaga                                              19

<210> SEQ ID NO 17
<211> LENGTH: 19
<212> TYPE: DNA
<213> ORGANISM: Artificial Sequence
<220> FEATURE:
<223> OTHER INFORMATION: Chemically synthesized - Control HER-2 Hybrid
      Sense

<400> SEQUENCE: 17
ttctccgaac gtgtcacgt                                              19

<210> SEQ ID NO 18
<211> LENGTH: 19
<212> TYPE: RNA
<213> ORGANISM: Artificial Sequence
<220> FEATURE:
<223> OTHER INFORMATION: Chemically synthesized - Control HER-2 Hybrid
      Antisense

<400> SEQUENCE: 18
acgagucacg uucggagaa                                              19

<210> SEQ ID NO 19
<211> LENGTH: 15
<212> TYPE: DNA
<213> ORGANISM: Artificial Sequence
<220> FEATURE:
<223> OTHER INFORMATION: Chemically synthesized - HER-2 Antisense
      Oligonucleotide

<400> SEQUENCE: 19
tccatggtgc tcact                                                  15

<210> SEQ ID NO 20
```

-continued

```
<211> LENGTH: 31
<212> TYPE: PRT
<213> ORGANISM: Artificial Sequence
<220> FEATURE:
<223> OTHER INFORMATION: Chemically synthesized - HoKC

<400> SEQUENCE: 20

Lys Lys His Lys Lys Lys Lys His Lys Lys Lys Lys His Lys Lys Lys
1               5                   10                  15

Lys His Lys Lys Lys Lys His Lys Lys Lys Lys His Lys Lys Cys
            20                  25                  30

<210> SEQ ID NO 21
<211> LENGTH: 21
<212> TYPE: DNA
<213> ORGANISM: Artificial Sequence
<220> FEATURE:
<223> OTHER INFORMATION: Chemically synthesized - FLIP Sense
<220> FEATURE:
<221> NAME/KEY: misc_feature
<222> LOCATION: (1)..(19)
<223> OTHER INFORMATION: nucleic acids are RNA

<400> SEQUENCE: 21
gcagucuguu caaggagcat t                                              21

<210> SEQ ID NO 22
<211> LENGTH: 21
<212> TYPE: DNA
<213> ORGANISM: Artificial Sequence
<220> FEATURE:
<223> OTHER INFORMATION: Chemically synthesized - FLIP Antisense
<220> FEATURE:
<221> NAME/KEY: misc_feature
<222> LOCATION: (1)..(19)
<223> OTHER INFORMATION: nucleic acids are RNA

<400> SEQUENCE: 22
ugcuccuuga acagacugct t                                              21
```

PREPARATION OF ANTIBODY OR AN ANTIBODY FRAGMENT-TARGETED IMMUNOLIPOSOMES FOR SYSTEMIC ADMINISTRATION OF THERAPEUTIC OR DIAGNOSTIC AGENTS AND USES THEREOF

CROSS REFERENCE TO RELATED APPLICATIONS

The present application is a continuation-in-part of U.S. application Ser. No. 10/113,927, filed Apr. 2, 2002, which is a continuation-in-part of U.S. application Ser. No. 09/914,046, filed Oct. 1, 2001. U.S. application Ser. No. 09/914,046, is a U.S. National Phase Application under 35 U.S.C. §371 of PCT/US00/04392, filed Feb. 22, 2000, which claims the benefit of U.S. Provisional Application No. 60/121,133, filed Feb. 22, 1999. U.S. application Ser. No. 10/113,927 also claims the benefit of U.S. Provisional Application No. 60/280,134, filed Apr. 2, 2001. The disclosures of each of these applications are incorporated by reference herein in their entireties for all purposes.

BACKGROUND OF THE INVENTION

1. Field of the Invention

The present invention is in the fields of drug delivery, cancer treatment and pharmaceuticals. This invention provides a method of making antibody- or antibody fragment-targeted immunoliposomes and antibody- or antibody fragment-targeted polymers useful for the systemic delivery of molecules to treat diseases. The liposome and polymer complexes are useful for carrying out targeted gene delivery and efficient gene expression after systemic administration. The specificity of the delivery system is derived from the targeting antibodies or antibody fragments.

2. Related Art

The ideal therapeutic for cancer would be one that selectively targets a cellular pathway responsible for the tumor phenotype and would be nontoxic to normal cells. To date, the ideal therapeutic remains just that—an ideal. While cancer treatments involving gene therapy have substantial promise, there are many issues that need to be addressed before this promise can be realized. Perhaps foremost among the issues associated with macromolecular treatments is the efficient delivery of the therapeutic molecules to the site(s) in the body where they are needed. The ideal delivery vehicle would be one that could be systemically administered and then home to tumor cells wherever they occur in the body. A variety of delivery systems ("vectors") have been tried, including viruses and liposomes. The infectivity that makes viruses attractive as delivery vectors also poses their greatest drawback. Residual viral elements can be immunogenic, cytopathic or recombinogenic. The generation of novel viruses with new targets for infection also raises the theoretical possibility that, once introduced into patients, these viruses could be transformed via genetic alteration into new human pathogens. Consequently, a significant amount of attention has been directed at non-viral vectors for the delivery of molecular therapeutics. The liposome approach offers a number of advantages over viral methodologies for gene delivery. Most significantly, they lack immunogenicity. Moreover, since liposomes are not infectious agents capable of self-replication, they pose no risk of evolving into new classes of infectious human pathogens.

Targeting cancer cells via liposomes can be achieved by modifying the liposomes so that they selectively deliver their payload to tumor cells. Surface molecules can be used to target liposomes to tumor cells, because the molecules that decorate the exterior of tumor cells differ from those on normal cells. For example, if a liposome has the protein transferrin (Tf) or an antibody that recognizes transferrin receptor (TfR) on its surface, it will home to cancer cells that have higher levels of the TfR. Such liposomes designed to home to tumors have been likened to "smart" bombs capable of seeking out their target.

Failure to respond to therapy represents an unmet medical need in the treatment of many types of cancer, including prostate cancer. Often when cancer recurs, the tumors have acquired increased resistance to radiation or chemotherapeutic agents. The incorporation into currently used cancer therapies of a new component which results in radio-/chemo-sensitization would have immense clinical relevance. One way in which such sensitization could be achieved is via gene therapy (i.e., delivery of a gene the expression of which results in increased sensitization). In PCT patent application WO 00/50008 (published 31 Aug. 2000), incorporated herein by reference, we provided proof-of-principle that an anti-transferrin receptor single chain antibody (TfRscFv) can be chemically conjugated to a cationic liposome. Moreover, this TfRscFv directed liposome delivery system can deliver genes and other molecules systemically and specifically to tumors.

Immunoliposomes and Cationic Polymers as Gene Transfer Vehicles

As noted above, some of the problems associated with using viral vectors could be circumvented by non-viral gene transfer vectors. Progress has been made toward developing non-viral, pharmaceutical formulations of genes for in vivo human therapy, particularly cationic liposome-mediated gene transfer systems (31, 32). Cationic liposomes are composed of positively charged lipid bilayers and can be complexed to negatively charged, naked DNA by simple mixing of lipids and DNA such that the resulting complex has a net positive charge. The complex can be bound and taken up by cells in culture with moderately good transfection efficiency (33). Features of cationic liposomes that make them versatile and attractive for DNA delivery include: simplicity of preparation; the ability to complex large amounts of DNA; versatility in use with any type and size of DNA or RNA, including siRNA; the ability to transfect many different types of cells, including non-dividing cells; and lack of immunogenicity or biohazardous activity (reviewed in 34, 35). More importantly from the perspective of human cancer therapy, cationic liposomes have been proven to be safe and efficient for in vivo gene delivery (33, 34, 36). At least 75 clinical trials have been approved using cationic liposomes for gene delivery (37), and liposomes for delivery of small molecule therapeutics (e.g., antifungal agents) are already on the market.

Researchers also have considered the suitability of cationic polymers as transfer vectors for delivery of therapeutic agents in vivo. For example, Polyethyleneimine (PEI) is the organic macromolecule with the highest cationic-charge-density potential, and a versatile vector for gene and oligonucleotide transfer in vitro and in vivo, as first reported by Boussif et al. (66). Since then, there has been a flurry of research aimed at this polycation and its role in gene therapy (73). Cell-binding ligands can be introduced to the polycation to 1) target specific cell types and 2) enhance intracellular uptake after binding the target cell (13). Erbacher et al. (67) conjugated the integrin-binding peptide 9-mer RGD via a disulfide bridge and showed physical properties of interest for systemic gene delivery.

The transfection efficiency of both cationic liposomes and cationic polymers, such as PEI, can be increased dramatically when they bear a ligand recognized by a cell surface receptor.

Receptor-mediated endocytosis represents a highly efficient internalization pathway present in eukaryotic cells (38, 39). The presence of a ligand on a liposome facilitates the entry of DNA into cells through initial binding of ligand by its receptor on the cell surface followed by internalization of the bound complex. Transferrin receptor (TfR) levels are elevated in various types of cancer cells including prostate cancers (40), even those prostate cell lines derived from human lymph node and bone metastases (40-43). Elevated TfR levels also correlate with the aggressive or proliferative ability of tumor cells (44). Therefore, TfR is a potential target for drug delivery in the therapy of malignant cell growth (45, 46). In our laboratory, we have prepared transferrin-complexed cationic liposomes with tumor cell transfection efficiencies in SCCHN of 60%-70%, as compared to only 5-20% by cationic liposomes without ligand (47). Also see published PCT patent application WO 00/50008.

In addition to the use of ligands that are recognized by receptors on tumor cells, specific antibodies also can be attached to the liposome surface (48) enabling them to be directed to specific tumor surface antigens (including but not limited to receptors) (49). These "immunoliposomes," especially the sterically stabilized immunoliposomes, can deliver therapeutic drugs to a specific target cell population (50). Parks et al. (51) found that anti-HER-2 monoclonal antibody (MAb) Fab fragments conjugated to liposomes could bind specifically to a breast cancer cell line, SK-BR-3, that overexpresses HER-2. The immunoliposomes were found to be internalized efficiently by receptor-mediated endocytosis via the coated pit pathway and also possibly by membrane fusion. Moreover, the anchoring of anti-HER-2 Fab fragments enhanced their inhibitory effects. More recently, Park et al. (23) used an anti-HER-2 immunoliposome composed of long circulating liposomes chemically conjugated to anti-HER-2 monoclonal antibody scFv fragments to deliver doxorubicin to breast cancer tumors even though HER-2 was not overexpressed. A number of other studies have been published which have employed antibodies against tumor specific antigens coupled to liposomes, primarily sterically stabilized liposomes, to target tumor cells for delivery of prodrugs and drugs in vitro or in vivo (52-56). These studies demonstrated the utility of immunoliposomes for tumor-targeting drug delivery. The combination of cationic liposome-gene transfer and immunoliposome techniques appears to be a promising system for targeted gene therapy and is the subject of this proposal.

Progress in biotechnology has allowed the derivation of specific recognition domains from MAb (57). The recombination of the variable regions of heavy and light chains and their integration into a single polypeptide provides the possibility of employing single-chain antibody derivatives (designated scFv) for targeting purposes. Thus, a scFv based on the anti-TfR MAb 5E9 (52) contains the complete antibody binding site for the epitope of the TfR recognized by this MAb as a single polypeptide chain of approximate molecular weight 26,000. This TfRscFv is formed by connecting the component VH and VL variable domains from the heavy and light chains, respectively, with an appropriately designed linker peptide. The linker bridges the C-terminus of the first variable region and N-terminus of the second, ordered as either VH-linker-VL or VL-linker-VH. The binding site of an scFv can replicate both the affinity and specificity of its parent antibody combining site.

The TfRscFv has advantages in human use over the Tf molecule itself or even an entire MAb to target liposomes or cationic polymers to cancer cells with elevated levels of the TfR for a number of reasons. First, the size of the scFv (~28 kDa) is much smaller than that of the Tf molecule (~80 kDa) or the parental MAb (~150 kDa). The scFv-liposome-therapeutic agent complex or scFv-polymer-therapeutic agent complex thus may exhibit better penetration into small capillaries characteristic of solid tumors. Second, the smaller scFv also has practical advantages related to its production as a recombinant protein. Large scale production of the TfRscFv will be required for the therapy disclosed herein to be taken into human trials. Third, the scFv is a recombinant molecule (not a blood product like Tf) and, therefore, presents no issues related to potential contamination with blood borne pathogens. Additional advantages of using the TfRscFv relate to the fact that Tf interacts with the TfR with high affinity only after the ligand is loaded with iron. Large-scale production of liposomes containing iron-loaded Tf may present practical challenges. Thus, use of TfRscFv enables the tumor cell TfR to be targeted by a liposomal therapeutic complex that does not contain iron (itself implicated in cancer (58)). Fourth, without the Fc region of the MAb, the problem of non-antigen-specific binding through Fc receptors is eliminated (57).

p53 Tumor Suppressor Gene and the Pathogenesis of Prostate Cancer

The tumor suppressor gene p53 plays a crucial role in diverse cellular pathways including those activated in response to DNA damage, such as DNA repair, regulation of the cell cycle and programmed cell death (apoptosis) (1). Malfunctions of these critical cell pathways are associated with the process of tumorigenesis. Loss of functional p53, which has been implicated in over 60% of human cancers, can occur either through mutations in the p53 gene itself (the most common occurrence), or through other mechanisms such as amplification of the MDM-2 gene (found in certain sarcomas, and other cancers), or association of p53 with the E6 protein of human papilloma virus (which likely plays a role in cervical carcinoma) (2).

The loss of p53 function is of relevance to a broad array of cancer types, with non-functional p53 associated with, for example, 15-50% of breast cancer, 25-70% of metastatic prostate cancer, 25-75% of lung cancer, and 33-100% of head and neck cancers (3). The presence of mutant p53 also has been associated with an unfavorable prognosis for many human cancers including lung, colon, and breast (3), and mutant p53 is rarely found in some of the most curable forms of cancer e.g., Wilm's tumor, retinoblastoma, testicular cancer, neuroblastoma and acute lymphoblastic leukemia (4). In addition, p53 protein transcriptionally regulates genes involved in angiogenesis, a process required for solid tumor growth (5). Volpert et al. have proposed that development of the angiogenic phenotype for these tumors requires the loss of both p53 alleles (6).

Since it appears that most anti-cancer agents work by inducing apoptosis (20), inhibition of or changes in this pathway may lead to failure of therapeutic regimens. A direct link has been suggested between mutations in p53 and resistance to cytotoxic cancer treatments (both chemo- and radiotherapy (21)). It has also been suggested that the loss of p53 function may contribute to the cross-resistance to anti-cancer agents observed in some tumor cells (22).

Restoration of p53 function could, therefore result in sensitization of primary prostate tumors and even metastases to radio-/chemo-therapy. The introduction of wtp53 has been reported to suppress, both in vitro and in mouse xenograft models, the growth of various types of malignancies, e.g., prostate (23,24), head and neck (25,26), colon (27), cervical (28) and lung (15,29) tumor cells. However, p53 alone, while being able to partially inhibit tumor growth, has not been shown to be able to eliminate established tumors. Significantly, however, we have demonstrated that the combination of systemically delivered liposome-p53 and radiation led to complete long-term tumor regression of established head and neck xenograft tumors (25,30).

In summary, the implication of the p53 gene in a significant fraction of human cancers makes it one of the premiere candidates for cancer gene therapy. Based on a growing body of evidence related to p53 functions, effective restoration of these functions in tumor cells might be expected to re-establish normal cell growth control, restore appropriate responses to DNA-damaging agents (e.g., chemotherapy and radiotherapy), and to impede angiogenesis.

The sensitization of tumors to chemotherapy and radiation could lower the effective dose of both types of anticancer modalities, correspondingly lessening the severe side effects often associated with these treatments. Until now the vast majority of p53 gene therapy protocols have employed wtp53 gene replacement alone. Based upon the current literature and our data (30, 59), it appears that wtp53 replacement alone, while able to inhibit tumor growth to some extent, is insufficient to eliminate tumors long term. Therefore, it appears that a combinatorial approach involving both standard therapy and targeted gene therapy has substantial promise as a novel and more effective clinical modality for cancer treatment. Moreover, the demonstrated tumor cell selectivity of our systemically delivered ligand-liposome wtp53 complex indicates the potential of this method to sensitize even the distant micrometastases that are the ultimate cause of so many prostate cancer deaths.

BRIEF SUMMARY OF THE INVENTION

In accordance with this invention a variety of immunoliposomes and polymer complexes have been constructed that are capable of tumor-targeted, systemic delivery of a variety of types of therapeutic molecules for use in treating human diseases. The antibody- or antibody fragment-targeted immunoliposomes or polymer complexes are made via a simple and efficient non-chemical conjugation method. These complexes are equally as effective as, or more effective than, similar complexes prepared by chemical conjugation of the antibody or antibody fragment to the liposome or polymer complex. If an antibody fragment is used, the resultant complex is capable of producing a much higher level of transfection efficiency than the same liposome-therapeutic agent or polymer-therapeutic agent complex bearing the complete antibody molecule.

In accordance with the present invention, the single chain protein is not chemically conjugated to the liposome or polymer. Rather, the antibody- or scFv-liposome-therapeutic or diagnostic agent complex or the antibody- or scFv-polymer-therapeutic or diagnostic agent complex is formed by simple mixing of the components in a defined ratio and order. In one embodiment, the antibody or single chain protein first is mixed with the cationic liposome or the polymer at a protein: lipid ratio in the range of about 1:20 to about 1:40 (w:w) or protein:polymer ratio in the range of about 0.1:1 to 10:1 (molar ratio). The antibody- or antibody fragment-liposome or antibody- or antibody fragment-polymer then is mixed with a desired therapeutic or diagnostic agent, such as nucleic acid (preferably DNA), at a ratio in the range of about 1:10 to 1:20 (μg therapeutic or diagnostic agent:nmole total lipid) or about 1:1 to 1:40 (μg therapeutic or diagnostic agent:nmole polymer) and incubated for 10-15 minutes at room temperature.

The resultant therapeutic or diagnostic agent-antibody-liposome or therapeutic agent-antibody-polymer complex can be administered to a mammal, preferably a human, to deliver the agent to target cells in the mammal's body. Desirably the complexes are targeted to a site of interest can be a cell which is a cancer cell or a non-cancer cell. The targeting agent is an antibody or antibody fragment, which in one preferred embodiment binds to a transferrin receptor, and the target cell is a cell which expresses or contains the target site of interest. If the antibody or antibody fragment binds to a transferrin receptor, the target cell is a cell which expresses a transferrin receptor. The therapeutic agent can be a nucleic acid, preferably a DNA molecule and more preferably a DNA molecule which encodes a wild type p53 molecule, Rb molecule or Apoptin molecule, an antisense oligonucleotide such as an antisense HER-2 oligonucleotide, or an siRNA. The complexes, preferably in a therapeutic composition, can be administered intravenously (IV), intramuscularly (IM), intradermally (ID), intraocularly (IO), intraperitoneally (IP), intratumorally (IT), intranasally (IN), intracereberally (IC) and/or subcutaneously (SQ).

In an additional embodiment, the present invention provides methods of preparing an antibody- or antibody fragment-targeted cationic immunoliposome complex comprising preparing an antibody or antibody fragment; mixing the antibody or antibody fragment with a cationic liposome to form a cationic immunoliposome, wherein the antibody or antibody fragment is not chemically conjugated to the cationic liposome; and mixing the cationic immunoliposome with one or more siRNA molecules to form the antibody- or antibody fragment-targeted-cationic immunoliposome complex. In suitable embodiments, the antibody fragment is a single chain Fv fragment, such as an anti-transferrin receptor single chain Fv (TfRscFv).

Suitable lipids useful in preparing the siRNA-comprising cationic immunoliposome complexes of the present invention include mixtures of one or more cationic lipids and one or more neutral or helper lipids. Suitably, the antibody or antibody fragment is mixed with said cationic liposome at a ratio in the range of about 1:20 to about 1:40 (w:w). In embodiments, the cationic liposomes comprise a mixture of dioleoyl-trimethylammonium phosphate with dioleoylphosphatidylethanolamine and/or cholesterol; or a mixture of dimethyldioctadecylammonium bromide with dioleoylphosphatidylethanolamine and/or cholesterol. In further embodiments, the cationic immunoliposome is mixed with siRNA at a ratio in the range of about 1:3.5 to about 1:14 (μg siRNA: nmol liposome), suitably at ratio of about 1:7 (μg siRNA: nmol liposome).

In suitable embodiments, siRNA for use in the practice of the present invention include, but are not limited to, HER-2 targeted siRNA, such as siRNA which comprises the following 19-mer sense strand with the following pattern of 2'-deoxyinosine (I) and 2'-O-methylribonucleotide (2'-OMe) residues:

```
TITITgcggugguuGICIT      (SEQ ID NO: 9)

AGAGACGCCACCAACCGUA.     (SEQ ID NO: 16)
```

In an additional embodiment, the present invention provides antibody- or antibody fragment-targeted cationic immunoliposome complexes comprising a cationic liposome, an antibody or antibody fragment, and siRNA, wherein the antibody or antibody fragment is not chemically conjugated to the cationic liposome. The siRNA may be encapsulated within the cationic liposome, contained within a hydrocarbon chain region of the cationic liposome, associated with an inner or outer monolayer of the cationic liposome, or any combination thereof.

The present invention also provides methods of treating a patient suffering from, or predisposed to, a disease state, such as cancer, comprising administering the siRNA-comprising cationic immunoliposome complexes of the present invention to the patient. Additional disease states include, but are not limited to, viral disease, infectious diseases, diabetes, cardiovascular disease, macular degeneration and neurologic diseases. Suitably, the complexes are administered via intravenous administration, although additional administration routes as described herein can also be used (e.g., intramuscularly (IM), intradermally (ID), intraocularly (IO), intraperitoneally (IP), intratumorally (IT), intranasally (IN), intracereberally (IC) and/or subcutaneously (SQ)). In embodiments where the patient is suffering from or predisposed to cancer, the methods of the present invention can further comprise administering a chemotherapeutic agent or radiation to the patient, either before or after (e.g., at least 12 hours before or after) administration of the cationic immunoliposome complex). Suitable chemotherapeutic agents include, but are not limited to, doxorubicin, cisplatin, gemcitabine, mitoxantrone, taxotere and CDDP. Suitable types of radiation treatment include, but are not limited to, X-rays and Gamma radiation (e.g., $^{137}$Cs). The present invention also provides methods of enhancing the effectiveness of a chemotherapeutic agent or radiation, comprising administering the siRNA-comprising cationic immunoliposomes of the present invention in conjunction with the chemotherapeutic agent or the radiation treatment to a patient, either before or after (e.g., at least 12 hours before or after) administration of the cationic immunoliposome complex.

BRIEF DESCRIPTION OF THE DRAWINGS/FIGURES

FIGS. 6A and 6B show the results of an XTT cytotoxicity assay showing the chemosensitivity to GEMZAR® (gemcitabine) induced in pancreatic cancer cell lines (Colo 357 and Panc I) treated with TfRscFv-liposome-p53 prepared by simple mixing.

FIG. 8 shows the effect of the combination of systemically administered TfRscFv-liposome A-p53 prepared by simple mixing and radiation on DU145 human prostate xenograft tumors.

FIG. 9 shows the results of an XTT cytotoxicity assay showing chemosensitivity to GEMZAR® (gemcitabine) induced Panc I cells treated with TfRscFv-liposome-AS HER-2 ODN.

FIG. 60 shows scL mediated targeting of siRNA to primary tumors in orthotopic prostate cancer tumor mouse models.

DETAILED DESCRIPTION OF THE INVENTION

Figure 1:
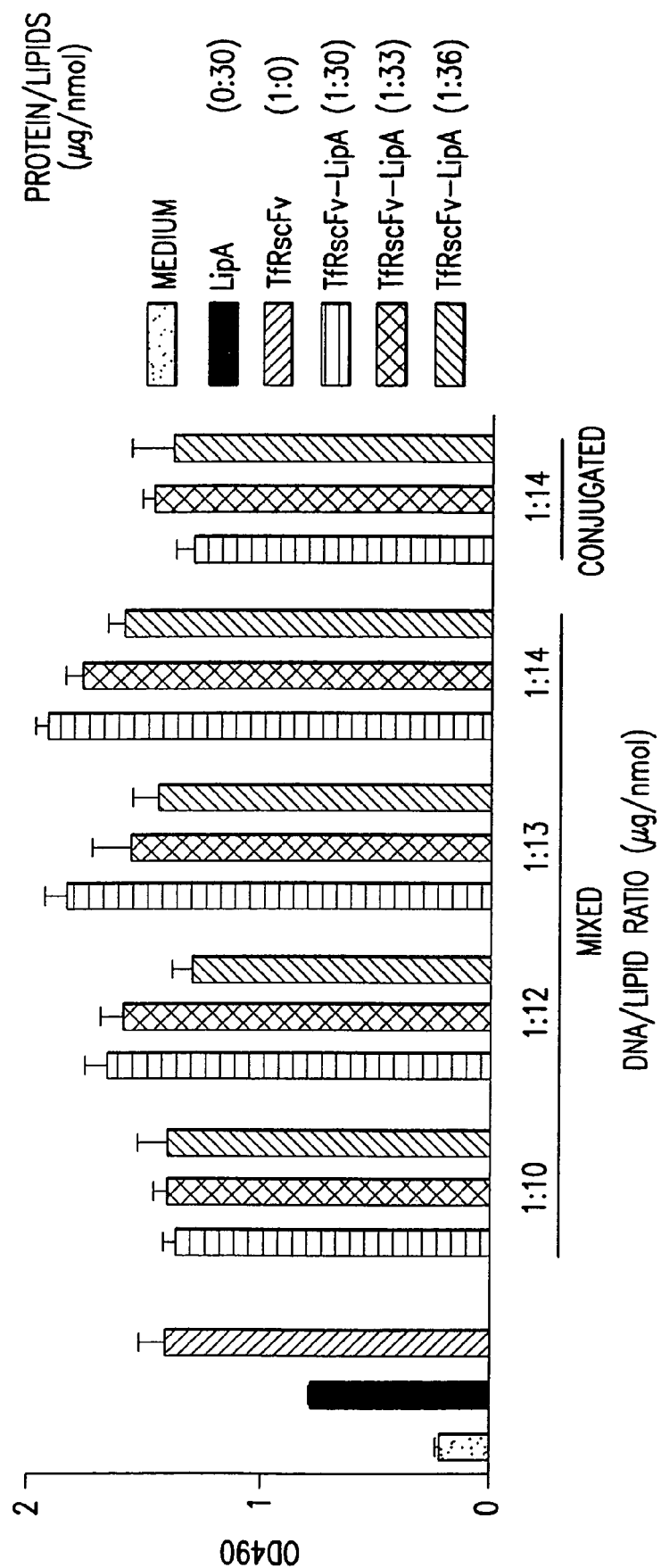
FIG. 1 shows the results of an ELISA assay showing binding of TfRscFv-liposome-DNA complex, made by simple mixing, to DU145 cells at various ratios of protein/lipid and DNA/lipid.

Antibody- or antibody fragment-targeted cationic liposome or cationic polymer complexes in accordance with this invention are made by a simple and efficient non chemical conjugation method in which the components of the desired complex are mixed together in a defined ratio and in a defined order. The resultant complexes are as effective as, or more effective than, similar complexes in which the antibody or antibody fragment is chemically conjugated to the liposome or polymer. The terms "immunocomplex," "immunoliposome," "complex," "nanocomplex," "immunonanocomplex," "liposome complex" are used interchangeably throughout to refer to the cationic liposomes of the present invention.

Either a whole antibody or an antibody fragment can be used to make the complexes of this invention. In a preferred embodiment, an antibody fragment is used. Preferably, the antibody fragment is a single chain Fv fragment of an antibody. One preferred antibody is an anti-TfR monoclonal antibody and a preferred antibody fragment is an scFv based on an anti-TfR monoclonal antibody. A suitable anti-TfR monoclonal antibody is 5E9 (see, e.g., Hayes, B. F., et al., "Characterization of a Monoclonal Antibody (5E9) that Defines a Human Cell Surface Antigen of Cell Activation," *J. Immunol.* 127:347-352 (1981); Batra, J. K., et al., "Single-chain Immunotoxins Directed at the Human Transferring Receptor Containing *Pseudomonas* Exotoxin A or Diphtheria Toxin: Anti-TFR(Fv)-PE40 and DT388-Anti-TFR(Fv)," *Mol. Cell. Biol.* 11:2200-2205 (1991); the disclosures of which are incorporated herein by reference). Another preferred antibody is an anti-HER-2 monoclonal antibody, and another preferred antibody fragment is an scFv based on an anti-HER-2 monoclonal antibody. An scFv based on 5E9 antibody contains the complete antibody binding site for the epitope of the TfR recognized by this MAb as a single polypeptide chain of approximate molecular weight 26,000. An scFv is formed by connecting the component VH and VL variable domains from the heavy and light chains, respectively, with an appropriately designed linker peptide, which bridges the C-terminus of the first variable region and N-terminus of the second, ordered as either VH-linker-VL or VL-linker-VH.

In a preferred embodiment, a cysteine moiety is added to the C-terminus of the scFv. Although not wishing to be bound by theory, it is believed that the cysteine, which provides a free sulfhydryl group, may enhance the formation of the complex between the antibody and the liposome. With or without the cysteine, the protein can be expressed in *E. coli* inclusion bodies and then refolded to produce the antibody fragment in active form, as described in detail in the Examples below.

Unless it is desired to use a sterically stabilized immunoliposome in the formation of the complex, a first step in making the complex comprises mixing a cationic liposome or combination of liposomes or small polymer with the antibody or antibody fragment of choice. A wide variety of cationic liposomes are useful in the preparation of the complexes of this invention. Published PCT application WO99/25320 describes the preparation of several cationic liposomes. Examples of desirable liposomes include those that comprise a mixture of dioleoyltrimethylammonium phosphate (DOTAP) and dioleoylphosphatidylethanolamine (DOPE) and/or cholesterol (chol), a mixture of dimethyldioctadecylammonium bromide (DDAB) and DOPE and/or chol. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio).

Suitable polymers are DNA binding cationic polymers that are capable of mediating DNA compaction and can also mediate endosome release. A preferred polymer is polyethyleneimine. Other useful polymers include polysine, protamine and polyamidoamine dendrimers.

The antibody or antibody fragment is one which will bind to the surface of the target cell, and preferably to a receptor that is differentially expressed on the target cell. The antibody or antibody fragment is mixed with the cationic liposome or polymer at room temperature and at a protein:lipid ratio in the range of about 1:20 to about 1:40 (w:w) or a protein polymer ratio in the range of about 0.1:1 to 10:1 (molar ratio).

The antibody or antibody fragment and the liposome or polymer are allowed to incubate at room temperature for a short period of time, typically for about 10-15 minutes, then the mixture is mixed with a therapeutic or diagnostic agent of choice. Examples of therapeutic molecules or agents which can be complexed to the antibody and liposome include genes, high molecular weight DNA (genomic DNA), plasmid DNA, antisense oligonucleotides, peptides, ribozymes, nucleic acids (including siRNA and antisense), viral particles, immunomodulating agents, proteins and chemical agents. Preferred therapeutic molecules include genes encoding p53, Rb94 or Apoptin. RB94 is a variant of the retinoblastoma tumor suppressor gene. Apoptin is a gene that induces apoptosis in tumor cells only. In another preferred embodiment, the agent is an antisense oligonucleotide, such as HER-2. A preferred HER-2 antisense oligonucleotide has the sequence 5'-TCC ATG GTG CTC ACT-3' (SEQ. ID NO: 19). A third type of preferred agent is a diagnostic imaging agent, such as an MRI imaging agent, such as a Gd-DTPA agent. If the agent is DNA, such as the coding region of p53, it can be positioned under the control of a strong constitutive promoter, such as an RSV or a CMV promoter.

The antibody or antibody fragment and liposome combination is mixed with the therapeutic or diagnostic agent at a ratio in the range of about 1:10 to 1:20 (µg of agent:nmole of total lipid) or 1:10 to 1:40 (ug of agent:nmole of total polymer) and incubated at room temperature for a short period of time, typically about 10 to 15 minutes. The size of the liposome complex is typically within the range of about 50-400 nm as measured by dynamic light scattering using a Malvern Zetasizer 3000.

In one embodiment of this invention, the liposome used to form the complex is a sterically stabilized liposome. Sterically stabilized liposomes are liposomes into which a hydrophilic polymer, such as PEG, poly(2-ethylacrylic acid), or poly(n-isopropylacrylamide (PNIPAM) have been integrated. Such modified liposomes can be particularly useful when complexed with therapeutic or diagnostic agents, as they typically are not cleared from the blood stream by the reticuloendothelial system as quickly as are comparable liposomes that have not been so modified. To make a sterically stabilized liposome complex of the present invention, the order of mixing the antibody or antibody fragment, the liposome and the therapeutic or diagnostic agent is reversed from the order set forth above. In a first step, a cationic liposome as described above is first mixed with a therapeutic or diagnostic agent as described above at a ratio in the range of about 1:10 to 1:20 (μg of agent:nmole of lipid). To this lipoplex is added a solution of a PEG polymer in a physiologically acceptable buffer and the resultant solution is incubated at room temperature for a time sufficient to allow the polymer to integrate into the liposome complex. The antibody or antibody fragment then is mixed with the stabilized liposome complex at room temperature and at a protein:lipid ratio in the range of about 1:5 to about 1:30 (w:w).

The liposomal or polymer complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a human patient to be benefited by administration of the therapeutic or diagnostic molecule of the complex. The complexes are sized appropriately so that they are distributed throughout the body following i.v. administration. Alternatively, the complexes can be delivered via other routes of administration, such as intratumoral (IT), intralesional (IL), aerosal, percutaneous, endoscopic, topical, intramuscular (IM), intradermal (ID), intraocular (IO), intraperitoneal (IP), intranasal (IN), intracereberal (IC) or subcutaneous administration. Preparation of formulations for delivery via such methods, and delivery using such methods, are well known in the art.

In one embodiment, compositions comprising the antibody- or antibody fragment-targeted liposome (or polymer) and therapeutic agent complexes are administered to effect human gene therapy. The therapeutic agent component of the complex comprises a therapeutic gene under the control of an appropriate regulatory sequence. Gene therapy for various forms of human cancers can be accomplished by the systemic delivery of antibody or antibody fragment-targeted liposome or polymer complexes which contain a nucleic acid encoding wt p53 or RB94. The complexes can specifically target and sensitize tumor cells, both primary and metastatic tumors, to radiation and/or chemotherapy both in vitro and in vivo.

The complexes can be optimized for target cell type through the choice and ratio of lipids, the ratio of antibody or antibody fragment to liposome, the ratio of antibody or antibody fragment and liposome to the therapeutic or diagnostic agent, and the choice of antibody or antibody fragment and therapeutic or diagnostic agent.

In one embodiment, the target cells are cancer cells. Although any tissue having malignant cell growth can be a target, head and neck, breast, prostate, pancreatic, brain, including glioblastoma, cervical, lung, liver, liposarcoma, rhabdomyosarcoma, choriocarcinoma, melanoma, retinoblastoma, ovarian, urogenital, gastric and colorectal cancers are suitable targets.

The complexes made by the method of this invention also can be used to target non-tumor cells for delivery of a therapeutic molecule or any nucleic acid. While any normal cell can be a target, preferred cells are dendritic cells, endothelial cells of the blood vessels, lung cells, breast cells, bone marrow cells, thymus cells and liver cells. Undesirable, but benign, cells can be targeted, such as benign prostatic hyperplasia cells, over-active thyroid cells, lipoma cells, and cells relating to autoimmune diseases, such as B cells that produce antibodies involved in arthritis, lupus, myasthenia gravis, squamous metaplasia, macular degeneration, cardiovascular disease, neurologic disease such as Alzheimer's disease, dysplasia and the like.

The complexes can be administered in combination with another therapeutic treatment, such as either a radiation treatment or chemotherapeutic agent. The therapeutic treatments, or a combination of therapeutic treatments, can be administered before or subsequent to the administration of the complex, for example within about 12 hours to about 7 days. Chemotherapeutic agents include, for example, doxorubicin, 5-fluorouracil (5FU), cisplatin (CDDP), docetaxel (TAXOTERE®), gemcitabine (GEMZAR®), paclitaxel, vinblastine, etoposide (VP-16), camptothecia, actinomycin-D, mitoxantrone and mitomycin C. Radiation therapies/treatments include gamma radiation ($^{137}$Cs), X-rays, UV irradiation, microwaves, electronic emissions and the like.

Diagnostic agents also can be delivered to targeted cells via the liposome or polymer complexes. Agents which can be detected in vivo following administration can be used. Exemplary diagnostic agents include electron dense materials, iron, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. Imaging agents disclosed by Low et al. in U.S. Pat. No. 5,688,488, incorporated herein by reference, are useful in the present invention.

The complexes made in accordance with the method of this invention can be provided in the form of kits for use in the systemic delivery of a therapeutic molecule by the complex. Suitable kits can comprise, in separate, suitable containers, the liposome, the antibody or antibody fragment, and the therapeutic or diagnostic agent. The components can be mixed under sterile conditions in the appropriate order and administered to a patient within a reasonable period of time, generally from about 30 minutes to about 24 hours, after preparation. The kit components preferably are provided as solutions or as dried powders. Components provided in solution form preferably are formulated in sterile water-for-injection, along with appropriate buffers, osmolarity control agents, etc.

siRNA

In a further embodiment, the present invention provides compositions and methods for delivering siRNA oligonucleotides using the complexes described herein. The use of small interfering (si) RNAs to suppress expression of specific transcripts is a useful technique to probe gene function in cells. The HER-2 gene, a transmembrane tyrosine kinase with homology to the epidermal growth factor receptor, is found to be over expressed in many cancers. Because of its established crucial role in signal transduction, and in many different cancers, HER-2 is an attractive target for anti-cancer therapies. One method of down-modulating HER-2 expression is by means of siRNA technology. Trilink Biotechnologies, Inc. (San Diego, Calif.) has developed modified hybrid (Sense DNA-Antisense RNA) siRNA analogs directed against HER-2, which is readily delivered using the liposome complexes disclosed throughout. The present invention also provides compositions and methods for delivery of any siRNA.

Short interfering RNAs (siRNA) are 21-25 nucleotide RNA duplexes with a characteristic structure of a symmetric 2 nucleotide 3'-end overhang and a 5' phosphate and 3' hydroxy group. They were first identified in plants and *Drosophila* where they were associated with sequence specific inhibition of gene expression (Reviewed in Schutze, N. "siRNA Technology," *Molecular & Cellular Endocrinology*, 213: 115-119 (2004); and Scherr, M., Morgan, M. A., and Eder, M. "Gene silencing mediated by small interfering RNAs in mammalian cells." *Current Medicinal Chemistry*, 10: 245-256 (2003) the disclosures of which are incorporated herein by reference).

Interferon (IFN)-Like Effects of siRNA.

Transfection of siRNA has been shown to result in IFN-mediated activation of the Jak-Stat pathway and global upregulation of IFN-stimulated genes Sledz, C. A., et al., *Nat Cell. Biol.* 5: 834-839 (2003). This effect is mediated by the dsRNA-dependent protein kinase, which is activated by relatively short 21-mer siRNA.

Structural Modulation of Potency and Off-Target Effects.

A key step in the RNA interference (RNAi) pathway is assembly of the RNA-induced silencing nanocomplex (RISC) that mediates target RNA cleavage through an active form (RISC*) which contains only the antisense strand of the siRNA. Inappropriate incorporation of the sense strand of siRNA into RISC* can lead to off-target RNA cleavage at sites homologous to the sense-strand complement (Webster, M. A., et al., Molecular & Cellular Biology, 18: 2344-2359 (1998)). Recent thermodynamic analyses have led to proposed sequence selection rules to favor incorporation of the antisense strand. Ideally, such asymmetric loading would abrogate sense-strand-mediated off-target cleavage, as well as increase potency due to increased concentration of RISC* loaded with the antisense strand (Khvorova, A., et al., Cell 115: 209-216 (2003). More specifically, it was proposed that active siRNA should exhibit enhanced flexibility at the 5' antisense terminus and an overall low internal stability profile, in particular within the 9-14 basepair region of the duplex. It was further suggested that altering the chemical or structural nature of the siRNA duplex (introducing mismatches and chemical modifications), which will alter the internal stability profiles to resemble the desirable one, might be a means for optimization of siRNA activity. Preliminary support for thermodynamic manipulation of RNAi activity is found in more recent studies using 3'-end mismatches in novel constructs called "fork-siRNA duplexes" Hohjoh, H., *FEBS Lett.* 557: 193-198 (2004).

Chemically Modified siRNA.

There have been a number of publications indicating that enhancement of RNAi activity in mammalian cells can be obtained with modified siRNAs. Activity is preserved with phosphorothioate (PS) linkages at the 5' and 3' ends, or at alternating linkages, and with 2'-fluoro (F) at all pyrimidines. Harborth, J., et al., *Antisense nucleic Acid Drug Dev.* 13: 83-105 (2003). Others found that activity is maintained with alternating 2'-O-methyl (OMe) linkages or several PS and OMe modifications at 5' and 3' ends. Amarzguioui, M., et al., *Nucleic Acids Res.* 31: 589-595 (2003). Activity has been preserved with more extensive modification with variable numbers of PS, OMe, and locked nucleic modifications.

Design of Improved siRNA Analogs (Modified Hybrid of Sense DNA-Antisense RNA)

The use of hybrid sense-DNA/antisense-RNA can induce RNAi activity in human cells. Hohjoh, H., *FEBS Lett.* 521: 195-199 (2002). In addition, such DNA/RNA constructs exhibit RNAi activity which is greater in both duration and percent knockdown than that shown by conventional siRNA. In addition to these advantages, hybrid DNA/RNAs are thought to be free of an IFN response induced by double-stranded RNA, possibly abrogating the cellular resistance mediated by the specific siRNA binding protein(s). Since unmodified DNA bound to RNA provides a substrate for RNase H, the unmodified DNA/RNA constructs which have been traditionally used to induce RNAi are subject to competitive degradation by RNase H which lessens their RNAi potency. Trilink Biotechnologies (San Diego, Calif.) has utilized a proven antisense oligonucleotide analog substituent-blocking strategy to prevent RNase H degradation of the antisense RNA (R) strand by incorporation of OMe (O) substituents in the central region of the sense strand with DNA (D) flanks. This is termed "hybrid." In addition, blunt-ended 19-mer siRNA has been found to be as effective as the commonly employed 21-mer construct, with 2-basepair overhangs (termed "duplex"), called for by "Tuschl's rules." Harborth, J., et al., *Antisense nucleic Acid Drug Dev.* 13: 83-105 (2003). Consequently, TriLink took advantage of this structural simplification in the form of a "5-9-5" 19-mer design shown below that 1) limits usage of OMe residues, which are more costly than DNA, and 2) has helical-DNA/RNA "footprints" assumed to be too small to readily accommodate RNase H.

```
Sense        DDDDDOOOOOOOOODDDDD

Antisense    RRRRRRRRRRRRRRRRRRR
```

The sense-DNA strand in unmodified DNA/RNA can lead to off-target effects by binding to complementary or partially homologous mRNA and then cleavage by RNase H. Crooke, S T., *Annu. Rev. Med.* 55: 61-95 (2004). This undesired side-effect was abrogated by the OMe substitution pattern. In addition, the 3' and 5' DNA-ends of the construct are intended to be degraded by exonucleases thus leaving a relatively short OMe fragment with a low $T_m$ and, therefore, low hybridization potential toward inhibition of translation of off-target mRNA.

```
DDDDDOOOOOOOOODDDDD  ⟶    D's  +  OOOOOOOOO
    RNase H-inactive       exo        low T_m
```

In one embodiment, the present invention provides methods for the systemic delivery of siRNA (e.g., duplex, hybrid, or a chemically-modified analog) via the cationic immunoliposome complexes disclosed throughout. The use of the complexes improves circulation time and increases delivery and uptake of the siRNA molecules. In embodiments where an anti-HER-2 siRNA is utilized, HER-2 intracellular signaling pathways are effected, resulting in sensitization of both primary and metastatic tumors (e.g., pancreatic, breast, prostate) to first-line chemotherapeutic agents (such as gemcitabine, taxotere, mitoxantrone) leading to an improved therapeutic modality for the treatment of tumors. As many targets (e.g., HER-2) and the pathways involved are known, the present invention provides for tumor-targeted delivery of any siRNA molecules, including chemically-modified HER-2 siRNA analogs.

In further embodiments, the present invention provides cationic liposomal complexes wherein one or more siRNA molecules encapsulated within the interior of the liposome, contained within the hydrocarbon chain region of the bilayer, complexed/associated with the inner and/or outer monolayer (e.g., via static interaction or chemical/covalent interaction), or a combination of any or all of these possibilities. Suitably, the siRNA molecules will be encapsulated within the interior of the liposome and/or associated with an inner and/or outer monolayer, for example via charge-charge interaction between the negative charge of the siRNA and the positive charge of the cationic liposome. As described herein, the term "siRNA" refers to nucleotide RNA duplexes, DNA/RNA hybrids, modified DNA/RNA hybrids, modified RNA/RNA duplexes or DNA/modified RNA hybrids with or without a characteristic structure of a symmetric 2 nucleotide 3'-end overhang and a 5' phosphate and 3' hydroxy group. siRNA molecules can be any length, for example, about 21, about 22, about 23, about 24, of about 25 nucleotides in length. In additional embodiments, shorter length siRNA molecules can be used in the practice of the present invention, for example 15, 16, 17, 18, 19, or 20 nucleotide siRNA molecules can be used. In further embodiments, longer siRNA molecules can be used, for example 26, 27, 28, 29, or 30 nucleotide siRNA molecules can be used. Any siRNA molecule(s) can be utilized in the practice of the present invention since the encapsulation/association of an siRNA molecule with the cationic liposomes of the present invention depends upon the size and charge of the siRNA, and not its nucleic acid sequence. Thus, siRNAs of any nucleic acid sequence can be utilized.

Examples of siRNA molecules include any siRNA molecules designed to down-regulate target proteins related to any disease state, including, but not limited to, cancers (e.g., a breast cancer, a uterine cancer, an ovarian cancer, a prostate cancer, a testicular cancer, a lung cancer, a leukemia, a lymphoma, a colon cancer, a gastrointestinal cancer, a pancreatic cancer, a bladder cancer, a kidney cancer, a bone cancer, a neurological cancer, a head and neck cancer, a skin cancer, a sarcoma, an adenoma, a carcinoma and a myeloma); infectious diseases (e.g. bacterial diseases, fungal diseases, parasitic diseases and viral diseases (such as a viral hepatitis, a disease caused by a cardiotropic virus; HIV/AIDS; and the like)); cardiovascular disease, diabetes and genetic disorders (e.g., anemia, neutropenia, thrombocytopenia, hemophilia, dwarfism and severe combined immunodeficiency disease ("SCID"); autoimmune disorders (e.g., psoriasis, systemic lupus erythematosus and rheumatoid arthritis) and neurodegenerative disorders (e.g., various forms and stages of multiple sclerosis, Creutzfeldt-Jakob Disease, Alzheimer's Disease, and the like). In suitable embodiments, the siRNA molecules for use in the practice of the present invention will be targeted to down-regulate proteins and oncogenes associated with, and often over-expressed, in cancers. Examples of cancer targets, and siRNA molecules that can be used in the practice of the present invention, include, but are not limited to, siRNA molecules targeted toward, growth factor receptors such as HER-2 (erB-2), Epidermal Growth Factor receptor (EGFR), Insulin Growth Factor 1 receptor (IGF1R) and vascular endothelial growth factor (VEGF); telomerase; FLICE; as well as other targets and sequences that are known in the art or otherwise identifiable.

In one embodiment, the present invention provides methods and compositions for delivery of siRNA molecules that are designed to downregulate the HER-2 (erb-2) growth factor receptor. In suitable embodiments, the siRNA molecule will comprise one of the following sequences:

```
Construct 1 sense
5' r(GGAGCUGGCGGCCUUGUGCCG) 3'     (SEQ ID NO: 1)
(nt3-nt23)

Construct 1 antisense
5' r(GCACAAGGCCGCCAGCUCCAU) 3'     (SEQ ID NO: 2)
(nt1-nt21)
```

-continued
```
Construct 3 sense
5' r(UCUCUGCGGUGGUUGGCAUUC) 3'     (SEQ ID NO: 3)
(nt1964-nt1984)

Construct 3 antisense
5' r(AUGCCAACCACCGCAGAGACG) 3'     (SEQ ID NO: 4)
(nt1962-nt1982)

Control sense
5' r(UUCUCCGAACGUGUCACGUUU) 3'     (SEQ ID NO: 5)

Control antisense
5' r(ACGUGACACGUUCGGAGAAUU) 3'     (SEQ ID NO: 6)

Control sense:
5'-TIC Icc gaa cgu guC ICI T-3'    (SEQ ID NO: 7)

Control antisense:
5'-ACG UGA CAC GUU CGG AGA A-3'    (SEQ ID NO: 8)
``` where I represents 2'-deoxyinosine and lowercase letters indicate 2'-O-Me RNA.

An additional example of a homologous chemically-modified siRNA hybrid for use in the practice of the present invention includes the following 19-mer sense strand with the following pattern of 2'-deoxyinosine (I) and 2'-O-methylribonucleotide (2'-OMe) residues:

```
5'-                                 (SEQ ID NO: 9)
d(TITIT)-2'OMe(GCGGUGGUU)-d(GICIT).
```

Table 1 below represents exemplary sequences of Anti-HER-2 and Control HER-2 cognate oligonucleotides suitable for use in the practice of the present invention.

TABLE 1

| Abbr. | Name | 5'→3' Sense (Top) 3'→5' Antisense (Bottom) | |
|---|---|---|---|
| D-1 | HER-2 Duplex 1 | GGAGCUGGCGGCCUUGUGCCG UACCUCGACCGCCGGAACACG | (SEQ ID NO: 1) (SEQ ID NO: 2) |
| D-3 | HER-2 Duplex 3 | UCUCUGCGGUGGUUGGCAU AGAGACGCCACCAACCGUA | (SEQ ID NO: 10) (SEQ ID NO: 11) |
| H-1 | HER-2 Hybrid 1 | GGAGCTGGCGGCCTTGTGCCG GCACAAGGCCGCCAGCUCCAU | (SEQ ID NO: 12) (SEQ ID NO: 13) |
| H-3 | HER-2 Hybrid 3 | TCTCTGCGGTGGTTGGCAT AGAGACGCCACCAACCGUA | (SEQ ID NO: 14) (SEQ ID NO: 15) |
| mH-3 | HER-2 Modified Hybrid 3 | TITITgcggugguuGICIT AGAGACGCCACCAACCGUA | (SEQ ID NO: 9) (SEQ ID NO: 16) |
| C-H | Control HER-2 Hybrid | TTCTCCGAACGTGTCACGT AAGAGGCUUGCACUGAGCA | (SEQ ID NO: 17) (SEQ ID NO: 18) |

TABLE 1-continued

| Abbr. | Name | 5'→3' Sense (Top)<br>3'→5' Antisense (Bottom) | |
|---|---|---|---|
| C-mH | Control HER-2 Modified Hybrid | TICICcgaacguguCICIT<br>AAGAGGCUUGCACAGUGCA | (SEQ ID NO: 7)<br>(SEQ ID NO: 8) |

RNA=capital letters in normal font; DNA=capital letters in bold font; 2'OMe=lower case letters in normal font. (See, Hogrefe, R. I. et al., "Chemically Modified Short Interfering Hybrids (siHYBRIDS): Nanoimmunoliposome Delivery In Vitro and In Vivo for RNAi of HER-2," *Nucleoside, Nucleotides and Nucleic Acids* 25:889-907 (2006); and Pirollo, K. et al., "Tumor-Targeting Nanoimmunoliposome Complex for Short Interfering RNA Delivery," *Human Gene Therapy* 17:117-124 (2006), the disclosures of which are incorporated herein by reference.)

While the Examples section utilizes the anti-HER 2 siRNA molecules described above, it should be noted that any siRNA molecule can be encapsulated/associated with the cationic immunoliposomes of the present invention, and hence, the present invention is not limited to the use of any particular sequence(s) of siRNA. In addition, more than one type of siRNA molecule can be encapsulated/associated with the cationic immunoliposome complexes of the present invention. This includes different types of siRNA (i.e. duplex, hybrid and modified hybrid) as well as siRNAs with different targets. For example, the immunoliposome complexes of the present invention can be prepared such that they comprise siRNAs that target several different proteins/genes in a cell or different cells/tissues.

Additional exemplary sequences for use in the practice of the present invention include the FLIP, RNA duplex:

```
Sense:    5' gcagucuguucaaggagcaTT 3'  (SEQ ID NO: 21)
Antisense: 5' ugcuccuugaacagacugcTT 3'  (SEQ ID NO: 22)
```

As described herein, siRNAs are suitably encapsulated, contained or complexed/associated with the liposome complexes of the present invention by simply mixing the one or more siRNA molecules with the liposomes during processing. Suitable ratios of siRNA:liposome complexes are readily determined by the ordinarily skilled artisan. For example, the molar ratio of siRNA molecules to liposome complex is suitably in the range of about 1:1 to about 1:20 (μg siRNA:nmol liposome), suitably about 1:3.5 to about 1:14 (μg siRNA:nmol liposome), more suitably about 1:7 or about 1:5 (μg siRNA:nmol liposome). As described throughout, examples of desirable cationic liposomes for delivery of siRNA molecules include those that comprise a mixture of dioleoyltrimethylammonium phosphate (DOTAP) and dioleoylphosphatidylethanolamine (DOPE) and/or cholesterol (chol); and a mixture of dimethyldioctadecylammonium bromide (DDAB) and DOPE and/or chol. The ratio of the lipids can be varied to optimize the efficiency of uptake of the siRNA molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably about 1:(1-2) (molar ratio). Examples of ratios of various lipids useful in the practice of the present invention include, but are not limited to:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol).

In one embodiment, the present invention provides methods of preparing siRNA-comprising antibody- or antibody fragment-targeted cationic immunoliposome complexes comprising preparing an antibody or antibody fragment; mixing the antibody or antibody fragment with a cationic liposome to form a cationic immunoliposome, wherein the antibody or antibody fragment is not chemically conjugated to the cationic liposome; and mixing the cationic immunoliposome with one or more siRNA molecules to form said antibody- or antibody fragment-targeted-cationic immunoliposome complex.

In suitable embodiments, the antibody fragment is a single chain Fv fragment, for example, an anti-transferrin receptor single chain Fv (TfRscFv) or an anti-HER-2 antibody or antibody fragment. Examples of suitable lipids for use in preparing the siRNA-comprising cationic immunoliposomes are described herein, and include, mixtures of dioleoyltrimethylammonium phosphate with dioleoylphosphatidylethanolamine and/or cholesterol; and mixtures of dimethyldioctadecylammonium bromide with dioleoylphosphatidylethanolamine and/or cholesterol. Suitably the antibody or antibody fragment is mixed with the cationic liposome at a ratio in the range of about 1:20 to about 1:40 (w:w) to form a cationic immunoliposome. Suitably, the cationic immunoliposome is mixed with the siRNA molecule at a molar ratio in the range of about 1:1 to about 1:20 (μg siRNA:nmol liposome), suitably about 1:3.5 to about 1:14 (μg siRNA:nmol liposome), more suitably about 1:7 or about 1:5 (μg siRNA:nmol liposome). Exemplary siRNA molecules for use in the practice of the present invention include those described herein, as well as additional siRNA molecules known in the art and readily identifiable by the ordinarily skilled artisan. Suitably, the siRNA molecules are directed to anti-cancer targets, such as oncogenes or overexpressed proteins, for example, siRNA molecules directed toward HER-2 (erb-2), VEGF, and other upregulated growth factors, as well as others described herein or that will be familiar to the skilled artisan. In further embodiments, the siRNA molecules are directed to targets involved in disease states including, but not limited to, infectious diseases (e.g., bacterial diseases, fungal diseases, parasitic diseases and viral diseases (such as viral hepatitis, diseases caused by cardiotropic viruses, HIV/AIDS and the like)) cardiovascular disease, diabetes and genetic disorders (such as anemia, neutropenia, thrombocytopenia, hemophilia, dwarfism and severe combined immunodeficiency disease ("SCID"), autoimmune disorders (such as psoriasis, systemic lupus erythematosus and rheumatoid arthritis) and neurodegenerative disorders (such as various forms and stages of multiple sclerosis, Creutzfeldt-Jakob Disease, Alzheimer's Disease and the like). In a further embodiment, the present invention provides siRNA molecule-comprising cationic immunoliposome complexes prepared by the methods described herein.

In a further embodiment, the present invention provides antibody- or antibody fragment-targeted cationic immunoliposome complexes comprising a cationic liposome, an antibody or antibody fragment, and one or more siRNA molecules, wherein the antibody or antibody fragment is not chemically conjugated to the cationic liposome. The antibody or antibody fragment is suitably associated with the liposome via an interaction (e.g., electrostatic, van der Walls, or other non-chemically conjugated interaction) between the antibody or antibody fragment and the liposome, suitably between a cystein residue on the antibody or antibody fragment and the liposome surface. In general, a linker or spacer molecule (e.g., a polymer or other molecule) is not used to attach the antibodies and the liposome. The siRNA molecule(s) can be encapsulated within the cationic liposome, contained with a hydrocarbon chain region of the cationic liposome, associated with an inner or outer monolayer of the cationic liposome, or any combination thereof. Suitably, the cationic immunoliposomes of the present invention are unilamellar liposomes (i.e. a single bilayer), though multilamellar liposomes which comprise several concentric bilayers can also be used. Single bilayer cationic immunoliposomes of the present invention comprise an interior aqueous volume in which agents (e.g., siRNA molecules) can be encapsulated. They also comprise a single bilayer which has a hydrocarbon chain region (i.e., the lipid chain region of the lipids) in which agents (e.g., siRNA molecules that have been conditioned to be neutral or largely uncharged) can be contained. In addition, agents (e.g., siRNA molecules) can be complexed or associated with either, or both, the inner monolayer and/or the outer monolayer of the liposome membrane (i.e., the headgroup region of the lipids), e.g., via a charge-charge interaction between the negatively charged siRNA and the positively charged cationic liposomes. In further embodiments, agents (e.g., siRNA molecules) can be encapsulated/associated/complexed in any or all of these regions of the cationic immunoliposome complexes of the present invention.

In a still further embodiment, the present invention provides methods of treating a patient suffering from, or predisposed to, a disease state, comprising administering the siRNA molecule-comprising cationic immunoliposome complexes of the present invention to the patient. The immunoliposome complexes can be administered via any desired route, including, but not limited to, intravenous, oral, topical, via inhalation, intramuscular injection, intratumoral injection, intradermal injection, intraperitoneal injection, intranasal injection, intraocular injection, intracranial injection, or other routes. As used herein, the term patient includes both animal patients (e.g., mammals such as dogs, cats, pigs, sheep, etc) as well as humans.

Suitably, the methods of the present invention are used to treat patients suffering from, or predisposed to, cancer. In further embodiments, the methods of treating patients suffering from, or predisposed to, cancer can further comprise administering a chemotherapeutic agent to the patient in addition to the administration of the siRNA molecule-comprising immunoliposome complex. In still further embodiments, the methods of treating patients suffering from, or predisposed to, cancer can further comprise administering radiation treatment to the patient in addition to the administration of the siRNA molecule-comprising immunoliposome complex. In suitable embodiments, the methods of the present invention comprise administering an immunoliposome complex comprising a siRNA molecule (e.g., and anti-HER-2 siRNA), in conjunction with a chemotherapeutic agent selected from the group consisting of doxorubicin, 5-fluorouracil (5FU), cisplatin (CDDP), docetaxel (TAXOTERE®), gemcitabine (GEMZAR®), pacletaxel, vinblastine, etoposide (VP-16), camptothecin, actinomycin-D, mitoxantrone and mitomycin C, or an antibody therapy, such as a monoclonal antibody, e.g., HERCEPTIN® (Genentech, San Francisco Calif.). The siRNA molecule-comprising immunoliposome complex and the chemotherapeutic agent (or antibody therapy) can be administered at the same time, or can be administered at different times (i.e., "in conjunction with" encompasses administration of both the complex and the agent at the same time or at different times). Suitably, the chemotherapeutic agent (or antibody therapy) is administered either before or after the siRNA molecule-comprising immunoliposome complex, (e.g., at least 1 hour before or after, at least 6 hours before or after, at least 12 hours before or after, at least 24 hours before or after, at least 48 hours before or after, etc., administration of the cationic immunoliposome complex).

Appropriate dosages of the siRNA molecule-comprising immunoliposome complexes and the chemotherapeutic agents (or antibody therapy) for administration in humans are easily determined by those of skill in the art, based on information contained herein and that is readily available in the art. Furthermore, such amounts can be estimated by extrapolating from experiments performed on animals, e.g., mouse, rat, dog or other studies. For example, the amount of siRNA delivered using the immunoliposomes of the present invention can be on the order of about 1-100 mg/Kg; the amount of gemcitabine (GEMZAR®) about 10-500 mg/Kg) and the amount of (docetaxel) TAXOTERE® (TXT) about 3-100 mg/Kg.

In additional embodiments, the methods of the present invention comprise administering an immunoliposome complex comprising a siRNA molecule (e.g., and anti-HER-2 siRNA), in conjunction with radiation treatment (radiation therapy). Examples of suitable radiation treatments include, but are not limited to, gamma radiation (e.g., $^{137}Cs$), X-rays, UV irradiation, microwaves, electronic emissions and the like. The siRNA molecule-comprising immunoliposome complex and the radiation treatment can be administered at the same time, or can be administered at different times (i.e., "in conjunction with" encompasses administration of both the complex and the radiation treatment at the same time or at different times). Suitably, the radiation treatment is administered either before or after the siRNA molecule-comprising immunoliposome complex, (e.g., at least 1 hour before or after, at least 6 hours before or after, at least 12 hours before or after, at least 24 hours before or after, at least 48 hours before or after, etc., administration of the cationic immunoliposome complex). Appropriate dosages (and durations) of the siRNA molecule-comprising immunoliposome complexes and the radiation treatment are easily determined by those of skill in the art, based on information contained herein and that is readily available in the art.

In a further embodiment, the present invention provides methods of enhancing the effectiveness of a chemotherapeutic agent, or radiation treatment, comprising administering a cationic immunoliposome complex of the present invention (e.g., a cationic immunoliposome complex comprising one or more siRNA molecules) in conjunction with the chemotherapeutic agent, or the radiation treatment, to a patient. Suitable siRNA molecules, chemotherapeutic agents and radiation treatments include those described throughout as well as those known in the art. The siRNA molecule-comprising immunoliposome complex and the chemotherapeutic agent, or radiation treatment, can be administered at the same time, or can be administered at different times. Suitably, the chemotherapeutic agent or the radiation treatment is administered either before or after the siRNA molecule-comprising immunoliposome complex, (e.g., at least 1 hour before or after, at least 6 hours before or after, at least 12 hours before or after, at least 24 hours before or after, at least 48 hours before or after, etc., administration of the cationic immunoliposome complex).

In a still further embodiment, the present invention provides methods for introducing an siRNA oligonucleotide into a cell, comprising incubating the cell with an siRNA cationic immunoliposome complex of the present invention, whereby the siRNA enters the cell. Thus, the present invention also provides methods for use in transfection of cell lines in in vitro settings, that is where the cells are maintained outside of a living organism (e.g., in cell culture or in in situ settings). The ordinarily skilled artisan will readily be able to determine appropriate concentrations of cells, siRNA and immunoliposomes for various in vitro settings based upon knowledge available in the art and provided throughout the Examples. Suitably the cell lines are cancer cells lines, e.g., breast, prostate, melanoma, pancreatic, uro-genitals, head and neck, or other cancer cells.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Construction and Purification of TfRscFv with a 3'-cysteine

Plasmid expression vector pDFH2T-vecOK was obtained from Dr. David Fitzgerald, NCI. This vector encodes the single chain fragment for the 5E9 antibody, which recognizes the human transferrin receptor (CD71). The VH-linker-Vκ TfRscFv was obtained by PCR amplification of the desired fragment. A cysteine moiety was added at the 3' end of the TfRscFv protein. Two forms of this vector were constructed. The first contains a pelB leader signal sequence, for transport to the periplasmic space, and a His Tag. The presence of the His Tag aids in detection of the protein, thus simplifying development of the purification protocol. Although this form was used for the initial testing, FDA guidelines recommend that no extraneous sequences be present for use in clinical trials. Therefore, a second form minus both of these sequences also was made.

Using PCR amplification the nucleotide sequence for the cysteine residue and a NotI restriction site were introduced at the 3' end. Similarly, a 5' NcoI site also was incorporated. The PCR product was cloned into NcoI and NotI sites of the commercial vector pET26b(+) (Novogen) thus producing a protein product containing both the pelB leader signal sequence and the His Tag. Growth in bacterial culture containing IPTG yielded an approximate 100 fold increase in single chain protein expression which was maximum at approximately 10 hours of IPTG induction. This protein was found primarily in the insoluble fraction (inclusion bodies).

The above construct also was modified to eliminate both the His Tag and pelB sequences in the final protein product. To accomplish this, the pET26b(+) vector was cut at the Nde I enzyme site 5' of the pelB sequence. PCR amplification inserted an Nde I site at the 5' end of the VH-linker-Vκ scFv for the TfR sequence. In addition to the nucleotide sequence for the cysteine residue and the NotI restriction site at the 3' end, a DNA stop codon was introduced adjacent to the cysteine sequence and before the NotI site. The PCR product was cloned into the NdeI and NotI sites of commercial expression vector pET26b(+) (Novogen). Thus, the protein product of this construct will not contain either the pelB sequence or the His-tag.

The majority of the cys-TfRscFv protein (also described as "sc" throughout) (approximately 90%) was found not to be soluble but to be contained within inclusion bodies. Therefore, the protein from the constructs described above was isolated from the inclusion bodies by sonication, treatment with 6 M guanidine-HCl, 200 mM NaCl (6 M GuHCl buffer) and purified via SEPHACRYL® S-200 gel filtration column chromatography. Refolding of the cys-TfRscFv protein was accomplished by dialysis at 4° C. against decreasing concentrations of guanidine-HCl. Alternatively, the cys-TfRscFv protein was prepared by isolation of the inclusion bodies by sonication with Triton X-100 followed by solubilization in 6 M Guanidine-HCl, 0.1 M tris-HCl pH=8.0, 2 mM EDTA pH=8.0 and dithioerythritol. Refolding was accomplished by mixing with a buffer composed of 0.1 M Tris-HCl pH=8.0, 0.5M L-arginine-HCl, 2 mM EDTA and 0.9 mM glutathionine and holding at 4° C. for 36-48 hours, followed by dialysis at 4° C. for 20-24 hours against 20 mM Tris-HClI (pH=9.0), 100 mM Urea, and 2 mM EDTA (pH=8.0). After dialysis, the cys-TfRsav was purified by ion exchange chromatography with Q-SEPHAROSE® (filtration gel), followed by concentration (an using AMICON® ultrafiltration device) and dialysis at 4° C. for 30 hours against PBS (pH=7.4) plus 0.06 M sodium chloride. After purification, SDS-PAGE showed a single band of the solublized, refolded cys-TfRscFv protein with the correct molecular weight of approximately 28-30 kDa (as described in WO 00/50008). The cys-TfRsav protein was stored at −80° C.

Example 2

Preparation of cys-TfRscFv-Liposome by Simple Mixing

Published PCT application WO 99/25320, incorporated herein by reference, describes the preparation of several cationic liposomes. The cationic liposomes prepared are clear solutions, their compositions and ratios are as follows:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol)

It is well known by those knowledgeable in the field that conjugated TfRscFv-immunoliposome retains its immunologic activity. We have established that the cys-TfRscFv can be chemically conjugated to lipoplex (PCT application WO 00/50008) and can efficiently transfect human prostate tumor cells in vitro and in vivo. It is common practice for single chain antibody fragments to be attached to liposomes using various chemical conjugation methods. We performed studies to determine if a simple mixing of the cys-TfRscFv and the cationic liposome, instead of chemical conjugation, would result in formation of an immunologically active complex that could still efficiently bind to and transfect tumor cells. A series of cys-TfRscFv-immunoliposome complexes was prepared by mixing the cys-TfRscFv with liposome A at defined ratios of single chain protein to liposome ranging from 1/25 to 1/36 (w/w). Based upon the ELISA data with the conjugated cys-TfRscFv complex the ratio of DNA to n moles total lipid in the mixed complex also was varied from 1/8 to 1/18. The preparation of the complexes was in accordance with the following general procedure: The appropriate amount of 2 mM liposome (A-H described above) is mixed with any volume of water (suitably deionized water) required to give a desired volume and inverted to mix. To the liposome-water the appropriate amount of cys-TfRscFv is added to give the desired ratio and mixed by gentle inversion 5-10 seconds. This mixture is kept at room temperature for 10 minutes (again inverted gently for 5-10 seconds after approximately 5 minutes). At the same time, the appropriate amount of DNA is mixed by inversion for 5-10 seconds with any volume of water (suitably deionized water) required to give a desired volume. Typically, for use in an in vitro assay, it is desirable that the concentration of DNA is in the range of about 0.01 μg to about 2 μg per well; for in vivo use, it is desirable to provide about 5 μg to about 50 μg of DNA per injection. The DNA solution is quickly added to the cys-TfRscFv-liposome solution and the mixture is inverted for 5-10 seconds. The final mixture is kept at room temperature for 10 minutes, gently inverting again for 5-10 seconds after approximately 5 minutes. For use in vivo dextrose or sucrose is added to a final concentration of about 1-50% (V:V) dextrose or sucrose, suitably 5% dextrose or 10% sucrose, and mixed by gentle inversion for 5-10 seconds. A specific example at a preferred ratio of 1:30 (cys-TfRscFv:liposome, w:w) and 1:14 (μg DNA:n mole total Lipid) is as follows: For 40 μg of DNA in a final volume of 800 μl mix 183 μl water with 280 μl of 2 mM liposome solution. Add 34 μl of cys-TfRscFv (with a concentration of 0.4 μg/ml). Mix 183 μl water with 40 μl of 1 μg/1 μl DNA. Add 80 μl of 50% Dextrose as the last step.

The size of the final complex prepared by the method of this invention is between about 25-800 nm, suitably about 100 and 400 nm with a zeta potential of between about 1 and 35 as determined by dynamic light scattering using a Malvern Zetasizer 3000. This size is small enough to efficiently pass through the tumor capillary bed and reach the tumor cells.

Figure 2:
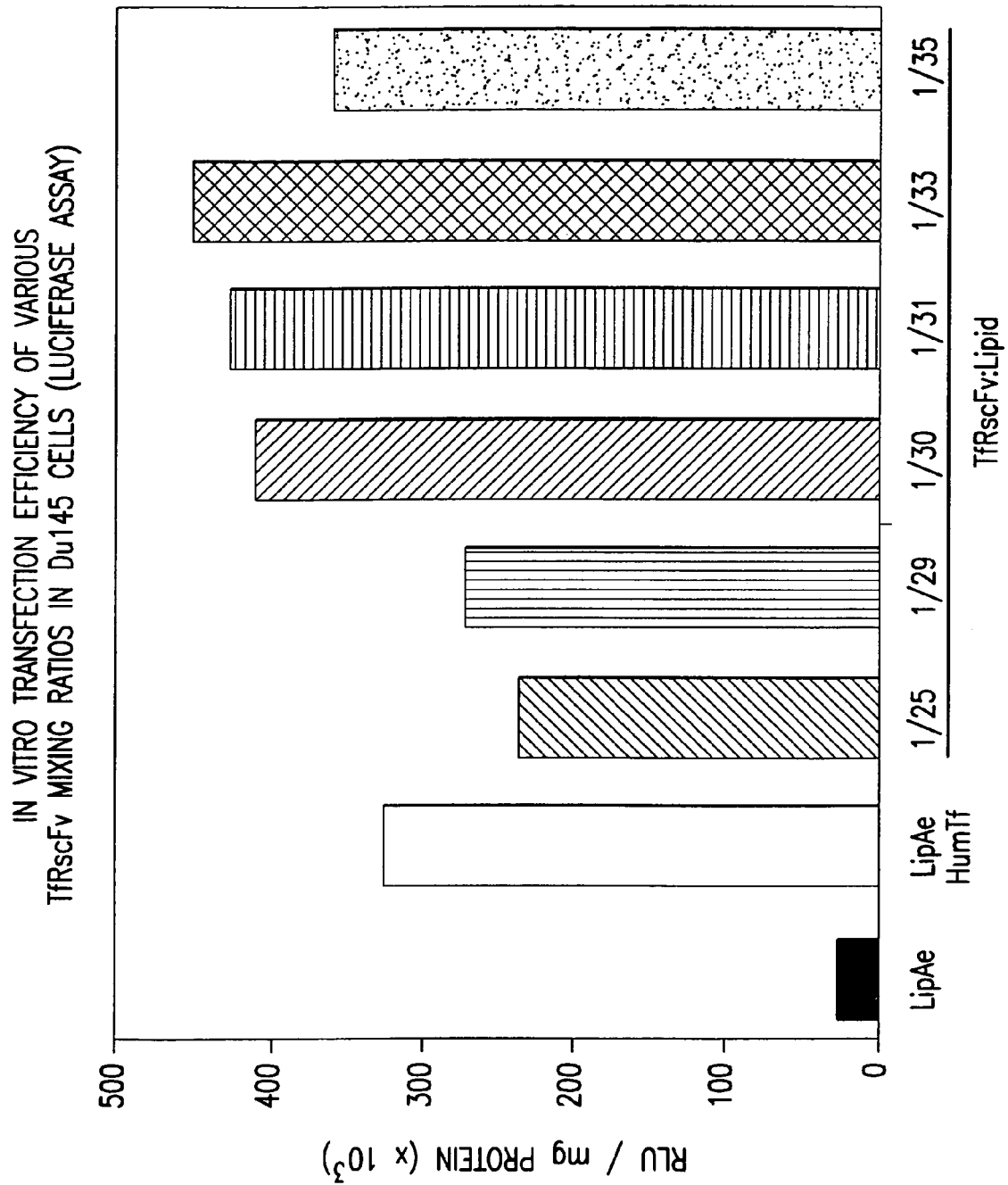
FIG. 2 shows the results of an in vitro transfection assay using different mixing ratios of TfRscFv:lipid in DU145 cells (Luciferase assay).
Figure 3:
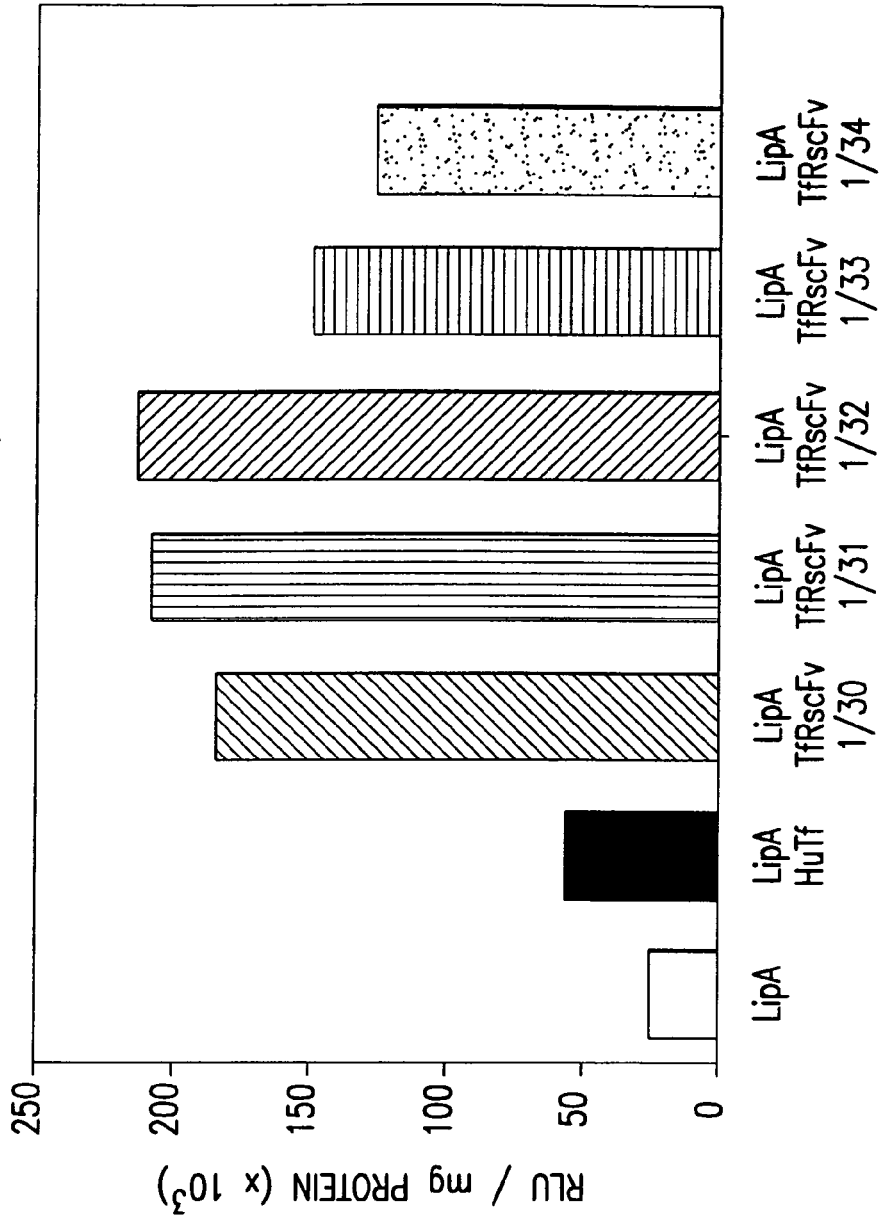
FIG. 3 shows the results of an in vitro transfection assay using different mixing ratios of TfRscFv:lipid in rat C6 cells (Luciferase assay).

An ELISA assay to assess the binding ability of the mixed complex to human prostate cancer DU145 cells was performed. For comparison, the complexes made with the conjugated immunoliposome were also included in the assay. The results shown in FIG. 1 clearly demonstrate that the immunoliposome complex prepared by simple mixing of the cys-TfRscFv protein with the cationic liposome binds to DU145 cells at least as well as those prepared through conjugation. Similar to the conjugated complex, a ratio of 1/30 protein to lipid and 1/14 DNA to lipid was found to have the highest binding ability. As was also previously observed with the conjugated complexes, the binding decreased in a DNA dose dependent manner. These findings indicate that simple mixing of components can form a complex that retains its immunologic activity. Identical optimal ratios were found in human prostate DU145 cells, and RAT C6 cells using the Luciferase assay (FIGS. 2 and 3) and in human pancreatic cancer cell line Panc I (Table 2, 3) using enhanced green fluorescence protein (EGFP) to assess the transfection efficiency.

TABLE 2

Transfection Efficiency of cys-TfRscFv-Liposome A in Panc I Cells Prepared by Simple Mixing Assessed Using the EGFP Reporter Gene I

| Ratio DNA:Total Lipids (μg: n moles) | % Fluorescent Cells |
| --- | --- |
| 1:8 | 20 |
| 1:10 | 22 |
| 1:12 | 35 |
| 1:14 | 50 |
| 1:16 | 24 |
| 1:18 | 20 |

The ratio of cys-TfRscFv:Liposome was 1:3 (w:w)

TABLE 3

Transfection Efficiency of cys-TfRscFv-Liposome A in Panc I Cells Prepared by Simple Mixing Assessed Using the EGFP Reporter Gene II

| Ratio cys-TfRscFv:Lipids (w:w) | % Fluorescent Cells |
| --- | --- |
| 1:26 | 14 |
| 1:28 | 14 |
| 1:30 | 30 |
| 1:32 | 28 |
| 1:34 | 15 |
| 1:36 | 18 |

Figure 4:
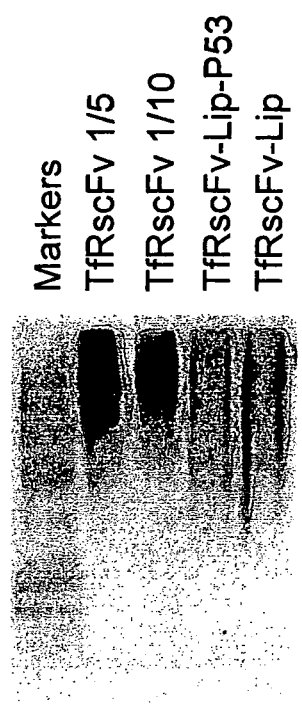
FIG. 4 shows a non-denaturing polyacrylamide gel demonstrating that >95% of the TfRscFv is bound to the liposome or liposome-p53 after simple mixing.

To establish the efficiency of the binding of the cys-TfRscFv to the liposome complex by simple mixing, a non-denaturing polyacylamide gel was used. Mixed cys-TfRscFv-liposome A-p53 complex and cys-TfRscFv-Liposome A without p53 DNA were loaded on the gel along with free cys-TfRscFv in amounts equal to ⅕ or ¹⁄₁₀ the amount of cys-TfRscFv used to prepare the complexes. The complexes were prepared using the ratio of cys-TfRscFv:liposome of 1:30 (w:w) and DNA:total lipid of 1:14 (μg:n mol total lipid). The free cys-TfRscFv complexes serve as quantitation standards, since under non-denaturing conditions the complex can not enter the gel, only free, unbound cys-TfRscFv can migrate into it. After transferring to membrane, the gel was probed with an anti-cys-TfRscFv antibody using the ECL Western Blot detection kit (Amersham). Comparison of the low signal level for the two complexes (with and without p53 DNA) shown in FIG. 4 with the signals from the free cys-TfEscFv standards indicates that greater than 95% of the cys-TfRscFv is incorporated into the complex by simple mixing of the components.

Example 3

In Vitro Chemosensitization of Human Cancer Cell Lines by cys-TfRscFv-Immunoliposome Delivered wtp53

Figure 5A:
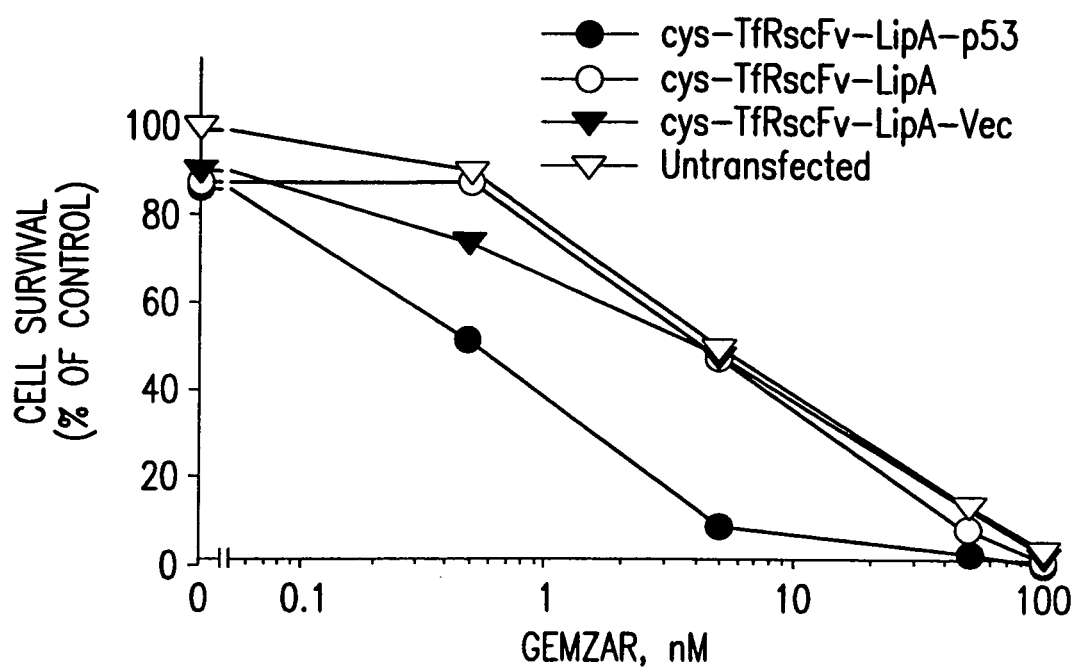
FIG. 5A shows the results of an XTT cytotoxicity assay showing the chemosensitivity to GEMZAR® (gemcitabine) induced in DU145 cells treated with TfRscFv-liposome-p53 prepared by simple mixing.

Experiments were performed to determine how effective the cys-TfRscFv-Liposome-p53 complex prepared by simple mixing would be in sensitizing prostate tumor cells to the drugs Gemzar® (gemcitabine HCl; manufactured by Eli Lilly and Co.) and Novantrone® (mitoxantrone, Immunex Corp.) both of which currently are used for the treatment of prostate cancer. The prostate tumor cell line DU145, which harbors mutant p53, was employed in these studies. The XTT cytotoxicity assay (66) was used to establish the level of chemosensitivity induced by the cys-TfRscFv-Liposome-p53 complex of this invention. $5 \times 10^3$ DU145 cells were plated/well of a 96 well plate. After 24 hours, the cells were transfected with the mixed cys-TfRscFv-Liposome-p53 complex. The cys-TfRscFv-Liposome-p53 complex was prepared by mixing at a ratio of 1:30 (w:w) (cys-TfRscFv:Liposome A) and 1:14 (μg p53 DNA:n moles total lipid). One day after transfection, anti-neoplastic agents were added at increasing concentrations (in triplicate). The XTT assay was performed approximately 3 days later and $IC_{50}$ values, the drug concentration yielding 50% growth inhibition, calculated. As shown in FIG. 5A, treatment with the cys-TfRscFv-Liposome-p53 complex increased the sensitivity of the cells to Gemzar® by 8-fold. For FIG. 5A, the $IC_{50}$ Values (nM) are as follows: cys-TfRscFv-LipA-p53: 0.5; cys-TfRscFv-LipA: 4.0; cys-TfRscFv-LipA-Vec: 4.0; Untransfected: 5.0. The fold sensitization for Vec vs p53=8 and for UT vs p53=10.

Figure 5B:
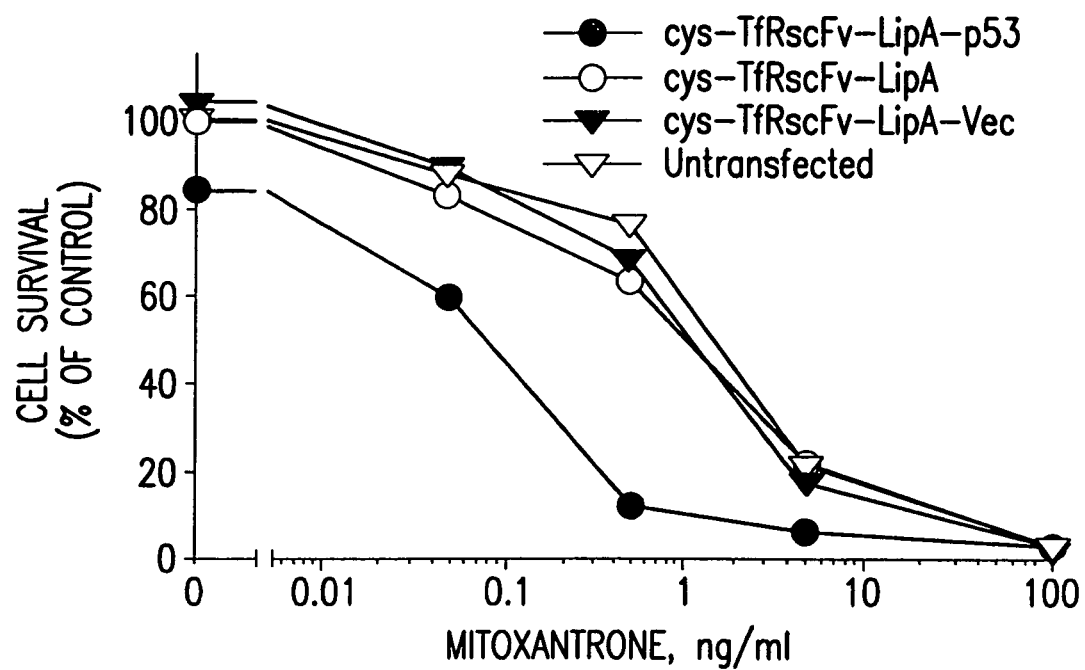
FIG. 5B shows the results of an XTT cytotoxicity assay showing the chemosensitivity to mitoxantrone induced in DU145 cells treated with TfRscFv-liposome-p53 prepared by simple mixing.

Similarly, DU145 cells were sensitized to the drug mitoxantrone by 17.5-fold (FIG. 5B). For FIG. 5B, the $IC_{50}$ values (ng/ml) were as follows: cys-TfRscFv-LipA-p53: 0.08; cys-TfRscV-LipA: 1.20; cys-TfRscFv-LipA-Vec: 1.40 and Untransfected: 1.80. The fold sensitization for Vec vs p53=17.5 and for UT vs p53=22.5. Similar studies were performed using human pancreatic cancer cell line Panc I. 4×103 Panc I cells per well were plated, and the XTT assay performed as above. A preferred ratio of 1:30 (cys-TfRscFv:liposome A w:w) and 1:14 (μg p53 DNA:n moles total lipid) also was used here. As with DU145 there was significant sensitization of the tumor cells to chemotherapeutic agents (FIGS. 6A and B). At a p53 DNA concentration of 0.06 μg/well there was a 23.8 fold increase in sensitization to Gemzar® using the mixed cys-TfRscFv-liposome DNA complex (FIG. 6A). For FIG. 6A, the IC50 values were as follows: cys-TfRscFvLipA-p53: 0.21 nM; cys-TfRscFv-LipA-Vec: 5.00 nM and TfLipA-p53: 0.30 nM. The IC50 of cys-TfRscFvLipA-Vec/IC50 of cys-TfRscFrLipA-p53=23.8. No sensitization was observed when empty vector in place of p53 was used. There was dramatic increase in response of the Panc I cells at a p53 DNA concentration of 0.08 μg DNA/well (FIG. 6B). Here an almost 200 fold increase in sensitization was observed. For FIG. 6B, the IC50 values were as follows: cys-TfRscFvLipA-p53: 1.8 nM; cys-TfRscFvLipA-Vec: 350 nM; and cys-TfRscFvLipA: 600 nM. The IC50 of cys-TfRscFvLipA-Vec/IC50 of cys-TfRscFvLipA-p53=194.44. Therefore, these in vitro studies demonstrate that the cys-TfRscFv-liposome, prepared by simple mixing, can efficiently transfect wtp53 into prostate tumor cells and sensitize them to conventional chemotherapeutic agents.

Example 4

In Vivo Tumor Targeting by the cys-TfRscFv-LipA-EGFP Prepared by Simple Mixing

Figure 7A:
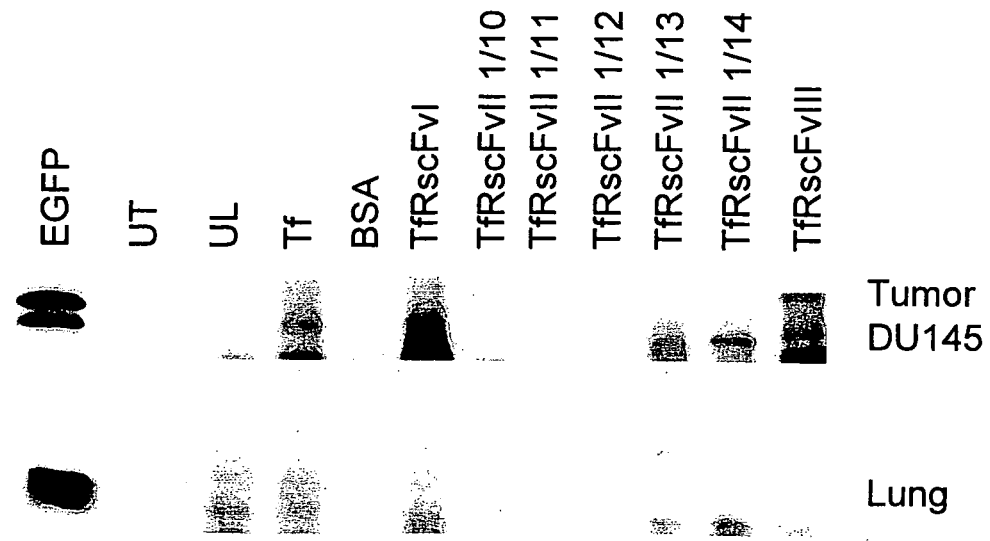
FIG. 7A shows the in vitro tumor targeting ability of the systemically administered TfRscFv-liposome-EGFP complex prepared by simple mixing at various ratios of DNA:lipid

DU145 tumors were subcutaneously induced in female athymic nude (NCR nu/nu) mice. Mice were I.V. tail vein injected three times over a 24 hour period with cys-TfRscFv-LipA-EGFP (enhanced green fluorescence protein) (TfRscFvII) prepared by simple mixing at a scFv:Liposome ratio of 1/30 but at various DNA:total lipid ratios (1/10, 1/11, 1/12, 1/13. 1/14) at 32 ug DNA/injection. For comparison, a complex at 1/30, 1/14 made via the conjugation method (TfRscFv III in FIG. 7B) and a different batch of single chain at 1/30, 1/14 (TfRscFv I in FIG. 7B) also were injected into mice. 60 hours post injection the mice were sacrificed, tumor and lung harvested and protein isolated for Western Blot Analysis using an anti-EGFP antibody. Unliganded LipA-EGFP complex (UL), Tf-LipA-EGFP complex (Tf) and BSA-LipA-EGFP complex (BSA) were injected into mice as controls. FIG. 7A—As shown in the DU145 tumor an EGFP band is observed in the positive controls Tf, TfRscFvIII, and in TfR-scFvI. More significantly, a strong EGFP signal was found in TfRscFvII at the DNA to lipid ratio of 1/14. In contrast only very low level of EGFP expression was evident in normal lung tissue. Therefore, the cys-TfRscFv-Lipoplex prepared by simple mixing can target tumor effectively after systemic administration.

Figure 7B:
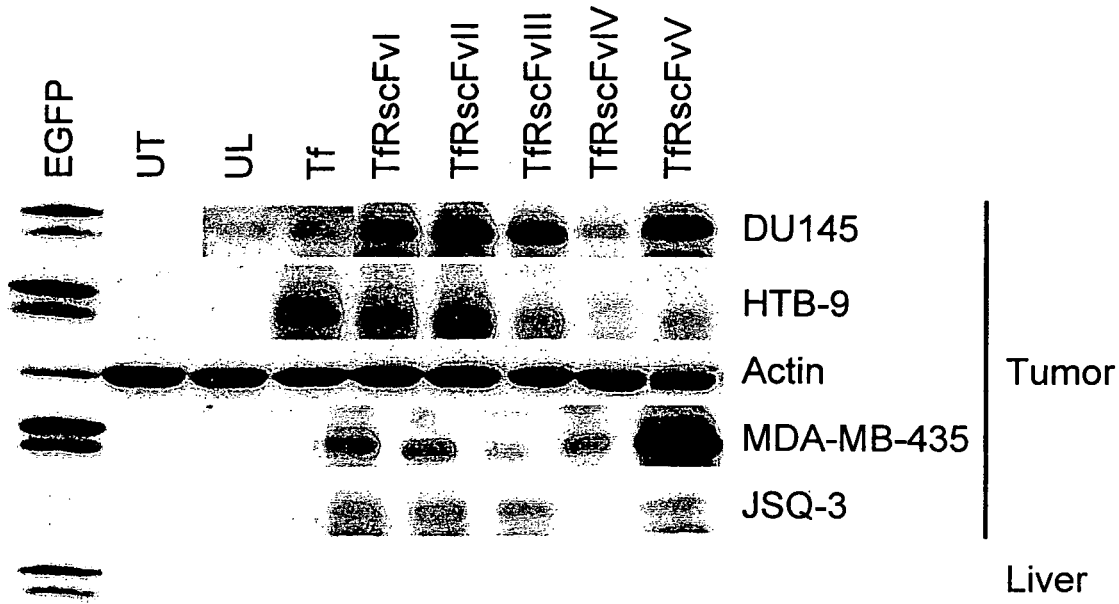
FIG. 7B shows the in vivo tumor targeting ability of the systemically administered TfRscFv-liposome-EGFP complex prepared by simple mixing in four different tumors and using multiple batches of the TfRscFv protein.

To assess the reproducibility of the mixing, different batches of cys-TfRscFv (I to V) were complexed to Liposome A-EGFP by simple mixing at the preferred ratio of 1:30 (scFv:liposome w:w) and 1:14 (μg DNA:n moles total lipid). Human prostate DU145, bladder HTB-9, breast MDA-MB-435 and head and neck JSQ-3 xenograft tumors were subcutaneously induced as above. The complexes also were I.V. tail vein injected three times over a 24 hour period. Tf-LipA-EGFP(Tf) and unliganded LipA-EGFP complex (UL) were used as controls. 60 hours after injection the mice were sacrificed and the tumor and liver were harvested and analyzed as above. Targeting is evident with all of the mixed complexes in the four tumor types (FIG. 7B). However, there is almost no signal in normal tissue (liver). The identical membrane was probed for Actin levels to show equal loading.

Example 5

Radio/Chemosensitization of Human Xenograft Tumors by Systemically Administered cys-TfRscFv-Liposome-p53 Prepared by Simple Mixing Efficacy studies were performed to further confirm the ability of the cys-TfRscFv-immunoliposome complex of this invention to bind and deliver wtp53 efficiently to tumor cells in vivo. Mice bearing subcutaneous DU145 tumors of approximately 60-90 mm$^3$ were injected, via the tail vein, three times a week (a total of 10 injections) with cys-TfR-scFv-Liposome-p53. This complex was prepared by simple mixing at a ratio of 1/30 (cys-TfRscFv:LiposomeA, w:w) and 1/14 (μg DNA/nmoles total lipid). The tumor area was selectively exposed to 2.0 Gy daily fractionated doses of γ-radiation to a total of 32 Gy (FIG. 8). The animals treated with the mixed cys-TFRfscFv-liposome A complex plus radiation had significant tumor growth inhibition. Similar findings also were observed using the combination of the anticancer drug GEMZAR® (gemcitabine) and the cys-TFRscFv-immunoliposome of this invention delivering tumor suppressor gene Rb94 to a human bladder carcinoma xenograft tumor (HTB-9), and in Panc I xenografts treated with GEMZAR® (gemcitabine) and cys-TFRscFv-Liposome carrying either another gene inducing apoptosis (Apoptin) or p53.

These findings demonstrate that a complex made by the method of this invention can comprise a variety of genes (incorporated into plasmid vectors) for effective delivery in vivo to cancer cells as a therapeutic treatment.

Example 6

Chemosensitization of Pancreatic Cancer Cells In Vitro by Antisense HER-2 Oligonucleotides Delivered by cys-TFRscFv-Liposome A Prepared by Simple Mixing This example demonstrates the usefulness of this invention in efficiently delivering molecules other than genes to tumor cells for therapeutic treatment. The complex was prepared as in Example 2, however, the DNA encapsulated here was an 18 mer phosphorothioated oligonucleotide (ODN) directed against the initiation codon of the HER-2 gene (AS HER-2) (51). The ratio used was as above for plasmid DNA 1:30 (cys-TfRscFv: liposome, w:w) and 1:14 (n moles ODN: n mole total lipids). Panc I cells, at $4 \times 10^3$ cells/well, were seeded in a 96 well plate. The cells were transfected 24 hours later by cys-TfRscFv-LipA-AS HER-2 prepared by the method of this invention. Tf-LipA-AS HER-2 and cys-TfR-scFv-LipA-SC ODN were used as controls. SC ODN is a scrambled ODN that has the same nucleotide composition as the AS HER-2 ODN but in random order. As shown in FIG. 9 the cys-TfRscFv-Lip A-AS HER-2 complex prepared by the method of this invention was-able to sensitize pancreatic cancer cell line Panc I to the effects of chemotherapeutic agent GEMZAR® (gemcitabine) by over 11 fold. This increase in sensitization is identical to that resulting from transfection with the positive control Tf-LipA-AS HER2 complex. For FIG. 9, the 1050 values were as follows: TfR-scFv-LipA3-AS-HER-2: 16 nM; Tf-LipAe-AS-HER-2: 14 nM and TfR-scFv-LipAe-SC: 200 nM. The 1050 of TfR-scFv-LipAe-SC/IC50 of TfR-scFv-LipAe-AS-HER-2-12.5.

Example 7

Figure 10A:
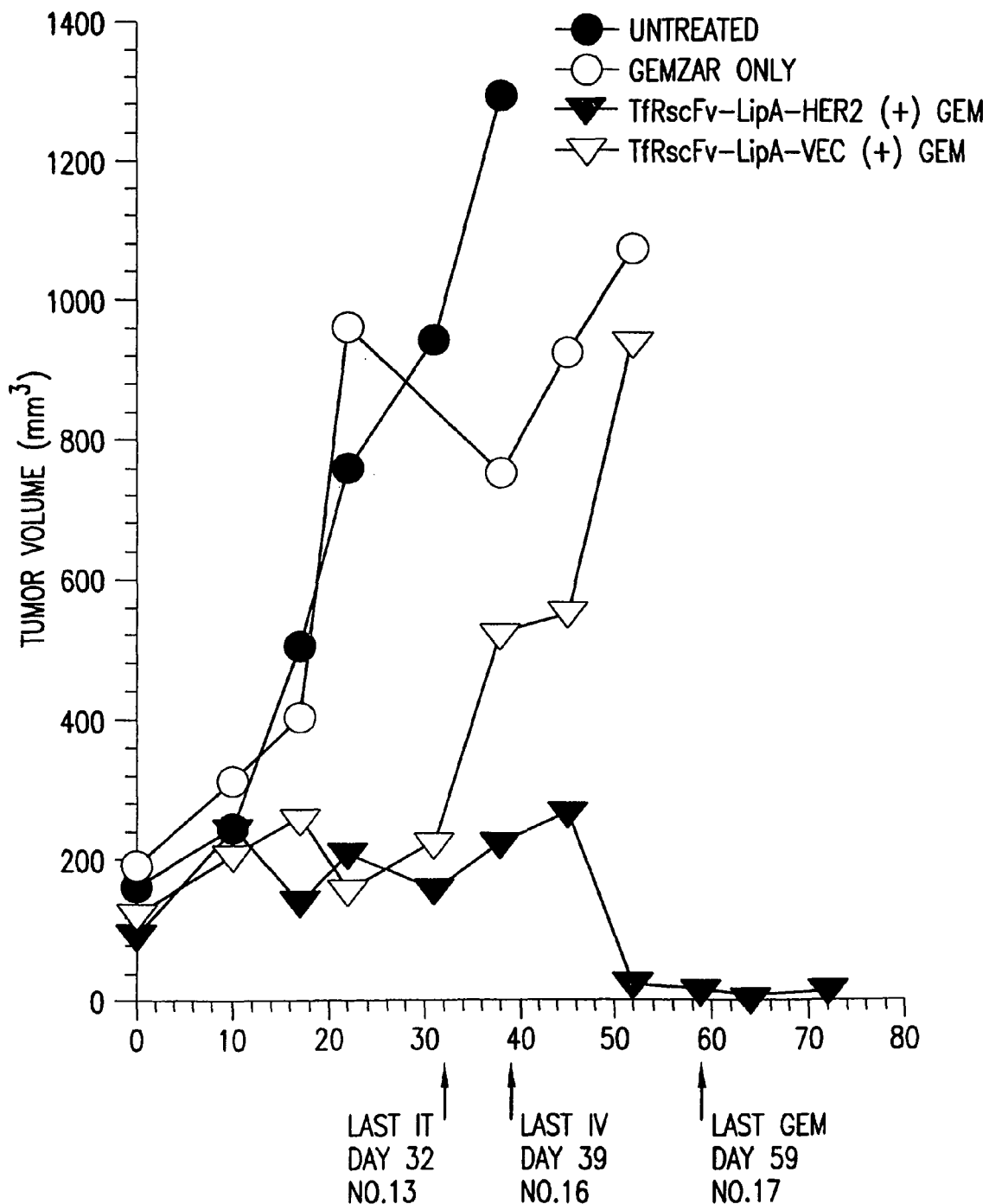
FIG. 10A shows the effect of the combination of systemically administered TfRscFv-liposome A-AS HER-2 ODN and GEMZAR® (gemcitabine) on Panc I human pancreatic xenograft tumors.

In Vivo Chemosensitization of Human Xenograft Tumors by Systemically Delivered cys-TFRscFv-LipA-AS HER-2 ODN Prepared by Simple Mixing In this example, the ability of the cys-TfRscFv liposome-DNA complex prepared by the method of this invention to deliver an antisense molecule to tumor cells in vivo after systemic delivery is demonstrated. To show the universality of this delivery system two different human xenograft mouse tumor models (pancreatic cancer and breast cancer) were employed. In the first (FIG. 10A) Panc I subcutaneous xenograft tumors were induced in female athymic nude (NCR nu/nu) mice. When the tumors were 100-200 mm³ in size the animals were injected with the chemotherapeutic agent GEMZAR® (gemcitabine) (intraperitoneally) and with cys-TfRscFv-LipA AS HER-2 prepared by the method of this invention (I.V.). The complex was made using the ratio of 1:30 (cys-TfRscFv: liposome, w:w) and 1:15 (n mole ODN: n mole total lipid). In addition to the I.V. injections the complex described above also was intratumorally injected. One group of animals received GEMZAR® (gemcitabine) only and a second control group received GEMZAR® (gemcitabine) plus the complex carrying empty vector. Treatment with GEMZAR® (gemcitabine) alone was not able to significantly inhibit pancreatic tumor growth. In contrast (FIG. 10A), the combination of GEMZAR® (gemcitabine) and AS-HER-2 ODN delivered by the cys-TfRscFv-Lip A complex prepared by the method of this invention not only significantly inhibited tumor growth but also resulted in tumor regression.

Figure 10B:
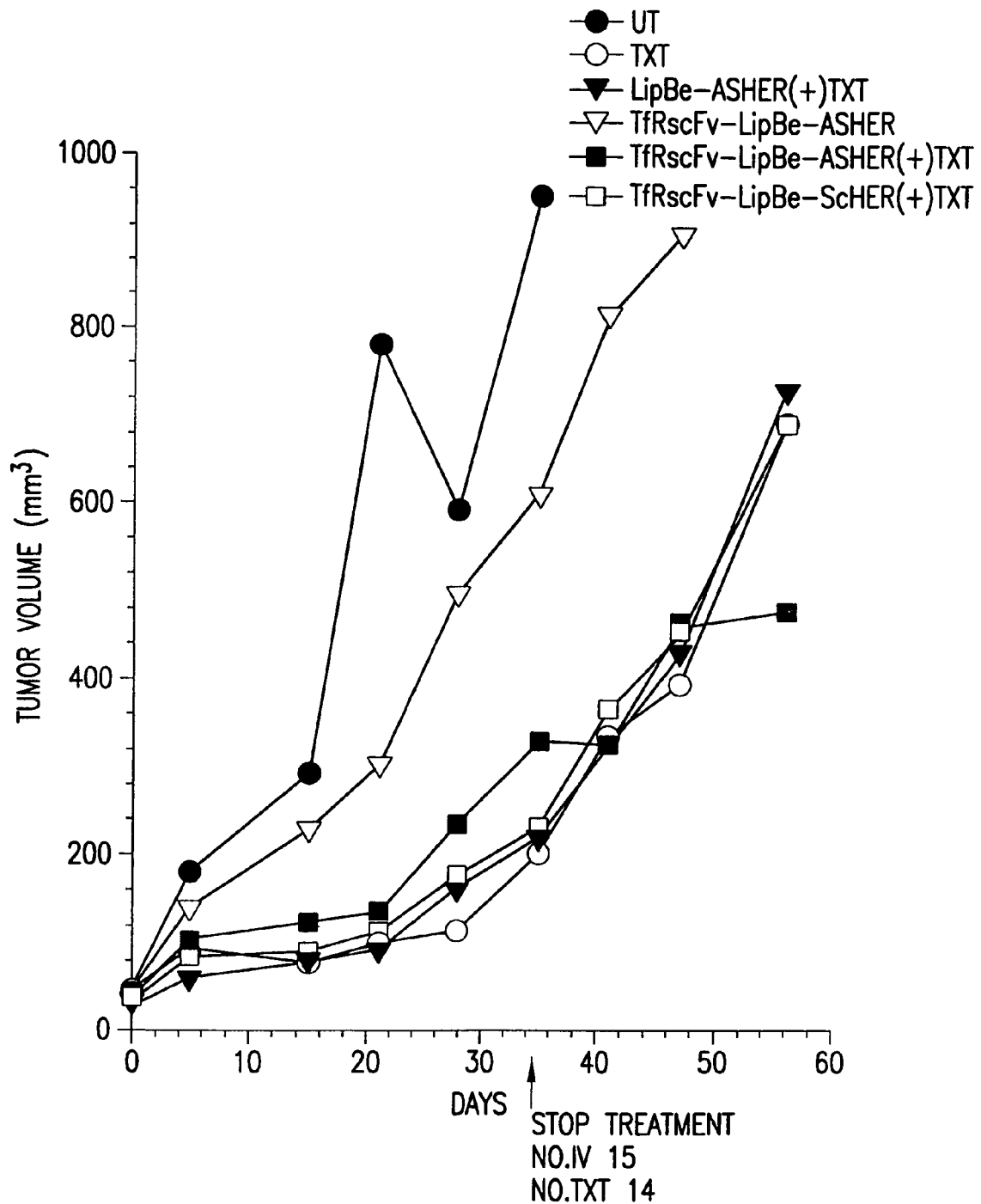
FIG. 10B shows the effect of the combination of systemically administered TfRscFv-liposome B-AS HER-2 ODN and Taxotere on MDA-MB-435 human breast xenograft tumors.

Significant tumor growth inhibition of human breast cancer xenograft tumors also was observed with the combination of the drug Taxotere® (docetaxel; manufactured by Aventis Pharmaceuticals, Collegeville, Pa.) and I.V. administered cys-TfRscFv-LipB AS HER-2 prepared by the method of this invention (FIG. 10B). While liposome formulation B was used in the breast tumor, the same ratios as described above for Panc I were employed.

Example 8

Enhancement of MRI Image by Delivery of Imaging Agent Magnivest® by cys-TFRscFv-Liposome A Prepared by Simple Mixing This example demonstrates the ability to encapsulate MRI imaging agents and form a cys-TfRscFv-Liposome-imaging agent complex by the method of this invention. The complex prepared by the method of this invention can be administered intravenously resulting in increased enhancement of the tumor image. These imaging agents can include, but are not limited to, Magnevist® (Gd-DTPA) (Schering AG). The ratios used to form the complex by simple mixing are the preferred ratios of 1:30 (cys-TfRscFv:liposome, w:w) and 1:14 (ug imaging agent nmoles lipid). In these studies 16 ul of Magnevist® were used in the complex.

Figure 11:
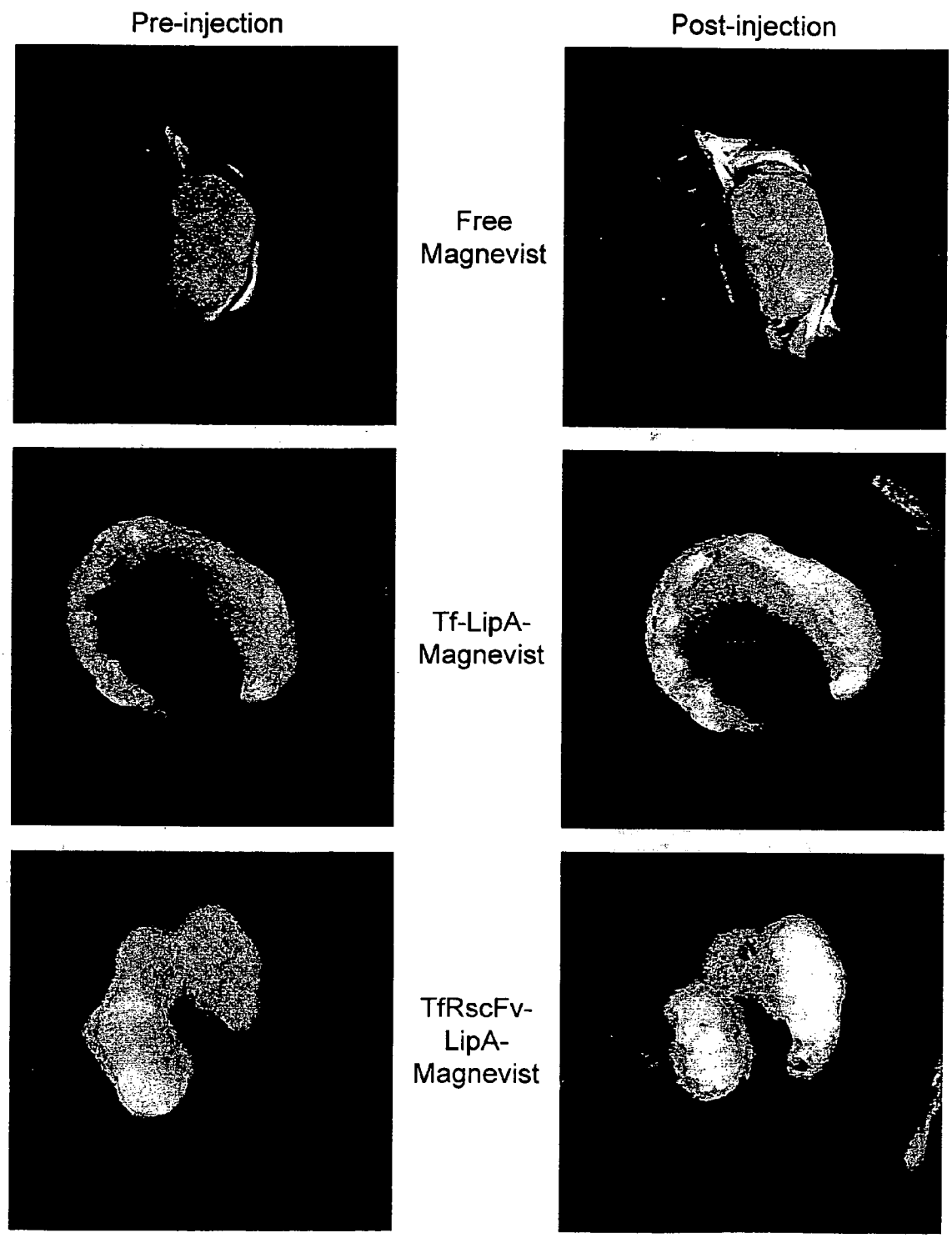
FIG. 11 shows the enhanced tumor imaging resulting from the systemic administration of the TfRscFv-liposome MAG-NEVIST® (Gd-DTPA) complex.

FIG. 11 shows the results from one I.V. injection of the cys-TfRscFv-LipA-MAGNEVIST® (Gd-DTPA) made by the method of this invention into mice bearing subcutaneous xenograft tumors of human head and neck (top panel), breast (middle panel) or prostate (bottom panel) origin. A higher level of imaging agent enhancement is evident in the tumor that received the cys-TfRscFv-LipA-MAGNEVIST® (Gd-DTPA) as compared to that receiving free MAGNEVIST® (Gd-DTPA) demonstrating the benefit of administering the imaging agent using the complex prepared by the method of this invention. In other experiments an increased uptake in the tumor as compared to the surrounding normal tissue also was observed.

Similar enhancement also was observed using syngenetic mouse lung metastasis model. $B_{16}/F_{10}$ mouse melanoma cells were injected intravenously into C57BL/6 mice. These cells form tumor nodules in the mouse lungs. The cys-TfRscFv-Liposome-MAGNEVIST® (Gd-DTPA) complex was prepared by the method of this invention also using the preferred ratios of 1:30 and 1:14. The complex was I.V. administered and the tumor modules imaged via MRI. Compared to free MAGNEVIST® (Gd-DTPA), the encapsulated imaging agent also has a prolonged uptake in the tumor since the peak enhancement with the complex is later than that of the free MAGNEVIST® (Gd-DTPA).

Example 9

Preparation of Sterically Stabilized Immunoliposomes by Simple Mixing

Liposomal complexes are rapidly cleared from the blood stream by the reticuloendothelial system. In an effort to prolong this circulation time sterically stabilized liposomes have been formulated that have a hydrophilic polymer such as PEG integrated into the liposome complex. Various methods have been devised to include a targeting ligand such as an antibody or antibody fragment in the PEG-liposome complex. Most, if not all, of these methodologies involve a chemical conjugation step to link the antibody or antibody fragment to the PEG. Such harsh chemical reactions and the method used to form the complex can result in loss or masking of antibody activity. In this example, we demonstrate that the cys-TfRscFv protein can be linked to a PEG-liposome molecule by simple mixing and that the resultant complex can more efficiently transfect human tumor cells.

To form this complex, a lipoplex consisting of one of the cationic lipid formulations given in Example 2 was mixed with nucleic acid at a ratio of 1:14 (ug DNA:n moles lipid) as described in Example 2. To this lipoplex was added the commercially available NHS-PEG-MAL polymer (2%) in 25 mM HEPE Buffer (pH 7.2). The solution was gently inverted for 3-5 seconds and incubated at room temperature for 1.5 hours. To form the cys-TfRscFv-PEG-Liposome-DNA complex, the cys-TfRscFv protein was added to the PEG-lipoplex at a ratio of 1:8 (cys-TfRscFv:liposome, w:w), inverted gently and kept at room temperature for 10 minutes to 1 hour, then used to transfect the cells in vitro. Other ratios in the range of 1:5 to 1:30 (cys-TfRscFv:liposome, w:w) could also be employed to form the complex. For in vivo use, 50% Dextrose was added to a final concentration of 5% after the incubation, mixed gently by inversion and injected into animals. Alternatively, the final complex could have been stored at 4° C. overnight (12-18 hr).

Figure 12:
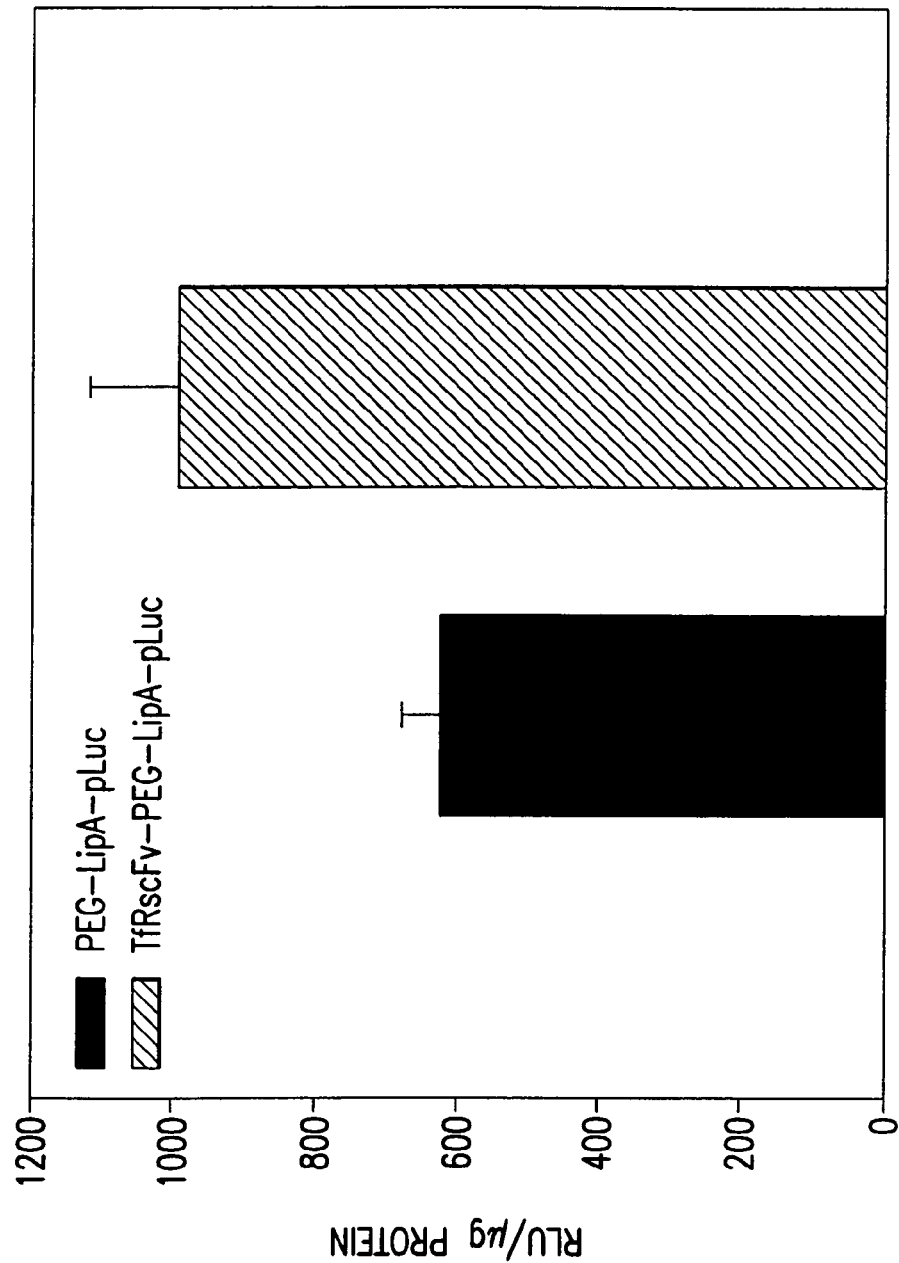
FIG. 12 shows the results of an in vitro transfection assay of sterically stabilized TfRscFv-PEG-liposome A-pLuc in MDA-MB-435 cells (Luciferase assay).

In the experiment shown here the nucleic acid was pLuc, a plasmid DNA that codes for the firefly luciferase gene. Human breast cancer cells MDA-MB-435 were plated at $5 \times 10^4$ cells/well. Twenty-four hours later they were transfected with the cys-TfRscFv-PEG-LipA-pLuc as described in Example 3 and the transfection efficiency assessed by the level of luciferase activity. As shown in FIG. 12 the cys-TfRscFv-PEG-LipA-pLuc complex prepared by the method of this invention was able to transfect the target cells with better efficiency than the PEG-LipA-pLuc without the targeting cys-TfRscF protein.

Thus the method of simple mixing described here also can be used as a simple, non-destructive means of preparing sterically stabilized targeted immunoliposomes.

Example 10

Figure 13:
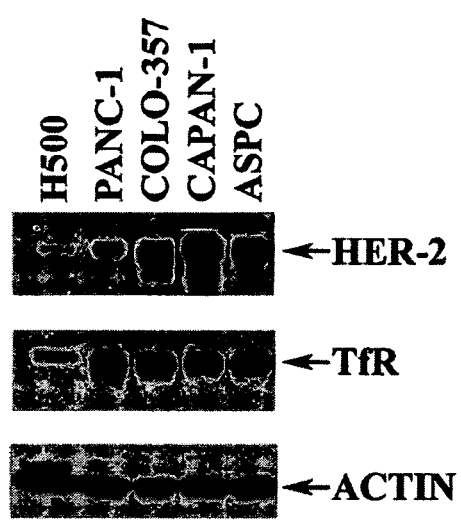
FIG. 13 shows the results of a Western blot analysis of HER-2 and TfR protein levels in various human pancreatic cancer cell lines.

Cell Lines and Immunocomplex Preparation and Characterization for siRNA Delivery Cell Lines Human pancreatic cancer cell lines (PANC-1 and Capan-1) and a human prostate cancer cell line (PC-3) were obtained from the Tissue Culture Shared Resource of the Lombardi Comprehensive Cancer Center (Washington, D.C.). Capan-1 cells were maintained in Iscove's modified DMEM (Biofluids Division of Biosource International, Rockville, Md.) containing 4 mM L-glutamine, sodium bicarbonate and supplemented with 2 mM L-glutamine, 50 µg/ml each of penicillin, streptomycin, and neomycin, with 20% non-heat-inactivated fetal bovine serum (FBS; Quality Biological, Gaithersburg, Md.). PC-3 cells were maintained in Ham's F12 medium supplemented with 10% heat-inactivated FBS plus L-glutamine and antibiotics as described above. The MDA435/LCC6 cell line was a gift from R. Clarke (Lombardi Comprehensive Cancer Center). MDA435/LCC6 is a tumorigenic cell line isolated from spontaneous ascites in mice inoculated in the mammary fat pad with the invasive and metastatic human breast cancer cell line MDA-MB-435 (Leonessa et al., *Br. J. Cancer* 73:154-161 (1996)). Both MDA435/LCC6 and PANC-1 cells were maintained in improved minimum essential medium (IMEM; Biofluids Division of Biosource International) supplemented with L-glutamine and antibiotics as described above, plus 5 or 10%, respectively, heat-inactivated FBS. FIG. 13 shows the results of a Western blot analysis of HER-2 and TfR protein levels in various human pancreatic cancer cell lines.

Immunoliposome Complex Formation

An exemplary targeting moiety for use in the practice of the present invention is an anti-transferrin receptor single-chain antibody fragment (TfRscFv). TfRscFv contains the complete antibody-binding site for the epitope of the TfR recognized by the monoclonal antibody 5E9. Cationic liposomal formulation LipA (DOTAP: DOPE or DDAB:DOPE at a 1:1 to 1:2 molar ratio) was prepared using the ethanol injection method as described herein and known in the art. TfRscFv/LipA/siRNA complexes were prepared as follows: After 10 minutes of incubation with rotation or stirring at room temperature of a mixture of LipA and TfRscFv (ratio of TfRscFv to LipA, 1:1 to 1:40 (wt/wt), more suitably 1:10 to 1:30 wt/wt), the siRNA at the appropriate concentration was added, mixed by inversion or stirring at room temperature, and incubated for 10 minutes. For animal injection, dextrose or sucrose was added to each sample to a final concentration of 1% to 20%, more suitably 5-10%. The ratio of siRNA to Liposome was from about 1:1 to about 1:20 (µg siRNA:nmol liposome), suitably about 1:3.5 to about 1:14 (µg siRNA: nmol liposome), more suitably about 1:7 (µg siRNA:nmol liposome). The size of the complex was determined by dynamic light scattering on a Malvern ZETAZISER® 3000HS particle sizer (Malvern Instruments, Malvern, UK).

Cationic liposomal formulation LipA-MPB (DOTAP: DOPE:MPB-DOPE or DDAB:DOPE:MPB-DOPE at a 1:1: 0.1 to 1:2:0.1 molar ratios) were prepared using the ethanol injection method. The LipA-HoKC liposome was then prepared using the coupling reaction between the cationic liposomes carrying the maleimide group and the peptide-carrying terminal cysteine group (HoKC) as described in Yu, W., et al., "Enhanced transfection efficiency of a systemically delivered tumor-targeting immunolipoplex by inclusion of a pH-sensitive histidylated oligolysine peptide." Nucleic Acids Research 32:e48 (2004), the disclosure of which is incorporated by reference herein in its entirety. The K[K(H)KKK]$_5$-K(H)KKC (HoKC or HK) (SEQ ID NO: 20) peptide was manufactured by Sigma-Genosys (The Woodlands, Tex.). An aliquot of 0.1 mmol of the peptide with a free thiol group on cysteine was added to 2 mmol of LipA-MPB in 10 mM HEPES (pH 7.4) solution and rotated at room temperature for 2 hours. The resulting LipA-HoKC had a lipid concentration of 1.4 mM. TfRscFv/LipA-HoKC/siRNA complexes were prepared as follows: After 10 minutes incubation with rotation or stirring at room temperature of a mixture of LipA-HoKC and TfRscFv (ratio of TfRscFv to LipA-HoKC, 1:1 to 1:40 (wt/wt), more suitably 1:10 to 1:30 (wt/wt)), the siRNA at the appropriate concentration was added mixed by inversion or stirring at room temperature and incubated for 10 minutes. For animal injection, dextrose or sucrose was added to each sample to a final concentration of 1% to 20%, more preferentially 5-10%. The ratio of siRNA to Liposome was from about 1:1 to about 1:20 (µg siRNA:nmol liposome), suitably about 1:3.5 to about 1:14 (µg siRNA:nmol liposome), more suitably about 1:7 (µg siRNA:nmol liposome).

Scanning Probe Microscopy (SPM)

Sample solutions of the nanocomplexes were freshly prepared and imaged within 2-3 hours. Samples consisted of (i) TfRscFv/LipA/siRNA, (ii) TfRscFv/LipA-HoKC/siRNA. Samples for SPM imaging were prepared as follows: For sample (i) a fresh dilution 1:3 by volume with deionized water was prepared and a 511 droplet was micropipetted onto an untrasonically cleaned silicon substrate used with native oxide coating. For sample (ii) a 5 µl droplet of undiluted solution was micropipetted onto an untrasonically cleaned silicon substrate. SPM imaging was performed using a Veeco MultiMode SPM with a Nanoscope IV controller. Topographic images were obtained in Tapping Mode using uncoated silicon high-resonant frequency Veeco RTESP cantilevers [resonant frequency ~320-360 kHz and spring constant ~20-60 N/m] and NTMDT NSC12 type C cantilevers [120-190 kHz and 3.5-12 N/m].

Physical Characterization Studies

SPM images surface topography in tapping mode by oscillating the tip and cantilever to which it is attached close to the cantilever resonance frequency. A feedback circuit maintains the oscillation of the cantilever at a constant amplitude. This constant amplitude is given by a set point which is somewhat smaller than that of the freely oscillating cantilever. Since the SPM tip interacts with the surface through various small forces, there is a phase shift between the cantilever excitation and its response at a given point on the surface. For an inhomogeneous surface, the tip-surface interactions will vary according to surface charge, steep topographical changes, and mechanical stiffness variations, for example. By changing the set point and observing how certain features respond to softer or harder tapping, we can correlate this with the response expected for a specific structure such as a liposome.

SPM allows for visualization of the size distribution of HK-conjugated and non-HK-conjugated complexes and performing direct sensing of the mechanical stiffness of the nanoparticle surface to establish that the peptide is indeed conjugated with the external surface of the liposome. The mechanical properties of the liposome surface are obtained by the phase imaging technique.

Figure 14:
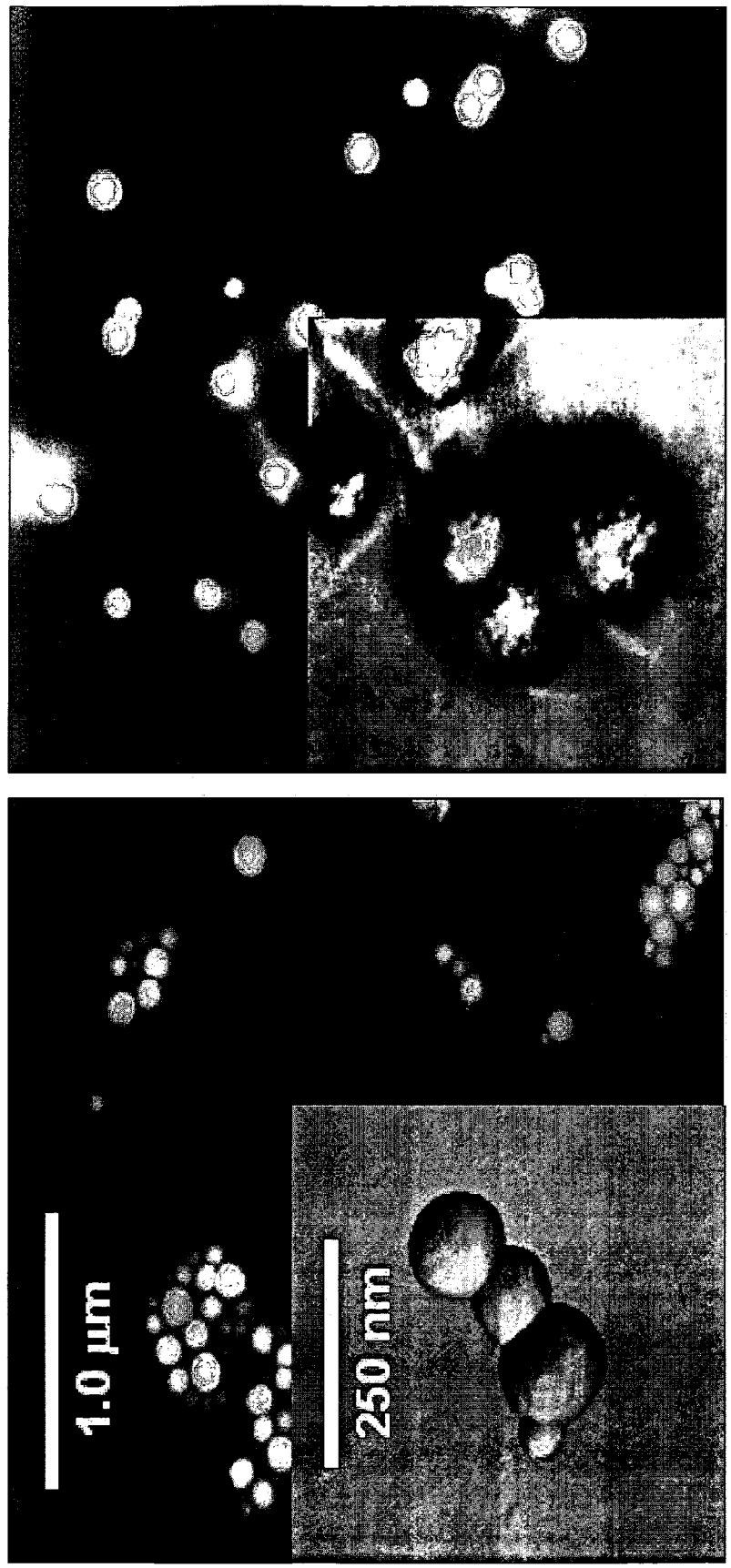
FIG. 14 shows scanning probe microscopy images of isolated and aggregated TfRscFv/LipA/siRNA nanoparticles on the left-hand side and TfRscFv/LipA-HoKC/siRNA nanoparticles on the right.

FIG. 14 presents SPM topographic images of isolated and aggregated TfRscFv/LipA/siRNA nanoparticles on the left-hand side and TfRscFv/LipA-HoKC/siRNA nanoparticles on the right. The size distribution of single non-HK-conjugated particles is in the range of 40-140 nm diameter, with an average diameter measured to be approximately 70 nm. The height/diameter ratio is 0.25. It is not expected that the liposomes remain spherical when bound to a substrate, and the preparation method requires that the liposomes be supported during drying. This ratio is important way of distinguishing between filled and unfilled liposomes as well as droplets formed during dewetting of lipids that have fallen apart.

For HoKC-conjugated liposomes, the average diameter is approximately 130 nm in the range of 90 to 160 nm and the height/diameter ratio is 0.44. The insets to each topographic image present higher magnification phase images of particle surfaces in which the non-HoKC-conjugated particles are evidently smooth, lacking surface features of any kind. In contrast, HoKC-conjugated particles have a definite structured appearance. FIG. 14 indicates that the size distribution of HoKC-conjugated particles appears to be larger and that the surface structure is considerably more inhomogeneous than the non HoKC-conjugated complex.

Throughout the remaining examples, unless otherwise indicated, the terms "hybrid," "H" and "H-3," refer to the anti HER-2 siRNA sequence Hybrid 3:

```
TCTCTGCGGTGGTTGGCAT      (SEQ ID NO: 14)

AGAGACGCCACCAACCGUA.     (SEQ ID NO: 15)
```

Throughout the remaining examples, unless otherwise indicated, the terms "duplex," "D" and "D-3," refer to the anti HER-2 siRNA sequence Duplex 3:

```
UCUCUGCGGUGGUUGGCAU      (SEQ ID NO: 10)

AGAGACGCCACCAACCGUA.     (SEQ ID NO: 11)
```

Throughout the remaining examples, unless otherwise indicated, the terms "modified hybrid," "mod. Hybrid" "mH" and "mH-3," refer to the anti-HER-2 siRNA sequence Modified Hybrid 3:

```
TITITgcggugguuGICIT      (SEQ ID NO: 9)

AGAGACGCCACCAACCGUA.     (SEQ ID NO: 16)
```

Example 11

Evaluation of HER-2 and Tf Receptor Levels in PanCA Cell Lines

For the ligand-targeting cationic liposomal gene therapy delivery system of the present invention to be useful as a therapeutic modality for cancer treatment, it was first determined if transferrin (Tf) receptor (TfR) levels were elevated in various pancreatic tumors. Using Western analysis, TfR levels were evaluated in a number of PanCa cell lines. The antibody used was the commercially available (ZYMED Laboratories, Inc. (Carlsbad, Calif.)) mouse anti-human TfR monoclonal antibody. Total cellular protein (20 µg) from human pancreatic cell lines, PANC-1, Colo 357, CaPan-1, and AsPC and normal fibroblast cell line H500 were separated by 8% discontinuous SDS polyacrylamide gel electrophoresis and hybridized with an anti-human HER-2 (Santa Cruz Biotechnology, Santa Cruz, Calif.)) and TfR (Zymed Laboratories) antibodies. Actin levels were determined as an internal control for protein loading. As shown in FIG. 13 (middle line), all four PanCa cell lines (CaPan-1, Colo 357, PANC I, and AsPC-1) possess elevated TfR levels as compared to H500, a normal human fibroblast cell line. Analysis of actin levels demonstrated that equal amounts of protein had been loaded in each lane. In addition, the TfR is known to rapidly recycle.

The level of HER-2 expression in the PanCa cell lines was also evaluated. While HER-2 expression varies among them (CaPan-1 being highest and PANC-1 lowest) all four cell lines demonstrate higher expression compared to H500 (FIG. 13).

Example 12 siRNA Delivery Via Immunoliposome Complexes

Effect of TfRscFV/LipA/siRNA in PanCa Cell Lines

In order to assess the effect on pancreatic cancer cell survival of anti-HER2 siRNA delivered via immunoliposomes of the present invention, the following experiment was performed. $4 \times 10^3$ PANC-1 cells were plated per well on a 96 well plate. After 24 hours, the cells were transfected with TfRscFv/liposome complexes containing Hybrid (H-1 (SEQ ID NO:12 & SEQ ID NO:13) or H-3 (SEQ ID NO:14 & SEQ ID NO:15)) or Duplex (D-1 (SEQ ID NO:1 & SEQ ID NO:2) or D-3 (SEQ ID NO: 10 & SEQ ID NO:11)) siRNA. Constructs H-3 and H-1 are both directed against the HER-2 gene but have different sequences. Duplex represents the "standard" form of siRNA which is a double stranded RNA molecule, with one sense and one antisense strand. Hybrid is a molecule in which the antisense strand is RNA while the sense strand is DNA. Cells were also transfected with control sequences (SEQ ID NOs: 17 & 18) analogous to Hybrid 3 (H-3) and Duplex 3 (D-3). The control sequences have the identical nucleotide makeup as the correlating siRNA, however in random order such that the molecule does not have homology to any known gene sequence. The siRNA concentration varied from 2 to 250 nM. The ratio of liposome to siRNA was 7 to 1 (nmol:ug). The XTT assays were performed 48 hours after transfection. $IC_{50}$ values are the siRNA concentrations yielding 50% cell growth inhibition.

Figure 15:
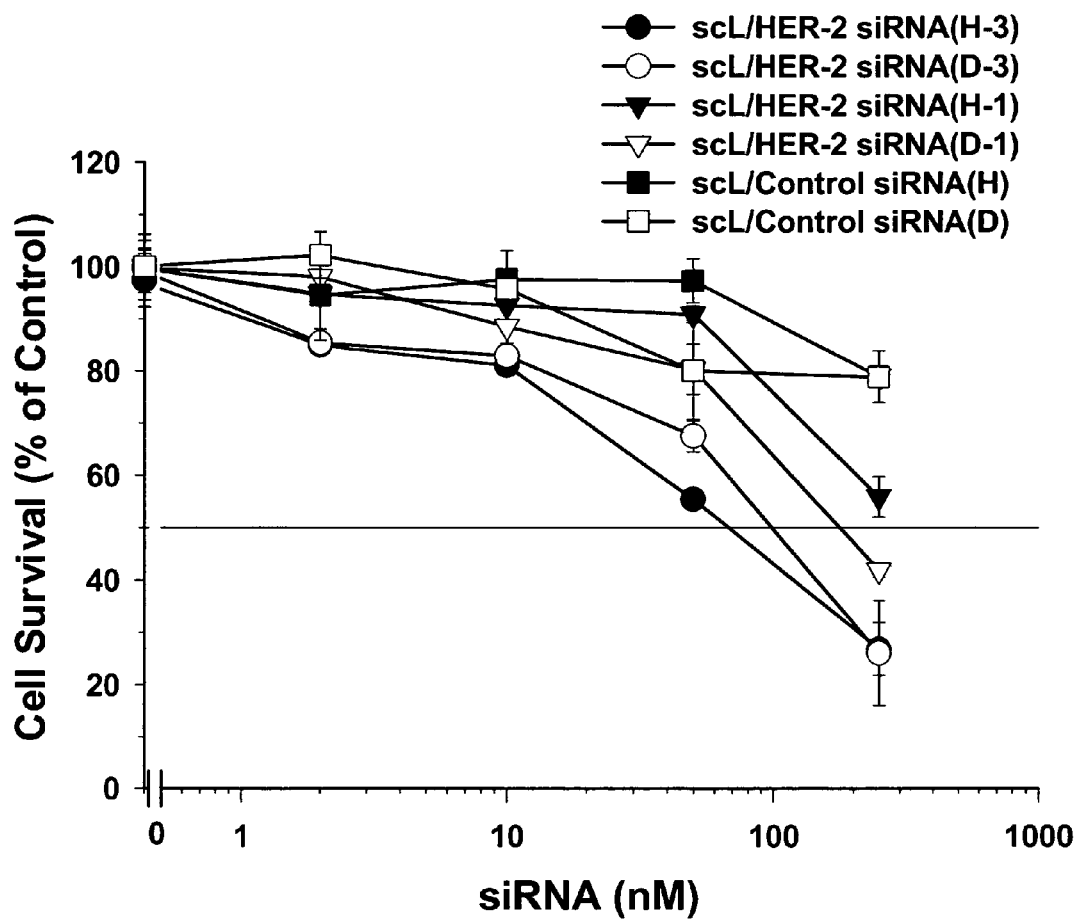
FIG. 15 shows a comparison of the effects of immunocomplex delivered HER-2 siRNA structures on PANC-1 cell survival.
Figure 16:
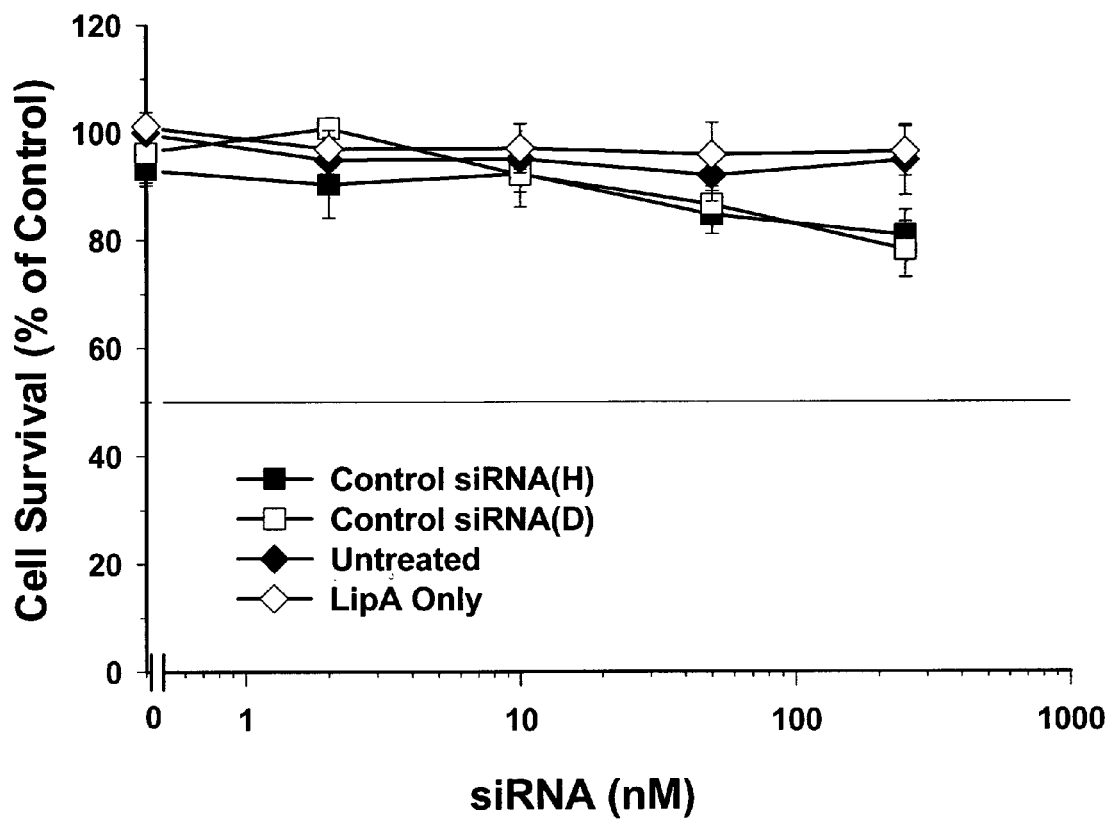
FIG. 16 shows a comparison of the effects of immunocomplex delivered HER-2 control siRNA structures on PANC-1 cell survival.

The dose-dependent effect of the HER-2 siRNA, hybrid (DNA/RNA) or duplex (RNA/RNA), and a control siRNA, on cell survival is shown in FIG. 15. Various concentrations of siRNAs were tested. At 250 nM concentration, both hybrid and duplex control siRNAs have some effect on cell survival, the treatment resulting in approximately 20% cell loss (see FIG. 16 also showing untreated and liposome (LipA) only treated cells as controls to demonstrate that the cell killing is siRNA specific). However, this concentration is much higher than that of the test siRNAs used in further experiments. Construct 3, both the hybrid, H-3 ($IC_{50}$:68 nM) and duplex, D-3 ($IC_{50}$:100 nM), seem to be more effective than hybrid and duplex forms of Construct 1 (H-1 and D-1) in reducing cell survival (hybrid-1 $IC_{50}$:>250 nM and duplex-1 $IC_{50}$:180 nM). It has been consistently observed that the hybrid form of Construct 3 (H-3) is more potent than the duplex form (D-3).

Figure 17:
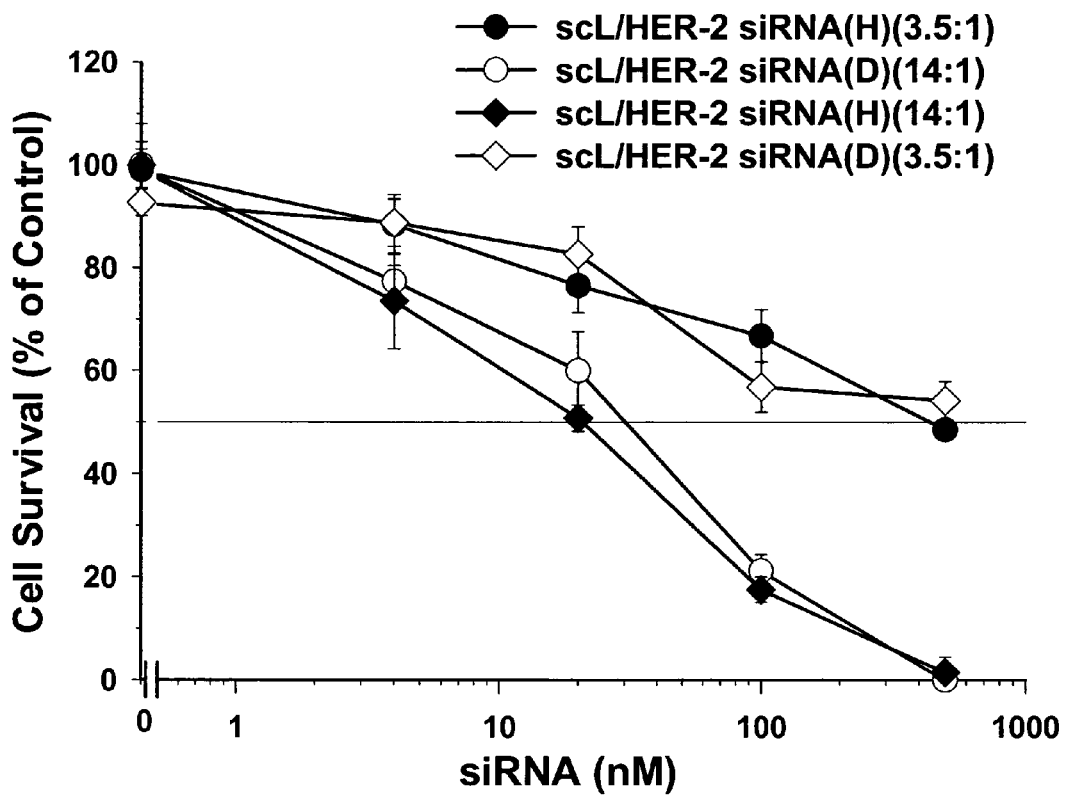
FIG. 17 shows a comparison of the effects of immunocomplex (scL) delivered HER-2 siRNA structure (Hybrid 3 (H-3) vs Duplex 3 (D-3)) and different ratios of scL:HER-3 siRNA on Capan-1 Cell Survival.

A comparison of the effects of scL delivered HER-2 siRNA structure (Hybrid 3 vs Duplex 3) and different ratios of scL:HER-3 siRNA on Capan-1 Cell Survival is shown in FIG. 17. The siRNA concentration was varied from 0.5 to 500 nM. The ratios of liposome to siRNA were 3.5 to 1 or 14 to 1 (nmol:μg). The XTT assays were performed 48 hours after transfection. $IC_{50}$ values are the siRNA concentrations yielding 50% cell growth inhibition. FIG. 17 demonstrates that the higher ratios of siRNA produced greater cell kill.

Figure 18:
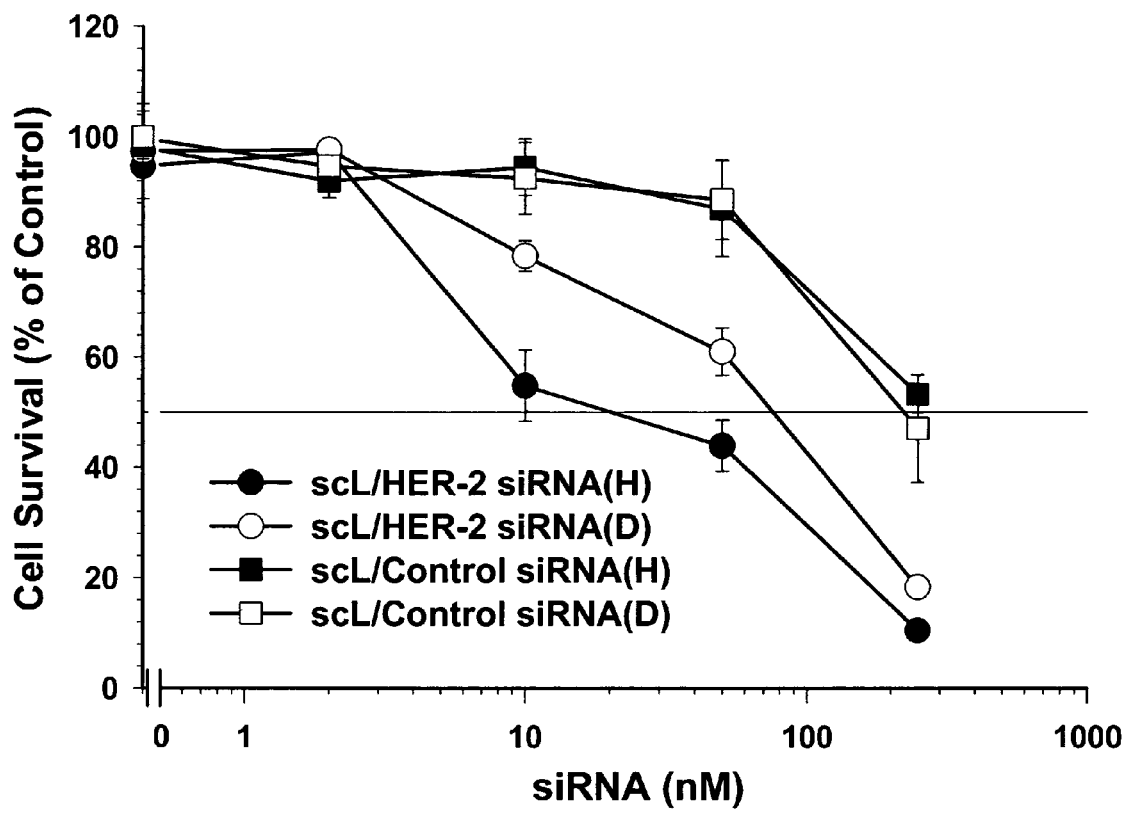
FIG. 18 shows a comparison of the effects of scL delivered HER-2 siRNA structure (Hybrid 3 vs Duplex 3) on PANC-1 cell survival.

A comparison of the effects of scL delivered HER-2 siRNA structure (Hybrid 3 vs Duplex 3) on PANC-1 cell survival is shown in FIG. 18. The control sequences have the identical nucleotide makeup as the correlating siRNA, however in random order such that the molecule does not have homology to any known gene sequence. The siRNA concentration varied from 2 to 250 nM. The ratio of liposome to siRNA was 14 to 1 (nmol:ug). The XTT assays were performed 48 hours after transfection. $IC_{50}$ values are the siRNA concentrations yielding 50% cell growth inhibition.

Figure 19:
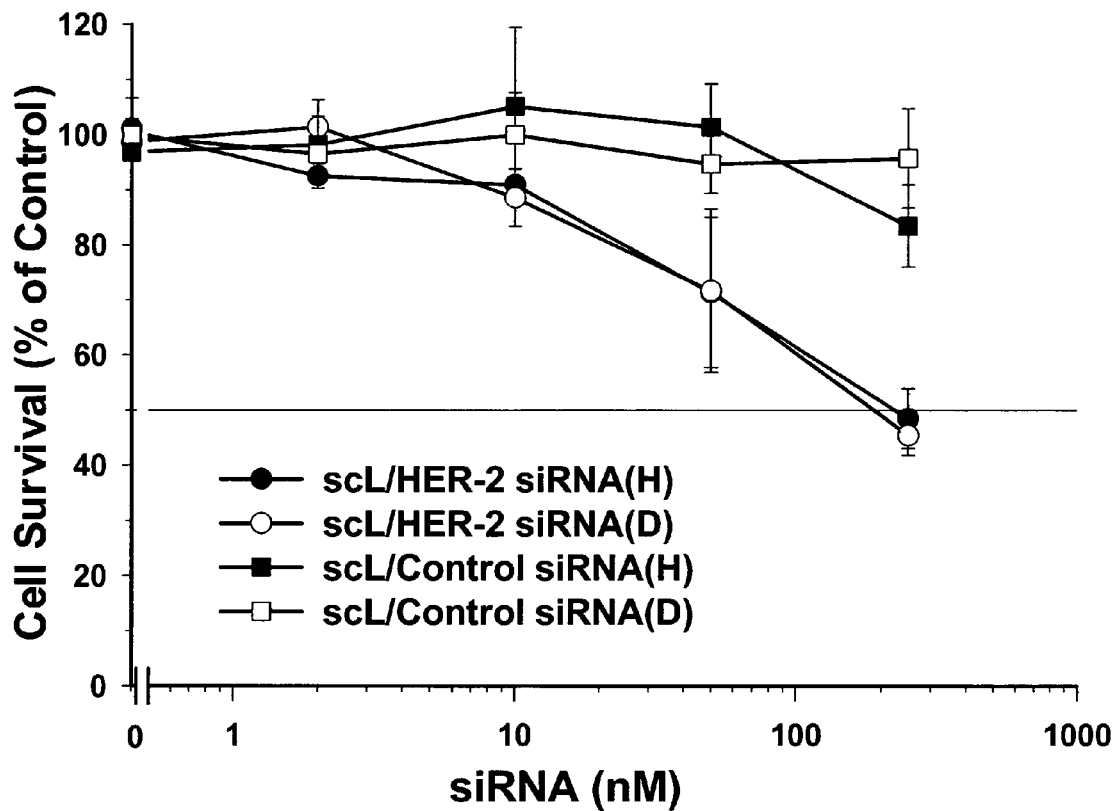
FIG. 19 shows a comparison of the effects of scL delivered HER-2 siRNA structure (Hybrid 3 vs Duplex 3) on Capan-1 cell survival.
Figure 20A:
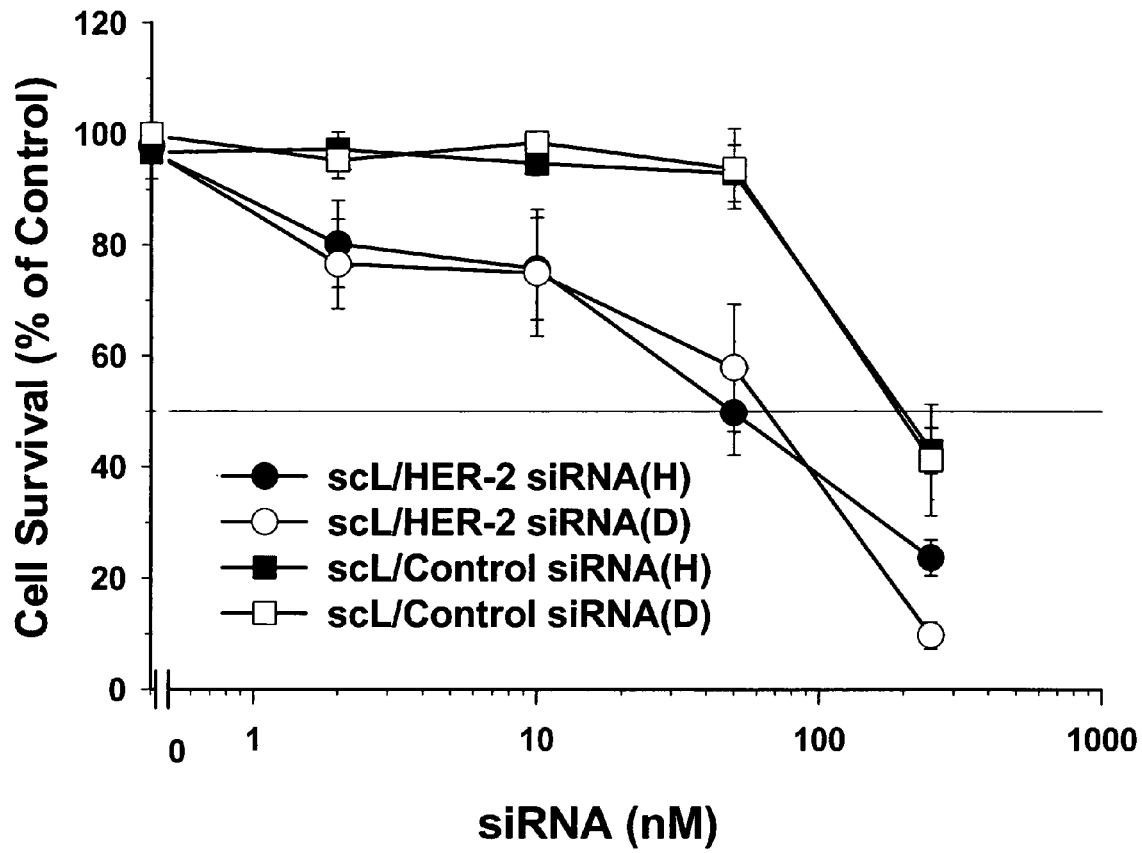
FIG. 20a shows a comparison of the effects of scL delivered HER-2 siRNA structure (Hybrid 3 vs Duplex 3) on Capan-1 cell survival.

A comparison of the effects of scL delivered HER-2 siRNA structure (Hybrid 3 vs Duplex 3) on Capan-1 cell survival is shown in FIG. 19. The control sequences have the identical nucleotide makeup as the correlating siRNA, however in random order such that the molecule does not have homology to any known gene sequence. The siRNA concentration varied from 2 to 250 nM. The ratios of liposome to siRNA were 3.5 to 1 (nmol:ug). The XTT assays were performed 48 hours after transfection. $IC_{50}$ values are the siRNA concentrations yielding 50% cell growth inhibition. A similar experiment showing the effects of scL delivered HER-2 siRNA structure (Hybrid 3 vs Duplex 3) on Capan-1 cell survival, where the ratios of liposome to siRNA were 14 to 1 (nmol:ug), is shown in FIG. 20a.

Figure 20B:
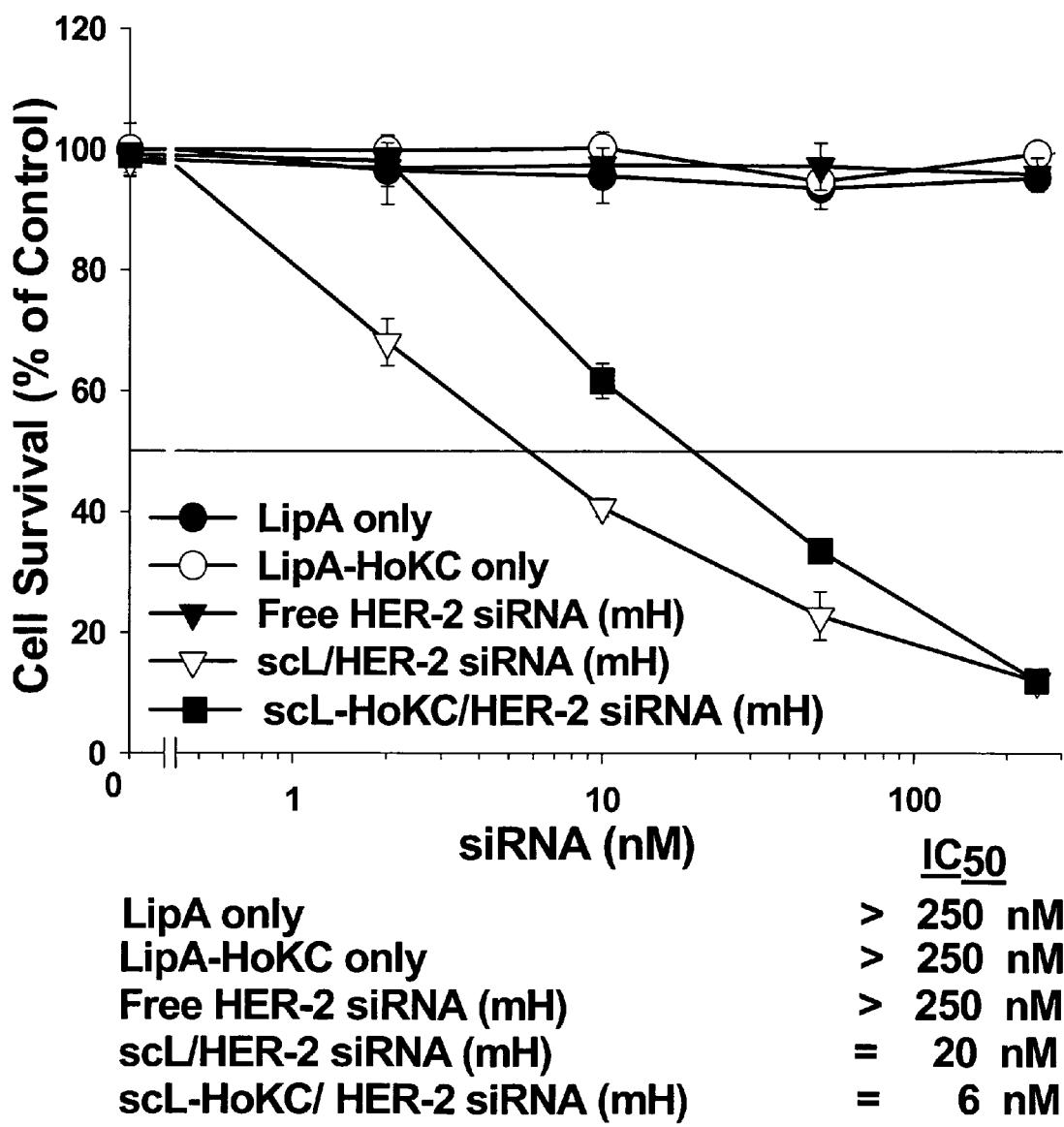
FIG. 20b shows a comparison of the effect of free (uncomplexed) siRNA, scL or scL-HoKC complexed mHsiRNA on MDA-MB-435 cell survival.

To demonstrate that the use of both the scL and the scL-HoKC immunoliposomes for delivery of siRNA is superior to the use of free (uncomplexed) siRNA, the level of cell killing (based upon the $IC_{50}$ values) was compared in vitro in MDA-MB-435 human breast cancer cells. $5 \times 10^3$ MDA-MB-435 cells were plated/well of a 96 well plate. After 24 hours, the cells were transfected with increasing concentrations of the modified hybrid anti-HER-2 siRNA either as free (uncomplexed) siRNA or complexed as part of the scL or scL-HoKC immunoliposomes of the present invention. The ratio of liposome to siRNA for both complexes was 7:1 (nmol/ug). As shown in FIG. 20b, the free (uncomplexed) siRNA, like the control liposome and liposome-HoKC, had no effect on the cells at doses up to 250 nM. In contrast, there was significant cell killing by the siRNA at low doses when delivered by both complexes with, as observed previously, the scL-HoKC yielding better results than the scL ($IC_{50}$ values being 20 nM and 6 nM, respectively).

These experiments demonstrate that this TfRscFv/Lip complex was able to efficiently delivery both duplex and hybrid siRNA to different cell types.

Example 13

Down-Modulation of HER-2 Expression In Vitro

Figure 21:
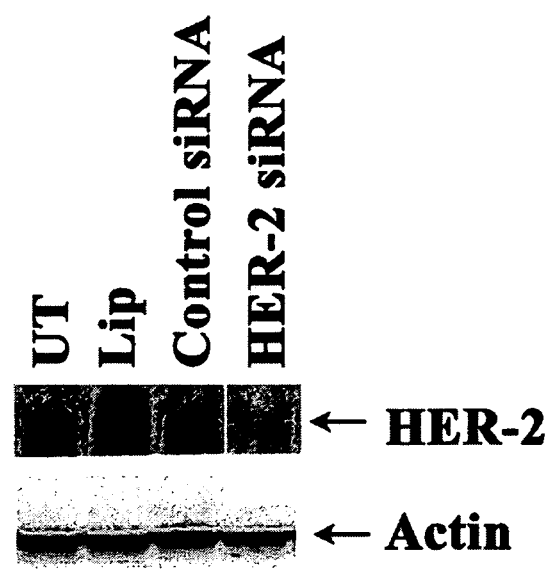
FIG. 21 shows the results of a Western analysis showing down-modulation of HER-2 protein in PANC-1 cells by TfRscFv-LipA-HER-2 siRNA.

Western analysis was used to assess the ability of the scL-HER-2siRNA hybrid to down modulate the expression of HER-2 in PanCa cell line PANC-1. The results of this experiment are shown in FIG. 21. $1.2 \times 10^6$ PANC-1 cells were seeded in a T75 flask and transfected 24 hours later with TfRscFv-LipA containing 50 nM of either HER-2 siRNA (hybrid (H-3)) or control siRNA (hybrid). 48 hours later, the cells were harvested, lysed in RIPA buffer, and protein isolated and concentration determined for use in Western analysis. 80 μg was loaded per lane of a 4-20% gradient polyacrylamide/SDS gel. To detect HER-2 protein expression the membrane was probed with the anti-human HER-2/Neu (C-18) rabbit polyclonal Ab (Santa Cruz Biotechnology) and the signal detected by ECL (Amersham). The identical membrane was subsequently probed with an antibody to actin to demonstrate equal loading. Untreated cells and liposome alone treated cells serve as additional controls. In this preliminary experiment, inhibition of HER-2 expression by the treatment with scLHER-2siRNA was observed.

Figure 22:
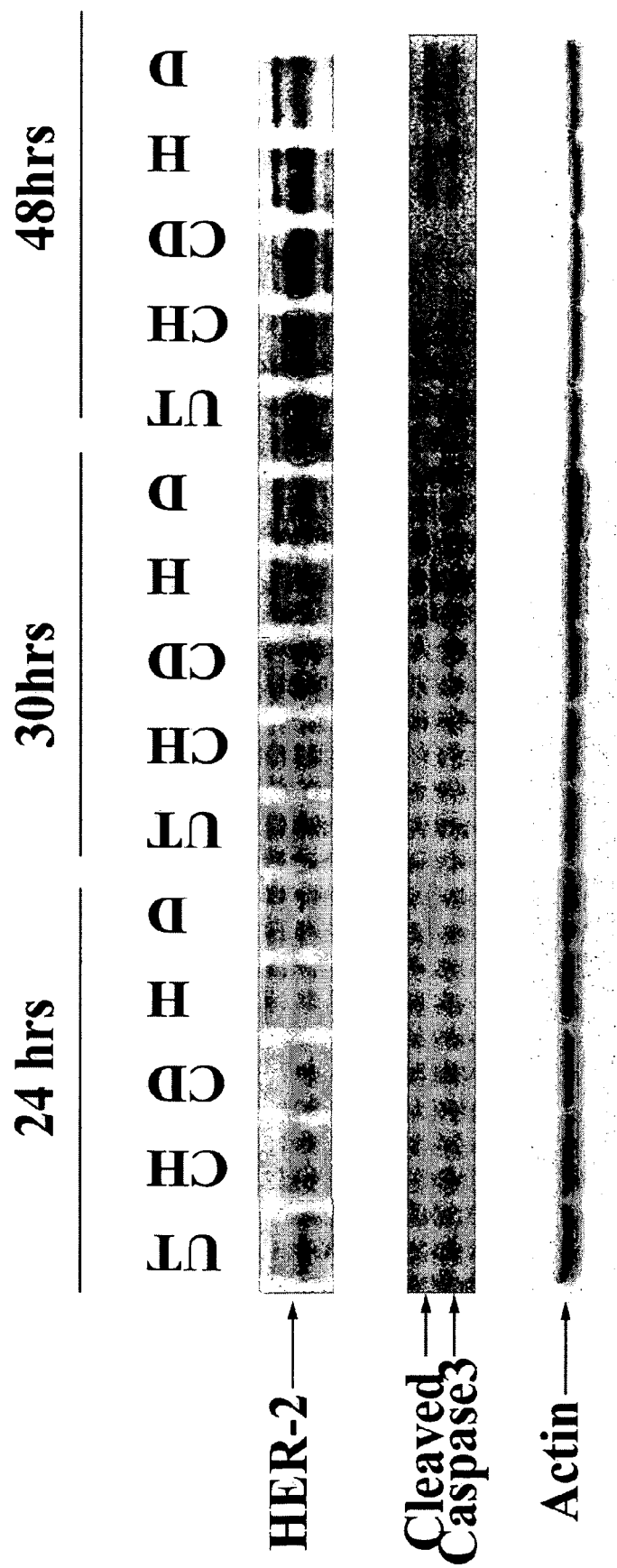
FIG. 22 shows the results of a Western analysis showing time dependent down-modulation of HER-2 and induction of apoptosis in pancreatic cancer cell line COLO357 treated with scL delivered HER-2 hybrid and duplex siRNA.

Down-modulation of HER-2 expression was also examined in a second pancreatic cancer cell line, COLO 357, over time. COLO 357 cells were seeded, and transfected 24 hours later with the scL-siRNA complex carrying 250 nM HER-2H siRNA (H-3) or control sequence. Untreated cells served as a control. At 24, 30 and 48 hours post-treatment, the cells were harvested, lysed in RIPA buffer, protein determined, run on a 4-20% gradient polyacrylamide/SDS gel and transferred to nitrocellulose membrane. For HER-protein expression the membranes were probed with the anti-human HER-2/Neu (C-18) rabbit polyclonal Ab (Santa Cruz Biotechnology) and the signal detected by ECL (Amersham). Inhibition of HER-2 expression was evident at 24 and 30 hrs post-treatment, as shown in FIG. 22. This effect was transient since the level of HER-2 began to recover by 48 hrs post-treatment. The induction of apoptosis was also evident after this treatment as shown by reprobing of the membrane for the presence of the 17 kDA fragment of cleaved caspase3 (Cell Signaling). The 17 kDa protein was evident only in the cells treated with the scL siRNA (H) complex, particularly 30 hrs after transfection. UT—Untransfected cells, H—Hybrid HER-2 siRNA, D—Duplex HER-2 siRA, CH—Control Hybrid siRNA, CD—Control Duplex siRNA.

Figure 23:
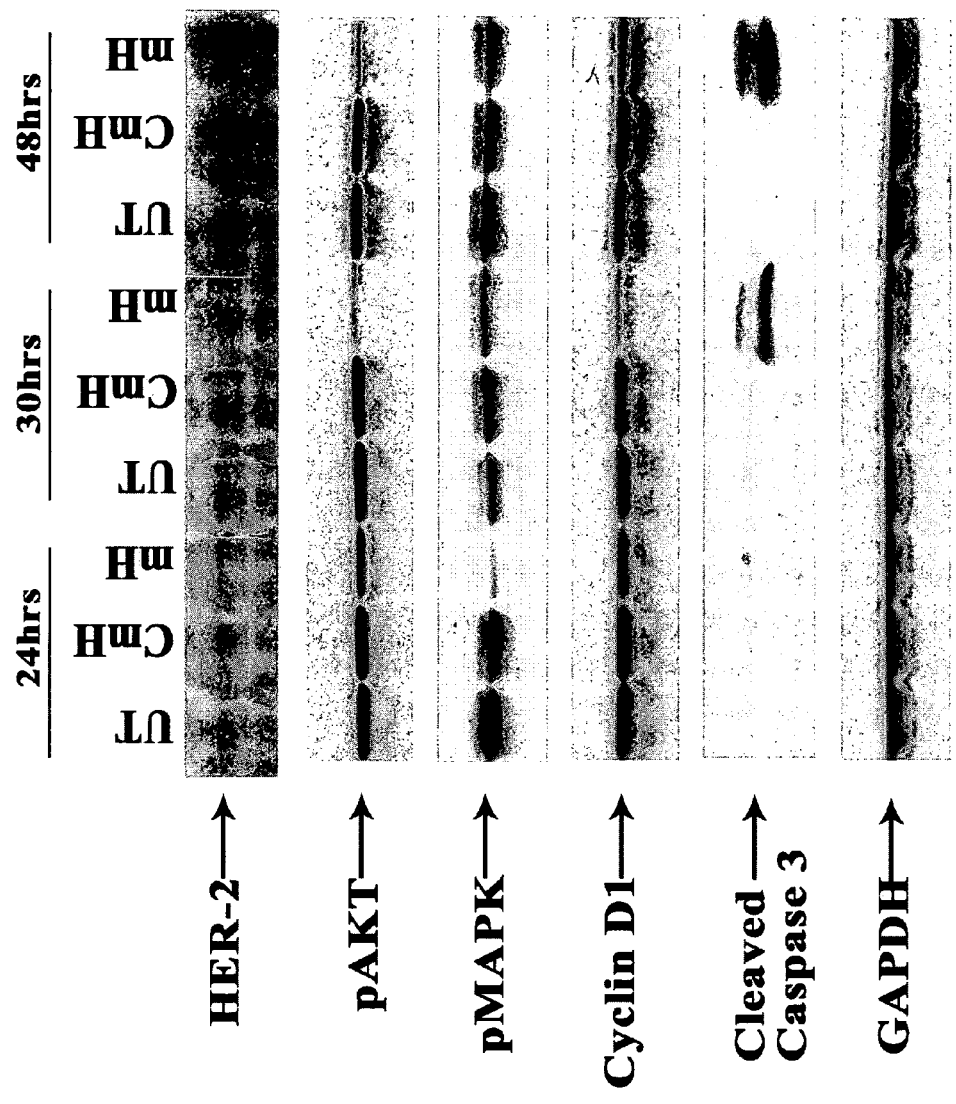
FIG. 23 shows the results of a Western analysis showing time dependent down-modulation of HER-2 and induction of apoptosis in pancreatic cancer cell line PANC-1 treated with scL delivered HER-2 siRNA hybrid and duplex.

Time dependent down-modulation of HER-2 and induction of apoptosis was also examined in PANC-1 Cells treated with scL-HoKC (peptide) delivered HER-2 modified Hybrid (mH) siRNA. PANC-1 were treated with 250 nM siRNA modified hybrid in complex with TfRscFv liposome-HoKC for 24, 30 or 48 hours. Forty micrograms of protein were separated by Criterion Precast 4-20% gradient gel. HER-2 protein was detected using Neu (C-18) rabbit polyclonal antibody, peroxidase conjugated goat antirabbit IgG and ECL Western Bloting reagents. GAPDH levels were determined as an internal control for protein loading. UT—Untransfected cells, mH—Modified Hybrid HER-2 siRNA, CmH—Control Modified Hybrid siRNA. pAKT and pMAPK, the active (phosphorylated) forms of proteins AKT and MAPK, are components of two signal transduction pathways influenced by HER-2. HER-2 is upstream of these two genes in the pathways. If HER-2 is activated these pathways can be constitutively activated and result in uncontrolled cell growth. Thus, silencing of HER-2 results in downmodulation of these proteins, shortcircuiting these signals (as is noted in FIG. 23). Caspase-3 is an important apoptotic protein. It has a key position in apoptosis. It is cleaved into a 12 and a 17 kDa fragment when it is activated (leading to cell death). Thus the presence of the 17 kDa fragment indicates that the apoptotic pathway is activated resulting in cell death. Thus, downmodulation of HER-2 in the cells via the siRNA/immunoliposome complexes turns off the pathways leading to cell growth and induce cell death.

Example 14

Sensitization to Chemotherapeutic Agents

In order to determine if the combination of various chemotherapeutic agents and tumor-targeted immunoliposome-HER-2 siRNA nanocomplex delivery could result in an increased response to the various agents, the following experiments were performed. The XTT cytotoxicity assay was used in these studies to establish the level of chemosensitivity induced by the liposome-HER-2 siRNA nanocomplexes.

Sensitization to Gemcitabine (GEMZAR®)

Figure 24:
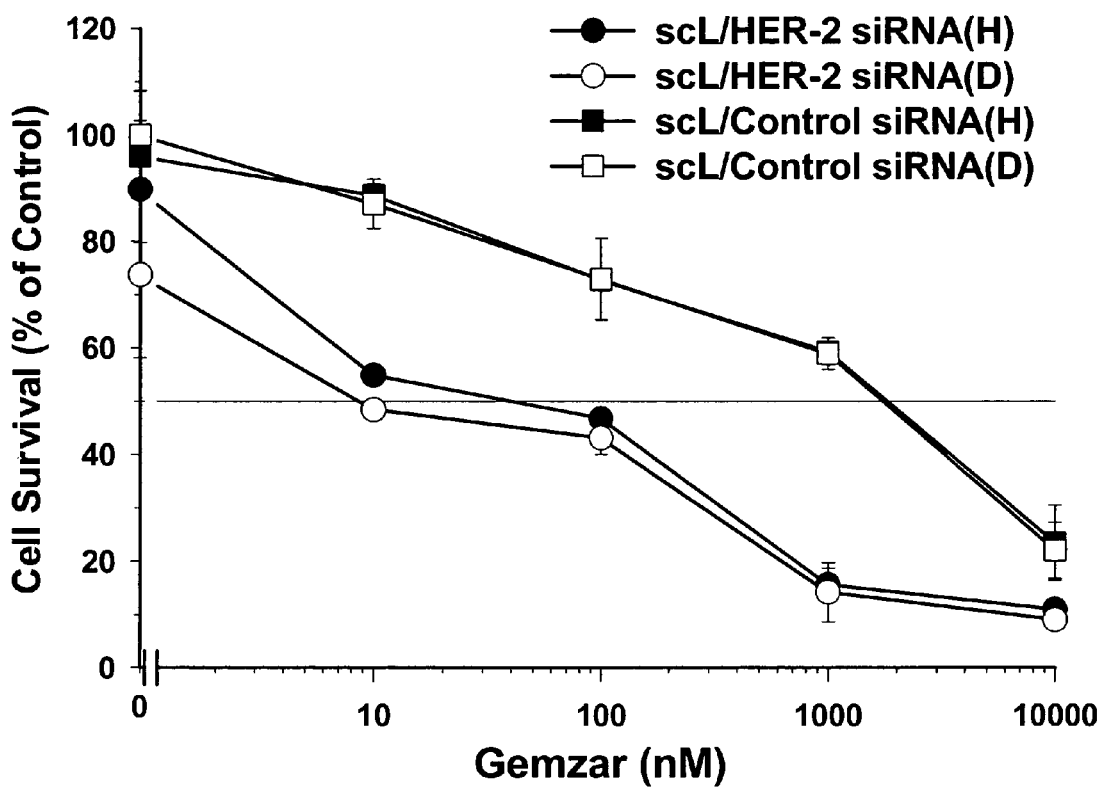
FIG. 24 shows a comparison of the effects of scL delivered HER-2 siRNA structure (Hybrid 3 vs Duplex 3) on sensitization of Capan-1 cells to gemcitabine (GEMZAR®).

$4 \times 10^3$ Capan-1 cells were plated per well of a 96 well plate. After 24 hours, the cells were transfected with TfRscFv/Liposome complexes containing 100 nM Hybrid 3, Duplex 3, or control siRNA. The ratio of liposome to siRNA was 7 to 1 (nmol:ug). 24 hours later gemcitabine was added in increasing concentrations (in triplicate). The XTT assays were performed 48 hours after addition of gemcitabine. $IC_{50}$ values are the gemcitabine (nM) concentrations yielding 50% cell growth inhibition. Significant chemosensitization was observed, as shown in FIG. 24. At an siRNA concentration of 100 nM treatment with the TfRscFv-LipA-HER-2 siRNA nanocomplex increased the response of PANC-1 cells to gemcitabine by over 35 fold compared to the control H molecule, and over 178-fold compared to the control duplex. These in vitro studies demonstrate that this siRNA therapy delivery system has the potential to significantly improve the treatment for PanCa.

The experiments presented below explore the effects of changes to siRNA concentrations, ratios of siRNA:liposome, cell type and siRNA structure on sensitization of cells to killing by chemotherapeutic agents.

Figure 25:
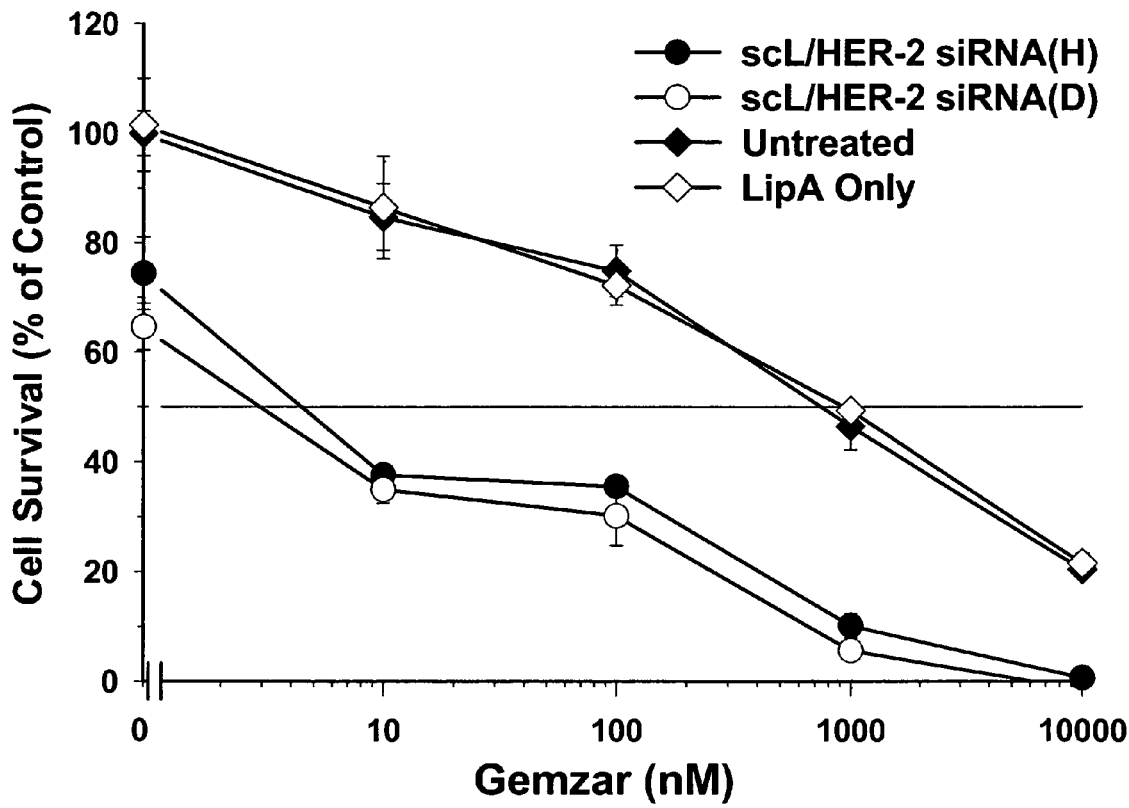
FIG. 25 shows a comparison of the effects of scL delivered HER-2 siRNA structure (Hybrid 3 vs Duplex 3) on sensitization of Capan-1 cells to gemcitabine (GEMZAR®).

In another experiment showing the effects of siRNA delivery relative to treated and liposome only treated cells, $4 \times 10^3$ Capan-1 cells were plated per well of a 96 well plate. After 24 hours, the cells were transfected with TfRscFv/Liposome complexes containing 100 nM Hybrid 3 or Duplex 3 siRNA, as well as liposome A only. The ratio of liposome to siRNA was 7 to 1 (nmol:ug). 24 hours later gemcitabine was added in increasing concentrations (in triplicate). The XTT assays were performed 48 hours after addition of gemcitabine, the results of which are shown in FIG. 25. $IC_{50}$ values are the gemcitabine (nM) concentrations yielding 50% cell growth inhibition. The scL delivery of the siRNA increased gemcitabine cell kill by over 20 fold.

Figure 26:
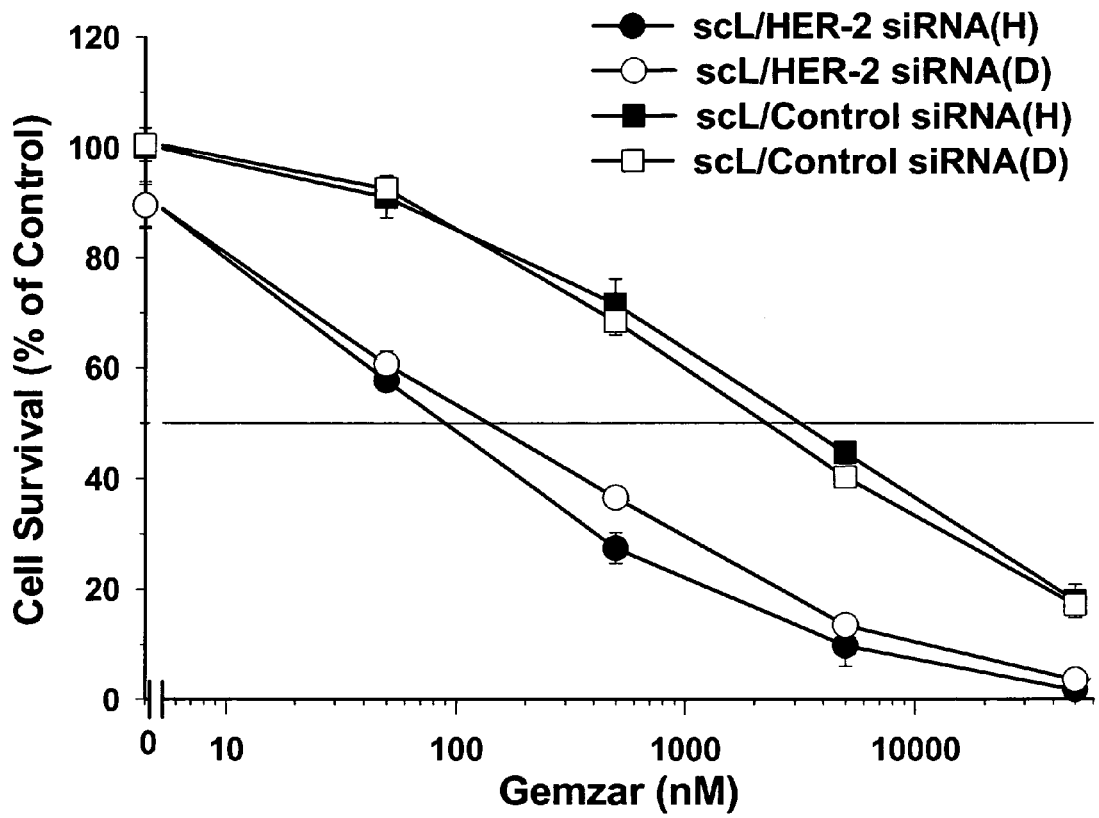
FIG. 26 shows a comparison of the effects of scL delivered HER-2 siRNA structure (Hybrid 3 vs Duplex 3) on sensitization of PANC-1 cells to gemcitabine (GEMZAR®).

In a further experiment on a different cell line, $4 \times 10^3$ PANC-1 cells were plated/well of a 96 well plate. After 24 hours, the cells were transfected with TfRscFv/Liposome complexes containing 50 nM Hybrid 3 or Duplex 3 siRNA, as well as control siRNA. The ratio of liposome to siRNA was 7 to 1 (nmol:ug). 24 hours later gemcitabine was added in increasing concentrations (in triplicate). The XTT assays were performed 48 hours after gemcitabine addition, the results of which are shown in FIG. 26. $IC_{50}$ values are the gemcitabine (nM) concentrations yielding 50% cell growth inhibition. The scL delivery of the siRNA increased gemcitabine cell kill by 16-35 fold.

Figure 27:
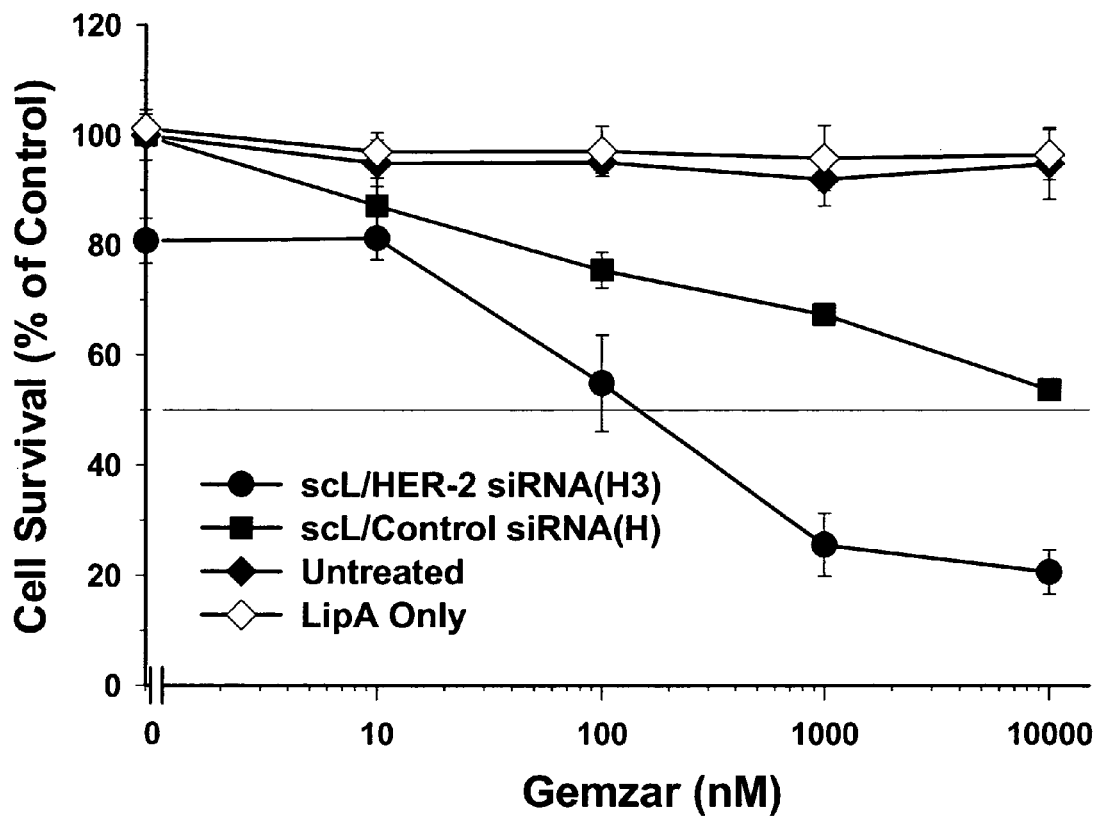
FIG. 27 shows a comparison of the effects of scL delivered HER-2 siRNA structure (Hybrid 3 vs Controls) on sensitization of PANC-1 cells to gemcitabine (GEMZAR®).

In an additional experiment examining the effects of siRNA versus three controls, $4 \times 10^3$ PANC-1 cells were plated/well of a 96 well plate. After 24 hours, the cells were transfected with TfRscFv/Liposome complexes containing 50 nM Hybrid 3, control siRNA, or transfected with liposome A only. The ratio of liposome to siRNA was 7 to 1 (nmol:ug). 24 hours later gemcitabine was added in increasing concentrations (in triplicate). The XTT assays were performed 48 hours after gemcitabine addition, the results of which are shown in FIG. 27. $IC_{50}$ values are the gemcitabine (nM) concentrations yielding 50% cell growth inhibition. The scL delivery of the siRNA increased gemcitabine cell kill by greater than 80 fold compared to controls.

Figure 28:
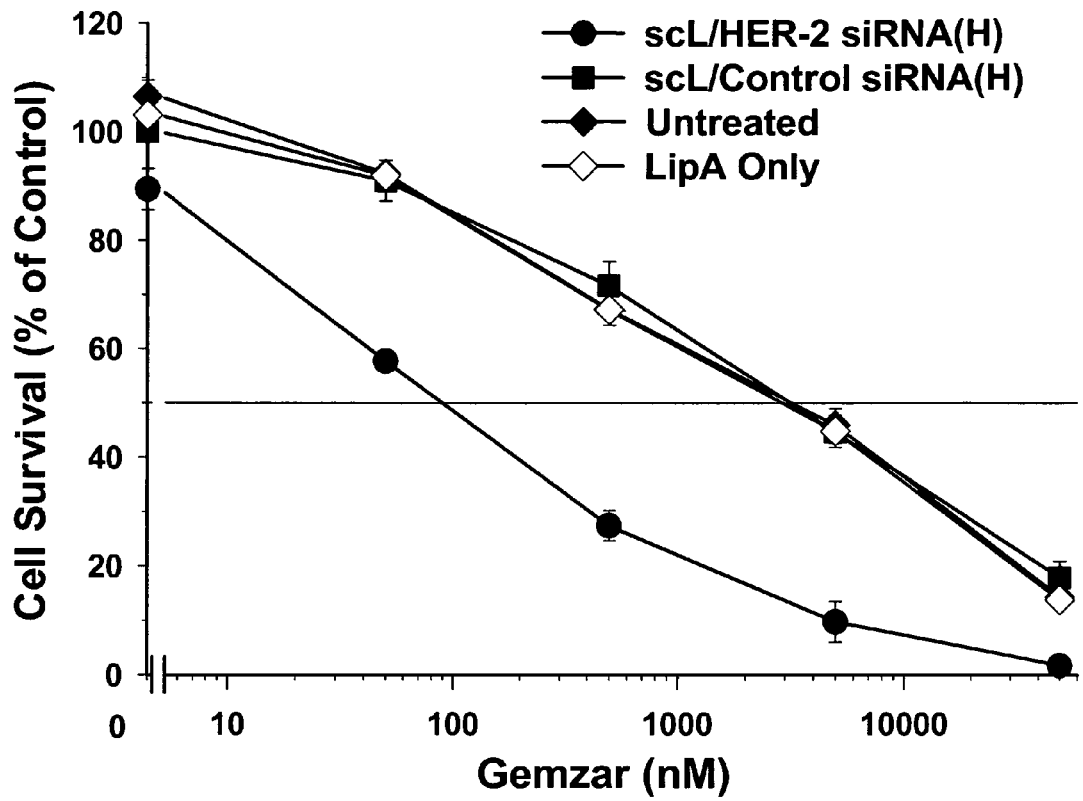
FIG. 28 shows a comparison of the effects of scL delivered HER-2 siRNA structure (Hybrid 3 vs Controls) on sensitization of PANC-1 cells to gemcitabine (GEMZAR®).

In another experiment examining the effects of siRNA versus three controls, $4 \times 10^3$ PANC-1 cells were plated/well of a 96 well plate. After 24 hours, the cells were transfected with TfRscFv/Liposome complexes containing 50 nM Hybrid 3, control siRNA, or transfected with liposome A only. The ratio of liposome to siRNA was 7 to 1 (nmol:ug). 24 hours later gemcitabine was added in increasing concentrations (in triplicate). The XTT assays were performed 48 hours after gemcitabine addition, the results of which are shown in FIG. 28. $IC_{50}$ values are the gemcitabine (nM) concentrations yielding 50% cell growth inhibition. The scL delivery of the siRNA increased gemcitabine cell kill by greater than 35 fold compared to controls.

Figure 29:
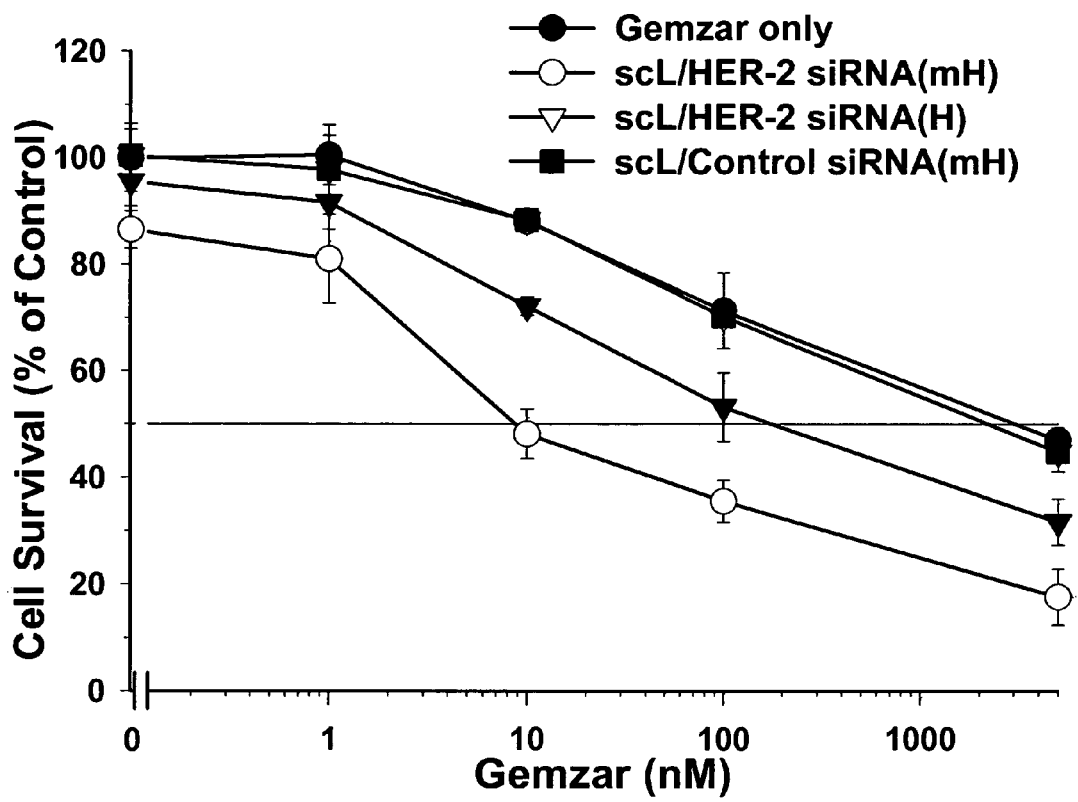
FIG. 29 shows a comparison of the effects of HER-2 siRNA structure (Hybrid vs modified Hybrid) on sensitization of Panc-1 Cells to gemcitabine (GEMZAR®).

In a further experiment examining the effects of the modified hybrid siRNA were examined. $4 \times 10^3$ PANC-1 cells were plated/well of a 96 well plate. After 24 hours, the cells were transfected with TfRscFv/LipA complex containing 100 nM Hybrid, modified Hybrid or control siRNA. The ratio of LipA to siRNA was 5 to 1 (nmol:ug). Gemcitabine was added in increasing concentrations (in triplicate). The cell viability XTT-based assay was performed 48 hours after gemcitabine addition, the results of which are shown in FIG. 29. $IC_{50}$ values are the gemcitabine (nM) concentrations yielding 50% cell growth inhibition. The IC50 values for the H and mH were 180 nM and 9 nM, respectively. Compared to Gem alone ($IC_{50}$ 300 nM), this represents a 16.7 and 333 fold increase, respectively, in sensitization by the siRNA with an almost 20 fold higher level of sensitization by mH over H (FIG. 29). The control mH had no real effect on sensitization ($IC_{50}$ 2200 nM). Therefore, it appears that the mH form of the siRNA is more effective than the hybrid. However, the immunoliposome complex can efficiently delivery both mH and H siRNA molecules.

Figure 30:
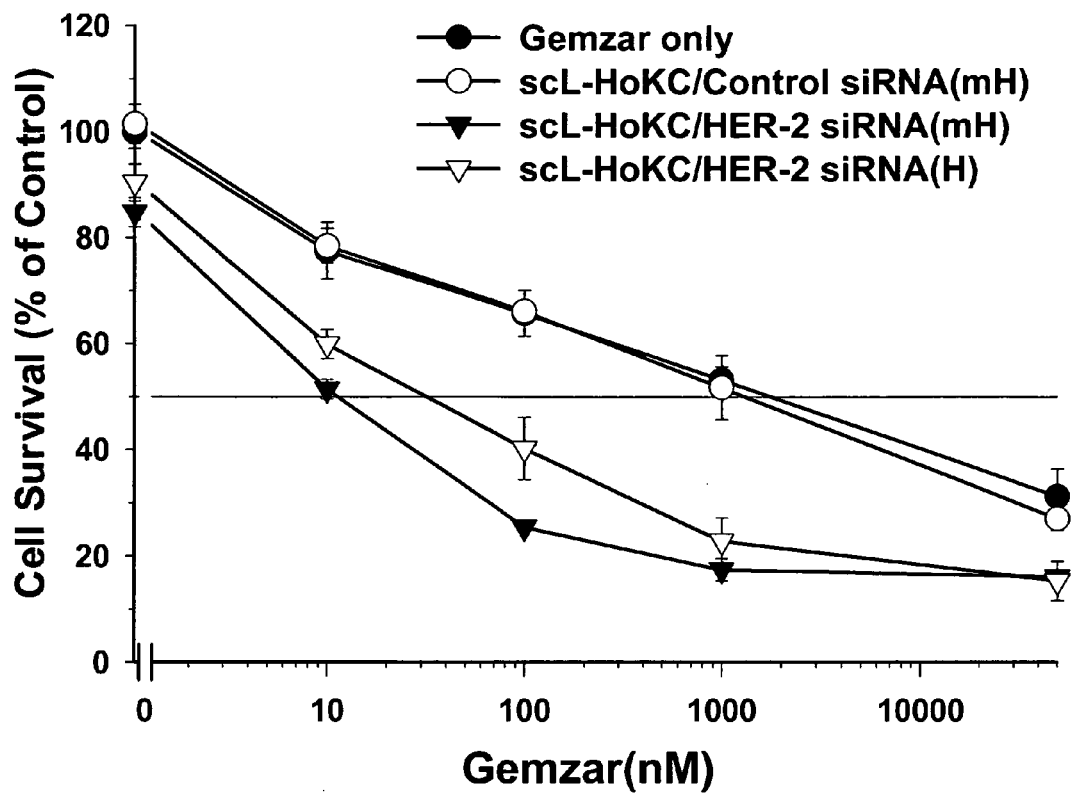
FIG. 30 shows a comparison of the effects of scL-HoKC mediated HER-2 siRNA structures (Hybrid vs modified Hybrid) on sensitization of Panc-1 cells to gemcitabine (GEMZAR®).

In an additional experiment a higher concentration of siRNA was examined. $4 \times 10^3$ PANC-1 cells were plated per well of a 96 well plate. After 24 hours, the cells were transfected with TfRscFv/Liposome-HoKC complex containing 125 nM Hybrid or modified Hybrid siRNA. The ratio of liposome to siRNA was 5 to 1 (nmol:ug). 24 hours later gemcitabine was added in increasing concentrations (in triplicate). The XTT assays were performed 48 hours after gemcitabine addition, the results of which are shown in FIG. 30. The $IC_{50}$ values are the gemcitabine concentrations that result in 50% survival. The peptide-containing immunoliposomes can also deliver both types of siRNA molecules.

Figure 31:
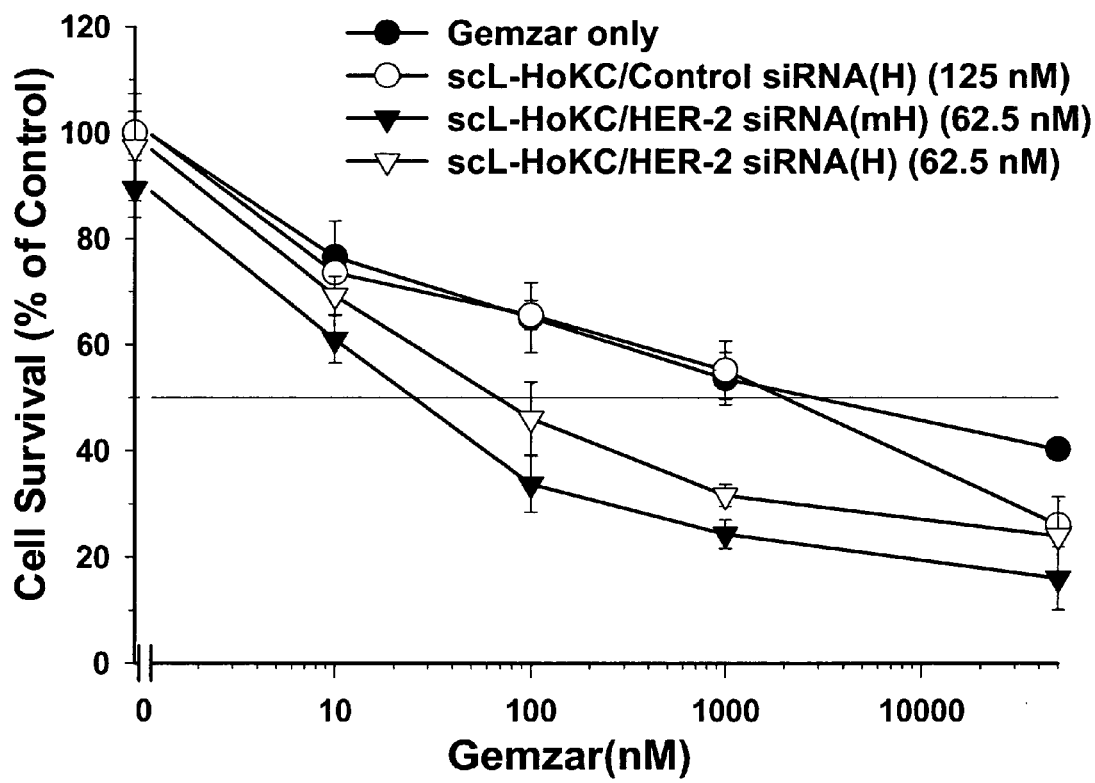
FIG. 31 shows a comparison of the effects of scL-HoKC mediated HER-2 siRNA structures (Hybrid vs modified Hybrid) on sensitization of Panc-1 cells to gemcitabine (GEMZAR®).

In another experiment examining the effects of modifying the siRNA concentration, $4 \times 10^3$ PANC-1 cells were plated per well of a 96 well plate. After 24 hours, the cells were transfected with TfRscFv/Liposome-HoKC complex containing 62.5 nM Hybrid or modified Hybrid siRNA, as well as control hybrid sequence (125 nM). The ratio of liposome to siRNA was 5 to 1 (nmol:ug). 24 hours later gemcitabine was added in increasing concentrations (in triplicate). The XTT assays were performed 48 hours after gemcitabine addition, the results of which are shown in FIG. 31. The $IC_{50}$ values are the gemcitabine concentrations that result in 50% survival. Thus, various concentrations can be delivered.

Figure 32:
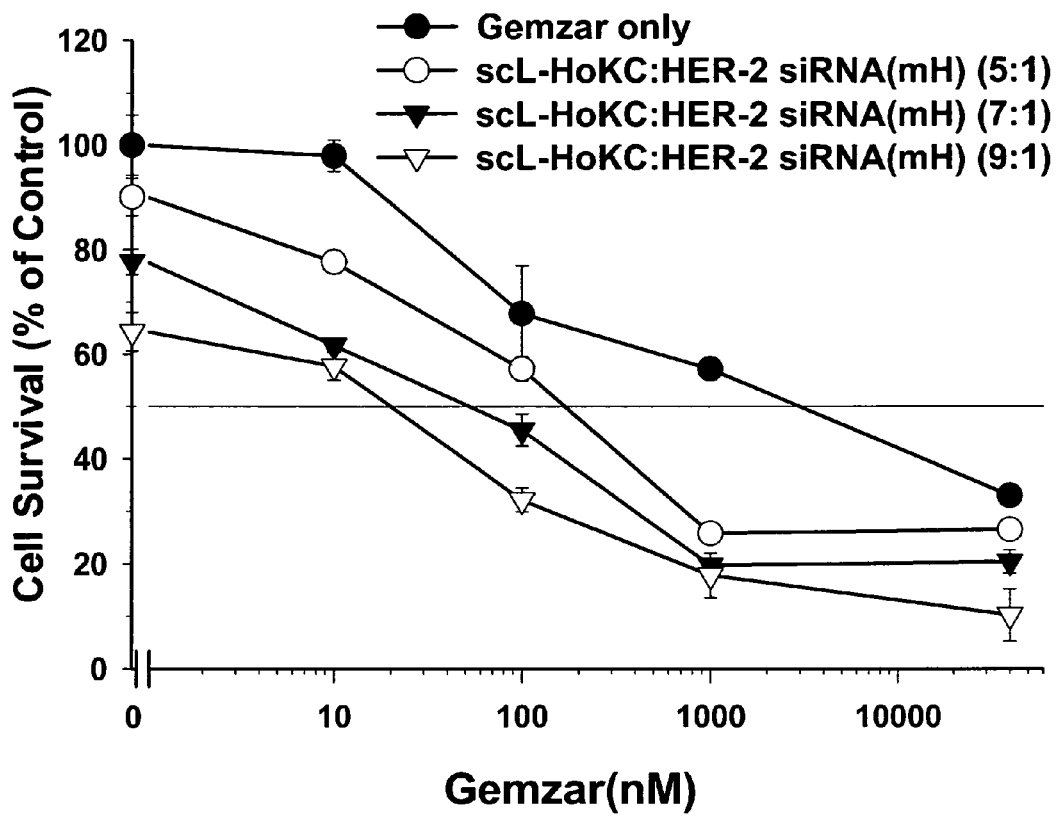
FIG. 32 shows a comparison of scL-HoKC:HER-2 siRNA ratios on sensitization of PANC-1 to gemcitabine (GEMZAR®).
Figure 33:
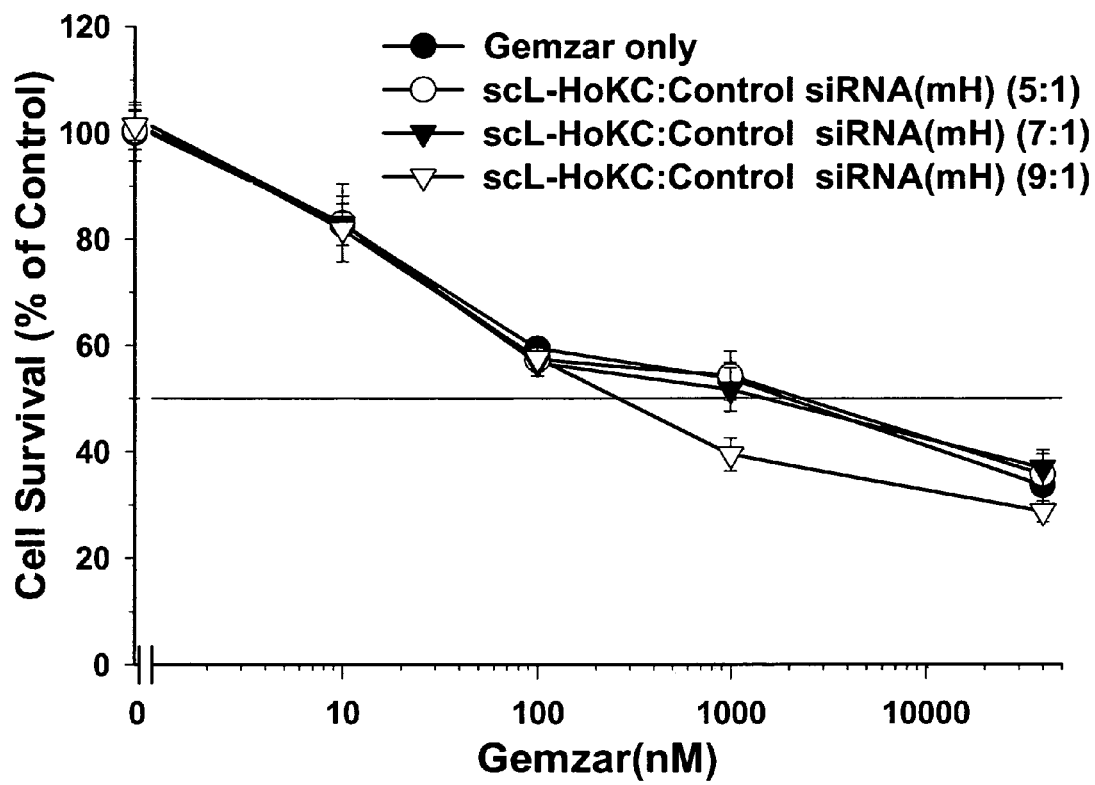
FIG. 33 shows a comparison of scL-HoKC:Control siRNA ratios on sensitization of PANC-1 to gemcitabine (GEMZAR®).

In an additional experiment examining the effects of modifying the ratio of liposome to siRNA, in the immunoliposome with the peptide $4 \times 10^3$ PANC-1 cells were plated per well of a 96 well plate. After 24 hours, the cells were transfected with TfRscFv/Liposome-HoKC complexes containing 125 nM modified Hybrid siRNA. The ratio of LipA-HoKC to siRNA was 5 to 1, 7 to 1 and 9 to 1 (nmol:ug). 24 hours later gemcitabine was added in increasing concentrations (in triplicate). The XTT assays were performed 48 hours after gemcitabine addition, the results of which are shown in FIG. 32. The $IC_{50}$ values are the gemcitabine concentrations that result in 50% survival. The controls for this experiment are shown in FIG. 33.

Figure 34:
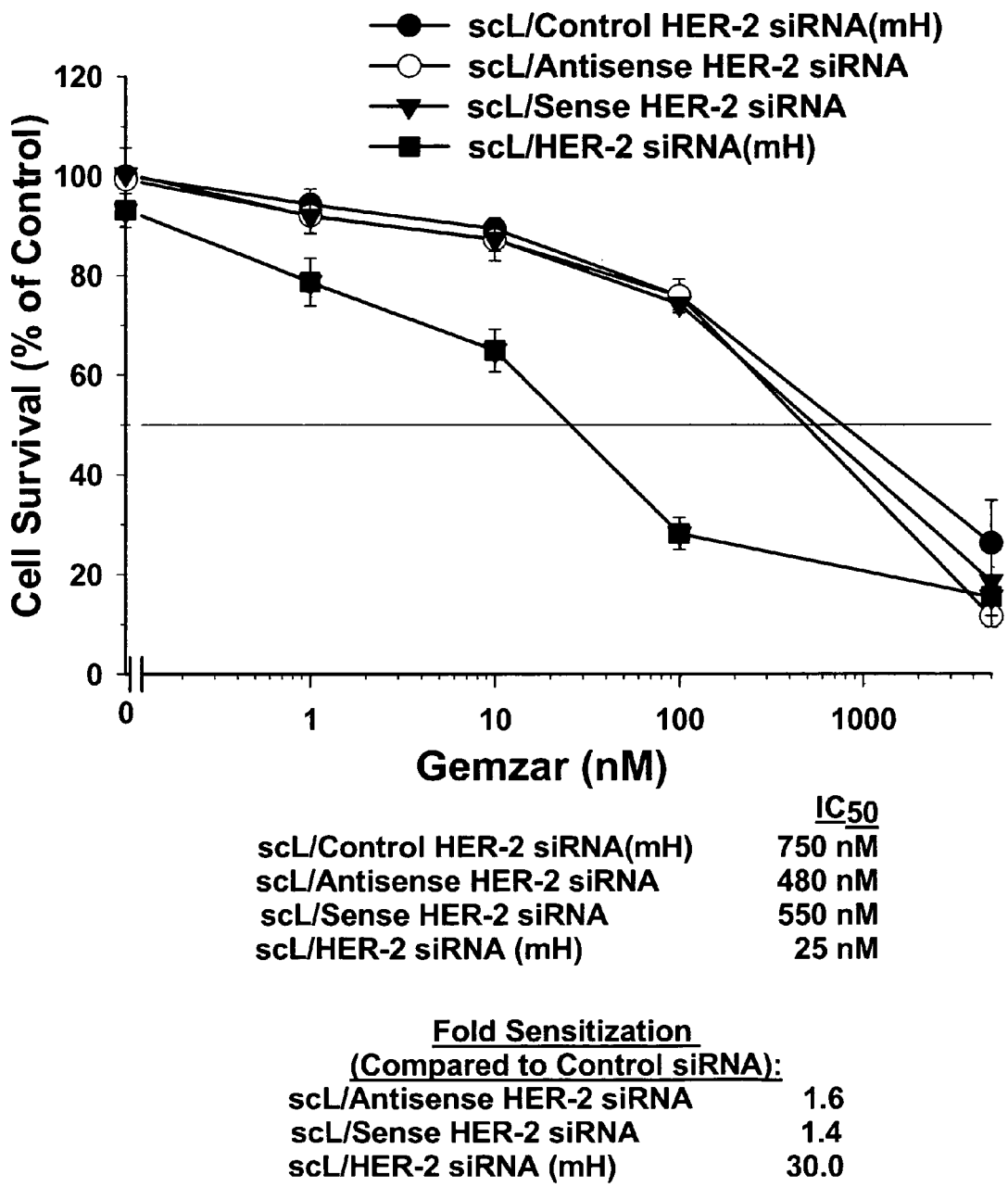
FIG. 34 shows a comparison of the effects of scL delivered complete double stranded and separate sense and antisense strands of the HER-2 siRNA structure on sensitization of PANC-1 cells to gemcitabine (GEMZAR®).

In another experiment examining the effects of the structure of the siRNA, $4 \times 10^3$ PANC-1 cells were plated per well of a 96 well plate. After 24 hours, the cells were transfected with TfRscFv/Liposome complexes containing 100 nM modified Hybrid, or the individual antisense, or sense strands of the mH HER-2 siRNA. The ratio of liposome to siRNA was 5 to 1 (nmol:ug). 24 hours later gemcitabine was added in increasing concentrations (in triplicate). The XTT assays were performed 48 hours after gemcitabine addition, the results of which are shown in FIG. 34. The $IC_{50}$ values are the concentrations that result in 50% survival. Thus, single stranded molecule can also be delivered by the method of this invention.

Figure 35:
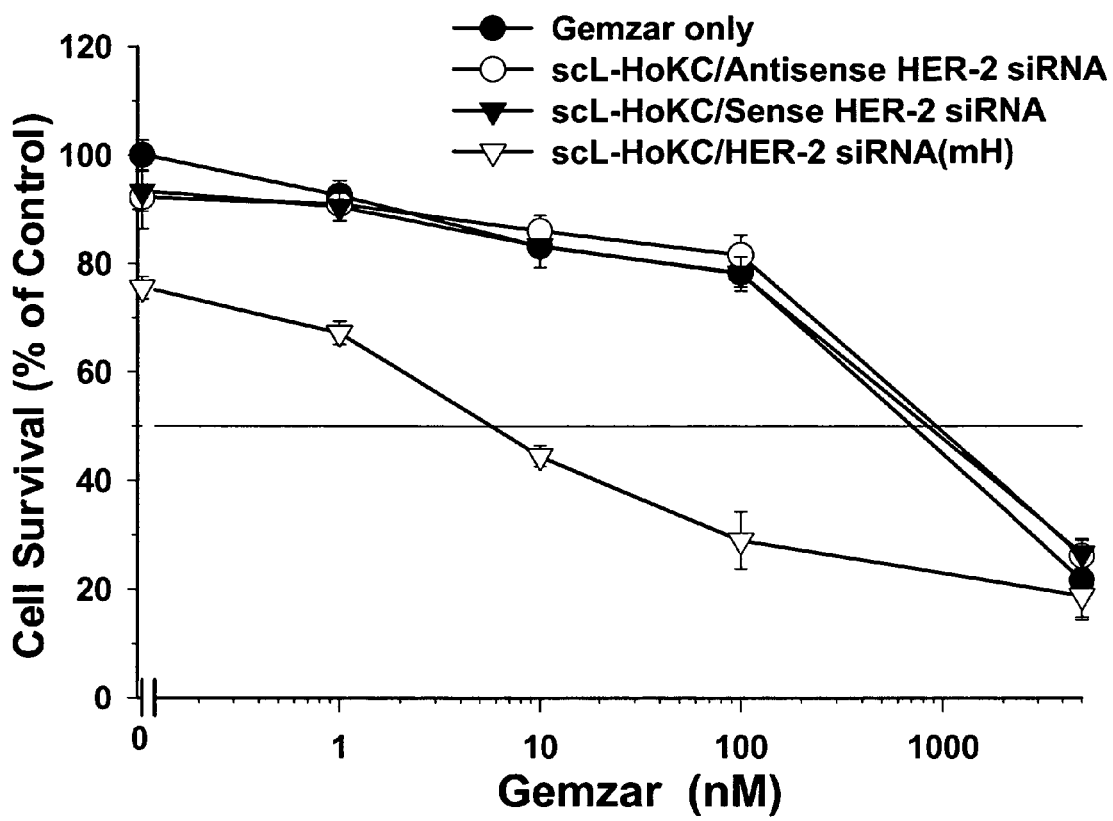
FIG. 35 shows a comparison of the effects of scL-HoKC delivered complete double stranded and separate sense and antisense strands of the HER-2 siRNA structure on sensitization of PANC-1 cells to gemcitabine (GEMZAR®).

In another experiment examining the effects of the structure of the siRNA, $4 \times 10^3$ PANC-1 cells were plated per well of a 96 well plate. After 24 hours, the cells were transfected with TfRscFv/LiposomeA-HoKC complexes containing 100 nM modified Hybrid siRNA, or the individual antisense, or sense strands of the mH HER-2 siRNA. The ratio of liposome to siRNA was 5 to 1 (nmol:ug). 24 hours later gemcitabine was added in increasing concentrations (in triplicate). The XTT assays were performed 48 hours after gemcitabine addition, the results of which are shown in FIG. 35. The $IC_{50}$ values are the concentrations that result in 50% survival. Thus, single stranded molecules can also be delivered by the method of this invention.

Figure 36:
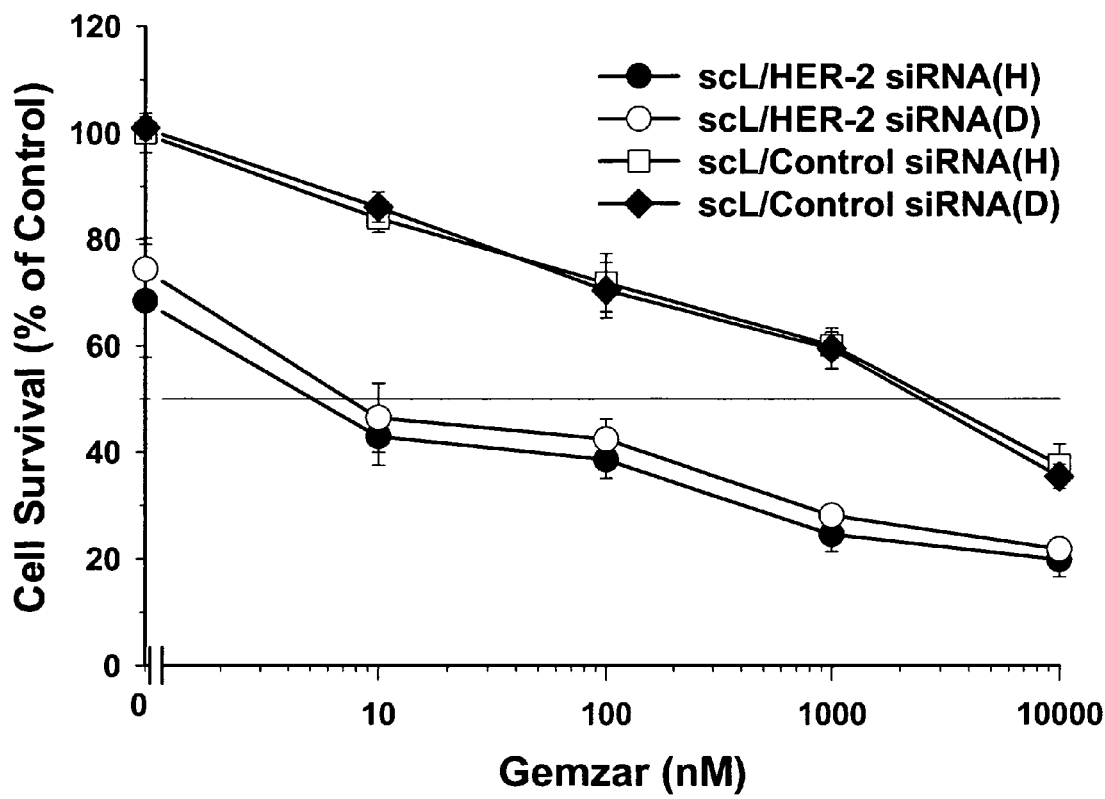
FIG. 36 shows a comparison of the effects of scL delivered HER-2 siRNA structure (Hybrid 3 vs Duplex 3) on sensitization of AsPC cells to gemcitabine (GEMZAR®).
Figure 37:
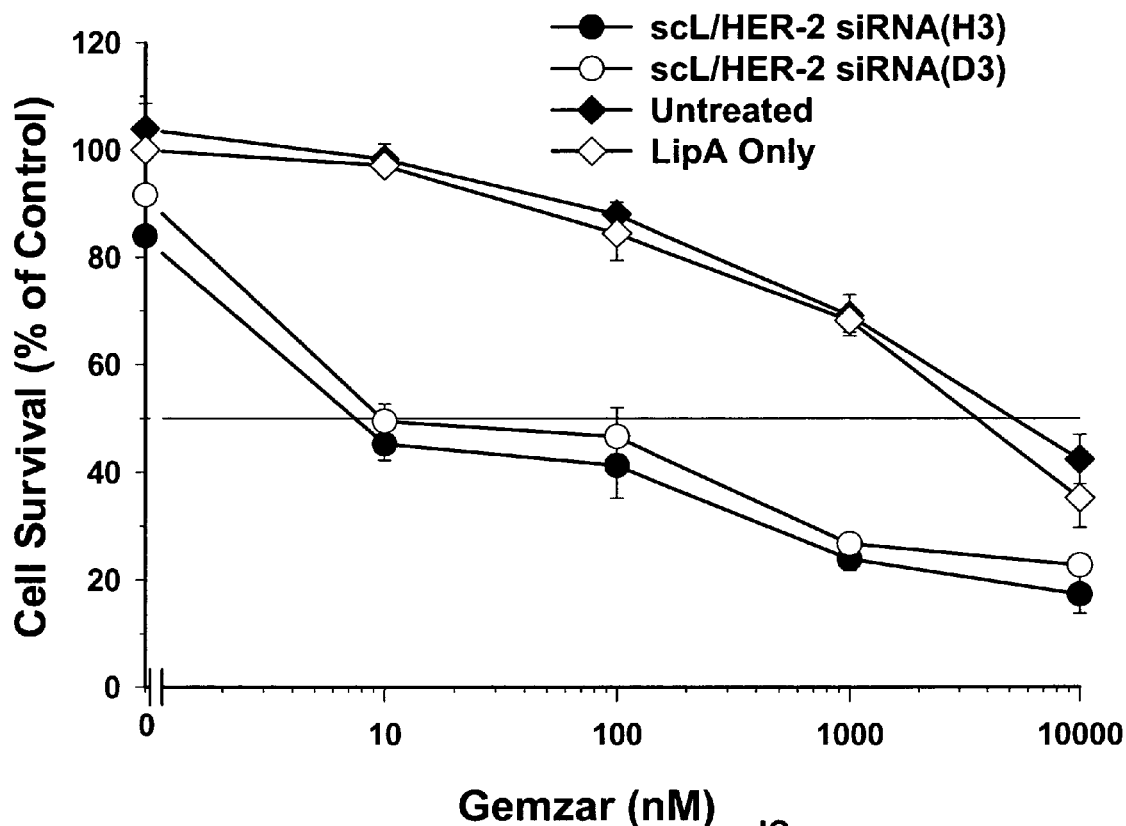
FIG. 37 shows a comparison of the effects of scL delivered HER-2 siRNA structure (Hybrid 3 vs Duplex 3) on sensitization of AsPC cells to gemcitabine (GEMZAR®).

Additional experiments were performed on other cancer cell lines. In one experiment, $4 \times 10^3$ AsPC cells were plated/well of a 96 well plate. After 24 hours, the cells were transfected with TfRscFv/Liposome complexes containing 100 nM Hybrid 3 or Duplex 3 siRNA as well as control siRNA. The ratio of liposome to siRNA was 7 to 1 (nmol:ug). 24 hours later gemcitabine was added in increasing concentrations (in triplicate). The XTT assays were performed 48 hours after addition of gemcitabine, the results of which are shown in FIG. 36. $IC_{50}$ values are the gemcitabine (nM) concentrations yielding 50% cell growth inhibition. In a similar experiment, $4 \times 10^3$ AsPC cells were plated/well of a 96 well plate. After 24 hours, the cells were transfected with TfRscFv/Liposome complexes containing 100 nM Hybrid 3 or Duplex 3 siRNA as well as liposome A only. The ratio of liposome to siRNA was 7 to 1 (nmol:ug). 24 hours later gemcitabine was added in increasing concentrations (in triplicate). The XTT assays were performed 48 hours after addition of gemcitabine, the results of which are shown in FIG. 37. $IC_{50}$ values are the gemcitabine (nM) concentrations yielding 50% cell growth inhibition. Since the controls in FIGS. 36 and 37 do not increase the sensitization to the chemotherapeutic agent, the response seen with the scL complexed siRNA is due to the delivered siRNA and is not due to non-specific cytotoxicity caused by the complex or the liposome alone.

Figure 38:
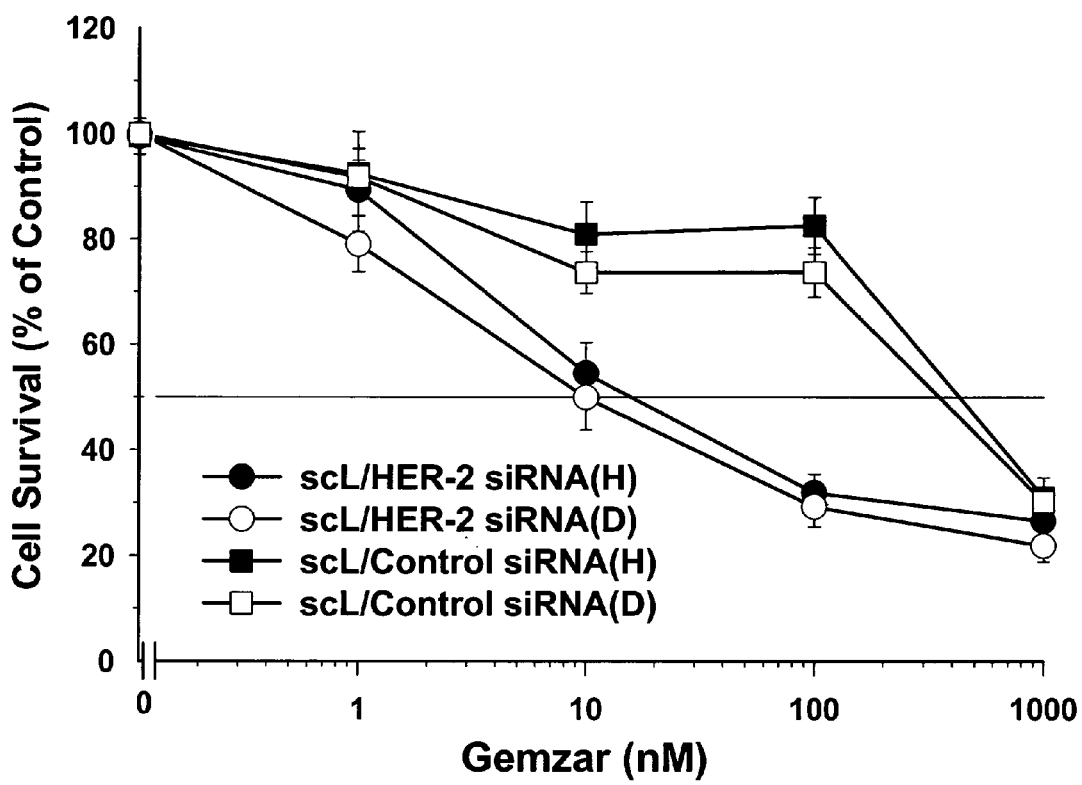
FIG. 38 shows a comparison of the effects of HER-2 siRNA structure (Hybrid 3 vs Duplex 3) on sensitization of Colo-357 cells to gemcitabine (GEMZAR®).
Figure 39:
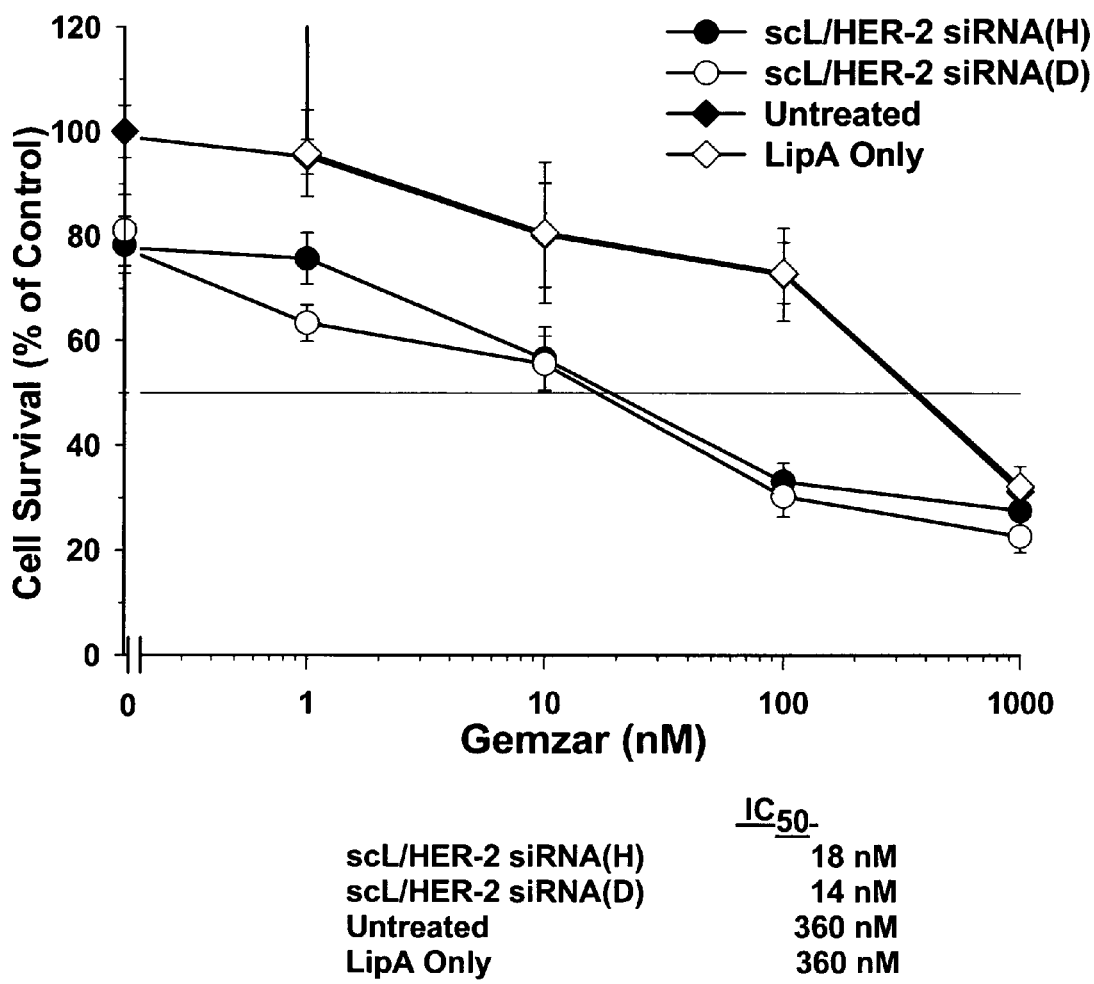
FIG. 39 shows a comparison of the effects of HER-2 siRNA structure (Hybrid 3 vs Duplex 3) on sensitization of Colo-357 cells to gemcitabine (GEMZAR®).

In another experiment in another cell line, $4 \times 10^3$ Colo-357 cells were plated per well of a 96 well plate. After 24 hours, the cells were transfected with TfRscFv/Liposome complexes containing either 100 nM Hybrid 3, Duplex 3 siRNA or control siRNA. The ratio of liposome to siRNA was 7 to 1 (nmol:ug). 24 hours later gemcitabine was added in increasing concentrations (in triplicate). The XTT assays were performed 48 hours after addition of gemcitabine, the results of which are shown in FIG. 38. $IC_{50}$ values are the gemcitabine (nM) concentrations yielding 50% cell growth inhibition. In an additional experiment, $4 \times 10^3$ Colo-357 cells were plated per well of a 96 well plate. After 24 hours, the cells were transfected with TfRscFv/Liposome complexes containing either 100 nM Hybrid 3 or Duplex 3 siRNA or transfected with liposome A only. The ratio of liposome to siRNA was 7 to 1 (nmol:ug). 24 hours later gemcitabine was added in increasing concentrations (in triplicate). The XTT assays were performed 48 hours after addition of gemcitabine, the results of which are shown in FIG. 39. $IC_{50}$ values are the gemcitabine (nM) concentrations yielding 50% cell growth inhibition. Since the controls in FIGS. 38 and 39 do not increase the sensitization to the chemotherapeutic agent, the response seen with the scL complexed siRNA is due to the delivered siRNA and is not due to non-specific cytotoxicity caused by the complex or the liposome alone.

Figure 40:
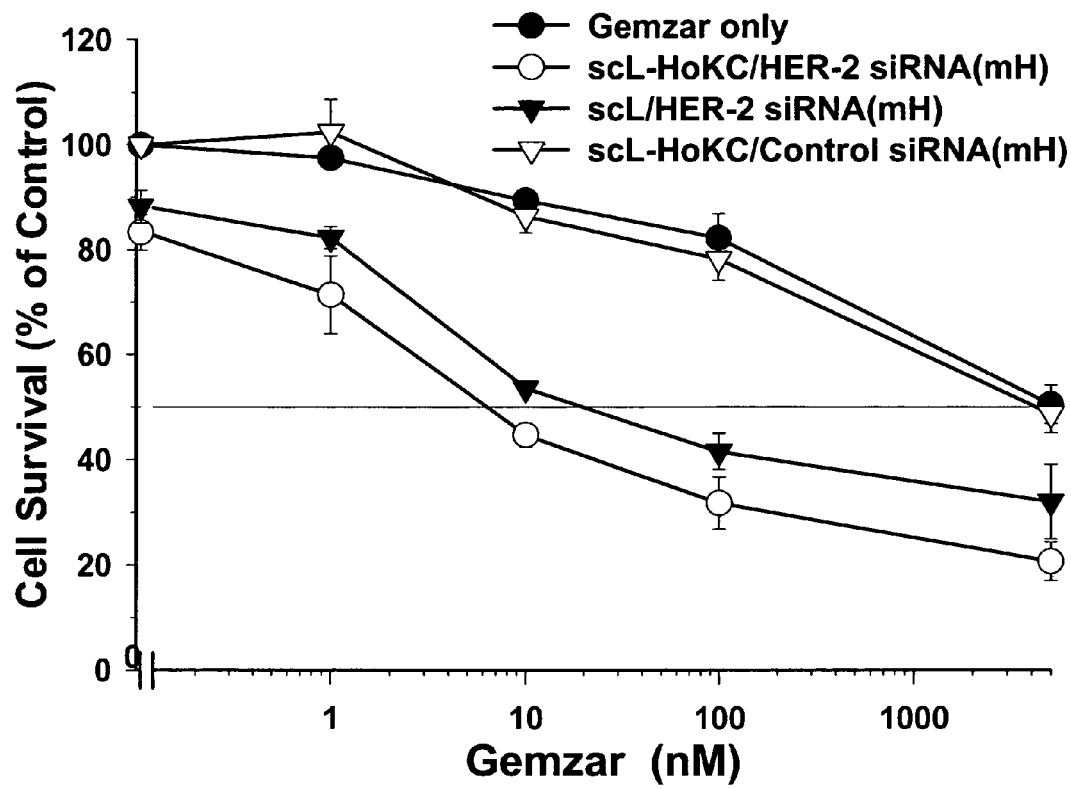
FIG. 40 shows a comparison of the effects of scL-HoKC and scL on HER-2 siRNA mediated sensitization of Panc-1 Cells to gemcitabine (GEMZAR®).

In an additional experiment comparing the effects of scL and scL-HoKC delivery of siRNA, $4 \times 10^3$ PANC-1 cells were plated/well of a 96 well plate. After 24 hours, the cells were transfected with TfRscFv/LipA (with or without the HoKC peptide) complex containing 100 nM Hybrid, modified Hybrid or control siRNA. The ratio of LipA to siRNA was 5 to 1 (nmol:ug). gemcitabine was added in increasing concentrations (in triplicate). The cell viability XTT-based assay was performed 48 hours after gemcitabine addition, the results of which are shown in FIG. 40. $IC_{50}$ values gemcitabine (nM) yielding 50% cell growth inhibition Sensitization to Docetaxel (TAXOTERE®)

Figure 41:
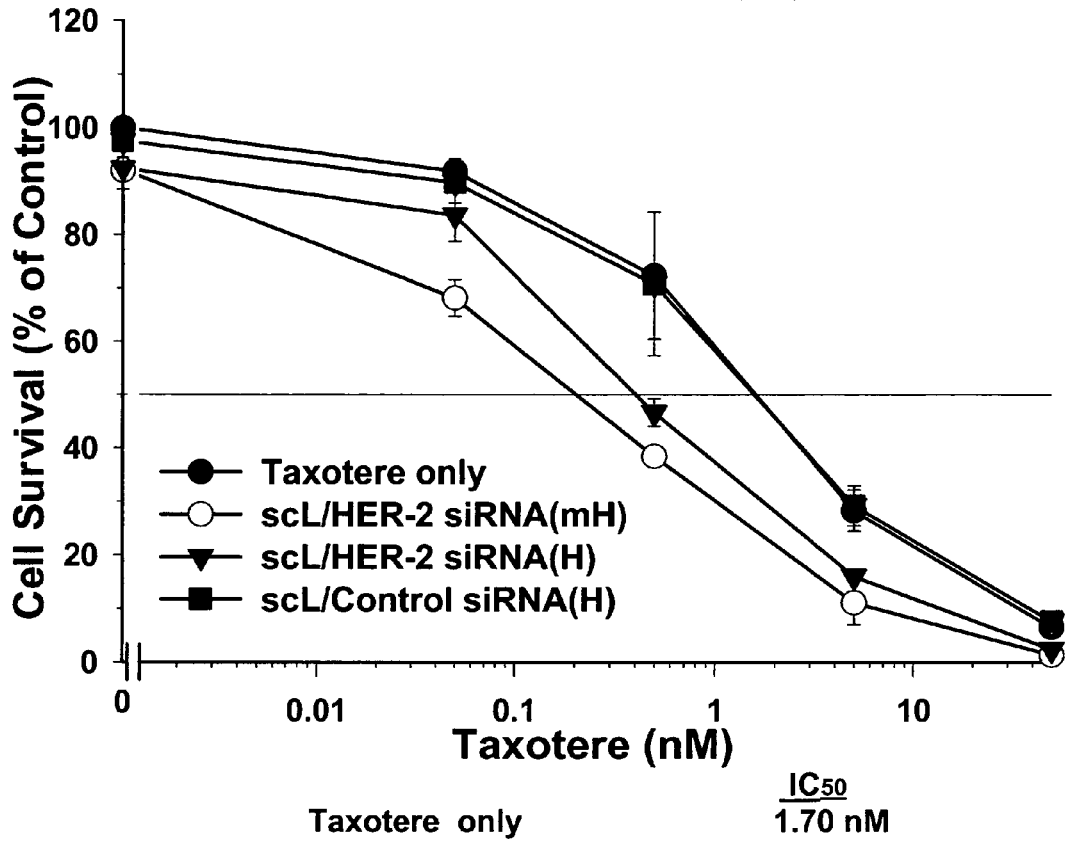
FIG. 41 shows a comparison of the effects of HER-2 siRNA structure (Hybrid vs modified Hybrid) on sensitization of MDA-MB-435 cells to docetaxel (TAXOTERE®).

In order to determine the effects of HER-2 siRNA structure (Hybrid vs modified Hybrid) on sensitization of human breast cancer cell line MDA-MB-435 cells to docetaxel, $5 \times 10^3$ MDA-MB-435 cells were plated/well of a 96 well plate. After 24 hours, the cells were transfected with TfRscFv/LipA complex containing 125 nM Hybrid, modified Hybrid or control siRNA. In the modified Hybrid, the sense strand is composed of DNA and modified RNA. The ratio of LipA to siRNA was 5 to 1 (nmol:ug). docetaxel was added in increasing concentrations (in triplicate). The cell viability XTT-based assay was performed 48 hours after addition, the results of which are represented in FIG. 41. $IC_{50}$ values docetaxel (nM) yielding 50% cell growth inhibition.

The experiments presented below explore the effects of changes to siRNA concentrations, ratios of siRNA:liposome, cell type and siRNA structure on the response to conventional chemotherapeutic agents (cell kill).

Figure 42:
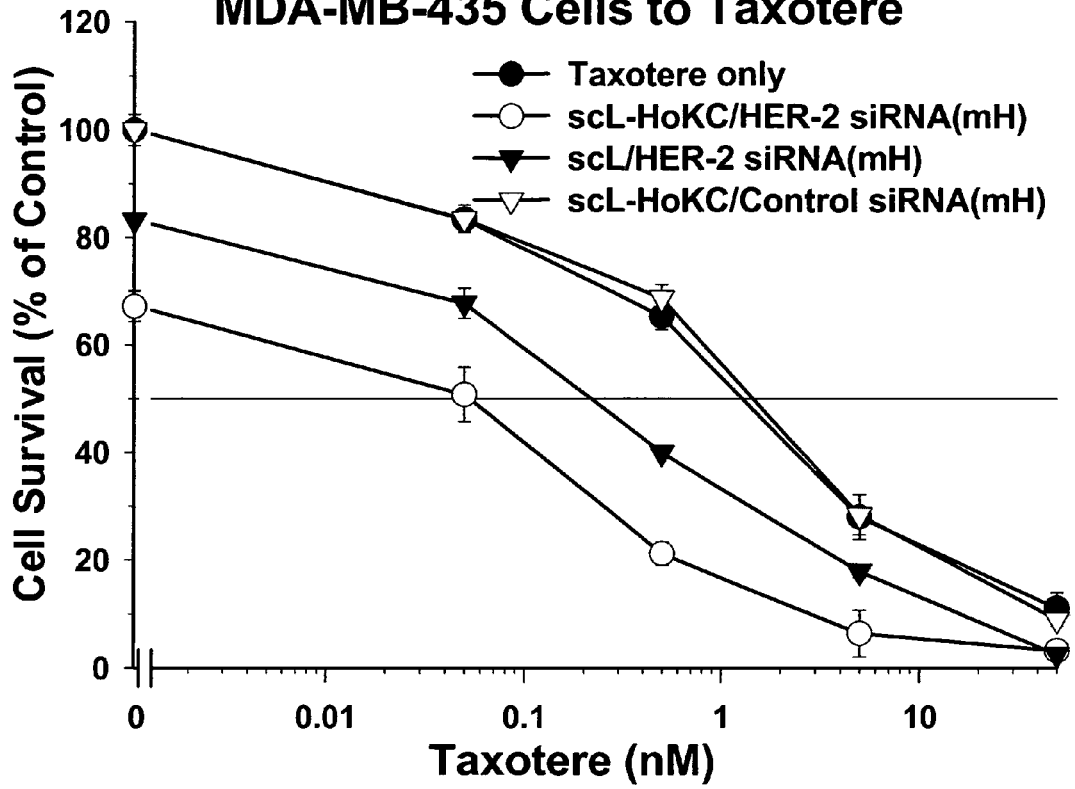
FIG. 42 shows a comparison of the effects of scL-HoKC and scL on HER-2 siRNA mediated sensitization of MDA-MB-435 cells to docetaxel (TAXOTERE®).

In another experiment comparing the effects of scL and scL-HoKC delivery of siRNA, $5 \times 10^3$ MDA-MB-435 cells were plated/well of a 96 well plate. After 24 hours, the cells were transfected with TfRscFv/LipA, or TfRscFv/LipA-HoKC complexes containing 125 nM modified Hybrid or control siRNA. The ratio of LipA to siRNA was 5 to 1 (nmol:ug). Docetaxel was added in increasing concentrations (in triplicate). The cell viability XTT-based assay was performed 48 hours after docetaxel addition, the results of which are shown in FIG. 42. $IC_{50}$ values docetaxel (nM) yielding 50% cell growth inhibition.

Figure 43:
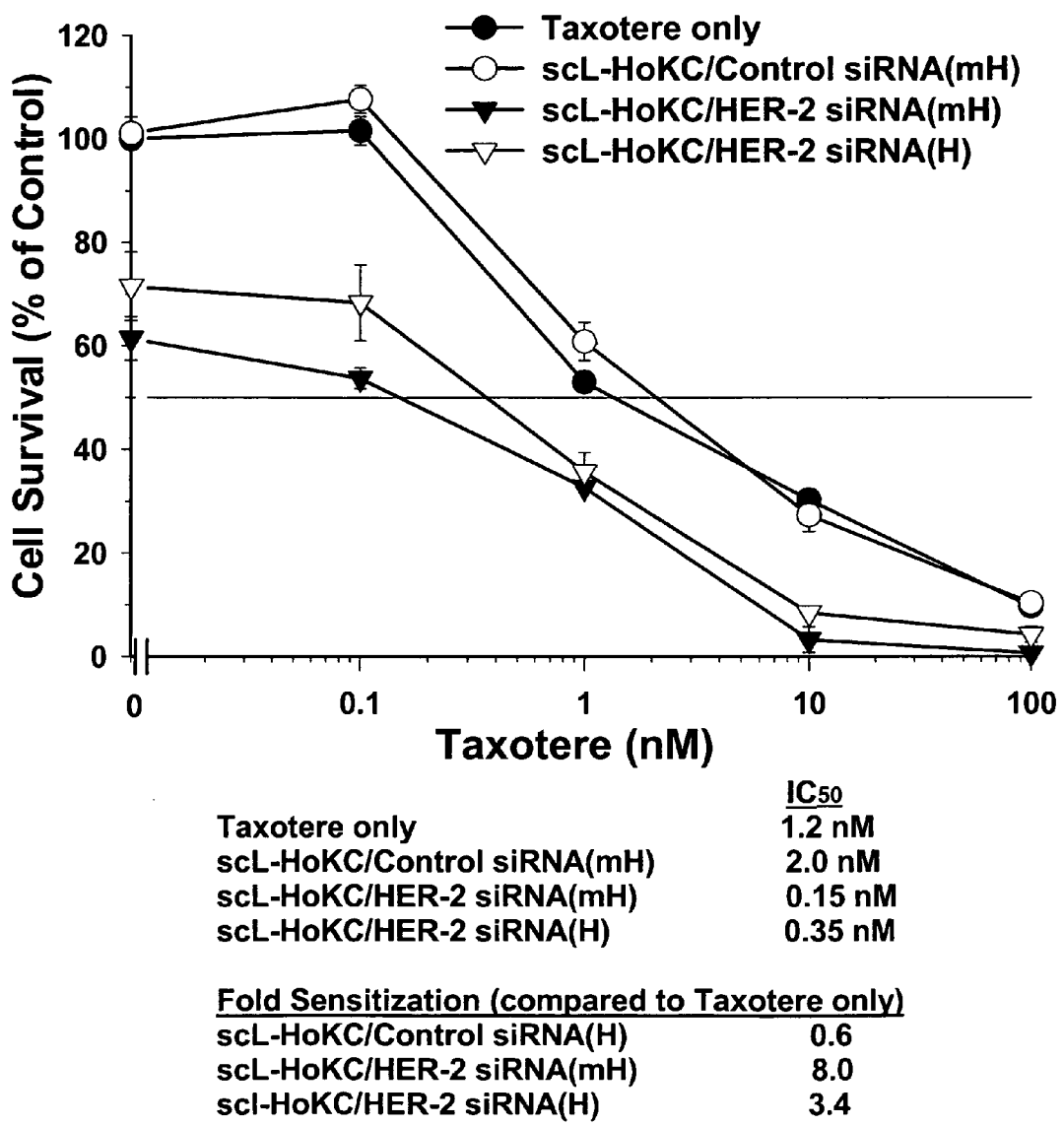
FIG. 43 shows a comparison of the effects of scL-HoKC mediated HER-2 siRNA structures (Hybrid vs modified Hybrid) on sensitization of MDA-MB-435 cells to docetaxel (TAXOTERE®).

In an additional experiment examining the effects of the siRNA structure (hybrid vs. modified hybrid), $4 \times 10^3$ MDA-MB-435 cells were plated per well of a 96 well plate. After 24 hours, the cells were transfected with TfRscFv/Liposome-HokC complex containing 125 nM Hybrid or modified Hybrid siRNA as well as control Hybrid sequence. The ratio of liposome to siRNA was 5 to 1 (nmol:ug). 24 hours later docetaxel was added in increasing concentrations (in triplicate). The XTT assays were performed 48 hours after docetaxel addition, the results of which are shown in FIG. 43. The $IC_{50}$ values are the docetaxel concentrations that result in 50% survival.

Figure 44:
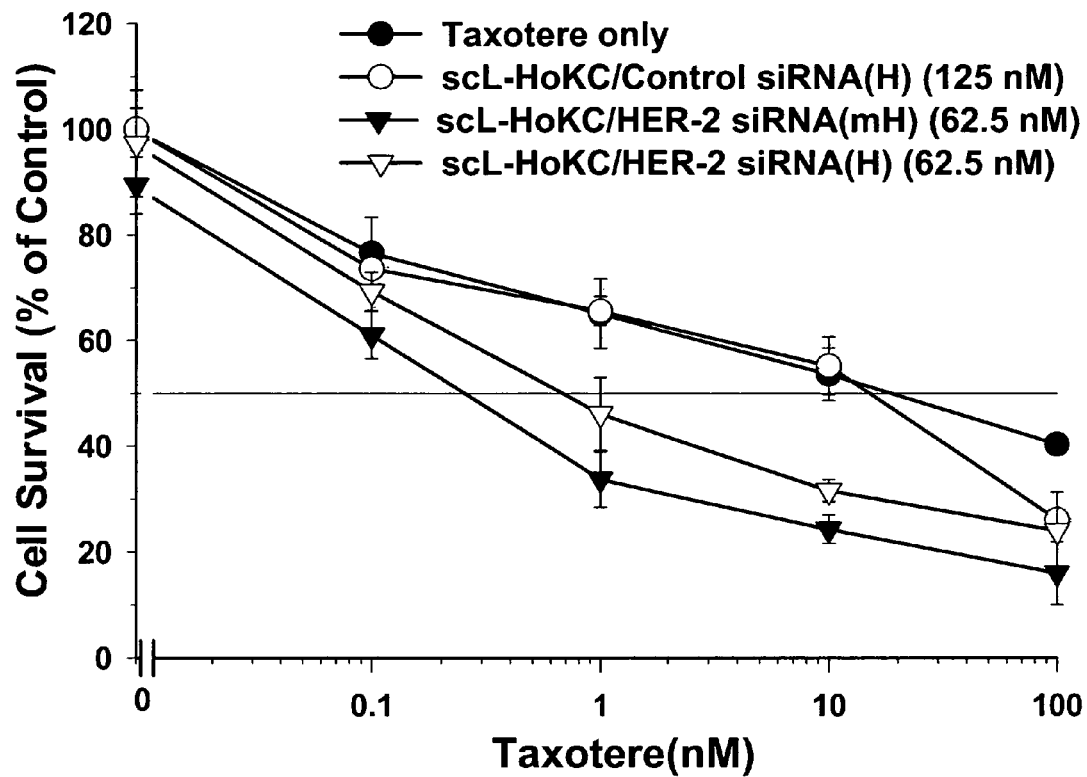
FIG. 44 shows a comparison of the effects of scL-HoKC mediated HER-2 siRNA structures (Hybrid vs modified Hybrid) on sensitization of MDA-MB-435 cells to docetaxel (TAXOTERE®).

In a further experiment examining the effects of varying the siRNA concentration, $4 \times 10^3$ MDA-MB-435 cells were plated per well of a 96 well plate. After 24 hours, the cells were transfected with TfRscFv/Liposome-HokC complex containing 62.5 nM Hybrid or modified Hybrid siRNA as well as control Hybrid sequence. The ratio of liposome to siRNA was 5 to 1 (nmol:ug). 24 hours later docetaxel was added in increasing concentrations (in triplicate). The XTT assays were performed 48 hours after docetaxel addition, the results of which are shown in FIG. 44. The $IC_{50}$ values are the docetaxel concentrations that result in 50% survival.

Figure 45:
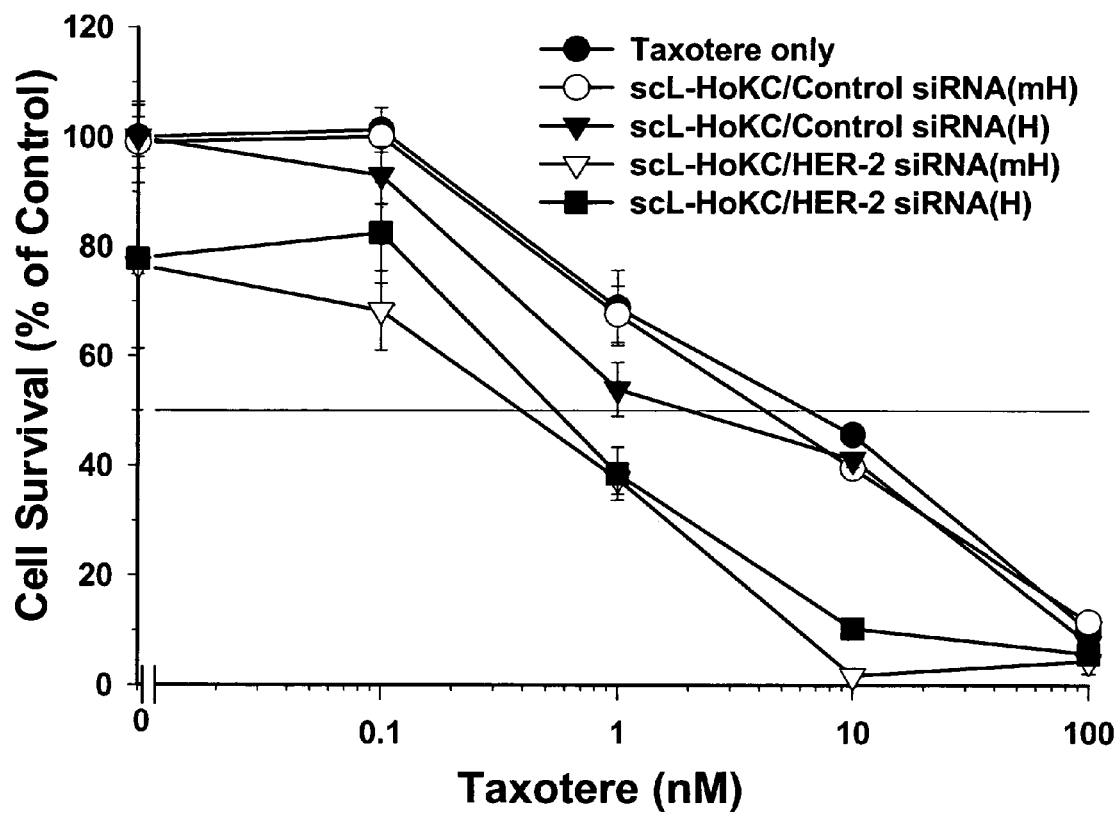
FIG. 45 shows a comparison of the effects of scL-HoKC mediated HER-2 siRNA structures (Hybrid vs modified Hybrid) on sensitization of MDA-MB-435 cells to docetaxel (TAXOTERE®).

In another experiment, $4 \times 10^3$ MDA-MB-435 cells were plated per well of a 96 well plate. After 24 hours, the cells were transfected with TfRscFv/Liposome-HokC complex containing 125 nM Hybrid or modified Hybrid siRNA as well as control Hybrid or modified Hybrid sequences. The ratio of liposome to siRNA was 5 to 1 (nmol:ug). 24 hours later docetaxel was added in increasing concentrations (in triplicate). The XTT assays were performed 48 hours after docetaxel addition, the results of which are shown in FIG. 45. The $IC_{50}$ values are the docetaxel concentrations that result in 50% survival.

Figure 46:
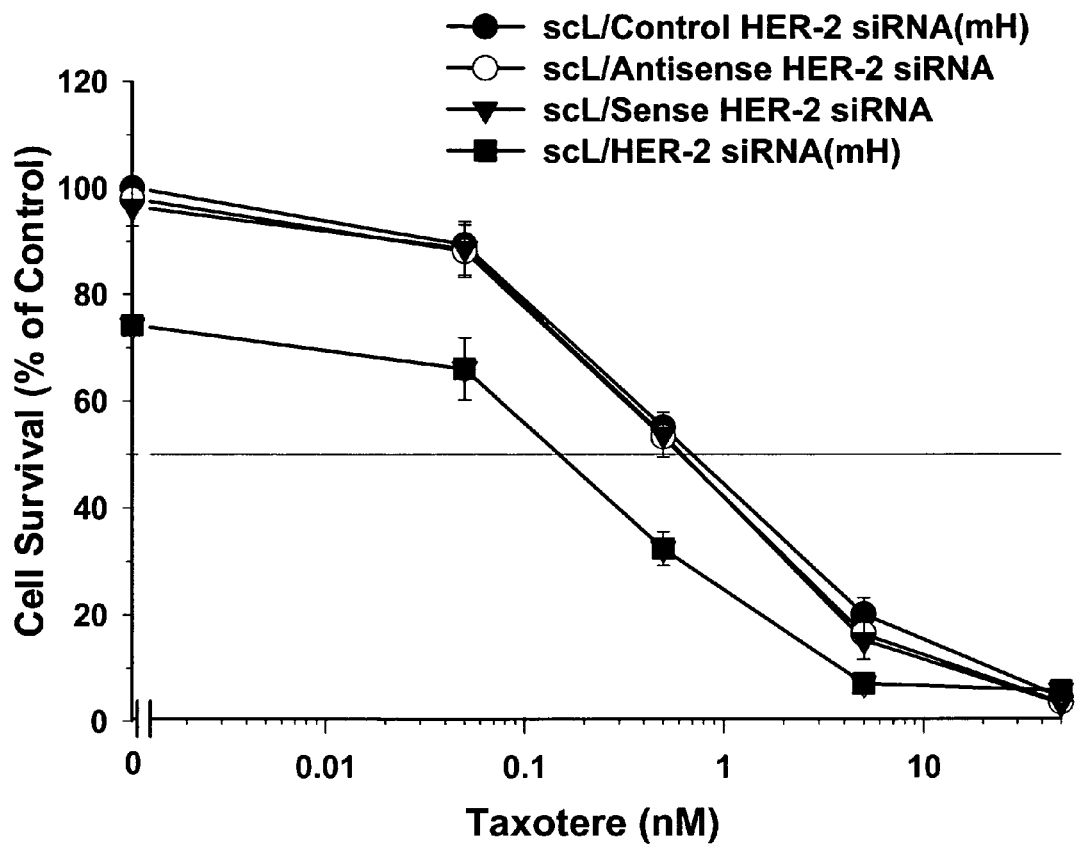
FIG. 46 shows a comparison of the effects of scL delivered complete double stranded and separate sense and antisense strands of the HER-2 siRNA structure on sensitization of MDA-MB-435 cells to docetaxel (TAXOTERE®).

In an additional experiment examining the effects of siRNA structure, $4 \times 10^3$ MDA-MB-435 cells were plated per well of a 96 well plate. After 24 hours, the cells were transfected with TfRscFv/LiposomeA complexes containing 125 nM modified Hybrid siRNA, or the individual antisense, or sense strands of the mH HER-2 siRNA. The ratio of liposome to siRNA was 5 to 1 (nmol:ug). 24 hours later docetaxel was added in increasing concentrations (in triplicate). The XTT assays were performed 48 hours after docetaxel addition, the results of which are shown in FIG. 46. The $IC_{50}$ values are the concentrations that result in 50% survival.

Figure 47:
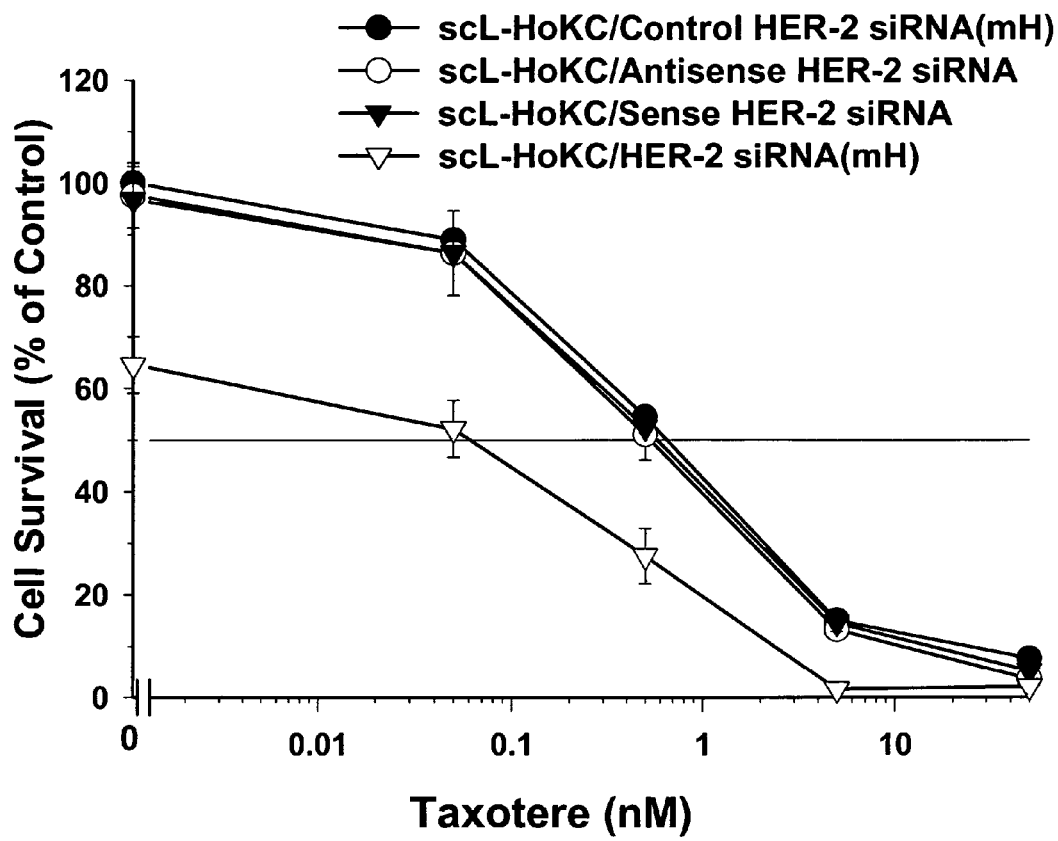
FIG. 47 shows a comparison of the effects of scL-HoKC delivered-HER-2 siRNA structure on sensitization of MDA-MB-435 cells to docetaxel (TAXOTERE®).

In a further experiment examining the effects of siRNA structure, $4 \times 10^3$ MDA-MB-435 cells were plated per well of a 96 well plate. After 24 hours, the cells were transfected with TfRscFv/LiposomeA-HokC complexes containing 125 nM modified Hybrid siRNA, or the individual antisense, or sense strands of the mH HER-2 siRNA. The ratio of liposome to siRNA was 5 to 1 (nmol:ug). 24 hours later docetaxel was added in increasing concentrations (in triplicate). The XTT assays were performed 48 hours after docetaxel addition, the results of which are shown in FIG. 47. The $IC_{50}$ values are the concentrations that result in 50% survival. These results demonstrate that the scL and scL-HoKC complexes can also delivery individual nucleic acid strands.

In another experiment, a comparison of commercial and SGT HER-2 siRNA delivery systems on sensitization of MDA-MB-435 cells was made. $4 \times 10^3$ MDA-MB-435 cells were plated per well of a 96 well plate. After 24 hours, the cells were transfected with either modified Hybrid HER-2 siRNA or Control siRNA delivered by means of commercial liposome Oligofectamine™ (Invitrogen, Carlsbad, Calif.), our scL or scL-HoKC complex. Transfection with the scL or scL-HoKC complexes was performed using our standard procedure described herein, while transfection with Oligofectamine™ was performed as per manufacturer's protocol as follows:

In order to make siRNA-Oligofectamine™ complex, siRNA and Oligofectamine™ Reagent (Invitrogen) were diluted separately in RNase free tubes. 50 µl of Oligofectamine™ was mixed with 150 µl of serum free media (SFM). 1 nmole of HER-2 or control siRNA was diluted in 800 µl of SFM. After 5 minutes at room temperature (RT), solution of siRNA was added to Oligofectamine™, mixed and left at RT for 20 minutes. The resulting concentration of siRNA is 1 µM.

Figure 48:
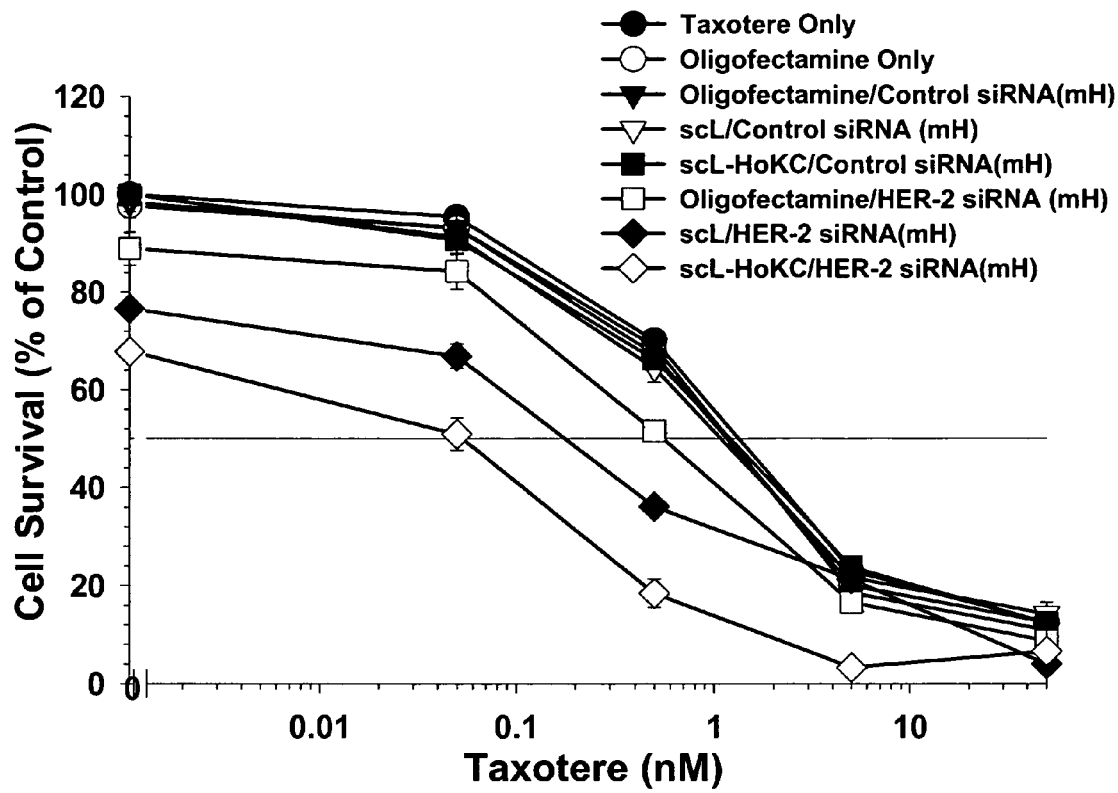
FIG. 48 shows a comparison of commercial and SGT HER-2 siRNA delivery systems on sensitization of MDA-MB-435 cells to docetaxel (TAXOTERE®).

All of the complexes were diluted to 250 nM by addition of SFM. For transfection of all complexes the growth media was replaced by fresh complete media, 50 µl per well. 50 µl of siRNA/Oligofectamine™ complex (250 nM siRNA) was added/well, resulting in 125 nM siRNA. After 5 hours incubation at 37° C., 50 µl of complete media (with 10% serum) was added per well. Cells were incubated for an additional 19 hours. Docetaxel, in media containing 5% serum, was added to the appropriate concentrations. 48-hours later the cell survival, XTT based, assay was performed. The $IC_{50}$ values are the concentrations that result in 50% survival. The results of this experiment are shown in FIG. 48. In all cases, siRNA delivered via the immunoliposomes of the present invention provided better cell kill than siRNA delivered via the untargeted commercial liposomes (3 to 8 fold better), with the liposome comprising the HoKC peptide provided the best results.

Sensitization to Mitoxantrone

Figure 49:
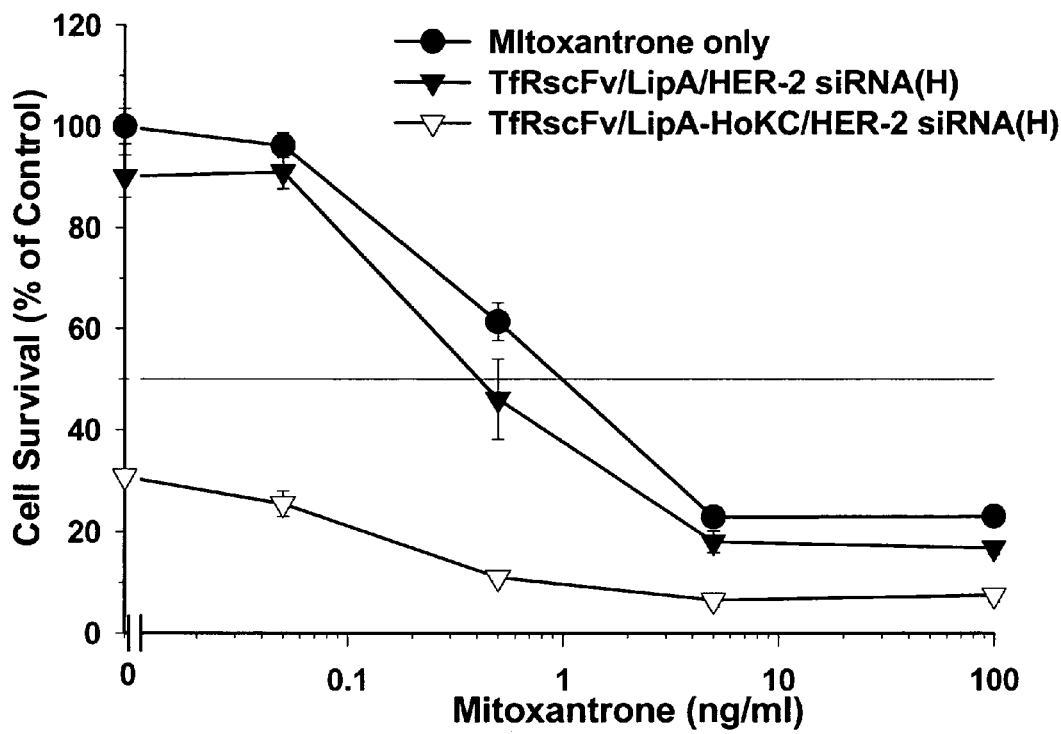
FIG. 49 shows a comparison of the effects of scL-HoKC vs. scL on HER-2 siRNA mediated sensitization of DU145 cells to Mitoxantrone.

In order to determine the effects of siRNA delivery via the immunoliposomes of the present invention on human prostate cancer cells, $5 \times 10^3$ DU145 cells were plated/well of a 96 well plate. After 24 hours, the cells were transfected with TfRscFv/LipA, or TfRscFv/LipA-HoKC complexes containing 75 nM Hybrid siRNA. The ratio of liposome to siRNA was 7 to 1 (nmol:ug). Mitoxantrone was added in increasing concentrations (in triplicate). The XTT assays were performed ~2 days after Mitoxantrone addition and $IC_{50}$ values (Mitoxantrone (ng/mL) yielding 50% growth inhibition) calculated, the results of which are shown in FIG. 49.

Figure 50:
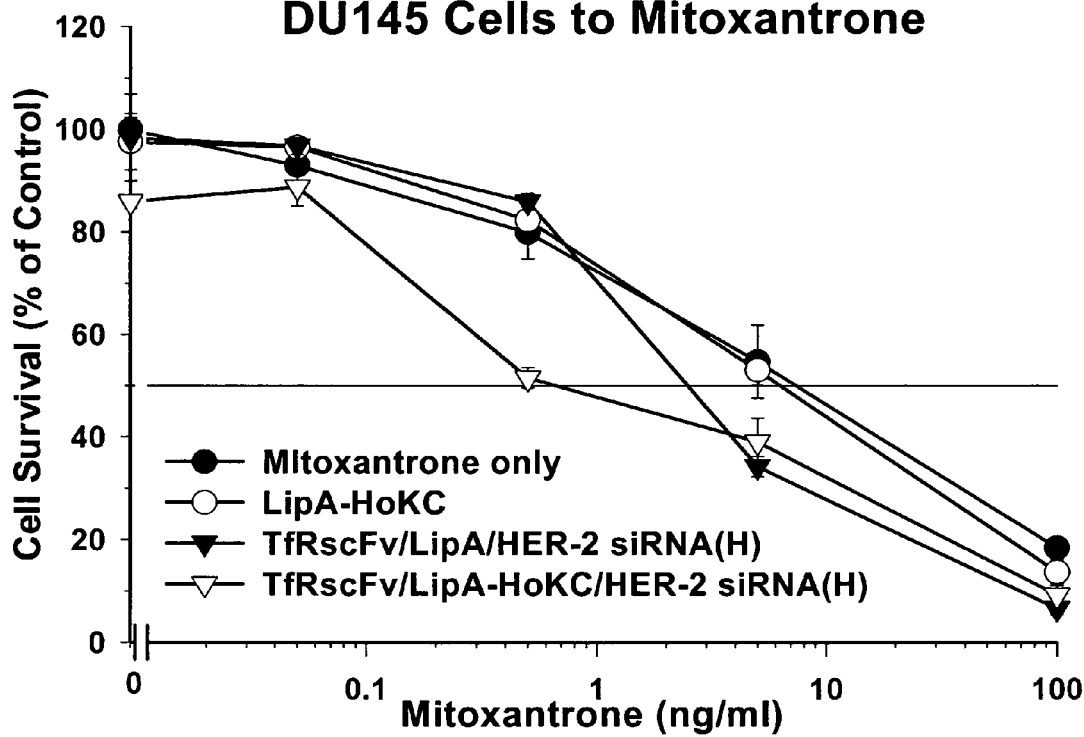
FIG. 50 shows a comparison of the effects of scL-HoKC vs. scL on HER-2 siRNA mediated sensitization of DU145 cells to mitoxantrone.

In an additional experiment examining the use of the HoKC peptide, $5 \times 10^3$ DU145 cells were plated per well of a 96 well plate. After 24 hours, the cells were transfected with TfRscFv/Liposome-HoKC containing 25 nM Hybrid siRNA or LipA-HoKC only complexes. The ratio of liposome to siRNA was 7 to 1 (nmol:ug). 24 hours later Mitoxantrone was added in increasing concentrations (in triplicate). The XTT assays were performed 48 hours after Mitoxantrone addition, the results of which are represented in FIG. 50. The $IC_{50}$ values are the Mitoxantrone concentrations that result in 50% survival.

Example 15

Sensitization to Radiation

The immunocomplexes of this invention (both scL and scL-HoKC) are also useful for the delivery of siRNA to cells treated in combination with conventional radiotherapy (radiation treatment) resulting in increased sensitization to this radiotherapy. Athymic nude mice are injected with $1 \times 10^4$ to $1 \times 10^7$ human cancer cells, either with or without the use of Matrigel. When the tumors reach a minimum of 50 mm³ in volume the animals are injected by intravenous administration with the scL or scL-HoKC complex carrying a suitable siRNA molecule (duplex, hybrid, modified hybrid), suitably the modified hybrid against HER-2 (SEQ ID NO: 9 & 16). The complex is administered 2-3 times per week during the course of radiation treatment. Radiation treatment, such as but not limited to gamma radiation ($^{137}$Cs), or X-rays, is administered at the conventional dose appropriate for that type of radiotherapy which is well known to one skilled in the art. An example is the administration of fractionated doses of $^{137}$Cs at 1-3 Gy/day given for 5 days in a row, followed by 2 days of no radiation treatment, for a period of 4 to 6 weeks. Suitably, radiation treatment begins the same day as the first administration of the complexes. Tumor sizes are monitored by measurements at least weekly with calipers throughout the course of treatment and for at least 30 days post treatment. Following these procedures a decrease in rate of tumor growth (tumor growth inhibition), or decrease in tumor size (tumor regression) are expected.

Example 16

Delivery of FLIP siRNA Using Immunoliposome Complexes

In order to examine the effectiveness of the immunoliposome complexes at delivering additional types of siRNA, the following experiments were performed using commercially available FLIP siRNA. FLIP siRNA is targeted to downregulated the FLICE-like inhibitory protein (FLIP).

Figure 51:
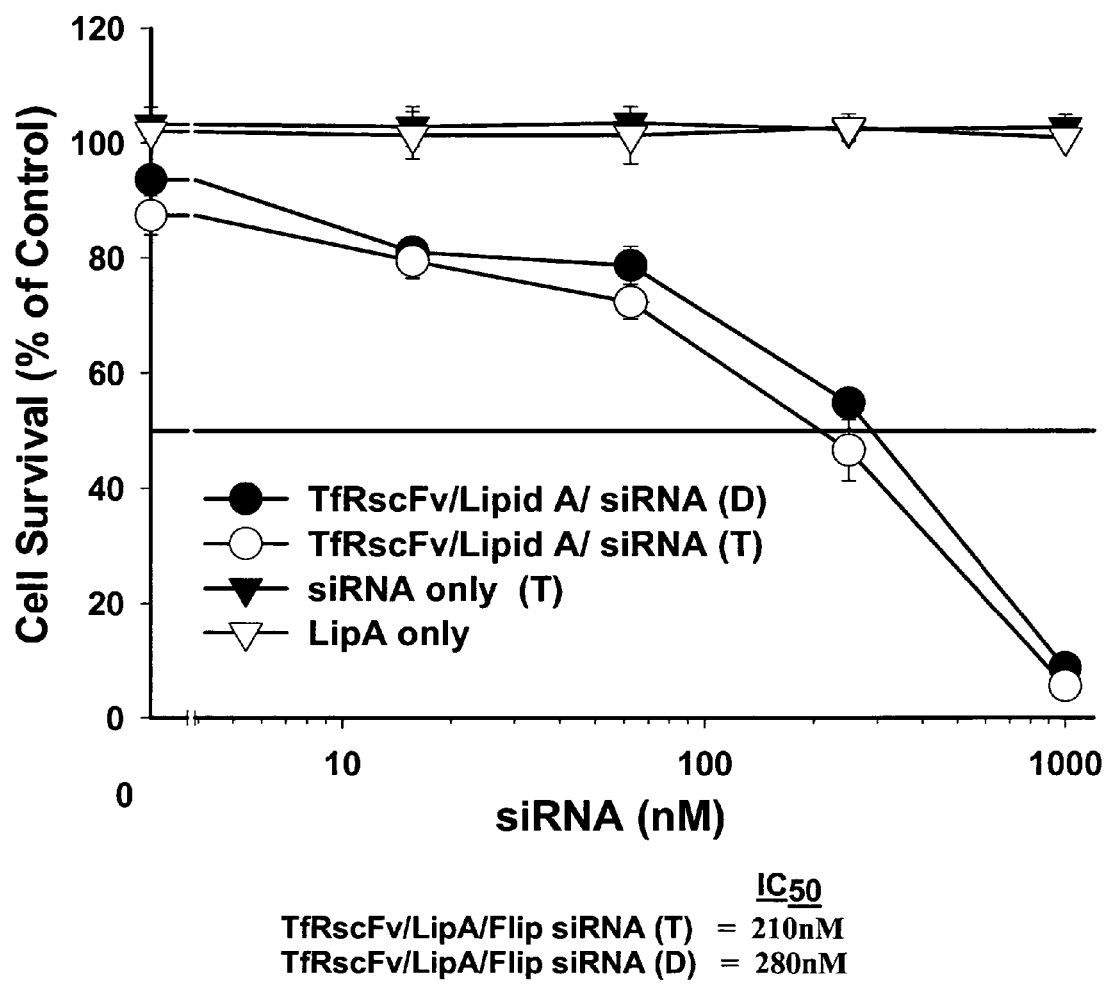
FIG. 51 shows a comparison of the effect of FLIP siRNA from two commercial sources delivered by scL on HCT116 cell survival.

In one experiment, 4.5×10$^3$ HCT116 human colon carcinoma cells were plated per well of a 96 well plate. After 24 hours, the cells were transfected with TfRscFv/Liposome complexes containing standard Duplex siRNA produced by two independent commercial entities, TriLink Biotechnologies, Inc. (San Diego, Calif.) (T), or Dharmacon RNA Technologies (Lafayette, Colo.) (D). The siRNA concentration varied from ~4 to 1000 nM. The ratio of LipA to siRNA was 3.5 to 1 (nmol:ug). The XTT assays were performed 48 hours after transfection, the results of which are shown in FIG. 51. The IC$_{50}$ values are the siRNA concentrations that result in 50% survival. In both cases, the FLIP siRNA was successfully delivered using the immunoliposome complexes, providing an enhanced cell kill.

Figure 52:
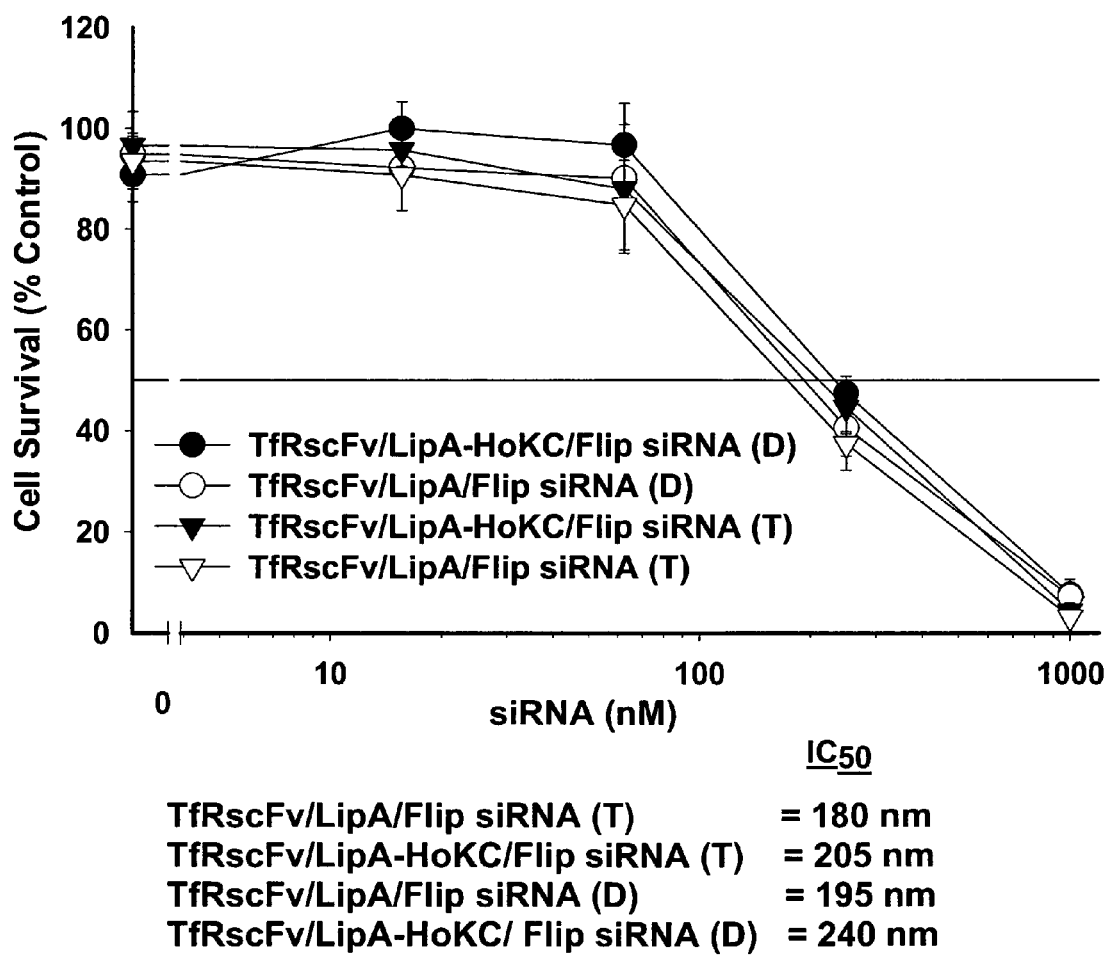
FIG. 52 shows a comparison of the effect of FLIP siRNA (standard duplex) from two commercial sources as free (uncomplexed) siRNA or delivered by scL or scL-HoKC on HCT116 cell survival.

In an additional experiment examining the use of the HoKC peptide, 4.5×10$^3$ HCT116 colon carcinoma cells were plated per well of a 96 well plate. After 24 hours, the cells were transfected with either TfRscFv/Liposome or TfRscFv/Liposome-HoKC complexes containing standard Duplex siRNA (T) and (D) as designated above. The siRNA concentration varied from ~4 to 1000 nM. The ratio of LipA to siRNA was 5 to 1 (nmol:ug). The XTT assays were performed 48 hours after transfection, the results of which are shown in FIG. 52. The IC$_{50}$ values are the siRNA concentrations that result in 50% survival.

Figure 53:
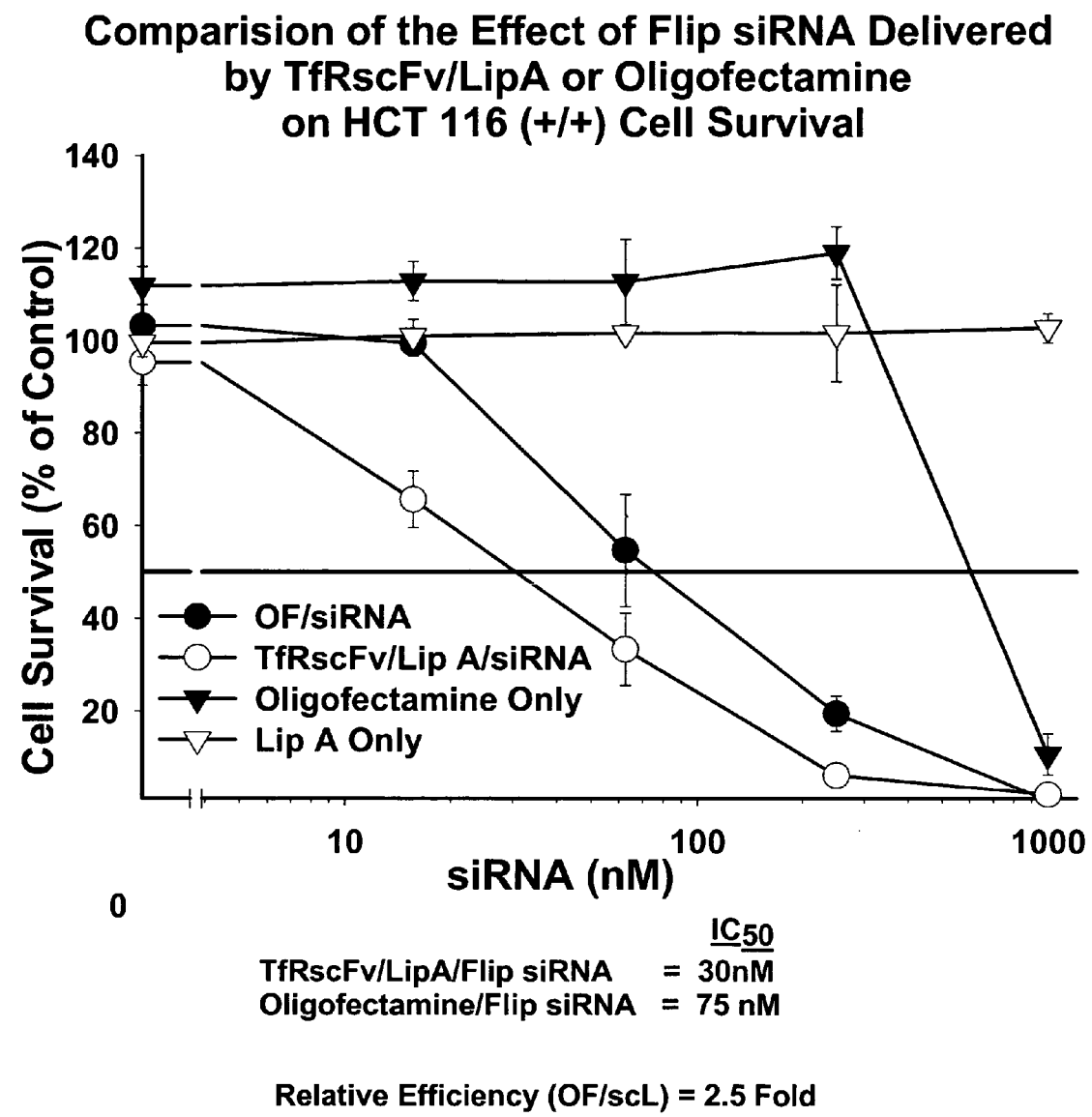
FIG. 53 shows a comparison of the effect of FLIP siRNA (standard duplex) delivered by scL or Oligofectamine™ on HCT116 cell survival.

In a further experiment comparing the use of the immunoliposomes of the present invention with a commercially available liposome, 4.5×10$^3$ HCT116 colon carcinoma cells were plated per well of a 96 well plate. After 24 hours, the cells were transfected with either TfRscFv/Liposome or commercially available liposome Oligofectamine™ (Invitrogen) complexes containing Duplex siRNA. Cells were also transfected with either Liposome A only or Oligofectamine™ only. Oligofectamine™ complex was prepared as described above in Example 14. The siRNA concentration varied from ~4 to 1000 nM. The ratio of LipA to siRNA was 5 to 1 (nmol:ug). The XTT assays were performed 48 hours after transfection, the results of which are shown in FIG. 53. The IC$_{50}$ values are the siRNA concentrations that result in 50% survival. Here, as in FIG. 48 with the anti-HER-2 siRNA, the immunoliposomes of the present invention provide enhanced cell kill (2.5 fold) as compared to untargeted commercial liposomes.

Example 17

In Vivo Delivery of siRNA Using Immunoliposome Complexes

Stability and Delivery of siRNA

Figure 54:
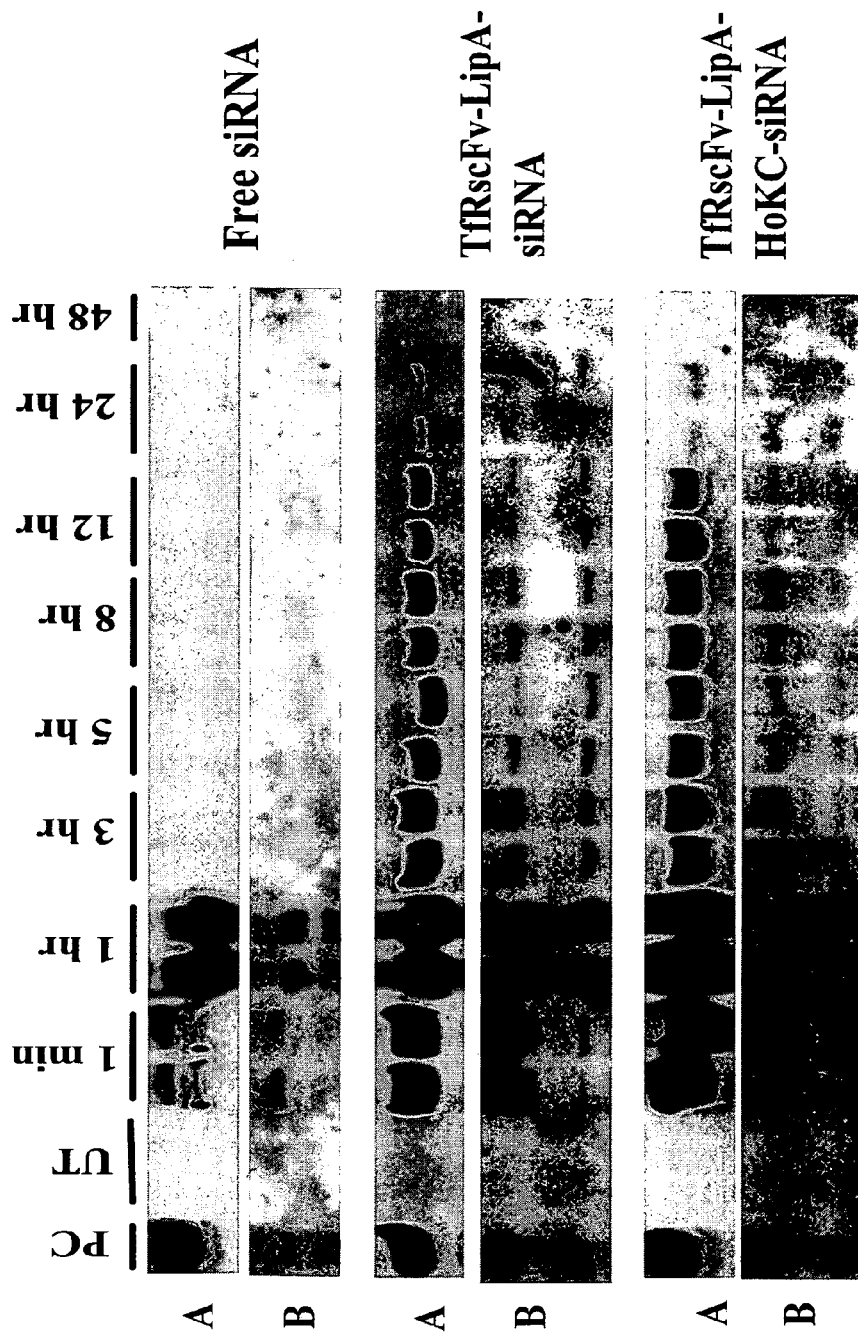
FIG. 54 shows the results examining stability of siRNA in plasma of non-tumor bearing BALB/c mice.

In order to compare the stability of siRNA in vivo, both as free nucleic acid and as complexed with the immunoliposome complexes of the present invention, BALB/c mice were injected once via the tail vein with modified hybrid anti HER-2 siRNA (at 9 mg/Kg) either as the free siRNA molecule, or in complex with TfRscFv-LipA, or TfRscFv-LipA-HoKC. Blood was collected from two mice of each group within 1 min, and at 1, 3, 5, 8, 12, 24, and 48 hours post-injection. Total RNA isolated from 10 µL of each plasma sample using TriZol (Invitrogen) was loaded per well on a 19% PAAG, with 7 M urea. The stability results are represented in FIG. 54. Row A—Membranes hybridized with deoxyribo oligonucleotide complementary to the sense strand of the siRNA (modified DNA/RNA strand). Row B—Membranes hybridized with deoxyribo oligonucleotide complementary to the anti-sense strand of siRNA (RNA strand). "PC" indicates Positive control (100 µg of modified hybrid anti HER-2 siRNA). "UT" indicates untreated mice. As seen in FIG. 54, free siRNA was no longer present in plasma after 3-5 hours, while delivery with both immunoliposomes prolonged stability to at least 12-24 hours with a small amount still detectable at 48 hours post-injection.

Figure 55:
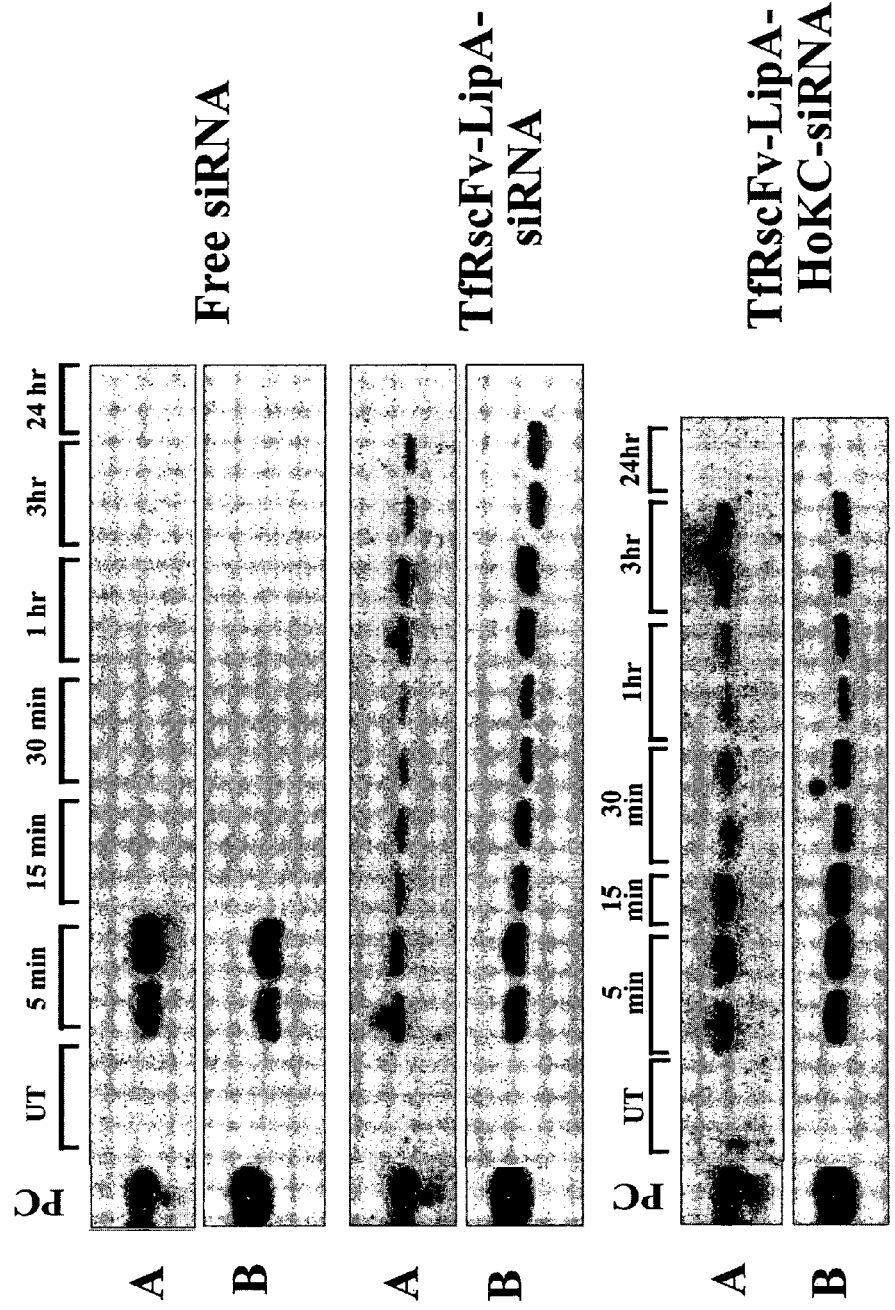
FIG. 55 shows the results of examining the fate of siRNA in blood of mice bearing human pancreatic cancer xenografts by systemically administered immunonanocomplexes.

In a further experiment, the stability of siRNA was examined in the blood of mice bearing human pancreatic cancer xenografts. PANC-1 human pancreatic cancer xenograft tumors were induced by the subcutaneous inoculation of tumor tissue suspended in 600 mL Matrigel collagen basement membrane. When the tumor was 150 mm$^3$, the animals were injected with control modified hybrid siRNA either as free (uncomplexed) siRNA or in complex with TfRscFv/LipA or TfRscFv/LipA-HoKC (9 mg siRNA per Kg). Blood was collected from one animal of each group of mice at 5 min, 15 min, 30 min, 1 hr 3 hr and 24 hr and plasma extracted from each sample. Total RNA was isolated from plasma using Trizol R reagent (Invitrogen). 10 mL was loaded per well on 19% PAAG, 7 M urea. The results of the stability assay are shown in FIG. 55. Row A—membrane hybridized with the deoxyribo oligonucleotide probe complementary to antisense strand of the siRNA to detect the antisense strand. Row B—membrane hybridized with the deoxyribo oligonucleotide probe complementary to the sense strand of the siRNA to detect the sense strand. "PC" indicates Positive control, 1 mg control modified hybrid siRNA. "UT" indicates untreated mice. Free siRNA is not observed after 15 minutes in the blood of these tumor bearing animals, while the immunoliposome complexes of the present invention extend stability to at least 3 or more hours.

Figure 56:
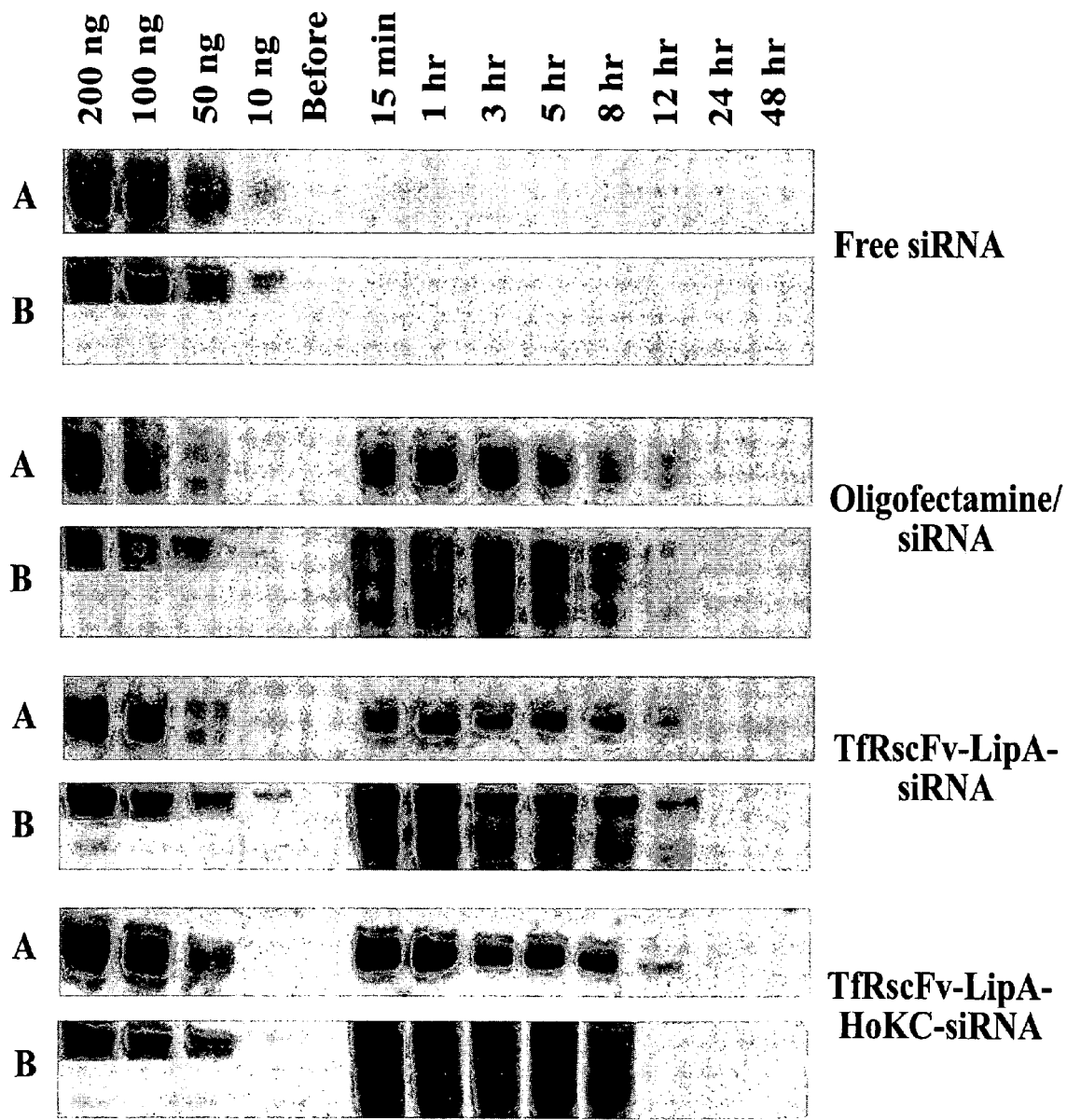
FIG. 56 shows the results examining stability of siRNA in plasma of non-tumor bearing BALB/c mice comparing the immunocomplexes of one embodiment of the present invention with a commercially available liposome transfection product.

In another experiment, the stability of siRNA in vivo in non-tumor bearing animals was examined using the immunocomplexes of the present invention, and comparing them to a commercially-available transfection liposomes system (OLIGOFECTAMINE®, Invitrogen). Non-tumor bearing BALB/c mice were injected once via the tail vein with free commercially obtained (Sigma) non-modified duplex anti- HER-2 siRNA, siRNA in complex with OLIGO-FECTAMINE®, siRNA in complex with TfRscFv/LipA, or siRNA in complex with TfRscFv-LipA-HoKC at 8 mg siRNA per kg. Blood was collected from one mouse of each group within 15 minutes and again at 1, 3, 5, 8, 12, 24, and 48 hours post-injection, and plasma was obtained. RNA was isolated from 10 uL of each plasma sample and loaded per well on 19% PAAG, 7M urea. The results of the stability assay are shown in FIG. 56. Row A—Membrane was hybridized with deoxyribo oligonucleotide complementary to the sense strand of siRNA (modified DNA/RNA strand). Row B—Membrane was hybridized with deoxyribo oligonucleotide complementary to the anti-sense strand of siRNA (RNA strand). PC—Positive control. 200, 100, 50, or 10 ng. of the duplex siRNA was mixed with RNA isolated from 10 uL of plasma obtained from an untreated mouse prior to loading on the gel. siRNA complexed with the immunocomplexes of the present invention shows at least comparable, if not better, stability compared to siRNA delivered using OLIGO-FECTAMINE®.

Figure 57:
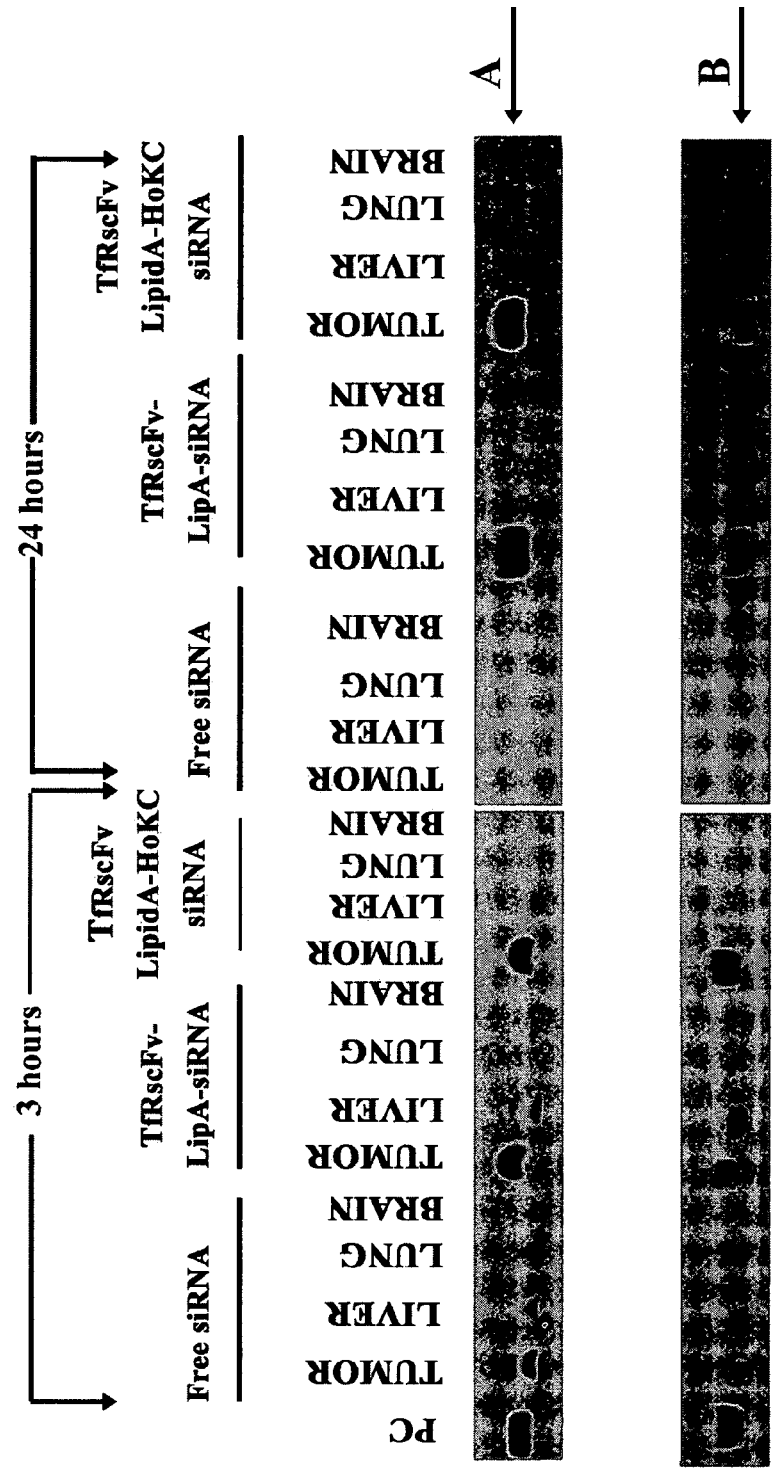
FIG. 57 shows the tumor specific delivery of siRNA to human pancreatic cancer xenografts by systemically administered scL or scL-HoKC immunonanocomplex.

In order to assess the tumor specific delivery of siRNA using the immunocomplexes of the present invention, PANC-1 human pancreatic cancer xenograft tumors were induced by the subcutaneous innoculation of tumor tissue suspended in 600 mL Matrigel collagen basement membrane. When the tumor was 150 mm$^3$, the animals were injected with control modified hybrid siRNA, either as free (uncomplexed) siRNA or complexed with TfRscFv/LipA or TfRscFv/LipA-HoKC (9 mg siRNA per Kg). After 3 hours and 24 hours one animal from each group was sacrificed and tumor, liver, lung and brain were removed. Total RNA was isolated from each tissue sample using Trizol R reagent (Gibco BRL). 20 mg of RNA was loaded per well on 19% PAAG, 7 M urea. The results of the delivery assay are shown in FIG. 57. Row A—membrane hybridized with the deoxyribo oligonucleotide probe complementary to antisense strand of the siRNA to detect the antisense strand. Row B—membrane hybridized with the deoxyribo oligonucleotide probe complementary to sense strand of the siRNA to detect the sense strand. "PC" indicates Positive control, 1 mg control modified hybrid siRNA. As represented in FIG. 57, the siRNA when delivered using either of the immunocomplexes of the present invention localizes in the tumor (especially after 24 hours). In contrast, free siRNA shows tumor specificity over liver at 3 hours and by 24 hours is not detectable in the tumor at all.

Figure 58:
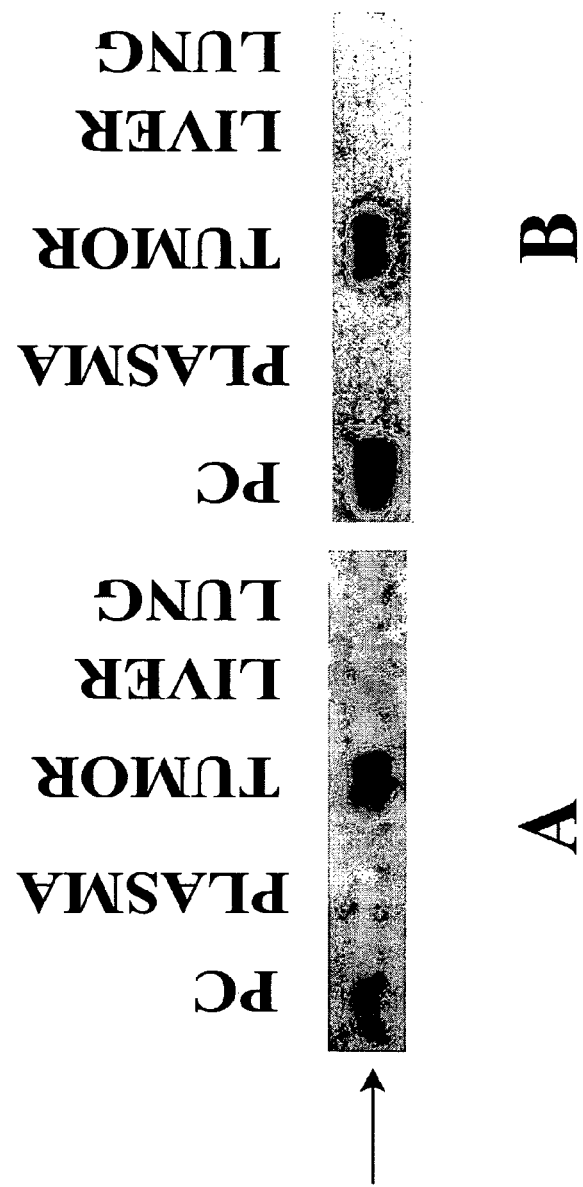
FIG. 58 shows the tumor specific delivery of siRNA to human colon cancer xenografts by systemically administered scL-HoKC immunonanocomplex.

An additional experiment examining siRNA delivery in vivo to a colon cancer cell line is shown in FIG. 58. HCT-116 human colon cancer xenograft tumors were induced by the subcutaneous innoculation of 2×10$^7$ cells suspended in MATRIGEL® collagen basement membrane (BD Biosciences, Bedford, Mass.). When the tumor reached approximately 150 mm$^3$, the animal was i.v. injected via the tail vein with TfRscFv-LipA HoKC (scLHK) complex carrying a 5'-FITC labeled control modified hybrid siRNA (9 mg/kg). After 3 hours, the mouse was sacrificed and plasma, tumor, liver and lungs were removed. Total RNA was isolated from each sample using TRIZOL® reagent (Invitrogen). 38.5 µg of RNA was loaded per well on 19% PAAG, 7 M urea. Row A—membrane hybridized with the 5' (FAM) modified control sense strand labeled by the Gene Images™ Alk Phos Direct™ Kit (Amersham Biosciences) to detect the antisense RNA strand. Row B—the same membrane hybridized with a deoxyoligonucleotide version of the antisense RNA strand of the siRNA to detect the hybrid sense strand. PC indicates positive control, 1 µg of control modified hybrid siRNA. The results shown in FIG. 58 demonstrate specific, high level, intact delivery of siRNA to the tumor tissue.

Figure 59:
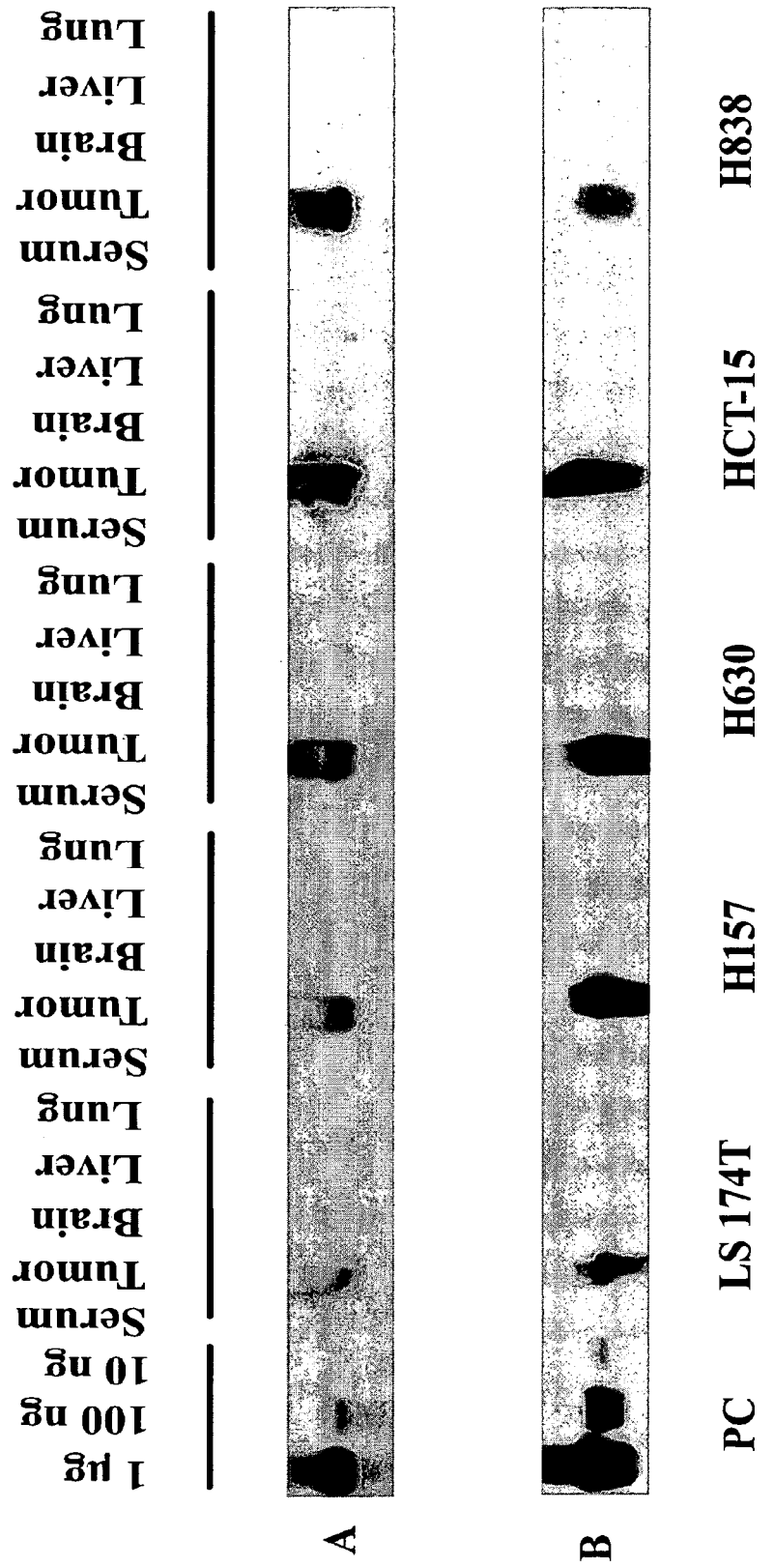
FIG. 59 shows the tumor specific delivery of HER-2 siRNA to human colon cancer xenografts by systemically administrated scL immunonanocomplex.

An additional experiment examining the tumor specific delivery of siRNA to numerous colon cancer xenografts is shown in FIG. 59. Human colon cancer xenograft tumors were induced by the subcutaneous inoculation of cells suspended in Matrigel collagen basement membrane. The LS 174T, H157, H630, HCT-15, and H838 colon cancer cells were injected on the upper and lower back at 5×10$^6$, 8×10$^6$, 1.1×10$^9$, and 1.4×10$^7$ cells per site. When the tumors reached approximately: LS 174T: 1050-1400 mm$^3$, H157: 500-550 mm$^3$, H630: 350-630 mm$^3$, HCT-15: 300-540 mm$^3$, and H838: 50-72 mm$^3$, the animals were injected via the tail vein with TfRscFv-LipA carrying the complex modified hybrid anti HER-2 siRNA at 9 mg per kg. After 24 hours, mice were sacrificed and blood, tumor, liver, and lung samples were collected. Total RNA was isolated from serum and organs using Trizol reagent (Gibco BRL). 25 µg of RNA from the organs or total RNA from 10 µl serum were loaded per well on 19% PAAG, 7 M urea. Row A—Membrane was hybridized with deoxyribo oligonucleotide complementary to the sense strand of the siRNA (modified DNA/RNA strand). Row B—Membrane was hybridized with deoxyribo oligonucleotide complementary to anti-sense strand of siRNA (RNA strand). "PC" indicates Positive control, modified hybrid siRNA in the amounts labeled. Again, tumor-specific delivery of siRNA using the immunocomplexes of the present invention is seen in all tumor cell lines.

In another experiment, the ability of the systemically administered scL nanocomplex to deliver siRNA specifically to tumors was assessed using 5'-FITC labeled control hybrid siRNA molecule as shown in FIG. 60. PC-3 human prostate cancer tumors were induced by the surgical implantation of <1 mm$^3$ slices of subcutaneous tumors into the mice. PC-3 was inserted into the capsule of the dorsal lobe of the prostate of male nude mice. 6-15 weeks post-surgery, the mice were i.v. injected (via the tail vein) with the scL complex (at 9 mg/kg control sequence). 20 min. later the animals were sacrificed, the tumors and liver excised, and examined for fluorescence using a Nikon EPI-Fluorescence Stereoscope. None of the tumors showed necrosis. Strong fluorescence was evident in the tumor cells while only low level signal is present in the normal liver. In the first panel in FIG. 60, one of the seminal vesicles (Left) is involved with the tumor. The fluorescence in this vesicle is brighter that of the right one which cannot be seen. The specificity of the complex to target tumors is evident as the blood vessels in the tumors are dark indicating that, although the complex passes through, there is no uptake. In the next panel to the right in FIG. 60, a cross section of the center of the tumor exhibits very high fluorescence showing the deep tumor penetrance of the complex. Thus, systemically administered scL nanocomplex is able to carry and efficiently deliver siRNA specifically to tumor cells.

Figure 61:
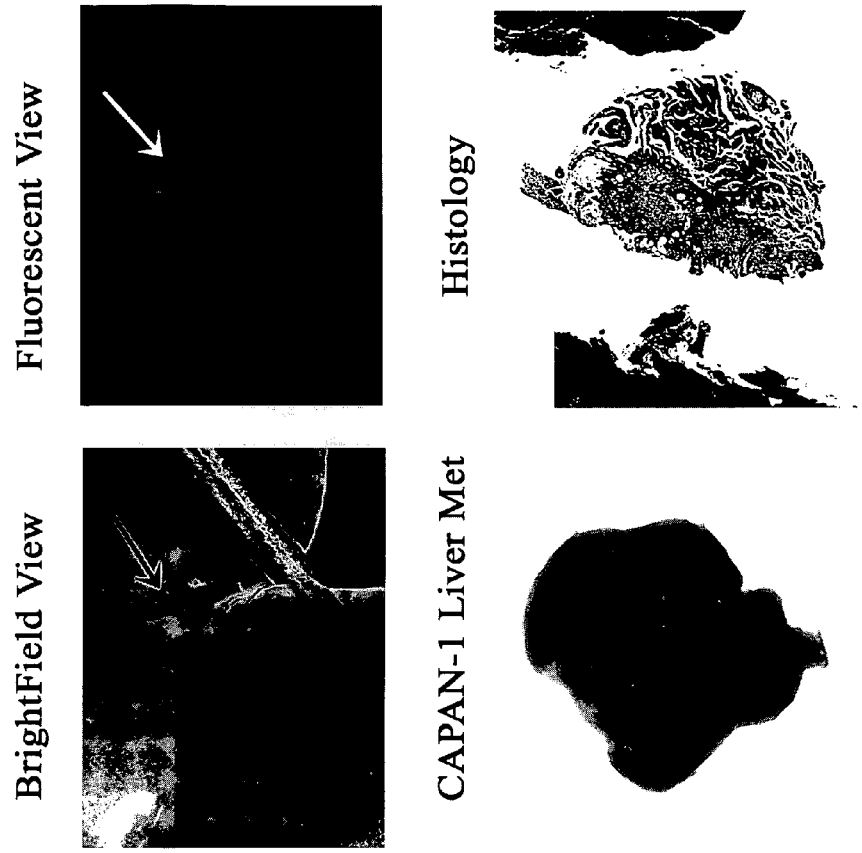
FIG. 61 shows scL mediated targeting of siRNA to metastatic tumors in pancreatic cancer orthotopic tumor mouse models.

The ability of systemically administered scL nanocomplex to deliver siRNA specifically to tumor metastases was assessed using the 5'-FITC labeled control hybrid siRNA molecule as shown in FIG. 61. Liver with metastasis derived from a CAPAN-1 orthotopic pancreatic tumor is shown. The identical field is shown in brightfield and fluorescent views with the arrows indicating the metastasis. As shown in FIG. 61, a fluorescent signal from the labeled siRNA is noted, indicating delivery of the siRNA to the metastasis.

Figure 62:
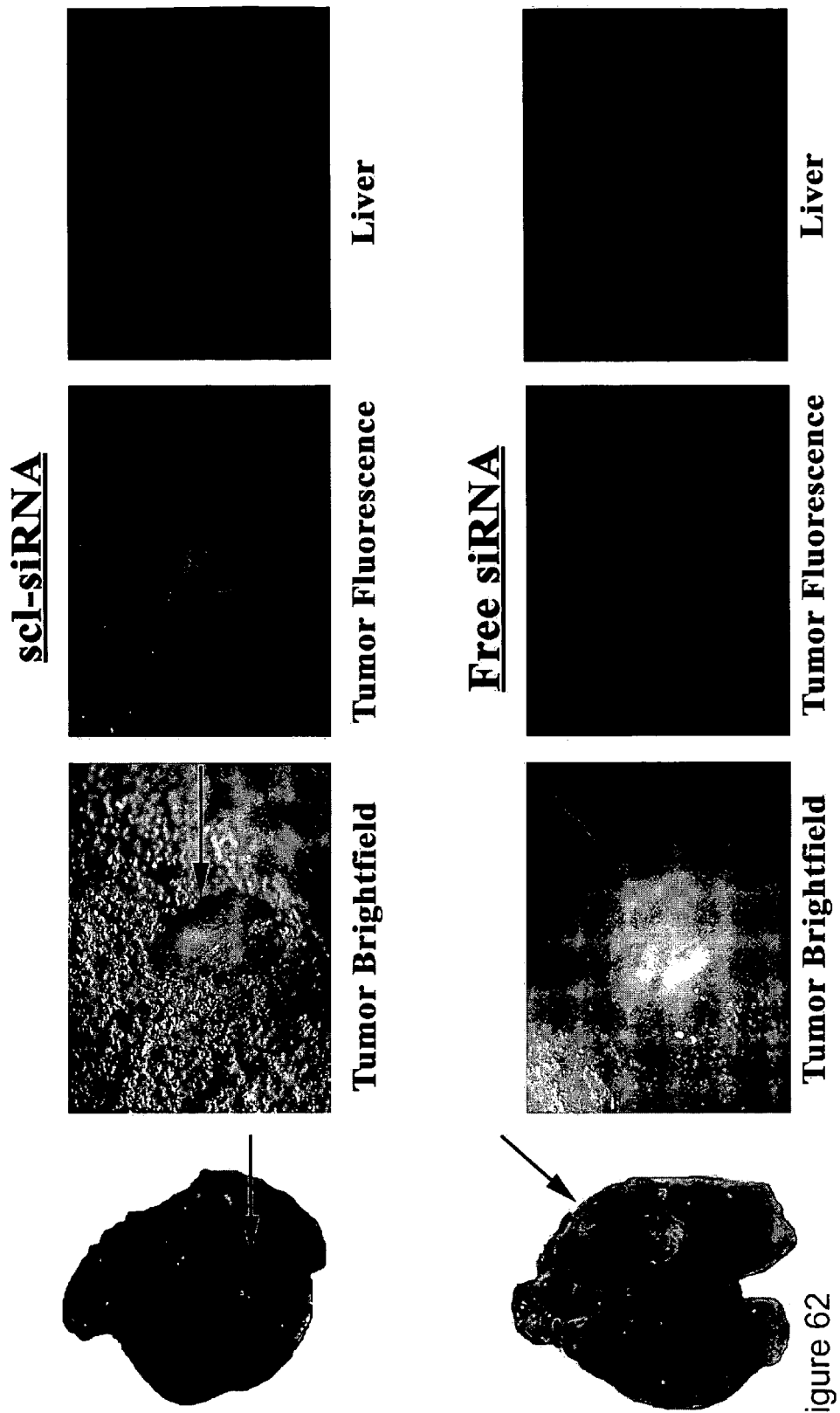
FIG. 62 shows a comparison of free and scL-mediated siRNA targeting to lung metastasis.

An additional experiment showing the comparison of free and scL-mediated siRNA targeting to lung metastases is shown in FIG. 62. Lung metastasis were induced by i.v. injection of MDA435/LCC6 cells. Approximately 8 weeks post-injection, the 6-FAM labeled siRNA at 9 mg/kg, either free or complexed with scL, was injected via the tail vein. Three hours later the animals were sacrificed. The upper row shows a small tumor nodule in the lung of the mouse that received the scL-siRNA. The arrow indicates this nodule in the photograph and the Brightfield view. The lower row shows a larger nodule in the lung from the mouse that received the free (uncomplexed) siRNA. The arrow indicates the nodule in the photograph and the brightfield view. The brightfield and the fluorescence views in both rows are of the identical field. All of the fluorescence images were taken with the identical settings, exposure time and magnification. Delivery of siRNA to the lung metastasis is noted when delivered with the immunoliposome complex.

Figure 63:
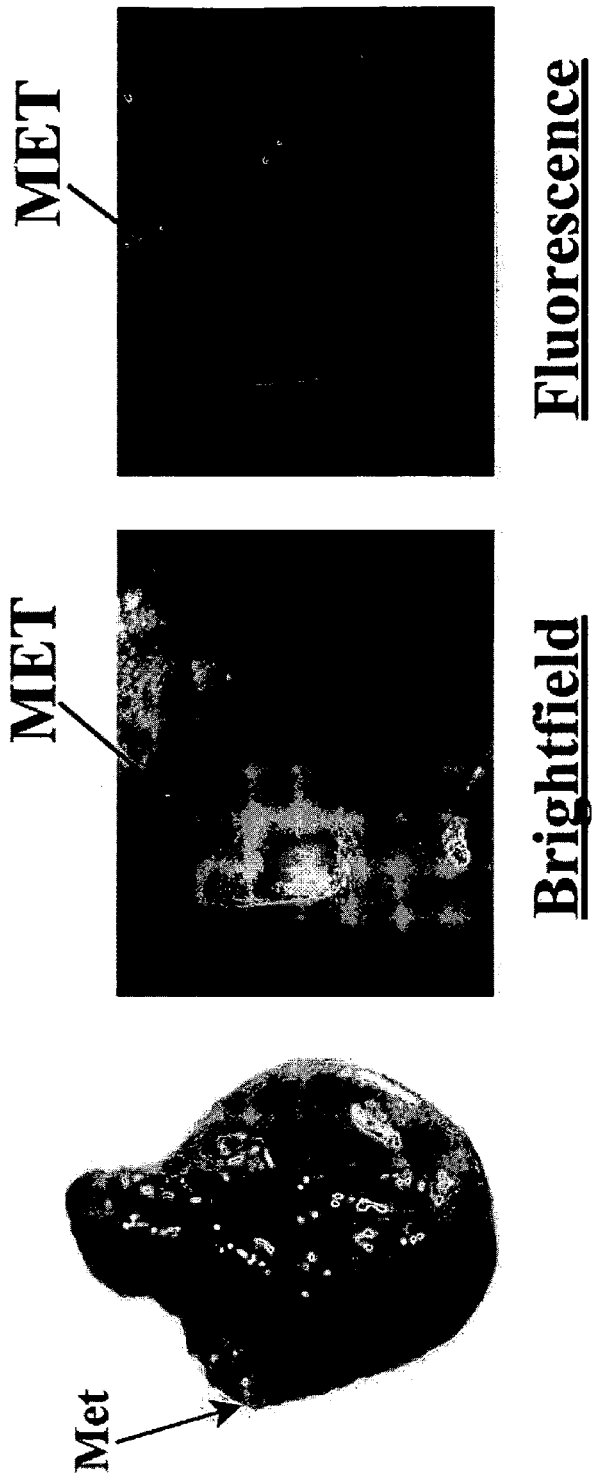
FIG. 63 shows delivery of Fl-siRNA to metastatic breast cancer cells by i.v. administered scL-HoKC complex.

In an additional experiment, delivery of Fl-siRNA to metastatic breast cancer cells by i.v. administered scL-HoKC complex is shown in FIG. 63. Lung metastasis were induced by i.v. injection of $8 \times 10^6$ MDA435/LCC6 cells. Approximately 8 weeks post-injection, the 6-FAM labeled siRNA at 9 mg/kg, complexed with scL-HoKC, was injected via the tail vein. Three hours later the animals were sacrificed. FIG. 63 shows a distinct tumor nodule in the lung of the mouse. The arrow indicates this nodule in the photograph, the brightfield and the fluorescent view, where it can clearly be seen that Fl-siRNA has been delivered. The brightfield and the fluorescence views are of the identical field.

Figure 64:
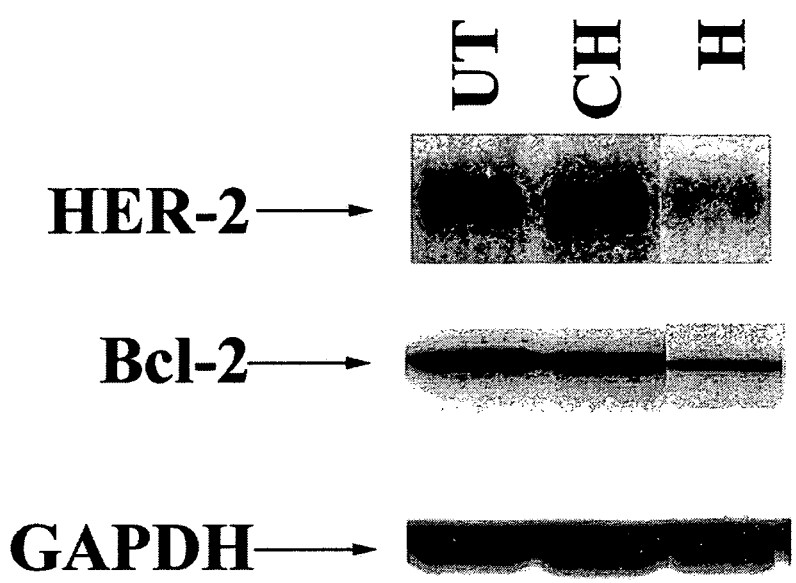
FIG. 64 shows down-modulation of HER-2 expression in tumors from mice treated with scL carrying hybrid siRNA.

Down-Modulation In Vivo Using the Immunoliposome Complexes of the Present Invention To demonstrate the effect on HER-2 levels in vivo, mice bearing human breast cancer xenograft tumor (MDA-MB-435) were i.v. injected through the tail vein three times over 24 hours with the scLsiRNA complex using Hybrid siRNA, or control sequence, both at 3 mg/kg/injection. Untreated mice serve as control. 20 hours after the last injection the mice were humanely euthanized, the tumor harvested, lysed in RIPA buffer, protein determined, and 40 ug of protein run on a precast 4-20% gradient polyacrylamide/SDS gel. After transfer to nitrocellulose, the membranes were probed with the anti-HER-2 antibody. The membrane was also probed with an antibody to Bcl-2 (SantaCruz) to assess the effect on apoptosis and GAPDH (for equal loading). UT=tumor from an untreated animal; H=hybrid siRNA; CH=control hybrid sequence. As shown in FIG. 64, there was no effect on HER-2 expression levels in the tumors of mice receiving the scL complex carrying the control (cH) sequence. However, there is significant down-modulation in the tumors from those treated with the scLsiRNA(H). This down-modulation of HER-2 also appears to be able to affect apoptosis as indicated by the decrease in expression of the anti-apoptotic protein Bcl-2.

Figure 65:
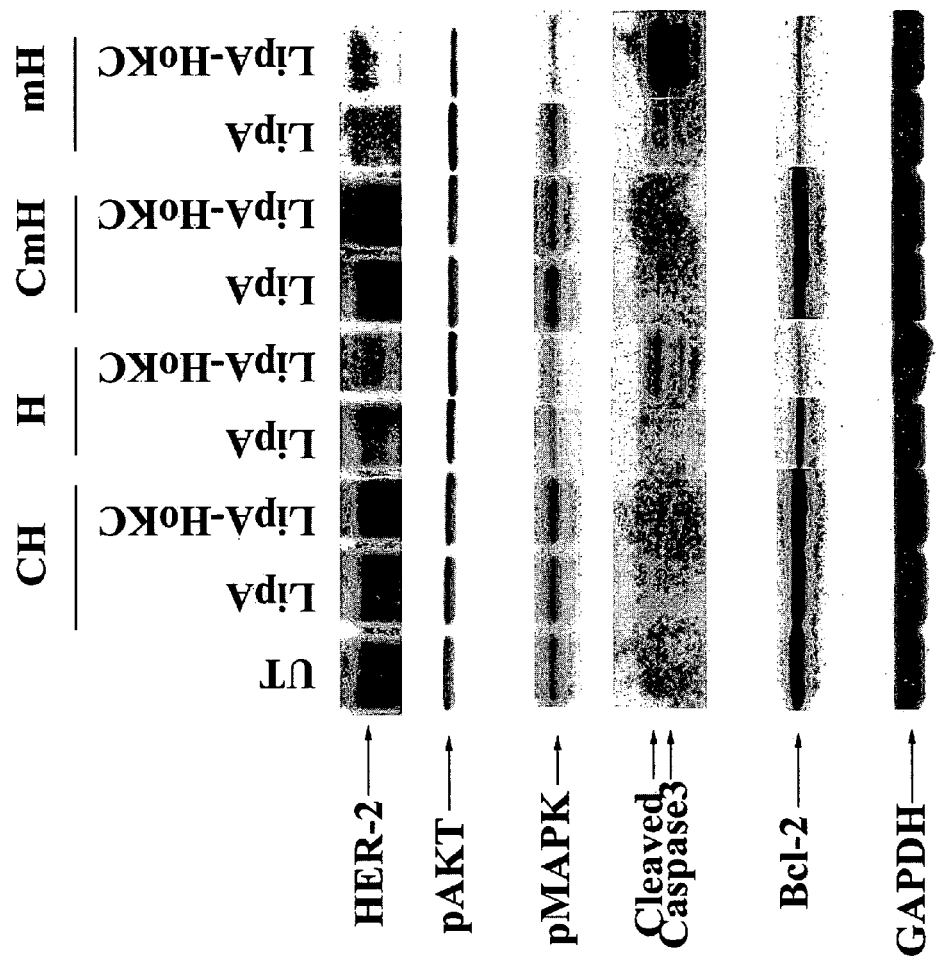
FIG. 65 shows the induction of apoptosis in MDA-MB-435 tumors treated with systemically Administered scL or scL-HoKC delivered hybrid or modified hybrid HER-2 siRNA.

In an additional experiment, the induction of apoptosis in MDA-MB-435 tumors treated with systemically administered scL or scL-HoKC delivered hybrid or modified hybrid HER-2 siRNA was assessed. Mice bearing MDA-MB-435 tumors were treated with 3 mg/kg hybrid or unmodified hybrid siRNA complexed with TfRscFv/liposome or TfRscFv/liposome-HoKC by i.v. injection three times with 18 hour time intervals between injections. 46 hours after first injection and 20 hours after last injection mice were sacrificed. Forty micrograms of protein isolated from each tumor were separated on Criterion Precast 4-20% gradient gel. "UT" indicates untransfected cells. "LipA" indicates TfRscFv LiposomeA delivering siRNA. "LipA-HoKC" indicates TfFscFv liposome/HoKC delivery siRNA. "H" indicates hybrid siRNA. "CH" indicates control hybrid siRNA, "mH" indicates modified hybrid siRNA and "CmH" indicates control modified hybrid siRNA.

pAKT and pMAPK are the active (phosphorylated) forms of proteins AKT and MAPK which are components of two signal transduction pathways influenced by HER-2. These pathways are important in regulating cell growth. HER-2 is upstream of these two genes in the pathways. If HER-2 is activated (such as in many types of cancers e.g. breast, ovarian, prostate, head and neck, pancreatic) these pathways can be constitutively activated and result in uncontrolled cell growth. Thus, silencing of HER-2 results in downmodulation of these proteins, shortcircuiting these signals. As demonstrated in FIG. 65, both the hybrid and the modified hybrid siRNA delivered using the immunocomplexes of the present invention down-modulated the HER-2 protein. Bcl-2 is an important component of apoptosis (programmed cell death). The Bcl-2 protein is "anti"-apoptotic. The ratio of Bcl-2 to other apoptotic proteins will influence whether a cell lives or goes into apoptosis. Modulating components upstream of Bcl-2, which can be done via the HER-2, AKT, and MAPK pathways (among others) will down-modulate BCL-2 and tip this balance towards cell death. Caspase-3 is an important apoptotic protein. It has a key position in apoptosis. It is cleaved into a 12 and a 17 kDa fragment when it is activated (leading to cell death). Thus the presence of the 17 kDa fragment indicates that the apoptotic pathway is activated resulting in cell death. Thus FIG. 65 demonstrates that delivery of siRNA using the immunoliposome complexes of the present invention efficiently silences HER-2 in these tumors, turning off the pathways leading to cell growth and induce cell death.

In Vivo Chemosensitization

Figure 66:
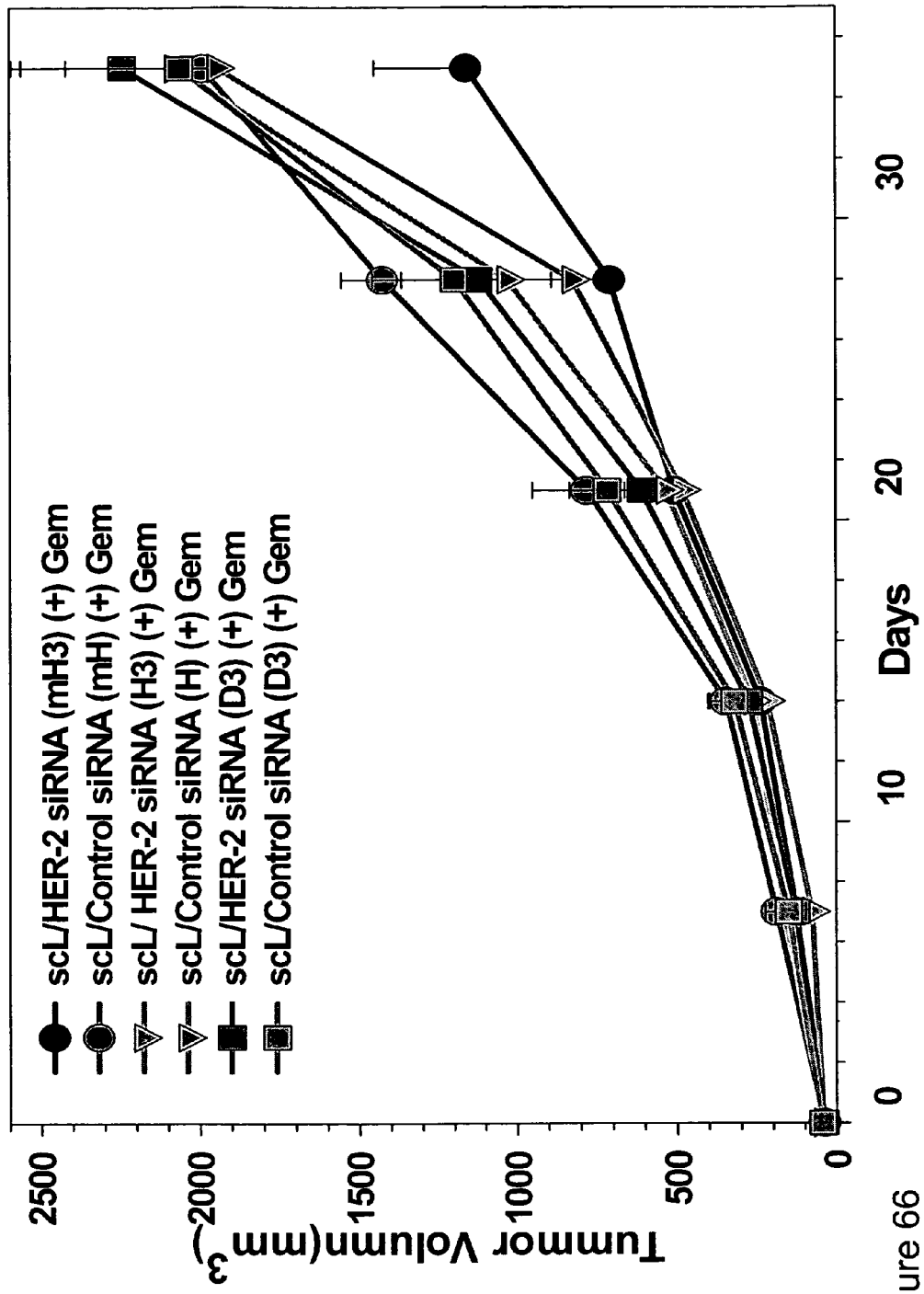
FIG. 66 shows the effect of the combination of scLsiRNA (H, mH and Duplex) and gemcitabine (Gem) on PANC-1 xenograft tumors in vivo.

The in vitro studies described herein demonstrate that treatment of Panc-1 cells with the scLsiRNA nano-complex carrying, for example, the modified hybrid or hybrid siRNA, could increase their response to gemcitabine (Gem). To assess the in vivo ability of the siRNA analogs to sensitize tumors to conventional chemotherapies, a combinatorial animal experiment was performed using a PANC-1 mouse model and Gem. Athymic nude mice (3 mice/group with two tumors/mouse) bearing subcutaneous xenograft tumors of 80-100 mm$^3$ were treated 3 times/week with the scLsiRNA nanocomplexes containing either Duplex (Dup), hybrid (H) or modified hybrid (mH) form of siRNA at 1 mg/kg/injection. As controls, one group of animals each received the combination of Gem and the nanocomplex carrying nonsense siRNA (Dup, H or mH). Gem was given i.p. twice weekly at 60 mg/kg. The animals received a total of 10 i.v. injections of nanocomplex and 7 of Gem. As shown in FIG. 66, effectiveness is evident when the mH siRNA is used. There was substantial tumor growth inhibition in this very aggressively growing tumor 10 days after the end of treatment with the scL delivered mHsiRNA. In comparison, the H and Dup forms were less effective. The controls had virtually no effect on tumor response to Gem. This also suggests that the siRNA effect is not due to non-specific cytotoxicity of the complex. The order of effectiveness, particularly evident after treatment has ended, is similar to that observed in vitro: mH>H>Dup. The weights of the animals as an indicator of toxicity was also monitored. No weight loss occurred and there was no significant difference between any of the treatment groups. Thus, it appears that the scLsiRNA has no major non-specific cytotoxicity, and that i.v. administration of the nanocomplex, in combination with Gem, has anti-tumor effects.

Figure 67:
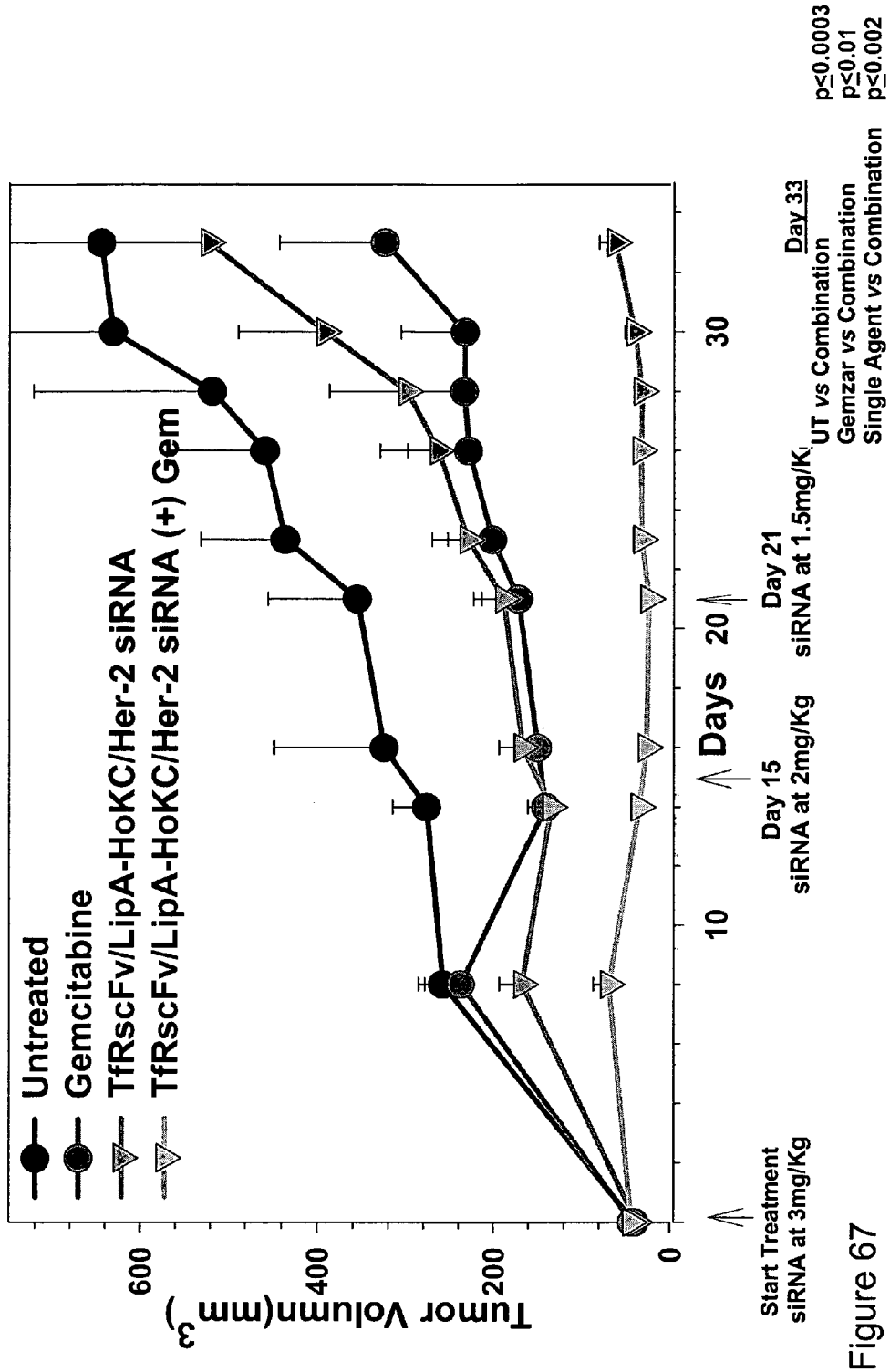
FIG. 67 shows the anti-tumor efficacy of the combination of systemically administered scL-HoKC delivered HER-2 siRNA (mHybrid) and gemcitabine (GEMZAR®) on growth of PANC-1 xenograft tumors.

In a further experiment, the anti-tumor efficacy of the combination of systemically administered scL-HoKC delivered HER-2 siRNA (mHybrid) and gemcitabine (GEMZAR®) was examined, the results of which are shown in FIG. 67. PANC-1 subcutaneous xenograft tumors were induced in female nude mice by the serial passage of 1 mm$^3$ pieces of PANC-1 tumor. Mice bearing tumors of ~50 mm$^3$ were i.v.

injected 3 times/week via the tail vein with scL-HoKC complex carrying the modified Hybrid HER-2 siRNA at 2-3 mg/Kg either alone or in combination with gemcitabine (GEMZAR®) (i.p injected twice weekly at 60 mg/Kg). Each point represents the mean+Std. Error of 8-20 tumors. As shown in FIG. 67, the combination of gemcitabine and siRNA delivered using the immunocomplexes of the present invention was very effective at limiting tumor volume.

Figure 68:
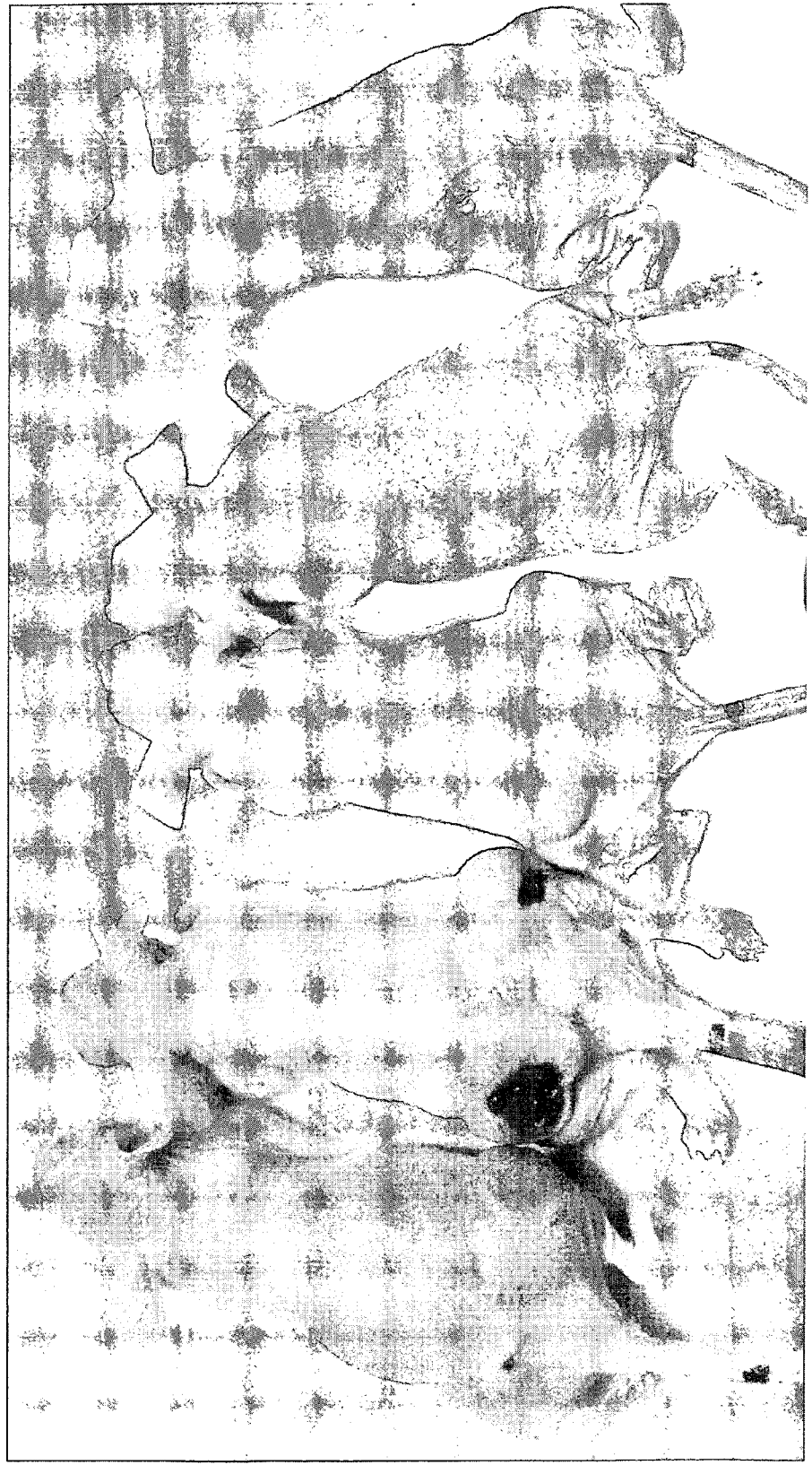
FIG. 68 shows photographs of representative mice from each of the groups in FIG. 67 at the end of treatment.
Figure 69:
FIG. 69 shows photographs of the mice in the combination treatment group (gemcitabine+siRNA delivered via immunocomplex) at the end of treatment.

Photographs of mice from each of the treatment groups described above (from FIG. 67) at the end of treatment are shown in FIG. 68. Photographs of the mice from the (gemcitabine+siRNA delivered via immunocomplex) at the end of treatment are shown in FIG. 69.

Figure 70:
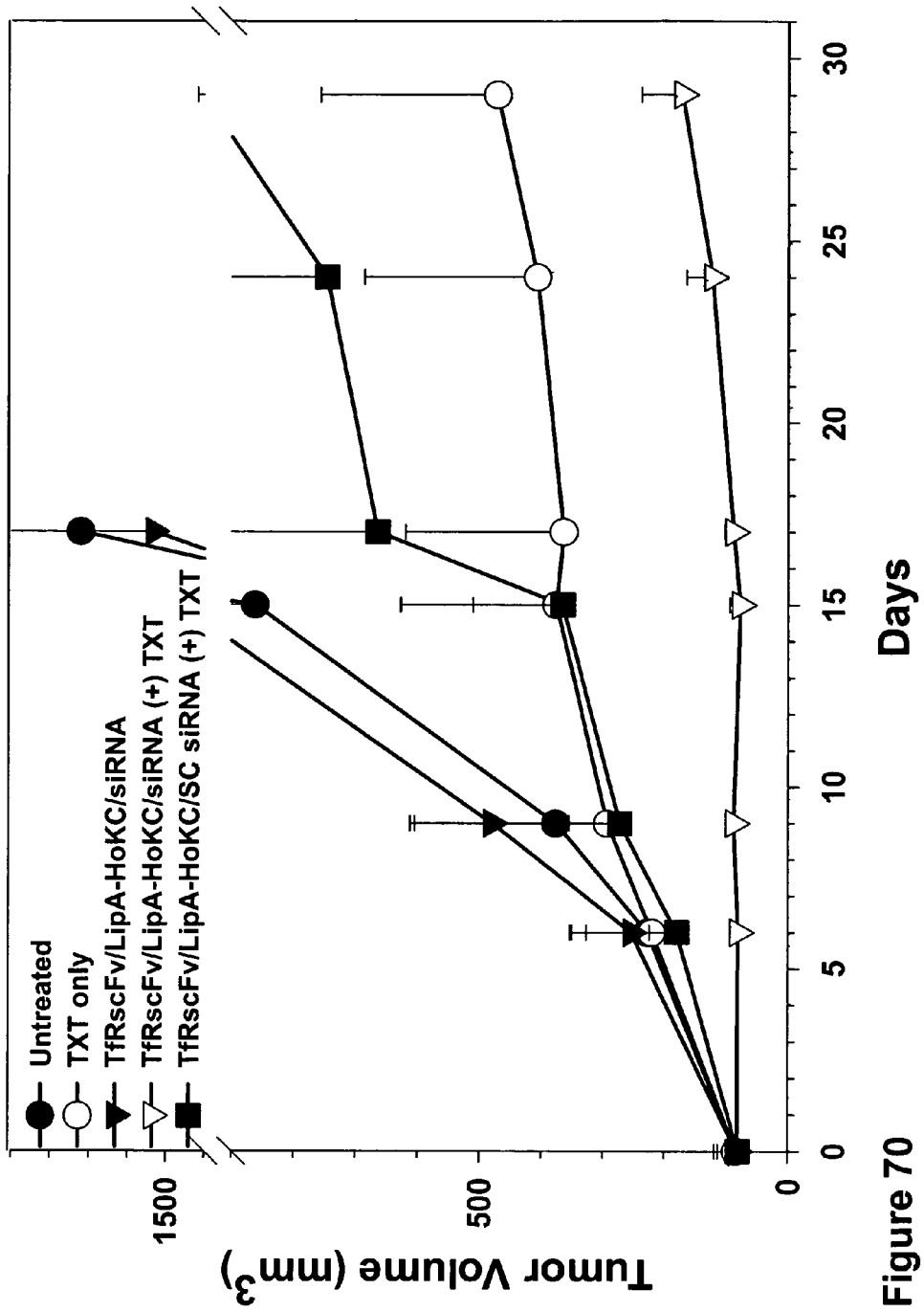
FIG. 70 shows the anti-tumor efficacy of the combination of scL-HoKC delivered anti-HER-2 mHsiRNA and Taxotere on MDA-MB-435 xenograft tumors.

In another experiment to demonstrate the versatility and applicability of the immunoliposome complexes of the present invention to deliver siRNA to various tumor types, the anti-tumor efficacy of the combination of systemically administered scL-HoKC delivered HER-2 siRNA (mHybrid) and docetaxel (Taxotere) was examined, the results of which are shown in FIG. 70. MDA-MB-435 subcutaneous xenograft tumors were induced in female nude mice by the subcutaneous inoculation of 2.5×106 cells suspended in Matrigel® collagen basement membrane. Mice bearing tumors of ~80 mm$^3$ were i.v. injected 3 times/week via the tail vein with scL-HoKC complex carrying the modified Hybrid HER-2 siRNA either alone or in combination with Taxotere (TXT) (i.v injected twice weekly at 6.5 to 7.5 mg/Kg). The first injection of complex was given at a dose of 2 mg/Kg at the ratio of siRNA to Liposome of 1:7 (ug/nmol). Subsequent injections were given at 1.5 mg/Kg at a ratio of siRNA to Liposome of 1:5 (ug/nmol). The ratio of TfRscFv to lip-HoKC was 1:30 (W:W). A total of 12 injections of complex and 7 of taxotere were administered. Tumor size was measured weekly using calipers. Each point represents the mean volume+Std. Error of 6-10 tumors. As shown in FIG. 70, the combination of Taxotere and siRNA delivered using the immunocomplexes of the present invention was very effective at limiting tumor volume.

LITERATURE CITED

1. Felgner, P. L., Tsai Y. J., Sukhu, L., Wheeler, C. J., Manthorpe M., Marshall, J. and Cheng S. H., Ann NY Acad. Sci., 772, 126-139 (1995).
2. Lewis, J. G., Lin, K. Y., Kothavale, A., Flanagan, W. M., Matteucci, M. D., DePrince, R. B., Mook, R. A., Hendren, R. W., and Wagner, R. W., Proc. Natl. Acad. Sci USA, 93, 3176-3181 (1996).
3. Aoki, K., Yoshida, T., Sugimura, T. and Terada, Cancer Res., 55, 3810-3816 (1997).
4. Clark, P. R., Hersh, E. M., Curr. Opin Mol. Ther, 1, 158-176 (1999).
5. Thierry, A. R., Lunardi-Iskandar, Y., Bryant, J. L., Rabinovich, P., Gallo, R. C. and Mahan, L. C., Proc Natl. Acad Sci, 92, 9742-9746 (1997).
6. The Journal of Gene Medicine Clinical Trials Database, http://www.wiley.co.uk/wileychi/genmed/clinical, September, (2001).
7. Cristiano, R. J. and Curiel, D. T., Cancer Gene Ther, 3(1), 49-57 (1996).
8. Cheng, P. W., Hum Gene Ther, 7, 275-282 (1996).
9. Keer, H. N., Kozlowski, J. M. and Tsai, M. C., J. Urol 143, 381-385 (1990).
10. Chackal-Roy, M., Niemeyer, C and Moore, M., J. Clin. Invest., 84, 43-50 (1989).
11. Rossi, M. C. and Zetter, B. R., PNAS, 89, 6197-6201 (1992).
12. Grayhack, J. T., Wendel, E. F. and Oliver, L., J. Urol. 121, 295-299 (1979).
13. Elliott, R. L., Elliott, M. C., Wang, F. and Head, J. F., Ann NY Acad Sci, 698, 159-166 (1993).
14. Miyamoto, T., Tanaka, N., Eishi, Y. and Amagasa, T., Int. J. Oral Maxillofac Surg 23, 430-433 (1994).
15. Thorstensen, K. and Romslo, I., Scad J. Clin Lab Invest. Suppl., 215, 113-120 (1993).
16. Xu, L., Pirollo, K. F. and Chang, E. H., Hum Gen Ther, 8, 467-475 (1997)
17. Xu, L., Pirollo, K. F., Tang, W-H., Rait, A., and Chang, E. H., Human Gene Therapy, 10, 2941-2952 (1999).
18. Xu, L., Frederik, P., Pirollo, K. F., Tang, W-H, Rait, A., Xiang, L-M, Huang, W., Cruz, I., Yin, Y. and Chang, E. H., Human Gene Therapy, 13, 1-13 (2002).
19. Allen, T. M., Hansen, C. B. & Zalipsky, S., Stealth Liposomes, 233-44 (1995).
20. Allen, T. M., Biochim Biophys Acta, 1237, 99-108 (1995).
21. Lasic, D. D., Vallner, J. J. and Working, P. K., Current Opinions in Molecular Therapeutics, 1, 177-185 (1999).
22. Park, J. W., Hong, K., Carter, P., Asgari, H., Guo, L. Y., Keller, G. A., Wirth, C., Shalaby, R., Kotts, C., Wood, W. I., Papahadjopoulos, D and Benz, C. C., Proc. Natl. Acad. Sci USA, 92, 1327-1331 (1995).
23. Park, J. W., Kirpotin, D. B., Hong, K., Shalaby, R., Shao, Y., Nielson, U. B., Marks, J. D., Papahadjopoulos, D., Benz, C. C., J. Control Release, 74 (1-3), 95-113 (2001).
24. Koning, G. A., Gorter, A., Scherphof, G. L. and Kamps, J. A., British Journal of Cancer, 80, 1718-1725 (1999).
25. Koning, G. A., Morselt, H. W., Velinova, M. J., Donga, J., Gorter, A., Allen, T. M., Zalipsky, S., Kamps, J. A. and Scherphof, G. L., Biochemica et Biophysica Acta, 1420, 153-167 (1999).
26. Nam, S. M., Kim, H. S., Ahn, W. S. and Park, Y. S., Oncology Research 11, 9-16 (1999).
27. Pagnan, G., Montaldo, P. G., Pastorino, F., Raffaghello, L., Kirchmeier, M., Allen, T. M. and Ponzoni, M., International Journal of Cancer, 81, 268-274 (1999).
28. Ng, K., Zhao, L., Liu, Y and Mahapatro, M., International Journal of Pharmaceutics, 193, 157-166 (2000).
29. Pirollo, K. F., Xu, L., Chang, E. H., Immunoliposomes: a targeted delivery tool for cancer treatment. In: Vector Targeting for Therapeutic Gene Delivery, D. Curiel (Ed.); Wiley Press (2002) In Press
30. Poon, R. Y., in Biotechnology International: International Developments in the Biotechnology Industry (eds. Fox F and Connor, T. H.) 113-128 (Universal Medical Press, Inc., San Francisco, Calif., 1997).
31. Weinberg, E. D., Biol. Trace Elements Res., 34, 123-140 (1992).
32. Reviews: p. 53. In: Oncogene Reviews. Jenkins, J. R., Banks L. M. (Eds), Stockton Press, London (1999): 18, 7617-777.
33. Sidransky, D., Hollstein, M., Annual Review of Medicine, 1996, 47, 285-301.
34. Ruley, H. E., In: Important Advances in Oncology 1996. Edited by DeVita, V. T., Hellman, S and S. A. Rosenberg, Philadelphia: Lippincott-Raven Publishers; 1996: 37-56.
35. Bristow, R. G., Benchimol, S., Hill, R. P.: Radiotherapy & Oncology, 40, 1996, 197-223.
36. Chiarugi, V., Magnelli, L., Gallo, O., Int. J. Mol. Med., 2, 715-719, 1998.
37. Volpert, O. V., Dameron, K. M., Bouck, N., Oncogene, 1997, 14, 1495-1502.
38. Kerr, J. F., Winterford, C. M. and Harmon, B. V., Cancer, 73, 1994, pp. 2013-2026.

39. Lowe, S. W., Curr. Opin Oncol., 7, 547-553 (1995).
40. Johnson, P., Gray, D., Mowat, M. and Benchimol, J. S., Mol. Cell Biol., 11, 1-11 (1991).
41. Yang, C., Cirielli, C., Capogrossi, M. C. and Passaniti, A., Cancer Res., 55, 4210-4213 (1995).
42. Srivastava, S., Katayose, D., Tong, Y. A., Craig, C. R., McLeod, D. G., Moul, J. W., Cowan, K. H. and Seth, P., Urology, 46, 843-848 (1995).
43. Pirollo, K. F., Zhengmei, H., Rait, A., Jang, Y. J., Fee, W. E., Ray, P., Chiang, Y. and Chang, E. H., Oncogene, 14, 1735-1746 (1997).
44. Liu, T. J., Zhang, W. W., Taylor, D. L., Roth, J. A., Goepfert, H. and Clayman, G. L., Cancer Res., 54, 3662-3667 (1994).
45. Miyashita, T., Krajewski, S., Krajewska, M., Wang, H. G., Lin, H. K., Liebermann, D. A., Hoffman, B. & Reed, J. C., Oncogene, 9(6), 1799-1805 (1994).
46. Hamada, K., Alemany, R., Zhang, W. W., Hittelman, W. N., Lotan, R., Roth, J. A. and Mitchell, M. F., Cancer Res., 56 (3), 3047-3054 (1996).
47. Fujiwara, T., Grimm, E. A., Mukhopadhyay, T., Zhang, W. W., Owen-Schaub, L. B. and Roth, J. A., Cancer Res, 54, 2287-2291 (1994).
48. Fujiwara, T., Grimm, E. A., Mukhopadhyay, T., Cai, D. W., Owen-Schaub, L. B. and Roth, J. A., Cancer Res, 53, 4129-4133 (1993).
49. Xu, L., Pirollo, K. F., Rait, A., Murray, A. L. and Chang, D. H., Tumor Targeting, 4, 92-104 (1999).
50. Xu, L., Pirollo, K. F., Tang, W., Rait, A. and Chang, E. H., Human Gene Therapy, 10, 2941-2952 (1999),
51. Rait, A., Pirollo, K., Rait, V., Krkygier, J., Xiang, L. and Chang, E. H., Cancer Gene Therapy 8, 728-739 (2001).
52. Yazdi, P. T., Wenning, L. A. and Murphy, R. M., Cancer Res., 55, 3763-3771 (1995).
53. Dube'D, Francis, M., Leroux J-C and Winnik, F. M., Bioconjugate Chemistry 10, On line article, 2002.
54. Haynes B F, Hemler M, Cotner T, Mann D L, Eisenbarth G S, Strominger J L and Fauci A S., Characterization of a monoclonal antibody (5E9) that defines a human cell surface antigen of cell activation. Journal of Immunology 127: 347-351 (1981).
55. Batra J K, Fitzgerald D J, Chaudhary V K and Pastan I., Single-chain immunotoxins directed at the human transferrin receptor containing *Pseudomonas* exotoxin A or diphtheria toxin: anti-TFR(Fv)-PE40 and DT388-anti-TFR(Fv). Molecular & Cellular Biology 11: 2200-2205 (1991).

All publications, patents and patent applications mentioned in this specification are herein incorporated by reference to the same extent as if each individual publication, patent or patent application was specifically and individually indicated to be incorporated by reference.

What is claimed is:

1. A method of preparing an antibody- or antibody fragment-targeted cationic immunoliposome complex comprising:

(a) preparing an antibody or antibody fragment;

(b) mixing said antibody or antibody fragment with a cationic liposome that does not comprise maleimido-phenylbutyrate-lipid (MPB-lipid) to form a cationic immunoliposome, wherein said antibody or antibody fragment is complexed with said cationic liposome but is not chemically conjugated to said cationic liposome and wherein said antibody or antibody fragment does not comprise a lipid tag; and (c) mixing said cationic immunoliposome with an siRNA to form said antibody- or antibody fragment-targeted-cationic immunoliposome complex, wherein the cationic immunoliposome complex is 50-400 nm in size.

2. The method of claim 1, wherein an antibody is mixed with said cationic liposome.

3. The method of claim 1, wherein an antibody fragment is mixed with said cationic liposome.

4. The method of claim 3, wherein said antibody fragment is a single chain Fv fragment.

5. The method of claim 4, wherein said antibody fragment is an anti-transferrin receptor single chain Fv (TfRscFv).

6. The method of claim 1, wherein said antibody or antibody fragment is an anti-HER-2 antibody or an anti-HER-2 antibody fragment.

7. The method of claim 1, wherein said antibody fragment comprises a cysteine moiety at a carboxy terminus prior to being mixed with said cationic liposome.

8. The method of claim 1, wherein said cationic liposome comprises a mixture of one or more cationic lipids and one or more neutral or helper lipids.

9. The method of claim 1, wherein said antibody or antibody fragment is mixed with said cationic liposome at a ratio in the range of about 1:20 to about 1:40 (w:w).

10. The method of claim 1, wherein said cationic liposome comprises a mixture of, dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

11. The method of claim 1, wherein said cationic immunoliposome is mixed with said siRNA at a ratio in the range of about 1:3.5 to about 1:14 (μg siRNA:nmol liposome.

12. The method of claim 1, wherein said cationic immunoliposome is mixed with said siRNA at a molar ratio of about 1:7 (µg siRNA:nmol liposome).

13. The method of claim 1, wherein said cationic immunoliposome is mixed with said siRNA at a molar ratio of about 1:5 (µg siRNA:nmol liposome).

14. The method of claim 1, wherein said siRNA is an anti-HER-2 siRNA.

15. The method of claim 14, wherein a sense strand of said anti-HER-2 siRNA comprises the sequence:
5'-d(TITIT)-2'OMe(GCGGUGGUU)-d(GICIT) (SEQ ID NO:9).

16. The method of claim 14, wherein said anti-HER-2 siRNA comprises the sequences:

```
TITITgcggugguuGICIT       (SEQ ID NO: 9)

AGAGACGCCACCAACCGUA.      (SEQ ID NO: 16)
```

17. A cationic immunoliposome complex prepared by a method comprising:
(a) preparing an antibody or antibody fragment;
(b) mixing said antibody or antibody fragment with a cationic liposome that does not comprise maleimido-phenylbutyrate-lipid (MPB-lipid) to form a cationic immunoliposome, wherein said antibody or antibody fragment is complexed with said cationic liposome but is not chemically conjugated to said cationic liposome and wherein said antibody or antibody fragment does not comprise a lipid tag; and
(c) mixing said cationic immunoliposome with an siRNA to form said antibody- or antibody fragment-targeted-cationic immunoliposome complex,
wherein said cationic immunoliposome complex is 50-400 nm in size.

18. An antibody- or antibody fragment-targeted cationic immunoliposome complex comprising a cationic liposome that does not comprise maleimido-phenylbutyrate-lipid (MPB-lipid), an antibody or antibody fragment, and an siRNA, wherein said antibody or antibody fragment is complexed with said cationic liposome but is not chemically conjugated to said cationic liposome and wherein said antibody or antibody fragment does not comprise a lipid tag, wherein said cationic immunoliposome complex is 50-400 nm in size.

19. The cationic immunoliposome complex of claim 18, wherein said siRNA is encapsulated within said cationic liposome.

20. The cationic immunoliposome complex of claim 18, wherein said siRNA is associated with an inner or outer monolayer of said cationic liposome.

21. The cationic immunoliposome complex of claim 18, wherein said antibody fragment is a single chain Fv fragment.

22. The cationic immunoliposome complex of claim 18, wherein said antibody fragment is an anti-transferrin receptor single chain Fv (TfRscFv).

23. The cationic immunoliposome complex of claim 18, wherein said antibody or antibody fragment is an anti-HER-2 antibody or an anti-HER-2 antibody fragment.

24. The cationic immunoliposome complex of claim 18, wherein said cationic liposome comprises a mixture of one or more cationic lipids and one or more neutral or helper lipids.

25. The cationic immunoliposome complex of claim 18, wherein said antibody or antibody fragment and said cationic liposome are present at a ratio in the range of about 1:20 to about 1:40 (w:w).

26. The cationic immunoliposome complex of claim 18, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

27. The cationic immunoliposome complex of claim 18, wherein said siRNA and said cationic immunoliposome are present at a ratio in the range of about 1:3.5 to about 1:14 (µg siRNA:nmol liposome).

28. The cationic immunoliposome complex of claim 18, wherein said siRNA and said cationic immunoliposome are present at a molar ratio of about 1:7 (µg siRNA:nmol liposome).

29. The cationic immunoliposome complex of claim 18, wherein said siRNA and said cationic immunoliposome are present at a molar ratio of about 1:5 (µg siRNA:nmol liposome).

30. The cationic immunoliposome complex of claim 18, wherein said siRNA is an anti-HER-2 siRNA.

31. The cationic immunoliposome complex of claim 30, wherein a sense strand of said anti-HER-2 siRNA comprises the sequence:

```
5'-                            (SEQ ID NO: 9)
d(TITIT)-2'OMe(GCGGUGGUU)-d(GICIT).
```

32. The cationic immunoliposome complex of claim 30, wherein said anti-HER-2 siRNA comprises the sequences:

```
TITITgcggugguuGICIT;      (SEQ ID NO: 9)
and

AGAGACGCCACCAACCGUA.      (SEQ ID NO: 16)
```

33. An antibody- or antibody fragment-targeted cationic immunoliposome complex comprising a cationic liposome, an antibody or antibody fragment, and an anti-HER-2-siRNA, wherein said antibody or antibody fragment is complexed with said cationic liposome but is not chemically conjugated to said cationic liposome, and wherein the sense strand of said anti-HER-2 siRNA comprises the sequence:
5'-d(TITIT)-2'OMe(GCGGUGGUU)-d(GICIT) (SEQ ID NO:9).

34. The cationic immunoliposome complex of claim 33, wherein said anti-HER-2 siRNA comprises the sequences:

```
TITITgcggugguuGICIT;      (SEQ ID NO: 9)
and

AGAGACGCCACCAACCGUA.      (SEQ ID NO: 16)
```

35. The cationic immunoliposome complex of claim 33, further comprising a K[K(H)KKK]$_5$-K(H)KKC (HoKC) (SEQ ID NO: 20) peptide associated with said complex.

36. The cationic immunoliposome complex of claim 33, wherein said antibody fragment is a single chain Fv fragment.

37. The cationic immunoliposome complex of claim 33, wherein said antibody fragment is an anti-transferrin receptor single chain Fv (TfRscFv).

38. The cationic immunoliposome complex of claim 33, wherein said antibody or antibody fragment is an anti-HER-2 antibody or an anti-HER-2 antibody fragment.

39. The cationic immunoliposome complex of claim 33, wherein said antibody or antibody fragment and said cationic liposome are present at a ratio in the range of about 1:20 to about 1:40 (w:w).

40. The cationic immunoliposome complex of claim 33, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

41. The cationic immunoliposome complex of claim 33, wherein said anti-HER-2-siRNA and said cationic immunoliposome are present at a ratio in the range of about 1:3.5 to about 1:14 (µg siRNA:nmol liposome).

42. The cationic immunoliposome complex of claim 33, wherein said anti-HER-2-siRNA and said cationic immunoliposome are present at a molar ratio of about 1:7 (µg siRNA:nmol liposome).

43. The cationic immunoliposome complex of claim 33, wherein said anti-HER-2-siRNA and said cationic immunoliposome are present at a molar ratio of about 1:5 (µg siRNA:nmol liposome).

44. The cationic immunoliposome complex of claim 17, wherein said siRNA and said cationic immunoliposome are present at a ratio in the range of about 1:3.5 to about 1:7 (µg siRNA:nmol liposome).

45. The cationic immunoliposome complex of claim 18, wherein said siRNA and said cationic immunoliposome are present at a ratio in the range of about 1:3.5 to about 1:7 (µg siRNA:nmol liposome).

46. An antibody- or antibody fragment-targeted cationic immunoliposome complex comprising a cationic liposome that does not comprise maleimido-phenylbutyrate-lipid (MPB-lipid), an antibody or antibody fragment, and siRNA, wherein said antibody or antibody fragment is complexed with said cationic liposome but is not chemically conjugated to said cationic liposome and said antibody or antibody fragment does not comprise a lipid tag, and wherein said siRNA and said cationic immunoliposome are present at a ratio in the range of about 1:3.5 to about 1:5 (µg siRNA:nmol liposome).

47. The cationic immunoliposome complex of claim 46, wherein said siRNA is an anti-HER-2 siRNA comprising the sequence:

5'-d(TITIT)-2'OMe(GCGGUGUU)-d(GICIT) (SEQ ID NO:9).

48. The cationic immunoliposome complex of claim 47, wherein said anti-HER-2 siRNA comprises the sequences:

```
TITITgcgguggguuGICIT;      (SEQ ID NO: 9)
and

AGAGACGCCACCAACCGUA.       (SEQ ID NO: 16)
```

49. The cationic immunoliposome complex of claim 46, wherein said antibody fragment is a single chain Fv fragment.

50. The cationic immunoliposome complex of claim 46, wherein said antibody fragment is an anti-transferrin receptor single chain Fv (TfRscFv).

51. The cationic immunoliposome complex of claim 46, wherein said antibody or antibody fragment is an anti-HER-2 antibody or an anti-HER-2 antibody fragment.

52. The cationic immunoliposome complex of claim 46, wherein said antibody or antibody fragment and said cationic liposome are present at a ratio in the range of about 1:20 to about 1:40 (w:w).

53. The cationic immunoliposome complex of claim 46, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

54. The cationic immunoliposome complex of claim 46, wherein said siRNA and said cationic immunoliposome are present at a molar ratio of 1:5 (µg siRNA:nmol liposome).

55. An antibody- or antibody fragment-targeted cationic immunoliposome complex comprising a cationic liposome, an antibody or antibody fragment, and siRNA, wherein said antibody or antibody fragment is complexed with said cationic liposome but is not chemically conjugated to said cationic liposome and said antibody or antibody fragment does not comprise a lipid tag, and wherein said siRNA and said cationic immunoliposome are present at a ratio in the range of about 1:3.5 to 1:5 (µg siRNA:nmol liposome) said complex further comprising a K[K(H)KKK]$_5$-K(H)KKC (HoKC) (SEQ ID NO: 20) peptide associated with said complex.

56. The cationic immunoliposome complex of claim 55, wherein said siRNA is an anti-HER-2 siRNA comprising the sequence:

5'-d(TITIT)-2'OMe(GCGGUGUU)-d(GICIT) (SEQ ID NO:9).

57. The cationic immunoliposome complex of claim 55, wherein said anti-HER-2 siRNA comprises the sequences:

```
TITITgcgguggguuGICIT;      (SEQ ID NO: 9)
and

AGAGACGCCACCAACCGUA.       (SEQ ID NO: 16)
```

58. The cationic immunoliposome complex of claim 55, wherein said antibody fragment is a single chain Fv fragment.

59. The cationic immunoliposome complex of claim 55, wherein said antibody fragment is an anti-transferrin receptor single chain Fv (TfRscFv).

60. The cationic immunoliposome complex of claim 55, wherein said antibody or antibody fragment is an anti-HER-2 antibody or an anti-HER-2 antibody fragment.

61. The cationic immunoliposome complex of claim 55, wherein said antibody or antibody fragment and said cationic liposome are present at a ratio in the range of about 1:20 to about 1:40 (w:w).

62. The cationic immunoliposome complex of claim 55, wherein said cationic liposome comprises a mixture of dioleoyltrimethylammonium phosphate with dioleoylphosphatidylethanolamine and cholesterol, a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

63. The cationic immunoliposome complex of claim 55, wherein said siRNA and said cationic immunoliposome are present at a molar ratio of 1:5 (μg siRNA:nmol liposome).

64. The cationic immunoliposome complex of claim 33, wherein said cationic immunoliposome complex is 50-400 nm in size.

65. The cationic immunoliposome complex of claim 46, wherein said cationic immunoliposome complex is 50-400 nm in size.

66. The cationic immunoliposome complex of claim 55, wherein said cationic immunoliposome complex is 50-400 nm in size.

* * * * *